United States Patent [19]
Paoletti et al.

[11] Patent Number: 5,688,920
[45] Date of Patent: Nov. 18, 1997

[54] NUCLEOTIDE AND AMINO ACID SEQUENCES FOR CANINE HERPESVIRUS GB, GC AND GD AND USES THEREFOR

[75] Inventors: Enzo Paoletti, Delmar; Keith J. Limbach, Troy, both of N.Y.

[73] Assignee: Virogenetics Corporation, Troy, N.Y.

[21] Appl. No.: 413,118

[22] Filed: Mar. 29, 1995

Related U.S. Application Data

[63] Continuation-in-part of Ser. No. 220,151, Mar. 30, 1994, Pat. No. 5,529,780.

[51] Int. Cl.⁶ ............................................. C07K 14/03
[52] U.S. Cl. .................. 530/395; 530/350; 530/403; 424/199.1; 424/184.1; 424/229.1; 424/232.1; 435/69.1; 435/69.3; 435/172.3; 435/235.1; 435/236; 435/237; 435/320.1
[58] Field of Search .................... 530/395, 350, 530/403; 435/69.1, 69.3, 172.3, 235.1, 236, 237, 320.1; 424/184.1, 229.1, 232.1

[56] References Cited

PUBLICATIONS

Ackermam, M., R. Longnecker, B. Roizman, and L. Pereira, Virology 150, 207–220 (1986).
Allen, G.P. and M.R. Yeargan, J. Virol. 61, 2454–2461 (1987).
Allen, G.P. and J.T. Bryans, In: Progress in Veterinary Microbiology and Immunology, vol. 2, ed. R. Pandey (Basel), pp. 78–144 (1986).
Allen, G.P., and L.D. Coogle, J. Virol. 62, 2850–2858 (1988).
Altenburger, W., C–P. Suter and J. Altenburger, Archives Virol. 105, 15–27 (1989).
Appel, M., In Virus Infections of Vertebrates, vol. 1, pp. 5–15. Edited by M. Appel. Amsterdam–Oxford–New York–Tokyo: Elsevier Science Publishers (1987).
Audonnet, J.–C., Winslow, J., Allen, G. & Paoletti, E., Journal of General Virology 71, 2969–2978 (1990).
Avery, R.J., and J. Niven, Infect. and Immun. 26, 795–801 (1979).
Babiuk, L.A., J. L'Italien, S. van Drunen Littel–van den Hurk, T. Zamb, M.J.P. Lawman, G. Hughes, and G.A. Gifford, J. Virol. 159, 57–66 (1987).
Baer, R., A.T. Bankier, M.D. Biggin, P.L. Deininger, P.J. Farrell, T.J. Gibson, G. Hatfull, G.S. Hudson, S.C. Satchwell, C. Seguin, P.S. Tuffnell, and S.G. Barrell, Nature 310, 207–211 (1984).
Baines, J., and B. Roizman, J. Virol. 67, 1441–1452 (1993).
Balachandran, N., S. Bacchetti, and W.E. Rawls, Infect. Immun. 37, 1132–1137 (1982).
Bause, E., Biochemical Journal 209, 331–336 (1983).
Behbehani, A.M., Microbiological Reviews 47, 455–509 (1983).
Ben–Porat, T., J. DeMarchi, J. Pendrys, R.A. Veach, and A.S. Kaplan, J. Virol. 57, 191–196 (1986).
Ben–Porat, T. and A.S. Kaplan, In: The Herpesviruses, vol. 3, ed. B. Roizman (Plenum Publishing Corp., New York) pp. 105–173 (1985).
Ben–Porat, T., F.J. Rixon, and M.L. Blankenship, Virology 95, 285–294 (1979).
Bergoin, M. and Dales, S., In Comparative Virology, eds. K. Maramorosch and E. Kurstak, (Academic Press, NY) pp. 169–205 (1971).
Berman, P.W., D. Dowbenko, L.A. Lasky, and C.C. Simonsen, Science 222, 524–527 (1983).
Bertholet, E., Drillien, R., and Wittek, R., Proc. Natl. Acad. Sci. USA 82, 2096–2100 (1985).
Blewett, E. & Misra, V., Journal of General Virology 72, 2083–2090 (1991).
Blobel, G., Proceedings of the National Academy of Sciences, U.S.A. 77, 1496–1500 (1980).
Boursnell, M.E.G., P.F. Green, J.I.A. Campbell, A. Deuter, R.W. Peters, F.M. Tomley, A.C.R. Samson, P. Chambers, P.T. Emmerson, and M.M. Binns, J. Gen. Virol. 71, 621–628 (1990a).
Boursnell, M.E.G., P.F. Green, J.I.A. Campbell, A. Deuter, R.W. Peters, F.M. Tomley, A.C.R. Samson, P.T. Emmerson, and M.M. Binns, Veterinary Microbiology 23, 305–316 (1990b).
Boursnell, M.E.G., P.F. Green, A.C.R. Samson, J.I.A. Campbell, A. Deuter, R.W. Peters, N.S. Millar, P.T. Emmerson, and M.M. Binns, Virology 178, 297–300. (1990c.).
Brockmeier, S., Lager, K., Tartaglia, J., Riviere, M., Paoletti, E. & Mengeling, W., Veterinary Microbiology 38, 41–58 (1993).
Buller, R.M.L., G.L. Smith, Cremer, K., Notkins, A.L., and Moss, B., Nature 317, 813–815 (1985).
Buller, R.M.L., Chakrabarti,S., Cooper, J.A., Twardzik, D.R., and Moss, B., J.Virol. 62, 866–874 (1988).
Bzik, D.J., B.A. Fox, N.A. DeLuca, and S. Person, Virology 133, 301–307 (1984).

(List continued on next page.)

*Primary Examiner*—Christine M. Nucker
*Assistant Examiner*—Laurie Scheiner
*Attorney, Agent, or Firm*—Curtis, Morris & Safford P.C.

[57] ABSTRACT

Disclosed and claimed are nucleotides for genes encoding the canine herpesvirus (CHV) gB, gC and gD homologues. These genes encode polypeptides of 879, 459 and 345 amino acids, respectively, which are also disclosed and claimed. The genes are useful as DNA probes or, for preparing PCR primers. The polypeptides are useful in antigenic, immunological or vaccine compositions. The nucleotides can be expressed in any suitable vector system, allowing for production of the polypeptides. Additionally, the vector system containing any or any combination of the nucleotides can be employed in an antigenic, immunological or vaccine composition, such as a poxvirus vector system, e.g., a CHV-vaccinia or avipox virus recombinant, as can the products from expression, i.e., the gB, gC and gD glycoproteins. Antibodies elicited by the glycoproteins or from expression of the vector containing the nucleotide(s) are also useful. Methods for making and using the composition are also disclosed and claimed. Also, specific canarypox-CHV gB, gC and gD recombinants vCP320, vCP322 and vCP294 and methods for making and using them are also disclosed and claimed.

18 Claims, 85 Drawing Sheets

OTHER PUBLICATIONS

Cadoz, M., A. Strady, B. Meignier, J. Taylor, J. Tartaglia, E. Paoletti and S. Plotkin, The Lancet, 339, 1429 (1992).

Cantin, E.M., R. Eberle, J.L. Baldick, B. Moss, D.E. Willey, A.L. Notkins, and H. Openshaw, Proc. Natl. Acad. Sci. USA 84, 5908–5912 (1987).

Carmichael, L., Strandberg, J. & Barnes, F., Proceedings of the Society of Experimental Biology and Medicine, 120, 644–650 (1965).

Carmichael, L., Journal of the American Veterinary Medical Association 156, 1714–1721 (1970).

Chambers, P., N.S. Millar, and P.T. Emmerson, J. Gen. Virol. 67, 2685–2694 (1986).

Chan. W., Immunol. 49, 343–352 (1983).

Child, S.J., Palumbo, G.J., Buller, R.M.L., and Hruby, D.E. Virology 174, 625–629 (1990).

Clewell, D.B., J. Bacterial, 110, 667–676 (1972).

Clewell, D.B. and D.R. Helinski, Proc. Natl. Acad. Sci. USA 62, 1159–1166 (1969).

Colinas, R.J., R.C. Condit and E. Paoletti, Virus Research 18, 49–70 (1990).

Compton, T., In: Cell Biology of Virus Entry, Replication, and Pathogenesis, eds. Compans, R.W., A. Helenius, and M.B.A. Oldstone (Alan R. Liss, Inc.) pp. 45–56 (1989).

Cooney E.L., Corrier A.C., Greenberg P.D., et al., Lancet 337, 567–572 (1991).

Corden, J., Wasylyk, B., Buchwalder, A., Sassone–Corsi, P., Kedinger, C. & Chambon, P., Science 209, 1406–1414 (1980).

Cranage, M.P., T. Kourzarides, A.T. Bankier, S. Satchwell, K. Weston, P. Tomlinson, B. Barrell, H. Hart, S.E. Bell, A.C. Minson, and G.L. Smith, EMBO J. 5, 3057–3063 (1986).

Cremer, K.J., M. Mackett, C. Wohlenberg, A.L. Notkins, and B. Moss, Science 228, 737–740 (1985).

Davis, W.B., J.A. Taylor, and J.E. Oakes, J. Infect. Dis. 140, 534–540 (1979).

Davison, A.J., and J.E. Scott, J. gen Virol. 67, 1759–1816 (1986).

Drillien, R., F. Koehren and A. Kirn, Virology 111, 488–499 (1981).

Eberle, R., and R.J. Courtney, J. Virol. 35, 902–917 (1980).

Edbauer, C., R. Weinberg, J. Taylor, A. Rey–Senelonge, J.F. Bouquet, P. Desmettre, and E. Paoletti, Virology 179, 901–904 (1990).

Engelke, D.R., Hoener, P.A., and Collins, F.S., Proc. Natl. Acad. Sci. USA 85, 544–548 (1988).

Espion, D., S. de Henau, C. Letellier, C.–D. Wemers, R. Brasseur, J.F. Young, M. Gross, M. Rosenberg, G. Meulemans and A. Burny, Arch. Virol. 95, 79–95 (1987).

Etinger H.M., Altenburger W., Vaccine 9, 470–472 (1991).

Fargeaud, D., C. Benoit Jeannin, F. Kato, and G. Chappuis, Arch. Virol. 80, 69–82 (1984).

Fenner, F., Virology 5, 502–529 (1958).

Fitzpatrick, D. R., Babiuk, L. A. & Zamb, T. J., Virology 173, 46–57 (1989).

Flexner, C., Hugen, A., and Moss, B., Nature 330, 259–262 (1987).

Flowers, C., Eastman, E. & O'Callaghan, D., Virology 180, 175–184 (1991).

Frame, M.C., H.S. Marsden, and D.J. McGeoch, J. gen. Virol. 67, 745–751 (1986).

Fries et al., 32nd Interscience Conference on Antimicrobial Agents and Chemotherapy, Anaheim, CA (Oct. 1992).

Frink, R.J., M.R. Eisenberg, G. Cohen, and E.K. Wagner, J. Virol. 45, 634–647 (1983).

Funahashi, S., T. Sato and H. Shida, J. Gen. Virol. 69, 35–47 (1988).

Garten, W., Kohama, T., and H–D. Klenk, J. Gen. Virol. 51, 207–211 (1980).

Ghendon, Y.Z., and Chernos, V.I., Acta Virol. 8, 359–368 (1964).

Gillard, S., Spehner, D., Drillien, R., and Kirn A., Proc. Natl. Acad. Sci. USA 83, 5573–5577 (1986).

Glorioso, J., C.H. Schroder, G. Kumel, M. Szczesiul, and M. Levine, J. Virol. 50, 805–812 (1984).

Glorioso, J., U. Kees, G. Kumel, H. Kirchner, and P. Krammer, J. Immunol. 135, 575–582 (1985).

Goebel, S. J., Johnson, G.P., Perkus, M.E., Davis, S.W., Winslow, J.P., Paoletti, E., Virology 179, 247–266 (1990a).

Goebel, S.J., G.P. Johnson, M.E. Perkus, S.W. Davis, J.P. Winslow and E. Paoletti, Virology 179, 517–563 (1990b).

Goldstein, D.J. and S.K. Weller, Virology 166, 41–51 (1988).

Gretch, D.R., B. Kari, L. Rasmussen, R.C. Gehrz, and M.F. Stinski, J. Virol. 62, 875–881 (1988).

Guo, P., Goebel, S., Davis, S., Perkus, M.E., Languet, B., Desmettre, P., Allen, G., and Paoletti, E., J. Virol. 63, 4189–4198 (1989).

Guo et al., J. Virol. 64, 2399–2406 (1990).

Hampl, H., T. Ben–Porat, L. Ehrlicher, K–O. Habermehl, and A.S. Kaplan, J. Virol. 52, 583–590 (1984).

Homma, M., and M. Ohuchi, J. Virol. 12, 1457–1465 (1973).

Honess, R. W., Journal of General Virology 65, 2077–2107 (1984).

Honess, R. W., Bodemer, W., Cameron, K. R., Niller, H.–H. & Fleckenstein, B., Proceedings of the National Academy of Sciences, U.S.A. 83, 3604–3608 (1986).

Hruby, D.E., R.A. Maki, D.B. Miller and L.A. Ball, Proc. Natl. Acad. Sci. USA 80, 3411–3415 (1983).

Hutchinson, L., Browne, H., Wargents, V., Doris–Poynter, N., Primorac, S., Goldsmith, K., Minson, A., and D.C. Johnson, J. Virol. 66, 2240–2250 (1992).

Hutchinson, L., Goldsmith, K., Snoddy, A., Ghash, H., Graham, F. and D. Johnson. J. Virol. 66, 5603–5609 (1992b).

Hruby, D.E. and L.A. Ball, J. Virol. 43, 403–409 (1982).

Ichihashi, Y. and Dales, S., Virology 46, 533–543 (1971).

Ihara, T., Kato, A., Ueda, S., Ishihama, A. & Hirai, K., Virus Genes 3, 127–140 (1989).

Ishii, H., Y. Kobayashi, M. Kuroki and Y. Kodama, J. gen. Virol. 69, 1411–1414 (1988).

Jacobson, J.G., D.A. Leib, D.J. Goldstein, C.L. Bogard, P.A. Schaffer, S.K. Weller and D.M. Coen, Virology 173, 276–283 (1989).

Jamieson, A.T., G.A. Gentry and J.H. Subak–Sharpe, J. Gen. Virol. 24, 465–480 (1974).

Kato, A., Sato, I., Ihara, T., Ueda, S., Ishihama, A. & Hirai, K., Gene 84, 399–405 (1989).

Kato, S., M. Takahashi, S. Kameyama and J. Kamahora, Biken's 2, 353–363 (1959).

Keller, P.M., A.J. Davison, R.S. Lowe, C.D. Bennett, and R.W. Ellis, Virology 152, 181–191 (1986).

Kieff, E., and D. Liebowitz, In: Virology, Second Edition, eds. Fields, B.N. et al. (Raven Press, Ltd., New York) pp. 1889–1920 (1990).

Kieny, M. P., Lathe, R., Drillien, R., Spehner, D., Skory, S., Schmitt, D., Wiktor, T., Koprowski, H., and Lecocq, J. P., Nature (London) 312, 163–166 (1984).

Klein, P., Kanehisa, M. & DeLisi, C., Biochimica Biophyscia Acta 815, 468–476 (1985).

Konishi et al., Virology 190, 454–458 (1992).

Kopp, A. & Mettenleiter, T., Journal of Virology 66, 2754–2762 (1992).

Kost, T.A., E.V. Jones, K.M. Smith, A.P Reed, A.L. Brown, and T.J. Miller, Virology 171, 365–376 (1989).

Kotwal, G.J., A.W. Hugin and B. Moss, Virology 171, 579–587 (1989a).

Kotwal, G.J. and B. Moss, J. Virol. 63, 600–606 (1989b).

Kotwal, G.J., S.N. Isaacs, R. McKenzie, M.M. Frank and B. Moss, Science 250, 827–830 (1990).

Kotwal, G.J. and Moss, B., Nature (Lond.) 335, 176–178 (1988).

Kouzarides, T., Bankier, A. T., Satchwell, S. C., Weston, K., Tomlinson, P. & Barrell, B. G., Virology 157, 397–413 (1987).

Kozak, M., Cell 44, 283–292 (1986).

Kuhn, J., Eing, B., Brossmer, R., Munk, K. & Braun, R., Journal of General Virology 69, 2847–2858 (1988).

Lai, A. C.-K. and B. G.-T. Pogo, Virus Res. 12, 239–250 (1989).

Lasky, L.A., D. Dowbenko, C.C. Simonsen, and P.W. Berman, Bio–Technology 2, 527–532 (1984).

Lawrence, W.C., R.C. D'Urso, C.A. Kundel, J.C. Whitbeck and L.J. Bello, J. Virol. 60, 405–414 (1986).

Le, L., R. Brasseur, C. Wemers, G. Meulemans, and A. Burney, Virus Genes 1, 333–350 (1988).

Long, D., Cohen, G., Muggeridge, M. & Eisenberg, R., Journal of Virology 64, 5542–5552 (1990).

Long, D., Wilcox, W., Abrams, W., Cohen, G. & Eisenberg, R., Journal of Virology 66, 6668–6685 (1992).

Longnecker, R., S. Chatterjee, R. Whitley, and B. Roizman, Proc. Natl. Acad. Sci. USA 84, 4303–4307 (1987).

Maeda, K., Horimoto, T., Norimine, J., Kawaguchi, T., Tomonaga, K., Niikura, M., Kai, C., Takahashi, E. & Mikami, T., Archives of Virology 127, 387–397.

Mandecki, W., Proc. Natl. Acad. Sci. USA 83, 7177–7182 (1986).

Maniatis, T., E.F. Fritsch, and J. Sambrook, Molecular Cloning: A Laboratory Manual, (Cold Spring Harbor Laboratory, New York) (1982).

Marchioli, C.C., R.J. Yancey, Jr., R.C. Wardley, D.R. Thomsen and L.E. Post, Am. J. Vet. Res. 4, 1577–1583 (1987).

Marchioli, C., R.J. Yancey, Jr., J.G. Timmins, L.E. Post, B.R. Young, and D.A. Povendo, Am. J. Vet. Res. 49, 860–864 (1988).

Marchioli, C.C., R.J. Yancey, Jr., E.A. Petrovskis, J.G. Timmins, and L.E. Post, J. Virol. 61, 3977–3982 (1987).

Matthews, R.E.F., Intervirology 17, 42–44 (1982).

McGeoch, D.J., M.A. Dalrymple, A.J. Davison, A. Dolan, M.C. Frame, D. McNab, L.J. Perry, J.E. Scott, and P. Taylor, J. gen. Virol. 69, 1531–1574 (1988).

McGinnes, L.W., and T.G. Morrison, Virus Research 5, 343–356 (1986).

McLaughlin–Taylor, E., D.E. Willey, E.M. Cantin, R. Eberle, B. Moss, and H. Openshaw, J. gen Virol. 69, 1731–1734 (1988).

Meas, R.K., S.L. Fritsch, L.L. Herr, and P.A. Rota, J. Virol. 51, 259–262 (1984).

Merz, D.C., A. Scheid, and P. Choppin, J. Exper. Med. 151, 275–288 (1980).

Misra, V., R.M. Blumenthal and L.A. Babiuk, J. Virol. 40, 367–378 (1981).

Morgan, A.J., Mackett, S. Finerty, J.R. Arrand, F.T. Scullion and M.A. Epstein, J. Med. Virol. 25, 189–195 (1988).

Moss, B., E. Winters and J. A. Cooper, J. Virol. 40, 387–395 (1981).

Nagai, Y., H.D. Klenk, and R. Rott, Virology 72, 494–508 (1976).

Nagai, Y., T. Yoshida, M. Hamaguchi, H. Naruse, M. Iinuma, K. Maeno, and T. Matsumoto, Microbiol. Immunol. 24, 173–177 (1980).

Nazerian, K., Lee, L., Yanagida, N. & Ogawa, R., Journal of Virology 66, 1409–1413 (1992).

Nicolson, L. & Onions, D. E., Virology 179, 378–387 (1990).

Norrby, E., and Y. Gollmar, Infect. and Immun. 11, 231–239 (1975).

Oakes, J.E., and H. Rosemond–Hornbeak, Infect. Immun. 21, 489–495 (1978).

Ogawa, R., N. Yanagida, S. Saeki, S. Saito, S. Ohkawa, H. Gotoh, K. Kodama, K. Kamogawa, K. Sawaguchi and Y. Iritani, Vaccine 8, 486–490 (1990).

Paez, E., S. Dallo and M. Esteban, Proc. Natl. Acad. Sci. USA 82, 3365–3369 (1985).

Palumbo, G. J., Pickup, D.J., Fredrickson, T.N., Mcintyre, L.J., and Buller, R.M.L., Virology 172, 262–273 (1989).

Panicali, D., S.W. Davis, S.R. Mercer, and E. Paoletti, J. Virol. 37, 1000–1010 (1981).

Panicali, D., and E. Paoletti, Proc. Natl. Acad. Sci. USA 79, 4927–4931 (1982).

Panicali, D., Davis, S.W., Mercer, S.R., and Paoletti, E., J. Virol. 37, 1000–1010 (1981).

Paoletti, E., B.R. Lipinskas, C. Samsonoff, S. Mercer, and D. Panicali, Proc. Natl. Acad. Sci. USA 81, 193–197 (1984).

Papp–Vid, G., and J.B. Derbyshire, Can. J. Comp. Med. 43, 231–233 (1979).

Patel, D.D. and Pickup, D.J., EMBO 6, 3787–3794 (1987).

Patel, D.D., Ray, C.A., Drucker, R.P., and Pickup, D.J., Proc. Natl. Acad. Sci. USA 85, 9431–9435 (1988).

Pearson, W. R. & Lipman, D. J., Proceedings of the National Academy of Sciences 85, 2444–2448 (1988).

Pellett, P.E., M.D. Biggin, B.L. Barrell, and B. Roizman, J. Virol. 56, 807–813 (1985).

Perkus, M.E., K. Limbach, and E. Paoletti, J. Virol. 63, 3829–3836 (1989).

Perkus, M.E., A. Piccini, B.R. Lipinskas, and E. Paoletti, Science 229, 981–984 (1985).

Perkus, M.E., Goebel, S.J., Davis, S.W., Johnson, G.P., Limbach, K., Norton, E.K., and Paoletti, E., Virology 179, 276–286 (1990).

Perkus, M. E., D. Panicali, S. Mercer and E. Paoletti, Virology 152, 285–297 (1986).

Perkus, M.E., S.J. Goebel, S.W. Davis, G.P. Johnson, E.K. Norton and E. Paoletti, Virology 180, 406–410 (1991).

Petrovskis, E.A., J.G. Timmins, M.A. Armentrout, C.C. Marchioli, R.J. Yancey, Jr., and L.E. Post, J. Virol. 59, 216–223 (1986).

Petrovskis, E.A., J.G. Timmins, and L.E. Post, J. Virol. 60, 185–193 (1986).

Piccini, A., M.E. Perkus, and E. Paoletti, Methods in Enzymology 153, 545–563 (1987).

Pickup, D.J., B.S. Ink, W. Hu, C.A. Ray and W.K. Joklik, Proc. Natl. Acad. Sci. USA 83, 7698–7702 (1986).

Pickup, D.J., B.S. Ink, B.L. Parsons, W. Hu and W.K. Joklik, Proc. Natl. Acad. Sci. USA 81, 6817–6821 (1984).

Pizer, L., Cohen, G. & Eisenberg, R., Journal of Virology 34, 142–153 (1980).

Plummer, G., Goodheart, C., Henson, D. & Bowling, C., Virology 39, 134–137 (1969).

Proudfoot, N. J. & Brownlee, G. G., Nature 163, 211–214 (1976).

Reed, L.J. and Muench, H., Am. J. Hyg. 27, 493–497 (1938).

Richman, D.D., A. Buckmaster, S. Bell, C. Hodgman and A.C. Minson, J. Virol. 57, 647–655 (1986).

Riggio, M.P., A.A. Cullinane, and D. E. Onions, J. Virol 63, 1123–1133 (1989).

Riviere, M., Tartaglia J., Perkus, M. E., Norton, E. K., Bongermino, C. M., Lacoste, F., Duret, C., Desmettre, P. & Paoletti, E., Journal of Virology 66, 3424–3434 (1992).

Robbins, A.K., R.J. Watson, M.E. Whealy, W.W. Hays, and L.W. Enquist, J. Virol. 58, 339–347 (1986).

Robbins, A.K., D.J. Dorney, M.W. Wathen, M.E. Whealey, C. Gold, R.J. Watson, L.E. Holland, S.D. Weed, M. Levine, J.C. Glorioso, and L.W. Enquist, J. Virol. 61, 2691–2701 (1987).

Roizman, B. and A.E. Sears, In: Virology, eds. Fields, B.N. and D.M. Knipe (Raven Press, Ltd., New York) pp. 1795–1841 (1990).

Roizman, B., In The Herpesviruses, vol. 1, pp. 1–23, Ed. B. Roizman, New York & London: Plenum Press (1982).

Rooney, J.F., C. Wohlenberg, K.J. Cremer, B. Moss, and A.L. Notkins, J. Virol. 62, 1530–1534 (1988).

Rosenthal, K.L., J.R. Smiley, S. South, and D.C. Johnson, J. Virol. 61, 2438–2447 (1987).

Ross, L., Sanderson, M., Scott, S., Binns, M., Doel, T. & Milne, B., Journal of General Virology 70, 1789–1804 (1989).

Rota, P.A., R.K. Maes, and W.T. Ruyechan, Virology 154, 168–179 (1986).

Rubenstein, A.S. and A.S. Kaplan, Virology 66, 385–392 (1975).

Sanger, F., S. Nicklen, and A. Coulson, Proc. Natl. Acad. Sci. USA 74, 5463–5467 (1977).

Schmidtt, J.F.C. and H.G. Stunnenberg, J. Virol. 62, 1889–1897 (1988).

Seligmann, E.B., In Laboratory Techniques in Rabies, eds. M.M. Kaplan and H. Koprowski, (World Health Organization, Geneva) pp. 279–285 (1973).

Shapira, S.K., Chou, J., Richard, F.V. and Casadaban, M.J., Gene 25, 71–82 (1983).

Shida, H., Virology 150, 451–462 (1986).

Shida, H., T. Tochikura, T. Sato, T. Konno, K. Hirayoshi, M. Seki, Y. Ito, M. Hatanaka, Y. Hinuma, M. Sugimoto, F. Takahashi–Nishimaki, T. Maruyama, K. Miki, K. Suzuki, M. Morita, H. Sashiyama and M. Hayami, EMBO 6, 3379–3384 (1987).

Shida, H., Hinuma, Y., Hatanaka, M., Morita, M., Kidokoro, M., Suzuki, K., Maruyzam, T., Takahashi–Nishimaki, F., Sugimoto, M., Kitamura, R., Miyazawa, T. and Hayami, M., J. Virol. 62, 4474–4480 (1988).

Shimizu, M., K. Satou, and N. Nishioka, Arch. Virol. 104, 169–174 (1989).

Sinclair, R., R.F. Cook, and J.A. Mumford, J. gen, Virol. 70, 455–459 (1989).

Slabaugh, M., N. Roseman, R. Davis and C. Mathews, J. Virol. 62, 519–527 (1988).

Smith, J.S., P.A. Yager and G.M. Baer, In Laboratory Techniques in Rabies, eds. M. M. Kaplan and H. Koprowski (WHO Geneva) pp. 354–357 (1973).

Sodora, D., Cohen, G., Muggeridge, M. & Eisenberg, R., Journal of Virology 65, 4424–4431 (1991).

Spaete, R., Saxena, A., Scott, P., Long, G., Probert, W., Britt, W., Gibson W., Rasmussen, L. & Pachl, C., Journal of Virology 64, 2922–2931 (1990).

Spear, P.G., In: The Basis for Serodiagnosis and Vaccines, Immunochemistry of Viruses, vol. 2, eds. M.H.V. Van Regenmortel and A.R. Neurath (New York), pp. 425–443 (1985a).

Spear, P.G., In: The Herpesvirus, vol. 3, eds. B. Roizman (New York), pp. 315–356 (1985b).

Stanberry, L. R., S. Kit and M. G. Myers, J. Virol. 55, 322–328 (1985).

Stevely, W.S., J. Virol. 22, 232–234 (1977).

Stokes, A., G.P. Allen, L.A. Pullen, and P.K. Murray, J. gen. Virol. 70, 1173–1183 (1989).

Sullivan, V. and G.L. Smith, J. gen. Virol. 68, 2587–2598 (1987).

Sullivan, V. and G.L. Smith, J. gen. Virol. 69, 859–867 (1988).

Swain, M.A., R.W. Peet, and D.A. Galloway, J. Virol. 53, 561–569 (1985).

Tabor, S., and C.C. Richardson, Proc. Natl. Acad. Sci. USA 84, 4767–4771 (1987).

Tartaglia, J. & E. Paoletti, In Immunochemistry of Viruses, II. The Basis for Serodiagnosis and Vaccines. M.H.V. van Regenmortel & A.R. Neurath, Eds. 125–151. Elsevier Sciences Publishers, Amsterdam (1990).

Tartaglia, J., J. Taylor, W. I. Cox, J.–C. Audonnet, M.E. Perkus, A. Radaelli, C. de Giuli Morghen, B. Meignier, M. Riviere, K. Weinhold & E. Paoletti, In *Aids Research Reviews*, W. Koff, F. Wong–Staal & R.C. Kenedy, Eds., vol. 3, Marcel Dekker, NY (In press) (1993a).

Tartaglia, J., Perkus, M.E., Taylor, J., Norton, E.K., Audonnet, J.–C., Cox, W.I., Davis, S.W., Van Der Hoeven, J., Meignier, B., Riviere, M., Languet, B., Paoletti, E., Virology 188, 217–232 (1992).

Tartaglia, J., Jarrett, O., Desmettre, P., Paoletti, E. (1993b) J. Virol., in press.

Taylor, J., C. Trimarchi, R. Weinberg, B. Languet, F. Guillemin, P. Desmettre and E. Paoletti, Vaccine 9, 190–193 (1991b).

Taylor, J., Weinberg, R., Kawaoka, Y., Webster, R.G., and Paoletti, E., Vaccine 6, 504–508 (1988a).

Taylor, J., R. Weinberg B. Lanquet, P. Desmettre, and E. Paoletti, Vaccine 6, 497–503 (1988b).

Taylor, J., R. Weinberg, J. Tartaglia, C. Richardson, G. Alkhatib, D. Briedis, M. Appel, E. Norton & E. Paoletti, Virology 187, 321–328 (1992).

Taylor, G., E. J. Stott, G. Wertz and A. Ball. J. Gen. Virol. 72, 125–230 (1991a).

Taylor, J., Edbauer, C., Rey–Senelonge, A., Bouquet, J.–F., Norton, E., Goebel, S., Desmettre, P., Paoletti, E., J. Virol. 64, 1441–1450 (1990).

Telford, E. A., Watson, M. S., McBride, K. & Davison, A. J. (1992). The DNA sequence of equine herpesvirus–1. *Virology* 189, 304–316.

Tikoo, S. K., Fitzpatrick, D. R., Babiuk, L. A. & Zamb, T. J., Journal of Virology 64, 5132–5142 (1990).

Toyoda, T., T. Sakaguchi, K. Imai, N. M. Inocencio, B. Gotoh, M. Hamaguchi, and Y. Nagai, Virology 158, 242–247 (1987).

Wachsman, M., L. Aurelian, J.C.R. Hunter, M.E. Perkus, and E. Paoletti, Bioscience Reports 8, 323–334 (1988).

Wachsman, M., J.H. Luo, L. Aurelian, M.E. Perkus, and E. Paoletti, J. gen. Virol. 70, 2513–2520 (1989).

Wachsman, M., L. Aurelian, C.C. Smith, B.R. Lipinskas, M.E. Perkus, and E. Paoletti, J. Infect. Dis. 155, 1188–1197 (1987).

Wathen, M.W. and L.M.K. Wathen, J. Virol. 58, 173–178 (1986).

Wathen, M.W. and L.M.K. Wathen, J. Virol. 51, 57–62 (1984).

Wathen, L.M.K.,K.B. Platt, M.W. Wathen, R.A. Van Deusen, C.A. Whetstone, and E.C. Pirtle, Virus Res. 4, 19–29 (1985).

Weir, J.P., M. Bennett, E.M. Allen, K.L. Elkins, S. Martin, and B.T. Rouse, J. gen. Virol. 70, 2587–2594 (1989).

Weir, J.P. and B. Moss, J. Virol. 46, 530–537 (1983).

Whalley, J.M., G.R. Robertson, N.A. Scott, G.C. Hudson, C.W. Bell, and L.M. Woodworth, J. gen Virol. 70, 383–394 (1989).

Whealy, M.E., A.K. Robbins and L.W. Enquist, J. Virol. 63, 4055–4059 (1989).

Whitbeck, J.C., L.Z. Bello, and W.C. Lawrence, J. Virol. 62, 3319–3327 (1988).

Wilcox, W. C., Long, D., Sodora, D. L., Eisenberg, R. J. & Cohen, G. H., Journal of Virology 62, 1941–1947 (1988).

Wittmann, G. and H.-J. Rziha, In: Herpesvirus Diseases of Cattle, Horses and Pigs, ed. G. Wittman (Kluwer Academic Publishers) pp. 230–325 (1989).

Xuan, X., Horimoto, T., Limcumpao, J. A., Takumi, A., Tohya, Y., Takahashi, E. & Mikami, T., Archives of Virology 116, 185–195 (1991).

Zamb, T., Abstract No. 330, 68th Annual Meeting of Conference of Research Workers in Animal Disease, 16 and 17 Nov. 1987, Chicago, IL., USA (1987).

Zarling, J.M., P.A. Moran, R.L. Burke, C. Pachl, P.W. Berman, and L.A. Lasky, J. Immunol. 136, 4669–4673 (1986a).

Zarling, J.M., P.A. Moran, L.A. Lasky, and B. Moss, J. Virol. 59, 506–509 (1986b).

Zezulak, K.M., and P.G. Spear, J. Virol. 49, 741–747 (1984).

Zhou, J., L. Crawford, L. McLean, X. Sun, M. Stanley, N. Almond and G.L. Smith, J. Gen. Virol. 71, 2185–2190 (1990).

FIG. IA

| | | | |
|---|---|---|---|
| TTTTCTGGAT | TTCAGCTATG | TCCTTCGGGA | 30 |
| GTTTATATAA | CTTATGAAGA | AAACTGTCCT | 60 |
| TTGGTAGCAG | TTTTACAAAG | CGGTGTAAAT | 90 |
| TGCGAAATTG | GACCAACTAC | AACTGTAATA | 120 |
| TACGACAGTG | ATATTTTTC | TCTTCTTTAT | 150 |
| ACCGTTCTTC | AAAAATTGGC | TCCTGGTGTT | 180 |
| AATATAGAAA | TTTGATAAGT | ATGTTTCAT<br>M F S> | 210<br>3 |
| TGTATCTATA<br>L Y L Y | TATTTTTTT<br>I F F | ATTATTTATA<br>I I Y> | 240<br>13 |
| CTTTAATAAT<br>T L I I | ATGTGATCCA<br>C D P | ACAACACCGG<br>T T P> | 270<br>23 |
| AAAGTACTAT<br>E S T I | TAATCCATTA<br>N P L | AATCATCACA<br>N H H> | 300<br>33 |
| ATTTATCAAC<br>N L S T | ACCTAAACCT<br>P K P | ACTTCGGATG<br>T S D> | 330<br>43 |
| ATATTCGTGA<br>D I R E | AATTTTACGT<br>I L R | GAATCCCAAA<br>E S Q> | 360<br>53 |
| TTGAATCTGA<br>I E S D | TGATACATCA<br>D T S | ACATTTTACA<br>T F Y> | 390<br>63 |
| TGTGCCCACC<br>M C P P | ACCATCGGGA<br>P S G | TCAACATTGG<br>S T L> | 420<br>73 |
| TGCGTTTGGA<br>V R L E | GCCACCTAGA<br>P P R | GCATGTCCTA<br>A C P> | 450<br>83 |
| ACTATAAACT<br>N Y K L | TGGTAAAAAT<br>G K N | TTTACAGAAG<br>F T E> | 480<br>93 |

FIG. IB

| | | | | |
|---|---|---|---|---|
| GAATTGCTGT | AATATTTAAG | GAAAATATTT | 510 | |
| G I A V | I F K | E N I> | 103 | |
| CTCCTTATAA | ATTTAAAGCT | AATATATACT | 540 | |
| S P Y K | F K A | N I Y> | 113 | |
| ACAAAAATAT | TATTATCACC | ACTGTATGGT | 570 | |
| Y K N I | I I T | T V W> | 123 | |
| CTGGAAGCAC | ATATGCAGTA | ATTACTAATA | 600 | |
| S G S T | Y A V | I T N> | 133 | |
| GATATACAGA | TCGTGTACCT | ATAGGTGTTC | 630 | |
| R Y T D | R V P | I G V> | 143 | |
| CTGAAATTAC | AGAGTTGATT | GATAGAAGAG | 660 | |
| P E I T | E L I | D R R> | 153 | |
| GTATGTGTTT | ATCAAAAGCT | GATTATATTC | 690 | |
| G M C L | S K A | D Y I> | 163 | |
| GTAATAATTA | TGAATTTACC | GCATTTGATA | 720 | |
| R N N Y | E F T | A F D> | 173 | |
| AGGATGAAGA | CCCCAGAGAA | GTTCATTTAA | 750 | |
| K D E D | P R E | V H L> | 183 | |
| AGCCTTCAAA | GTTTAATACA | CCAGGATCCC | 780 | |
| K P S K | F N T | P G S> | 193 | |
| GTGGATGGCA | TACAGTTAAT | GATACTTACA | 810 | |
| R G W H | T V N | D T Y> | 203 | |
| CAAAAATTGG | GGGTTCTGGA | TTTTATCATT | 840 | |
| T K I G | G S G | F Y H> | 213 | |
| CTGGAACATC | TGTAAATTGT | ATAGTTGAAG | 870 | |
| S G T S | V N C | I V E> | 223 | |
| AAGTTGATGC | CAGATCTGTT | TATCCATATG | 900 | |
| E V D A | R S V | Y P Y> | 233 | |

FIG. 1C

| | | | | |
|---|---|---|---|---|
| ATTCATTTGC<br>D  S  F  A | TATCTCCACC<br>I  S  T | GGGGATATAA<br>G  D  I> | 930 | 243 |
| TTCATATGTC<br>I  H  M  S | CCCTTTTTTT<br>P  F  F | GGATTACGAG<br>G  L  R> | 960 | 253 |
| ATGGTGCTCA<br>D  G  A  H | TACTGAATAT<br>T  E  Y | ATTAGTTATT<br>I  S  Y> | 990 | 263 |
| CAACTGATAG<br>S  T  D  R | ATTTCAACAA<br>F  Q  Q | ATAGAAGGTT<br>I  E  G> | 1020 | 273 |
| ATTATCCTAT<br>Y  Y  P  I | CGACTTAGAT<br>D  L  D | ACTAGACTAC<br>T  R  L> | 1050 | 283 |
| AGCTTGGTGC<br>Q  L  G  A | ACCAGTTTCT<br>P  V  S | AGGAATTTTT<br>R  N  F> | 1080 | 293 |
| TAACAACACA<br>L  T  T  Q | ACACGTTACT<br>H  V  T | GTTGCTTGGA<br>V  A  W> | 1110 | 303 |
| ATTGGGTTCC<br>N  W  V  P | AAAAATTCGT<br>K  I  R | GAAGTGTGTA<br>E  V  C> | 1140 | 313 |
| CTTTGGCTAA<br>T  L  A  K | ATGGCGTGAA<br>W  R  E | ATTGATGAAA<br>I  D  E> | 1170 | 323 |
| TTATTCGTGA<br>I  I  R  D | TGAGTATAAG<br>E  Y  K | GGATCTTACA<br>G  S  Y> | 1200 | 333 |
| GATTTACAGC<br>R  F  T  A | AAAATCAATA<br>K  S  I | TCTGCAACAT<br>S  A  T> | 1230 | 343 |
| TTATTTCTGA<br>F  I  S  D | TACTACTCAA<br>T  T  Q | TTTGATATTG<br>F  D  I> | 1260 | 353 |
| ATCGTGTAAA<br>D  R  V  K | GTTAAGTGAT<br>L  S  D | TGTGCCAAAC<br>C  A  K> | 1290 | 363 |
| GTGAAGCCAT<br>R  E  A  I | AGAAGCTATT<br>E  A  I | GATAAGATCT<br>D  K  I> | 1320 | 373 |

FIG. 1D

| | | | | |
|---|---|---|---|---|
| ACAAAAAAAA<br>Y K K K | ATATAATAAA<br>Y N K | ACTCATATTC<br>T H I> | 1350<br>383 | |
| AAACAGGAGA<br>Q T G E | ATTGGAAACA<br>L E T | TACTTGGCTA<br>Y L A> | 1380<br>393 | |
| GAGGGGGATT<br>R G G F | TATTATAGCA<br>I I A | TTTAGACCAA<br>F R P> | 1410<br>403 | |
| TGATTAGTAA<br>M I S N | TGAGTTAGCA<br>E L A | AAATTGTATA<br>K L Y> | 1440<br>413 | |
| TAAATGAGTT<br>I N E L | AGTAAGATCT<br>V R S | AATCGTACGG<br>N R T> | 1470<br>423 | |
| TTGATTTGAA<br>V D L K | ATCTCTTTTA<br>S L L | AATCCATCTG<br>N P S> | 1500<br>433 | |
| TAAGAGGGGG<br>V R G G | GGCTAGAAAG<br>A R K | AGAAGATCAG<br>R R S> | 1530<br>443 | |
| TAGAGGAAAA<br>V E E N | TAAAAGATCA<br>K R S | AAACGTAATA<br>K R N> | 1560<br>453 | |
| TTGAAGGTGG<br>I E G G | TATTGAAAAT<br>I E N | GTAAATAATT<br>V N N> | 1590<br>463 | |
| CAACAATAAT<br>S T I I | TAAGACAACT<br>K T T | TCATCTGTTC<br>S S V> | 1620<br>473 | |
| ATTTTGCTAT<br>H F A M | GCTTCAGTTT<br>L Q F | GCCTATGATC<br>A Y D> | 1650<br>483 | |
| ATATTCAATC<br>H I Q S | ACATGTTAAT<br>H V N | GAAATGCTTA<br>E M L> | 1680<br>493 | |
| GTAGAATTGC<br>S R I A | AACTGCATGG<br>T A W | TGTAATCTTC<br>C N L> | 1710<br>503 | |
| AAAATAAAGA<br>Q N K E | GAGAACCCTT<br>R T L | TGGAATGAAG<br>W N E> | 1740<br>513 | |

FIG. 1E

```
TTATGAAACT  TAATCCAACT  AGTGTGGCTT  1770
 V  M  K  L   N  P  T    S  V  A>    523

CGGTTGCTAT  GGATCAAAGA  GTTTCAGCAC  1800
 S  V  A  M   D  Q  R    V  S  A>    533

GAATGTTAGG  GGATGTTCTT  GCAGTTACTC  1830
 R  M  L  G   D  V  L    A  V  T>    543

AATGTGTTAA  TATATCAGGT  TCTAGTGTTT  1860
 Q  C  V  N   I  S  G    S  S  V>    553

TTATTCAAAA  TTCCATGCGT  GTTTTAGGGT  1890
 F  I  Q  N   S  M  R    V  L  G>    563

CAACAACTAC  ATGTTACAGT  CGTCCTCTTA  1920
 S  T  T  T   C  Y  S    R  P  L>    573

TATCATTTAA  AGCACTAGAA  AACTCAACTA  1950
 I  S  F  K   A  L  E    N  S  T>    583

ACTATATTGA  AGGACAACTT  GGGGAAAATA  1980
 N  Y  I  E   G  Q  L    G  E  N>    593

ATGAACTATT  AGTAGAACGA  AAGCTAATTG  2010
 N  E  L  L   V  E  R    K  L  I>    603

AACCATGTAC  AGCTAACCAT  AAAAGATATT  2040
 E  P  C  T   A  N  H    K  R  Y>    613

TTAAATTTGG  TGCAGATTAT  GTATATTTTG  2070
 F  K  F  G   A  D  Y    V  Y  F>    623

AAAACTATGC  ATATGTTCGA  AAGGTACCTC  2100
 E  N  Y  A   Y  V  R    K  V  P>    633

TTAATGAAAT  TGAAATGATC  AGTGCATATG  2130
 L  N  E  I   E  M  I    S  A  Y>    643

TAGATCTTAA  TATTACATTA  CTTGAGGATC  2160
 V  D  L  N   I  T  L    L  E  D>    653
```

FIG. 1F

| | | | | |
|---|---|---|---|---|
| GTGAATTTTT<br>R E F L | ACCACTAGAG<br>P L E | GTATATACTC<br>V Y T> | 2190 | 663 |
| GAGCAGAGTT<br>R A E L | AGAAGATACA<br>E D T | GGACTATTGG<br>G L L> | 2220 | 673 |
| ACTATAGTGA<br>D Y S E | GATTCAACGT<br>I Q R | AGAAATCAAC<br>R N Q> | 2250 | 683 |
| TACATGCACT<br>L H A L | TAAGTTTTAT<br>K F Y | GATATTGACA<br>D I D> | 2280 | 693 |
| GTGTTGTAAA<br>S V V K | AGTTGATAAT<br>V D N | AATGTTGTAA<br>N V V> | 2310 | 703 |
| TTATGAGGGG<br>I M R G | CATTGCAAAT<br>I A N | TTTTTCCAAG<br>F F Q> | 2340 | 713 |
| GACTTGGAGA<br>G L G D | TGTTGGAGCG<br>V G A | GGATTTGGAA<br>G F G> | 2370 | 723 |
| AAGTTGTTTT<br>K V V L | GGGTGCTGCA<br>G A A | AATGCTGTTA<br>N A V> | 2400 | 733 |
| TTGCAACTGT<br>I A T V | TTCTGGAGTG<br>S G V | TCCTCGTTTC<br>S S F> | 2430 | 743 |
| TTAATAACCC<br>L N N P | ATTTGGGGCG<br>F G A | CTAGCCGTTG<br>L A V> | 2460 | 753 |
| GATTGCTGAT<br>G L L I | TTTAGCTGGA<br>L A G | CTATTTGCAG<br>L F A> | 2490 | 763 |
| CGTTTTTGGC<br>A F L A | TTATAGATAT<br>Y R Y | GTTTCTAAAC<br>V S K> | 2520 | 773 |
| TTAAGTCAAA<br>L K S N | TCCAATGAAA<br>P M K | GCACTATACC<br>A L Y> | 2550 | 783 |
| CAGTAACTAC<br>P V T T | AAAAAATTTA<br>K N L | AAAGAAAGTG<br>K E S> | 2580 | 793 |

FIG. 1G

| | | | |
|---|---|---|---|
| TTAAGAATGG<br>V K N G | TAATTCTGGA<br>N S G | AATAATAGTG<br>N N S> | 2610<br>803 |
| ATGGAGAAGA<br>D G E E | AAATGATGAT<br>N D D | AATATCGATG<br>N I D> | 2640<br>813 |
| AAGAAAAGCT<br>E E K L | TCAACAAGCT<br>Q Q A | AAAGAAATGA<br>K E M> | 2670<br>823 |
| TTAAATATAT<br>I K Y M | GTCTCTAGTT<br>S L V | TCTGCTATGG<br>S A M> | 2700<br>833 |
| AACAGCAGGA<br>E Q Q E | ACATAAAGCT<br>H K A | ATTAAAAAAA<br>I K K> | 2730<br>843 |
| ATAGTGGCCC<br>N S G P | TGCCCTTCTA<br>A L L | GCAAGTCACA<br>A S H> | 2760<br>853 |
| TTACAAACCT<br>I T N L | ATCTCTTAAA<br>S L K | CATCGTGGTC<br>H R G> | 2790<br>863 |
| CAAAATACAA<br>P K Y K | ACGTTTGAAA<br>R L K | AATGTAAATG<br>N V N> | 2820<br>873 |
| AAAATGAAAG<br>E N E S | TAAAGTTTAA<br>K V * | TAAAAAATTT | 2850<br>879 |
| AAATATTACG | TAAAATTTTC | TGACTCTGCC | 2880 |
| CACTTTTTTT | ATAATATAAA | TTTTAGAAAA | 2910 |
| TTTTACTCAT | TTTATTATCT | TTTATAAACC | 2940 |
| TCCAACTATT | TATAAAGGAT | AATAAATGGA | 2970 |
| CATTTCTGCG | GTGCCTGTAT | ATCCTACTAA | 3000 |

FIG. 3

| FIG. 3A |
|---|
| FIG. 3B |
| FIG. 3C |
| FIG. 3D |
| FIG. 3E |
| FIG. 3F |

FIG. 3A

```
CHV   M-----------------------------------------------FSLYL-----------------------YIFFIIYTLIICDPTTPESTINPLNHHM
FHV   MST--RGDLGKRRRGSRWQGHSGYFRQRCFFPSLLGIAATGSRHGNGSSGLTRL----------------------ARYVSFIWIVLFLVGPRPVEGQSGSTSEQP
EHV1  MSSGCRS-VGGSTWGN-WRGDGGDLRQRRVLSPVCSAPAAGSWIGSQLGNVGNLLATPHPLGKPASSRVGTIVLACLLLFGSCVVRAVPTTPSPPT
PRV   MPAG--GGLWRGPRGHR-PGHHGGAGLGRLWPA--PHHAAARGAVALALLLALAAAPPCGAAAVTRA---------ASASPTPGTGATPNDV
VZV   M-----------------------------------------------------------------------------FVTAVVSVSPSSFYESL------
HSV1  MHQG-------APSWGRRW-------FVVWALL----------GLTLGVLVASAAPSSP-GTPGVARDPG---GERGPCHSGAAALGAAPTGDPK
HCMV  MES-----------------------------------------------------------------------------STHNGSHTSR
EBV   MTR--------RR-----------------VLSVVVLLAALACRLGAQ--T-----------------------PEQPAPPATT
       *

LST-------PKPTSD-----D-I--REILRESQIESDDTSTF-Y-M  C  PPPSGSTLVRLEPPRA  C  PNYKLGK-NFTEGIAVIFKENISP
      RRTVATPEVGGTPPKPTTDPTDMSD-M--REALRASQIEANGPSTF-Y-M  C  PPPSGSTVVRLEPPRA  C  PDYKLGK-NFTEGIAVIFKENIAP
      STPTSMSTHSHGTVDPTLLPTETPDPL--RLAVRESGILAED-GDF-Y-T  C  PPPTGSTVVRIEPPRT  C  PKFDLGR-NFTEGIAVIFKENIAP
      SAEASLEEIEAFSPGPSEAPDGEYGDLDARTAVRAA---ATERDRF-Y-V  C  PPPSGSTVVRLEPEQA  C  PEYSQGR-NFTEGIAVLFKENIAP
      ------QVEPTQSEDITRSAHLGDGDEIREAIHKSQ-DAETKPTF-Y-V  C  PPPTGSTIVRLEPTRT  C  PDYHLGK-NFTEGIAVVYKENIAA
      PKKNKKPKNPTPPRPAGDNATVAAGHATLREHLRDIKAENTD-ANF-Y-V  C  PPPTGATVVQFEQPRR  C  PTRPEGQ-NYTEGIAVVFKENIAP
      TTSAQTRSVYSQHVTSSEAVSHRANETIYNITLKYGDVVGVNTTKYPYRV  C  SMAQGTDLIRFERNII  C  TSMKPINEDLDEGIMVVYKRNIVA
      VQPTATR-------------------------------QQTSFPFRV  C  ELSSHGDLFRFSSDIQ  C  PSF-GTRENHTEGLLMVFKDNIIP
                                                          *                  *            **        ** **
                                                                                    100
```

FIG. 3B

```
                                                                                               YKFKANIYYKNIIITTVWSGSTYAVITNRYTDRVPIGVPEITELIDRRGM   C   LSKADYIRNNYEFTAFDKDE-DPREVHLKPSKFNTPGSRGWHT
                                                                                               YKFKANIYYKNIIMTTVWSGSSYAVTTNRYTDRVPKVQEITDLIDRRGM   C   LSKADYVRNNYQFTAFDRDE-DPRELPLKPSKFNTPQSRGWHT
                                                                                               YKFRANVYYKDIVVTRVWKGYSHTSLSDRYNDRVPVSVEEIFGLIDSKGK   C   SSKAEYLRDNIMHHAYHDDE-DEVELDLCRPSLQLRGARAWQT
                                                                                               HKFKAHIYYKNIVIVTTVWSGSTYAAITNRFTDRVPVPVQEITDVIDRRGK   C   VSKAEYVRNNHKVTAFDRDE-NPVEVDLRPSRLNALGTRGWHT
                                                                                               YKFKATVYYKDVIVSTAWAGSSYTQITNRYADRVPIPVSEITDTIDKFGK   C   SSKATYVRNNHKVEAFNEDK-NPQDMPLIASKYNSVGSKAWHT
                                                                                               YKFKATMYYKDVTVSQVWFGHRYSQFMGIFEDRAPVPFEEVIDKINAKGV   C   RSTAKYVRNNLETTAFHRDD-HETDMELKPANAATRTSRGWHT
                                                                                               HTFKVRVYQKVLTFRRSYAYIYTYLLGSNTEYVAPPMWEI-HHINKFAQ   C   YSSYSRVIGGTVFVAYHRDSYENKTMQLIPDDYSNTHSTRYVT
                                                                                               YSFKVRSYTKIVTNILIYNGWYADSVTNRHEEKFSVDSYET-DQMDTIYQ   *   YNAVKMTKDGLTRVYVDRDGV-NITVNLKPTGGLANGVRRYAS

200
        NDTYTKIGGSGFYH-SGTSVN   C   IVEEVDARSVYPYDSFAISTGDIIHMSPFFGLRDGAHTEYISYS--TDRFQQIEGYYPI-DLDTRLQLGAP
        NETYTKIGAAGFHH-SGTSVN   C   IVEEVDARSVYPYDSFAISTGDVIHMSPFFGLRDGAHVEHTSYS--SDRFQQIEGYYPI-DLDTRLQLGAP
        NDITSYVGWMPWRHYTSTSVN   C   IVEEVEARSVYPYDSFALSTGDIVYASPFYGLRAAARIEHNSYA--QERFRQVEGYRPR-DLDSKLQAEEP
        TNDTYTKIGAAGFYH-TGTSVN   C   IVEEVEARSVYPYDSFALSTGDIVYMSPFFYGLREGAHGEHIGYA--PGRFQQVEHYYPI-DLDSRLRASES
        NDTYMVAGTPGTYR-TGTSVN   C   IIEEVEARSIFPYDSFGLSTGDIIYMSPFFGLRDGAYREHSNYA--MDRFHQFEGYRQR-DLDTR-ALLEP
        DLKYNPSRVEAFHRY-GTTVN   C   IVEEVDARSVYPYDEFVLATGDFVYMSPFPFYGYREGSHTEHTTYA--ADRFKQVDGFYAR-DLTTKARATAP
        KDQWHSRGS-TWLYRETCNLN   C   MLTITTARSKYPYHFFATSTGDVVYISPFY---NGTNRNASYFGENADKFFIFPNYTIVSDFGRPNAAPET
        QIELYDAPGWLIWTYRTRTTVN   C   LITDMMAKSNSPFDFFVTTGQIVEMSPFY---DGKNKET--FHERADSFHVRTNYKIV-DYDNRGTNPQG
                              *   *                                              ***                  *
```

FIG. 3C

```
        300
VS-RNFLTTQHVTVAWNWVPKIREV C TLAKWREIDEIIRDEYK-GSYRFTAKSISATFISDTT-QFDIDRVKLSD C AKREAIEAIDKIYKKK
VS-RNFLETPHVTVAWNWTPKCGRV C TLAKWREIDEMLRDEYQ-GSYRFTVKTISATFISNTS-QFEINRIRLGD C ATKEAAEAIDRIYKSK
VT-KNFITTPHVTVSWNWTEKKVEA C TLTKWKEVDELVRDEFR-GSYRFTIRSISSTFISNTT-QFKLESAPLTE C VSKEAKEAIDSIYKKQ
VT-RNFLRTPHFTVAWDWAPKTRRV C SLAKWREAEEMTRDETRDGSFRFTSRALGASFVSDVT-QLDLQRVHLGD C VLREASEAIDAIYRRR
AA-RNFLVTPHLTVGWNWJKPRTEV C SLVKWREVEDVVRDEYAH-NFRFTMKTLSTTFISETN-EFNLNQIHLSQ C VKEEARAIINRIYTTR
TT-RNLLTTPKFTVAWDWVPKRPSV C TMTKWQEVDEMLRSEY-GGSFRFSSDAISTTFTNLI-EYPLSRVDLGD C IGKDARDAMDRIFARR
HRLVAFLERADSVISWDIQDEKNVT C QLTFWEASERTIRSE-AEDSYHFSSAKMTATFLSKKQ-EVNNSDSAL-D C VRDEAINKLQQIFNTS
ER-RAFLDKGTYTLSWKL-ENRTAY C PLQHWQTFDSTIATE-TGKSIHFVTDEGTSSFVTNTIVGIELPD-AF-K C IEEQVNKTMHEKYEAV
                            *                 *                                  *
          400
YMKTHIQTGEL-ETYLARGGFIIAFRPMISNELAKLYINELVRSNRTVDLKSLLNPSVRGGA-------RKRRSV--------EEN--------KRSKRN
YSKTHIQTGTL-ETYLARGGFLIAFRPMISNELAKLYINELARSNRTVDLSALLNPSGETVQ-------RTRGSV--------PSNQH-------HRSRRS
VESTHVFSGDV-EYYLARGGFVVAFRPMLSNELARLYLNELVRSNRTYDLKNLLNPNANNNNNTTRRRRSLLSVPEPQPTQDGVHREQILHRLHKR
HSTHVLAGDRPEVYLARGGFVVAFRPLISNELAQLYARELER----LGLAGVVGPAAPAAARRARRSPGPAGTPEPPAVNGTGH----------
NSSHVRTGDI-QTYLARGGFVVFQPLLSNSLARLYLQELVRENTN-------HSPQKHPTRNTRSRRSV------PVELRANRT----------
YNATHIKVGQ-PQYYLANGGFLIAYQPLLSNTLAELYVREHLREQS--------------------RKPPNPTPPPPGASANAS---------
YNQIYEK-YGNVSVFETSGGLVFWQGIKQKSLVEL--------------ERLANRSSLNITH-------------------RTRRS
QDRYTKGQEAITYFITSGGLLLAWLPLTPRSLATV----------------KNLTELTPTSSPPSSPPSPPAPSAARGSTPAAVLRRRRR
          **                  *
```

FIG. 3D

```
-IEGGIENVNNSI------IIKTTSSVHFAMLQFAYDHIQSHVNEMLSRIATAW  C  NLQNKERTLWNEVMKLNPTSVASVAMDQRVSARMLGDVL
 TIEGGIETVNNAS------LLKTTSSVEFAMIQFAYDYIQAHVNEMLSRIATAW  C  TLQNREHVLWTETLKLNPGGVVSMALERRVSARLLGDAV
 AVEATAGTDSSNVTAKQLELIKTTSSIEFAMLQFAYDHIQSHVNEMLSRIATAW  C  TLQNKERTLWNEMVKINPSAIVSATLDERVAARVLGDVI
 ---------------------LRITTGSAEFARLQFTYDHIQAHVNDMLGRIAAAW  C  ELQNKDRTLWSEMSRLNPSAVATAALGQRVSARMLGDVM
 ---------------------ITTTSSVEFAMLQFTYDHIQEHVNEMLARISSSW  C  QLQNRERALWSGLFPINPSALASTILDQRVKARILGDVI
 ---------------------VERIKTTSSIEFARLQFTYNHIQRHVNDMLGRVAIAW  C  ELQNHELTLWNEARKLNPNAIASVTVGRRVSARMLGDVM
 TSDNNTTHLS-----SMESVH---NLVYAQLQFTYDTLRGYINRALAQIAEAW  C  VDQRRTLEVFKELSKINPSAILSAIYNKPIAARFMGDVL
 DAGNATTPVPPTAPGKSLGTLN---NPATVQIQFAYDSLRRQINRMLGDLARAW  C  LEQKRQNMVLRELTKINPTTVMSSIYGKAVAAKRLGDVI
                                                          . **                                    *  *
```

```
AVTQ  C  VNISGS-SVFIQNSMRVLGSTTT  C  YSRPLISFKALENSTN--YIEGQLGENNELLVERKLIEP  C  TANHKRYFKFGADYYFENYA
 AVTQ  C  VNISSG-HVYIQNSMRVTGSSTT  C  YSRPLVSFRALNDS-E--YIEGQLGENNDLLVERKLIEP  C  TVNNKRYFKFGADYVYFEDYA
 AITH  C  AKIEG--NVYLQNSMRSMDSNT-  C  YSRPPVTFTITKNANNRGSIEGQLGEENEIFTERKLIEP  C  ALNQKRYFKFGKEYVYYENYT
 AISR  C  VEVRGG--VYVQNSMRVPGERGT  C  YSRPLVTF-----EHNGTGVIEGQLGDDNELLISRDLIEP  C  TGNHRRYFKLGSGYVYYEDYN
 SVSN  C  PELGSDTRIILQNSMRVSGSTTR  C  YSRPLISISVSLN---GSGTVEGQLGTDNELIMSRDLLEP  C  VANHKRYFLFGHHYVYYEDYR
 AVST  C  VPVAAD-NVIVQNSMRISSRPGA  C  YSRPLVSFRY---EDQGPLVEGQLGENNELRLTRDAIEP  C  TVGHRRYFTFGGGYVYFEEYA
 GLAS  C  VTIN-QTSVKVLRDMNVKESPGR  C  YSRPVVIFNFANSSY---VQYGQLGEDNEILLGNHRTEE  C  QLPSLKIFIAGNSAYEYVDYL
 SVSQ  C  VPVN-QATVTLRKSMRVPGSETM  C  YSRPLVSFSFSFINDTK---TYEGQLGTDNEIFLTKKMTEV  C  QATSQYYFQSGNEIHVYNDYH
          *                         ****                                       *
                                        600
```

FIG. 3E

```
                                                                          700                                            800
YVRKVPLNEIEMISAYVDLNITLLEDREFLPLEVYTRAELEDTGLLDYSEIQRRNQLHALKFYDIDSVVK---VDNNVVIMRGIANFFQGLGDVGA
YVRKVPLSEIELISAYVDLNLTLLEDREFLPLEVYTRAELEDTGLLDYSEIQRRNQLHALKFYDIDSIVR---VDNNLVIMRGMANFFQGLGDVGA
FVRKVPPTEIEVISTYVELNLTLLEDREFLPLEVYTRAELEDTGLLDYSEIQRRNQLHALRFYDIDSVVN---VDNTAVIMQGIASFFKGLGKVGE
YVRMVEVPET--ISTRVTLNETLLEDREFLPLEVYTREELADTGLLDYSEIQRRNQLHALKFYDIDRVVK---VDHNVVLLRGIANFFQGLGDVGA
YVREIAVHDVGMISTYVDLNLTLLKDREFMPLQVYTRDELRDTGLLDYSEIQRRNQMHSLRFYDIDKVVQ---YDSGTAIMQGMAQFFQGLGTAGQ
YSHQLSRADITTVSTFIDLMITMLEDHEFVPLEVYTRHEIKDSGLLDYTEVQRRNQLHDLRFADIDTVIH---ADANAAMFAGLGAFFEGMGDLGR
FKRMIDLSSISTVDSMIALDIDPLENTDFRVLELYSQKELRSSNVFDLEEIMREFNSYKQRV----KYVEDKVVDPLPPYLKGLDDLMSGLGAAGK
HFKTIELDGIATLQTFISLNTSLIENIDFASLELYSRDEQRASNVFDLEGIFREYNFQAQNIAGLRKDLDNAVSNGRNQFVDGLGELMDSLGSVGQ
 :    . :  :    .:       .        .   .    *    :       *.        *               *...:* .   *

GFGKVVLGAANAVIATVSGVSSFLNNPFGALAVGLLILAGLFAAFLAYRYVSKLKSNPMKALYP--VTTKNLKE----------SVKNGNSGNNSD
GFGKVVLGAASAVISTVSGVSSFLNNPFGALAVGLLILAGIVAAFLAYRYISRLRANPMKALYP--VTTRNLKQ----------TAKSPASTAGGD
AVGTLVLGEAAGAVVSTVSGVSSFLNNPFGGLAIGLLVIAGLVLAGLVLAGLLVLAGLVAAFLAYRYVMQIRSNPMKALYP----ITTKALKN----------KAKTS---YGQN
AVGKVVLGATGAVISAVGGMVSFLSNPFGALAIGLLVLAGLVLAGLVLAGLVAAFLAYRHISRLRRNPMKALYP--VTIKTLKE-----------
AVGHVVLGATGALLSIVHGFTTFLSNPFGALAVGLLVLAGLVAAFFAYRYVLKLKTSPMKALYP--LTTKGLKQLPEGMDPFAEKPNATDTPIEEI
AVGKVVMGLVGGVVSAVSGVSSFMSNPFGALAVGLLVLAGLAAAFFAFRYVMRLQSNPMKALYP--LTTKELKN---------PTNPDASGE
AVGVAIGAVGAVASVVEGVATFLKNPFGAFTIILVAIAVVIITYLIYTQRRLCTQPLQNLFPYLVSADGTTVTSGSTKDTSLQAPPSYEESVYN
SITNLVSTVGGLFSSLVSGFISFFKNPFGGMLILVLVAGVVILVISLTRRTRQMSQQPVQMLYP-----------GIDELAQQHASG--------
    .       . .     .  .  ****  *.  .    .      .        *. .*       *.
```

FIG. 3F

```
GEENDDN------IDEEKLQQAKEMIKYMSLVSAMEQQEHKAIKKNSGPALLASHITNLSLK----HRGPKYKRLKNVNENESK----V
SDPGVDD------FDEEKLMQAREMIKYMSLVSAMEQQEHKAMKKNKGPAILTSHLTNMALR----RRGPKYQRLNNLDSGDDTETNLV
EEDDGSD------FDEAKLEEAREMIKYMSMVSALEKQEKKAIKKNSGVGLIASNVSKLALR----RRGPKYTRLQQNDTMEN--EKMV
DGVDEGD------VDEAKLDQARDMIRYMSIVSALEQQEHKARKKNSGPALLASRVGAMATR----RR--HYQRL-----ESEDPDAL
GDSQNTEPSVNSGFDPDKFREAQEMIKYMTLVSAAERQESKARKKNKTSALLTSRLTGLALR----NR-RGYSRVR-----TENVTGV
GEEGGD------FDEAKLAEAREMIRYMALVSAMERTEHKAKKGTSR-LLSAKVTDMVMRK---RRNTNYTQVPNKD--GDADEDDL
SGRKGPGPPSSDASTAAPPYTNEQAYQMLLALARLDAEQR--AQQNGTDSLDGQTGTQDKGQKPNLLDRLRHRKNGYRHLKDSDEEENV
---EGPG-------INPISKTELQAIMLALHEQNQEQKRAAQRAAGPSVASRALQAARDRFPGLRRRRYHDPETAAALLG-EAETEF
```

| FIG. 4A |
|---|
| FIG. 4B |
| FIG. 4C |
| FIG. 4D |
| FIG. 4E |

| | | | |
|---|---|---|---|
| CGAGCCCTAA | TTATTGGTTT | GTATATGACT | 30 |
| GTTGGAATTT | GTTACATTTT | TATTAAAACA | 60 |
| ATAAATTAAA | TTTTTTAAAC | TATATTACGG | 90 |
| TTGTGTGTGT | TTTAAGTTTT | AAATAAAGCA | 120 |
| ATATTTCGAA | TTCACATTTA | TCAAAAACAT | 150 |
| TAAAACCCAA | CACAAAAAAA | TTTCTATAAT | 180 |
| CATTAAGGTA | ATAAGTCAAA | ATGAGTTTTA<br>M  S  F> | 210<br>3 |
| AAAATTTTA<br>K  N  F  Y | TCTAATATAT<br>L  I  Y | GTAATTATAA<br>V  I  I> | 240<br>13 |
| TTTTTATAAA<br>I  F  I  N | CTCGATAATA<br>S  I  I | ACTTCGGCAT<br>T  S  A> | 270<br>23 |
| CTACATCCAA<br>S  T  S  K | ACCTTCAACA<br>P  S  T | CCTACCATAA<br>P  T  I> | 300<br>33 |
| TTCCAACTTC<br>I  P  T  S | AGCAAATGAA<br>A  N  E | TCACCTGCTT<br>S  P  A> | 330<br>43 |
| CCATAGATAC<br>S  I  D  T | AACTATAACA<br>T  I  T | AAACCTATAT<br>K  P  I> | 360<br>53 |
| CTACAGAGGC<br>S  T  E  A | AAATAATTTA<br>N  N  L | AAATCAGTAA<br>K  S  V> | 390<br>63 |
| GTACCTCAAT<br>S  T  S  I | TAAACCACCT<br>K  P  P | AAAAACTTAA<br>K  N  L> | 420<br>73 |
| AAAAAAAATT<br>K  K  K  L | ACTTAAATCT<br>L  K  S | AAATGTAGAG<br>K  C  R> | 450<br>83 |
| ATAATGTTAT<br>D  N  V  I | TTATAGGCCA<br>Y  R  P | TATTTTAGTC<br>Y  F  S> | 480<br>93 |
| AATTAGAAAT<br>Q  L  E  I | TAACTGTACT<br>N  C  T | ATAACTAAAA<br>I  T  K> | 510<br>103 |

FIG. 4B

```
AGCAAAATTT  AAGTAATCCT  TTAATTGAGT   540
 K  Q  N  L   S   N  P   L   I  E>   113

TATGGTTTAA  AGAACTTTCT  ACATATAATA   570
 L  W  F  K   E   L  S   T   Y  N>   123

AAACCAATGA  AAATGTTGAA  AGTTTAAAAA   600
 K  T  N  E   N   V  E   S   L  K>   133

CAGATATATC  AAAAAATATT  TTATTATTTT   630
 T  D  I  S   K   N  I   L   L  F>   143

CGACAAAAAA  TAATAGTGAT  AACTTTTATA   660
 S  T  K  N   N   S  D   N   F  Y>   153

ATGATTTTTT  ATTAGGTATA  CAAAATCAAC   690
 N  D  F  L   L   G  I   Q   N  Q>   163

CAGTAAATTA  TAAACTTTAC  GGTTCCCAAT   720
 P  V  N  Y   K   L  Y   G   S  Q>   173

TTTATGATAA  TGGAAACATA  TTACTAAATA   750
 F  Y  D  N   G   N  I   L   L  N>   183

TAAAGTCGGT  TGACTTTAAA  ACCTCTGGAA   780
 I  K  S  V   D   F  K   T   S  G>   193

TATATACTTG  GAAACTATAT  AATTCAAATA   810
 I  Y  T  W   K   L  Y   N   S  N>   203

ATGAAAGTAT  TTTTGAAACT  TTTAAAATTC   840
 N  E  S  I   F   E  T   F   K  I>   213

AAGTATATGC  ATATCATTCC  CCAAATGTAA   870
 Q  V  Y  A   Y   H  S   P   N  V>   223

ACTTAAAATC  AAACCCAAGT  TTATATAATG   900
 N  L  K  S   N   P  S   L   Y  N>   233

AAAACTACAG  CGCTATTTGT  ACAATAGCAA   930
 E  N  Y  S   A   I  C   T   I  A>   243

ATTACTTTCC  ATTGGAATCT  ACGGAAATAT   960
 N  Y  F  P   L   E  S   T   E  I>   253
```

FIG. 4C

| | | | | |
|---|---|---|---|---|
| TTTGGTTTAA | CGATGGACAA | CCTATTGATA | 990 |
| F  W  F  N | D  G  Q | P  I  D> | 263 |
| AAAAATATAT | AGATGAAACT | TATAGTGTAT | 1020 |
| K  K  Y  I | D  E  T | Y  S  V> | 273 |
| GGATTGACGG | TCTTATAACA | CGCACTTCAA | 1050 |
| W  I  D  G | L  I  T | R  T  S> | 283 |
| TATTATCCCT | TCCCTTTTCC | GAAGCCATGG | 1080 |
| I  L  S  L | P  F  S | E  A  M> | 293 |
| AAAGCCCCCC | CAATTTGCGA | TGTAATGTTG | 1110 |
| E  S  P  P | N  L  R | C  N  V> | 303 |
| AATGGTATAA | AAATTCAAAG | GCATCAAAAA | 1140 |
| E  W  Y  K | N  S  K | A  S  K> | 313 |
| AATTTTCAAA | TACCGTTATT | CCAAAAGTTT | 1170 |
| K  F  S  N | T  V  I | P  K  V> | 323 |
| ACTATAAACC | TTTTATATCT | ATAAATTTG | 1200 |
| Y  Y  K  P | F  I  S | I  K  F> | 333 |
| ATAATGGTTT | AGCTATTGT | GATGCTAAAT | 1230 |
| D  N  G  L | A  I  C | D  A  K> | 343 |
| GTGTTTCCG | TGAAAATAAT | AAATTACAAT | 1260 |
| C  V  S  R | E  N  N | K  L  Q> | 353 |
| GGTTAGTTAA | AGATATACCT | ATAAATGGTG | 1290 |
| W  L  V  K | D  I  P | I  N  G> | 363 |
| ATGATATTAT | AAGCGGCCCC | TGTTTAAACC | 1320 |
| D  D  I  I | S  G  P | C  L  N> | 373 |
| ACCCTGGTTT | GGTCAATATT | CAAAATAAAA | 1350 |
| H  P  G  L | V  N  I | Q  N  K> | 383 |
| TAGATATATC | GGATTATGAT | GAACCTGTTA | 1380 |
| I  D  I  S | D  Y  D | E  P  V> | 393 |

FIG. 4D

| | | | | |
|---|---|---|---|---|
| CCTATAAATG | TTCAATTATT | GGTTATCCAA | 1410 | |
| T Y K C | S I I | G Y P> | 403 | |
| TAATTTTTCC | CAACTTTTAT | GATGAAAGG | 1440 | |
| I I F P | N F Y | D E K> | 413 | |
| TGTTTGATGC | ATCGGATGAA | AATGTTAGTA | 1470 | |
| V F D A | S D E | N V S> | 423 | |
| AATCGATGTT | AATAAGTATT | ACCACAATAA | 1500 | |
| K S M L | I S I | T T I> | 433 | |
| TTGGTGGAGC | CATTTTTGTT | ATAGTATTGA | 1530 | |
| I G G A | I F V | I V L> | 443 | |
| TTTTTATAAC | AGCTTTATGT | TTTTATTGTT | 1560 | |
| I F I T | A L C | F Y C> | 453 | |
| CAAAAAATAA | TAAGATCTAA | TATCAATATT | 1590 | |
| S K N N | K I * | | 459 | |
| TACGTAAATG | GATTATATAA | TGTTATATTC | 1620 | |
| GTGTTATTAT | GATTTATAAG | TTCATCAAAT | 1650 | |
| TTAAAAATTT | GTATAGTATT | AAGATTTTA | 1680 | |
| ATAGGGGTAT | CGTTTAATAT | GGCTCAGTTA | 1710 | |
| | M | A Q L | 4 | |
| GTTTTAACTG | ATATTCCCCT | CGAAGATGTG | 1740 | |
| V L T D | I P L | E D V | 14 | |
| GAAAATAAAA | ATACTTCATC | CGACGAAGAA | 1770 | |
| E N K N | T S S | D E E | 24 | |
| ACAACTAACT | TAAACCAGAA | AAAATCAACA | 1800 | |
| T T N L | N Q K | K S T | 34 | |
| TGTCAATGTT | TATGTGTTAC | CCTTGGATTT | 1830 | |
| C Q C L | C V T | L G F | 44 | |
| TTTGCAGCTG | GAATTTTATT | AACCATAGCT | 1860 | |
| F A A G | I L L | T I A | 54 | |

FIG. 4E

| | | | |
|---|---|---|---|
| GCAATAATTT<br>A  I  I  F | TTACTTTTAT<br>T  F  I | TTTTACAGTA<br>F  T  V | 1890<br>64 |
| CCATTAGAAA<br>P  L  E  M | TGCTTGGATC<br>L  G  S | TATTAATTGT<br>I  N  C | 1920<br>74 |
| CCTCCATCTA<br>P  P  S  T | CATTTGGTAT<br>F  G  I | TGATAATGTT<br>D  N  V | 1950<br>84 |
| TGTATCGAAC<br>C  I  E  P | CAATAAAAAA<br>I  K  K | ATCTATTAAT<br>S  I  N | 1980<br>94 |
| TCTTATTCAG<br>S  Y  S  E | AATTATCTAA<br>L  S  K | AATATGTTAT<br>I  C  Y | 2010<br>104 |
| GATAGATTGT<br>D  R  L  S | CAAATCCGAT<br>N  P  I | AAATCAGAGT<br>N  Q  S | 2040<br>114 |
| ACTATTAACT<br>T  I  N  S | CCTTATTAAC<br>L  L  T | TGTTTTAAAT<br>V  L  N | 2070<br>124 |
| ATGTTTGCAG<br>M  F  A  D | ATAAAACTA<br>K  N  Y | TGAAAATGTT<br>E  N  V | 2100<br>134 |
| TATAATTGTA<br>Y  N  C  N | ATACAATGAG<br>T  M  S | TGAAAAAACA<br>E  K  T | 2130<br>144 |
| TGTAATTCAT<br>C  N  S  S | CAATAGCTAT<br>I  A  I | TTGTCAAACT<br>C  Q  T | 2160<br>154 |
| AATCATCCAC<br>N  H  P  L | TAAGTTCATT<br>S  S  L | GGGAAATTTT<br>G  N  F | 2190<br>164 |
| GTTATTAAAA<br>V  I  K  I | TTAGAAAAT<br>R  K  I | TTTTGGGTTT<br>F  G  F | 2220<br>174 |
| AAATAATAAA<br>K  * | TAAAATAAAT | AAACATTACT | 2250<br>175 |
| TTTTGTTTTT | GTCTTTATTA | AACAGTTGTA | 2280 |

FIG. 6

| | FIG. 6A |
|---|---|
| | FIG. 6B |
| | FIG. 6C |
| | FIG. 6D |

FIG. 6A

```
CHV   MS-FK---NFYLIYVIIIFI------------------NSIITSASTSKPSTPTIIPTSANES---
FHV   MRRYRMGRGIYLLYICLLYTYLQFGTSSTTAVSIENSDNSTAEMLSSTSMSATTPISQPTSPFTTPTRRSTNIATS
EIV1  MWLPNLVRFVAVAYLICAGAILTYASG--------ASASSSQSTPATPTHTTPNLTTAHG
HSV1  MAPGRVGLAVVLWSLL----WLGAGVSGGSETASTGPTITAGAVTNASEAPTSGSPGSAASPEVTPTSTPNPNNVT
                                                     *

-------PASIDTTITKP--------------------ISTEANNLKSVSTSIKPPKNLKKKL----LKSK
      SSTTQASQPTSTLTLTRSSTTIATSPSTTQAATFIGSSTDSNTILLKTTKKPKRKKNKNNGARFKLD
      AGSDNTTNANGTESTHSHETT-------------------IT
      QNKTTPTEPASPPTT-PKPTSTPKSPPTSTP------DPKPKNNTTPAKSGRPTK------PPGPVW
          *                                       *
```

```
C  R-DNV
C  GYKGV
C  T-KSL
C  DRRDP
   *
```

```
NLKSNPSLYNENYSAI  C  TIANYFPLESTEIFWFNDGQPID-KKYIDETYSVWIDGLITRTSILSLPFSEAMESP
NLTPRASLFNKTFEAV  C  AVANYFP-RSTKLTWYLDGKPIE-RQYISDTASVWIDGLITRSSVLAIPTTETDSEK
DLSVHPSLKGENYRAT  C  VVASYFPHSSVKLRWYKNAREVDFTKYVTNASVVWDGLITRISTVSIPVDPEEEYT
TLQPHAVMEGQPFKAT  C  TAAAYYPRNPVEFVWFEDDHQVFNPGQIDTQTHEHPDGFTTVSTVTSEAVGGQVP-P
                  *   *       *   *             * *  *    * *   *     *

3 0 0
PNLR  C  NVEWYKNSKASKKFSNTVIPKVYYKPFISIKFDNGLAI  C  DAK  C  VSRENNKLQWLVKDI----PIN
PDIR  C  DLEWHESPVSYKRFTKSVAPDVYYPPTVSVTFADTRAI  C  DVK  C  VPRDGISLMWKIGNYHLPKAMS
PSLR  C  SIDWYRDEVSFARIAKAGTPSVFVAPTVSVSVEDGDAV  C  TAK  C  VPSTGVFVSWSVND-HLP-GVP
RTFT  C  QMTWHRDSVTFSRRNATGLALVLPRPTITMEFGVRIVV  C  TAG  C  VP-EGVTFAWFLGDDPSPAAKS
         *                                          *          *
```

FIG. 6D

```
                                                      400
GDDIISGP  C  LNHPGLVNIQNKIDISDYDEPVTYK  C  SIIGYPIIFPNFYDEKVFDASD-ENVSKSMLISITTI
ADILITGP  C  IERPGLVNIQSMCDISETDGPVSYT  C  QTIGYPPILPGFYDTQVYDASP-EIVSESMLVSVVAV
SQDMTTGV  C  PSHSGLVNMQSRRPLSEENGEREYS  C  IIEGYPDGLPMFSDTVVYDASP-IVEDRPVLTSIIAV
A-VTAQES  C  -DHPGLATVRSTLPIS--YDYSEYI  C  RLTGYPAGIPVLEHHGSHQPPPRDPTERQVIEAIEWV
      *      *  **   ..  .    .     *      *** .   .     .     .        ..  .

IGGAIFVIVLIFITALCFYCSKNNK------I
ILGAVLITVFIFITALCLYYSHPRR------L
TCGAAALALVVLITAVCFYCSKPSQAPYKKSDF
GIGIGVLAAGVLVVTAIVYVVRTSQSR-QRHRR
 *     .      ..  . .       *
```

| | | | |
|---|---|---|---|
| GATATTTAAT | AAAACTATTA | TGAAACTTCT | 30 |
| TATAACTTAT | TTGTTTTTAT | TAAATGGGTT | 60 |
| GGGTTGGTTT | TAAAATTACA | TACGTGTATT | 90 |
| AAGAATTAAC | ATCATAAGG | ACACACCCAT | 120 |
| GAAAACATT | TAAATTCTAT | TAATTTGAAC | 150 |
| GGATTAAACA | TTTTCTCATT | TTAAGAGTTG | 180 |
| CTACGACTTT | TGATAGTAAA | ATGATTAAAC | 210 |
| | | M  I  K> | 03 |
| TTCTATTTAT | CTTATTTTAT | TTTAACCCAA | 240 |
| L  L  F  I | L  F  Y | F  N  P> | 13 |
| TAACTGGATA | TAAATGGGTA | GACCCTCCTC | 270 |
| I  T  G  Y | K  W  V | D  P  P> | 23 |
| GTAGGTATAA | TTACACCGTT | TTAAGAATGA | 300 |
| R  R  Y  N | Y  T  V | L  R  M> | 33 |
| TTCCAGATAT | TCCAAATCCA | ATGGATCCTT | 330 |
| I  P  D  I | P  N  P | M  D  P> | 43 |
| CTAAAAACGC | TGAAGTTCGG | TATGTAACTT | 360 |
| S  K  N  A | E  V  R | Y  V  T> | 53 |
| CTACTGACCC | ATGTGATATG | GTTGCTTTGA | 390 |
| S  T  D  P | C  D  M | V  A  L> | 63 |
| TTTCTAATCC | AAATATAGAA | TCTACAATTA | 420 |
| I  S  N  P | N  I  E | S  T  I> | 73 |
| AAACGATTCA | ATTTGTGCAA | AAGAAAAAT | 450 |
| K  T  I  Q | F  V  Q | K  K  K> | 83 |
| TTTACAATGC | ATCTCTTAGT | TGGTTTAAAG | 480 |
| F  Y  N  A | S  L  S | W  F  K> | 93 |
| TTGGAGATGA | TTGTACATAT | CCAATATATT | 510 |
| V  G  D  D | C  T  Y | P  I  Y> | 103 |

FIG. 7B

```
TAATTCAATA   TTTTGATTGT   GATCCTCAAA    540
 L  I  Q  Y    F  D  C     D  P  Q>     113

GAGAATTTGG   CATATGTTTA   AAAAGATCTC    570
 R  E  F  G    I  C  L     K  R  S>     123

CAGATTTTTG   GAAACCATCG   TTAGTTGGTT    600
 P  D  F  W    K  P  S     L  V  G>     133

ACACATTTTT   AACTGATGAT   GAATTGGAT     630
 Y  T  F  L    T  D  D     E  L  G>     143

TAGTTTTAGC   TGCCCCCGCT   CCATTTAATC    660
 L  V  L  A    A  P  A     P  F  N>     153

AAGGTCAATA   TAGACGGGTT   ATTCAAATTG    690
 Q  G  Q  Y    R  R  V     I  Q  I>     163

AAAATGAAGT   TTTTTATACT   GATTTTATGG    720
 E  N  E  V    F  Y  T     D  F  M>     173

TTCAATTACC   ACGAGAAACT   TGTTATTTTT    750
 V  Q  L  P    R  E  T     C  Y  F>     183

CTAAAGAAGA   TAAATTTGAA   CCAACTTTTA    780
 S  K  E  D    K  F  E     P  T  F>     193

TGGAATGGTG   TAAGGAATCT   AGATCTGTAG    810
 M  E  W  C    K  E  S     R  S  V>     203

GAGCATCAAA   AGTTGACGAT   GAACTTTTT     840
 G  A  S  K    V  D  D     E  L  F>     213

ATCTAAATAG   AGCTGGTCCC   CAAACCCTGC    870
 Y  L  N  R    A  G  P     Q  T  L>     223

TTAAATATTA   TGTTATTAAA   GATTTTTATA    900
 L  K  Y  Y    V  I  K     D  F  Y>     233

GACTTAACGG   TAGAGAACCT   CCAATAAAAT    930
 R  L  N  G    R  E  P     P  I  K>     243

TTAAAGAAGC   TCTTAGATAC   GATATACCAT    960
 F  K  E  A    L  R  Y     D  I  P>     253
```

FIG. 7C

| | | | |
|---|---|---|---|
| ATAAAGTGAA<br>Y  K  V  N | TGATAAATTT<br>  D  K  F | GATGATGAAT<br>  D  D  E> | 990<br>263 |
| TACCATCGAG<br>L  P  S  R | GCCACATATT<br>  P  H  I | AGTAATACTA<br>  S  N  T> | 1020<br>273 |
| TTAATAAAAC<br>I  N  K  T | TATTAAAGAA<br>  I  K  E | ATTGTAAATC<br>  I  V  N> | 1050<br>283 |
| TTGAAGATTA<br>L  E  D  Y | TTTTAAAAAT<br>  F  K  N | ACAAATGTTA<br>  T  N  V> | 1080<br>293 |
| TAGATACTAC<br>I  D  T  T | TACCCCAACA<br>  T  P  T | CCAATAAATA<br>  P  I  N> | 1090<br>303 |
| ATACCCCAAA<br>N  T  P  K | AAATATAACC<br>  N  I  T | GTGGGAATTG<br>  V  G  I> | 1140<br>313 |
| TTATAATTAT<br>V  I  I  I | ATTAATAATA<br>  L  I  I | CTATTTATAA<br>  L  F  I> | 1170<br>323 |
| TTGGATTTTT<br>I  G  F  F | TGTTTATAAA<br>  V  Y  K | AGACAAAAAA<br>  R  Q  K> | 1200<br>333 |
| TATATAATAA<br>I  Y  N  N | TTATAAAAA<br>  Y  K  K | TTAACAACAA<br>  L  T  T> | 1230<br>343 |
| ATGTTTAGCC<br>N  V  * | TTTATAAATT | AATTTACAGA | 1260<br>345 |
| ATAAACAACT | GGGCGGTCTT | TTGTTTAATA | 1290 |
| AAAATTCATG | TACCTACAAC | TTTTATTCAC | 1320 |

FIG. 9

| FIG. 9A |
|---|
| FIG. 9B |
| FIG. 9C |

FIG. 9A

```
CHV   MI-KLLF------------------------------------------------ILF------YF----
FHV   MMTRLHF-----------------------------------------------WW--C----------
EH'1  MPAVLLVLYVNPPPSVCILTQKLSLGLYNQWWRVCRSVPPPWYVFFNKRSMSTFKLMMDGRLVFAMAIAILSVVLSCGT
HSV1  MGGA---------------------------AARLGAV----------ILF-----VVIVGLHGVRGKYALADASLKM----AD
       *

-----NPITGYK--WVDPPRRYNYTVLRMIPDIPNPM-----DPSKNAEVRYVTSTDP  C  DMVALISNPNIESTIKTI
      SLTTPKTTTVYVKGFNIPPLRYNYTQARIVPKIPQAM-----DPKITAEVRYVTSMDS  C  GMVALISEPDIDATIRTI
      CEKAKRAVRGRQDRPKEFPPPRYNYTILTRYNATALASPFINDQVKNVDLRIVTATRP  C  EMIALIAKTNIDSILKEL
      PNRFRGKDLPVLDQLTDPPGVRRVYHI-----QAGLPNPF--QPPSLPITVYRRVERA  C  RSVLLNAPSEAPQIVRGA
       *.     *..*                        *.                 .:..  *
```

FIG. 9B

```
                                                             100
QFVQKKFYNASLSWFKVGDD    C   TYPIYLIQYFD    C   DPQREFGI   C   LKRSPDFWKPSLVGYTFLTDDELGLVLAAP
QLSQKKT-YNATISWFKVTQG   C   EYPMFLMDMRL    C   DPKREFGI   C   ALRSPSYWLEPLTKYMFLTDDELGLIMMAP
AAAQKT--YSARLTWFKIMPT   C   ATPIHDVSYMK    C   NPKLSFAM   C   DERSDILWQASLITMAAETDDELGLVLAAP
SEDVRKQPYNLTIAWFRMGGN   C   AIPITVMEYTE    C   SYNKSLGA   C   PIRTQPRWN-YYDSFSAVSEDNLGFLMHAP
  . :  *  **              *             *  .                *  .   *         .:  ..  **  **

200
APFNQGQYRRVIQIENEVFYTDFMVQL-PRET    C   YFSKEDKFEPTFMEW   C   KESRSVGASKVDDELFYLNRAGPQT
AQFNQGQYRRVITIDGSMFYTDFMVQL-SPTP    C   WFAKPDRYEEILHEW   C   RNVKTIGLDGARDYHYWVPYNPQP
AHSASGLYRRVIEIDGRRIYTDFSVTI-PSER    C   PIAFELNFGN--PDR   C   KTPEQYSRGEVFTRRFLGEFNFPQG
AFETAGTYLRLVKINDWTEITQFILEHRAKGS    C   KYTLPLRIPPSA---   C   LSPQAYQQGVTVDSIGMLPRFIPEN
 *    **:*   .* .  :     .            *                   *   .
```

FIG. 9C

```
.LKYYVIKDFYRLNGREPPIKFKEALRYDIPYKVNDK--FDDELPSRPHISNTINKTIKE-------IVNLEDYFKNT
.HKA-VLLYWYRTHGREPPVRFQEAIRYDRPAIPSGS-----EDSKRSNDSRG-ESSGPN----WIDIENYTPKN
.HMTWV-KFWFVYDGGNLPVQFYEAQAFARPVPPDNHPGFDSVESEITQNKTDPKPGQADPKPNQPFKWPSIKHLVPRL
QRT--VAVYSLKIAGWHGPRAPYTSTLLPPELPETPNATQPELAPEDPEDSALLEDPVGTVAPQIPPNWH------
        *                            *              *
   300
NVIDTTTPINNTPKN-------ITVGIVIIILILFIIG--FFVYK-RQKIYNNYKKL----TTNV-------
NVPIIISDDDVPTAPPKGMNNQSVVIPAIVLSCLIIALILGVIYIYILRVKRSRSTAYQQLPIIHTTHHP------
DEVDEVI-EPVTKPPKTSKSNSTFVGISVGLGIAGLVLVGVILYVCLRRKKELKVCTERLD--SPTLDL-------
--IPSIQDAATPYHPPATPNNMGLIAGAVGGSLLAALVICGIVYW-MRRRTRKAPKRIRLPHIREDDQPSSHQPLFY
   *                                                     *
```

| | | | |
|---:|---|---|---|
| 1 | TGAATGTTAA | ATGTTATACT | TTGGATGAAG |
| 31 | CTATAAATAT | GCATTGGAAA | AATAATCCAT |
| 61 | TTAAAGAAAG | GATTCAAATA | CTACAAAACC |
| 91 | TAAGCGATAA | TATGTTAACT | AAGCTTATTC |
| 121 | TTAACGACGC | TTTAAATATA | CACAAATAAA |
| 151 | CATAATTTTT | GTATAACCTA | ACAAATAACT |
| 181 | AAAACATAAA | AATAATAAAA | GGAAATGTAA |
| 211 | TATCGTAATT | ATTTTACTCA | GGAATGGGGT |
| 241 | TAAATATTTA | TATCACGTGT | ATATCTATAC |
| 271 | TGTTATCGTA | TACACTTTAC | AATTACTATT |
| 301 | ACGAATATGC | AAGAGATAAT | AAGATTACGT |
| 331 | ATTTAAGAGA | ATCTTGTCAT | GATAATTGGG |
| 361 | TACGACATAG | TGATAAATGC | TATTTCGCAT |
| 391 | CGTTACATAA | AGTCAGTTGG | AAAGATGGAT |
| 421 | TTGACAGATG | TAACTTAATA | GGTGCAAAAA |
| 451 | TGTTAAATAA | CAGCATTCTA | TCGGAAGATA |
| 481 | GGATACCAGT | TATATTATAC | AAAAATCACT |
| 511 | GGTTGGATAA | AACAGATTCT | GCAATATTCG |
| 541 | TAAAAGATGA | AGATTACTGC | GAATTTGTAA |
| 571 | ACTATGACAA | TAAAAGCCA | TTTATCTCAA |
| 601 | CGACATCGTG | TAATTCTTCC | ATGTTTTATG |
| 631 | TATGTGTTTC | AGATATTATG | AGATTACTAT |
| 661 | AAACTTTTTG | TATACTTATA | TTCCGTAAAC |
| 691 | TATATTAATC | ATGAAGAAAA | TGAAAAAGTA |
| 721 | TAGAAGCTGT | TCACGAGCGG | TTGTTGAAAA |
| 751 | CAACAAAATT | ATACATTCAA | GATGGCTTAC |
| 781 | ATATACGTCT | GTGAGGCTAT | CATGGATAAT |
| 811 | GACAATGCAT | CTCTAAATAG | GTTTTTGGAC |
| 841 | AATGGATTCG | ACCCTAACAC | GGAATATGGT |
| 871 | ACTCTACAAT | CTCCTCTTGA | AATGGCTGTA |
| 901 | ATGTTCAAGA | ATACCGAGGC | TATAAAAATC |
| 931 | TTGATGAGGT | ATGGAGCTAA | ACCTGTAGTT |
| 961 | ACTGAATGCA | CAACTTCTTG | TCTGCATGAT |
| 991 | GCGGTGTTGA | GAGACGACTA | CAAAATAGTG |
| 1021 | AAAGATCTGT | TGAAGAATAA | CTATGTAAAC |
| 1051 | AATGTTCTTT | ACAGCGGAGG | CTTTACTCCT |
| 1081 | TTGTGTTTGG | CAGCTTACCT | TAACAAAGTT |
| 1111 | AATTTGGTTA | AACTTCTATT | GGCTCATTCG |
| 1141 | GCGGATGTAG | ATATTTCAAA | CACGGATCGG |
| 1171 | TTAACTCCTC | TACATATAGC | CGTATCAAAT |
| 1201 | AAAAATTTAA | CAATGGTTAA | ACTTCTATTG |
| 1231 | AACAAGGTG | CTGATACTGA | CTTGCTGGAT |
| 1261 | AACATGGGAC | GTACTCCTTT | AATGATCGCT |
| 1291 | GTACAATCTG | GAAATATTGA | AATATGTAGC |

FIG. 17B

```
1321    ACACTACTTA    AAAAAATAA     AATGTCCAGA
1351    ACTGGGAAAA    ATTGATCTTG    CCAGCTGTAA
1381    TTCATGGTAG    AAAAGAAGTG    CTCAGGCTAC
1411    TTTTCAACAA    AGGAGCAGAT    GTAAACTACA
1441    TCTTTGAAAG    AAATGGAAAA    TCATATACTG
1471    TTTTGGAATT    GATTAAAGAA    AGTTACTCTG
1501    AGACACAAAA    GAGGTAGCTG    AAGTGGTACT
1531    CTCAAAATGC    AGAACGATGA    CTGCGAAGCA
1561    AGAAGTAGAG    AAATAACACT    TTATGACTTT
1591    CTTAGTTGTA    GAAAGATAG     AGATATAATG
1621    ATGGTCATAA    ATAACTCTGA    TATTGCAAGT
1651    AAATGCAATA    ATAAGTTAGA    TTTATTTAAA
1681    AGGATAGTTA    AAAATAGAAA    AAAAGAGTTA
1711    ATTTGTAGGG    TTAAAATAAT    ACATAAGATC
1741    TTAAAATTTA    TAAATACGCA    TAATAATAAA
1771    AATAGATTAT    ACTTATTACC    TTCAGAGATA
1801    AAATTTAAGA    TATTTACTTA    TTTAACTTAT
1831    AAAGATCTAA    AATGCATAAT    TTCTAAATAA
1861    TGAAAAAAAA    GTACATCATG    AGCAACGCGT
1891    TAGTATATTT    TACAATGGAG    ATTAACGCTC
1921    TATACCGTTC    TATGTTTATT    GATTCAGATG
1951    ATGTTTAGA     AAAGAAAGTT    ATTGAATATG
1981    AAAACTTTAA    TGAAGATGAA    GATGACGACG
2211    ATGATTATTG    TTGTAAATCT    GTTTTAGATG
2041    AAGAAGATGA    CGCGCTAAAG    TATACTATGG
2071    TTACAAAGTA    TAAGTCTATA    CTACTAATGG
2101    CGACTTGTGC    AAGAAGGTAT    AGTATAGTGA
2131    AAATGTTGTT    AGATTATGAT    TATGAAAAAC
2161    CAAATAAATC    AGATCCATAT    CTAAAGGTAT
2191    CTCCTTTGCA    CATAATTTCA    TCTATTCCTA
2221    GTTTAGAATA    CTTTTCATTA    TATTTGTTTA
2251    CAGCTGAAGA    CGAAAAAAT     ATATCGATAA
2281    TAGAAGATTA    TGTTAACTCT    GCTAATAAGA
2311    TGAAATTGAA    TGAGTCTGTG    ATAATAGCTA
2341    TAATCAGAGA    AGTTCTAAAA    GGAAATAAAA
2371    ATCTAACTGA    TCAGGATATA    AAAACATTGG
2401    CTGATGAAAT    CAACAAGGAG    GAACTGAATA
2431    TAGCTAAACT    ATTGTTAGAT    AGAGGGGCCA
2461    AAGTAAATTA    CAAGGATGTT    TACGGTTCTT
2491    CAGCTCTCCA    TAGAGCTGCT    ATTGGTAGGA
2521    AACAGGATAT    GATAAGCTG     TTAATCGATC
2551    ATGGAGCTGA    TGTAAACTCT    TTAACTATTG
2581    CTAAAGATAA    TCTTATTAAA    AAAAAATAAT
2611    ATCACGTTTA    GTAATATTAA    AATATATTAA
```

FIG. 17C

```
2641    TAACTCTATT    ACTAATAACT    CCAGTGGATA
2671    TGAACATAAT    ACGAAGTTTA    TACATTCTCA
2701    TCAAAATCTT    ATTGACATCA    AGTTAGATTG
2731    TGAAAATGAG    ATTATGAAAT    TAAGGAATAC
2761    AAAAATAGGA    TGTAAGAACT    TACTAGAATG
2791    TTTTATCAAT    AATGATATGA    ATACAGTATC
2821    TAGGGCTATA    AACAATGAAA    CGATTAAAAA
2851    TTATAAAAAT    CATTTCCCTA    TATATAATAC
2881    GCTCATAGAA    AAATTCATTT    CTGAAAGTAT
2911    ACTAAGACAC    GAATTATTGG    ATGGAGTTAT
2941    AAATTCTTTT    CAAGGATTCA    ATAATAAATT
2971    GCCTTACGAG    ATTCAGTACA    TTATACTGGA
3001    GAATCTTAAT    AACCATGAAC    TAAAAAAAAT
3031    TTTAGATAAT    ATACATTAAA    AAGGTAAATA
3061    GATCATCTGT    TATTATAAGC    AAAGATGCTT
3091    GTTGCCAATA    ATATACAACA    GGTATTTGTT
3121    TTTATTTTA     ACTACATATT    TGATGTTCAT
3151    TCTCTTTATA    TAGTATACAC    AGAAAATTCA
3181    TAATCCACTT    AGAATTTCTA    GTTATCTAG
```

| | | | |
|---|---|---|---|
| 1 | GATATCTGTG | GTCTATATAT | ACTACACCCT |
| 31 | ACCGATATTA | ACCAACGAGT | TTCTCACAAG |
| 61 | AAAACTTGTT | TAGTAGATAG | AGATTCTTTG |
| 91 | ATTGTGTTTA | AAAGAAGTAC | CAGTAAAAAG |
| 121 | TGTGGCATAT | GCATAGAAGA | AATAAACAAA |
| 151 | AAACATATTT | CCGAACAGTA | TTTTGGAATT |
| 181 | CTCCCAAGTT | GTAAACATAT | TTTTTGCCTA |
| 211 | TCATGTATAA | GACGTTGGGC | AGATACTACC |
| 241 | AGAAATACAG | ATACTGAAAA | TACGTGTCCT |
| 271 | GAATGTAGAA | TAGTTTTTCC | TTTCATAATA |
| 301 | CCCAGTAGGT | ATTGGATAGA | TAATAAATAT |
| 331 | GATAAAAAAA | TATTATATAA | TAGATATAAG |
| 361 | AAAATGATTT | TTACAAAAAT | ACCTATAAGA |
| 391 | ACAATAAAAA | TATAATTACA | TTTACGGAAA |
| 421 | ATAGCTGGTT | TTAGTTTACC | AACTTAGAGT |
| 451 | AATTATCATA | TTGAATCTAT | ATTGTTTTTT |
| 481 | AGTTATATAA | AAACATGATT | AGCCCCCAAT |
| 511 | CGGATGAAAA | TATAAAAGAT | GTTGAGAATT |
| 541 | TCGAATACAA | CAAAAGAGG | AATCGTACGT |
| 571 | TGTCCATATC | CAAACATATA | AATAAAATT |
| 601 | CAAAAGTAGT | ATTATACTGG | ATGTTTAGAG |
| 631 | ATCAACGTGT | ACAAGATAAT | TGGGCTTTAA |
| 661 | TTTACGCACA | ACGATTAGCG | TTAAAACTCA |
| 691 | AAATACCTCT | AAGAATATGC | TTTTGTGTCG |
| 721 | TGCCAAAATT | TCACACTACT | ACTTCTAGAC |
| 751 | ACTTTATGTT | TTTAATATCC | GGTCTTAAAG |
| 781 | AAGTCGCGGA | AGAATGTAAA | AGACTATGTA |
| 811 | TAGGGTTTTC | ATTGATATAT | GGCGTACCAA |
| 841 | AAGTAATAAT | TCCGTGTATA | GTAAAAAAT |
| 871 | ACAGAGTCGG | AGTAATCATA | ACGGATTTCT |
| 901 | TTCCATTACG | TGTTCCCGAA | AGATTAATGA |
| 931 | AACAGACTGT | AATATCTCTT | CCAGATAACA |
| 961 | TACCTTTTAT | ACAAGTAGAC | GCTCATAATA |
| 991 | TAGTACCTTG | TTGGGAAGCT | TCTGATAAAG |
| 1021 | AAGAATACGG | TGCACGAACT | TTAAGAAAAA |
| 1051 | AGATATTTGA | TAAATTATAT | GAATATATGA |
| 1081 | CAGAATTTCC | TGTTGTTCGT | AAACATCCAT |
| 1111 | ACGGTCCATT | TTCTATATCT | ATTGCAAAAC |
| 1141 | CCAAAAATAT | ATCATTAGAC | AAGACGGTAT |
| 1171 | TACCCGTAAA | ATGGGCAACG | CCTGGAACAA |
| 1201 | AAGCTGGAAT | AATTGTTTTA | AAAGAATTTA |
| 1231 | TAAAAAACAG | ATTACCGTCA | TACGACGCGG |
| 1261 | ATCATAACAA | TCCTACGTGT | GACGCTTTGA |
| 1291 | GTAACTTATC | TCCGTGGCTA | CATTTGGTC |

FIG. 20B

```
1321    ATGTATCCGC    ACAACGTGTT    GCCTTAGAAG
1351    TATTAAAATG    TATACGAGAA    AGCAAAAAAA
1381    ACGTTGAAAC    GTTTATAGAT    GAAATAATTG
1411    TAAGAAGAGA    ACTATCGGAT    AATTTTTGTT
1441    ACTATAACAA    ACATTATGAT    AGTATCCAGT
1471    CTACTCATTC    ATGGGTTAGA    AAAACATTAG
1501    AAGATCACAT    TAATGATCCT    AGAAAGTATA
1531    TATATTCCAT    TAAACAACTC    GAAAAGCGG
1561    AAACTCATGA    TCCTCTATGG    AACGCGTCAC
1591    AAATGCAGAT    GGTGAGAGAA    GGAAAAATGC
1621    ATAGTTTTTT    ACGAATGTAT    TGGGCTAAGA
1651    AGATACTTGA    ATGGACTAGA    ACACCTGAAG
1681    ACGCTTTGAG    TTATAGTATC    TATTTGAACA
1711    ACAAGTACGA    ACTAGACGGC    ACGGATCCTA
1741    ACGGATACGT    AGGTTGTATG    TGGTCTATTT
1771    GCGGATTACA    CGATAGAGCG    TGGAAAGCAA
1801    GACCGATATT    TGGAAAGATA    AGATATATGA
1831    ATTATGAGAG    TTCTAAGAAG    AAATTTGATG
1861    TTGCTGTATT    TATACAGAAA    TACAATTAAG
1891    ATAAATAATA    TACAGCATTG    TAACCATCGT
1921    CATCCGTTAT    ACGGGAATA     ATATTACCAT
1951    ACAGTATTAT    TAAATTTTCT    TACGAAGAAT
1981    ATAGATCGGT    ATTTATCGTT    AGTTTATTTT
2011    ACATTTATTA    ATTAAACATG    TCTACTATTA
2041    CCTGTTATGG    AAATGACAAA    TTTAGTTATA
2071    TAATTTATGA    TAAAATTAAG    ATAATAATAA
2101    TGAAATCAAA    TAATTATGTA    AATGCTACTA
2141    GATTATGTGA    ATTACGAGGA    AGAAAGTTTA
2161    CGAACTGGAA    AAAATTAAGT    GAATCTAAAA
2191    TATTAGTCGA    TAATGTAAAA    AAAATAAATG
2221    ATAAAACTAA    CCAGTTAAAA    ACGGATATGA
2251    TTATATACGT    TAAGGATATT    GATCATAAAG
2281    GAAGAGATAC    TTGCGGTTAC    TATGTACACC
2311    AAGATCTGGT    ATCTTCTATA    TCAAATTGGA
2341    TATCTCCGTT    ATTCGCCGTT    AAGGTAAATA
2371    AAATTATTAA    CTATTATATA    TGTAATGAAT
2401    ATGATATACG    ACTTAGCGAA    ATGGAATCTG
2431    ATATGACAGA    AGTAATAGAT    GTAGTTGATA
2461    AATTAGTAGG    AGGATACAAT    GATGAAATAG
2491    CAGAAATAAT    ATATTTGTTT    AATAAATTTA
2521    TAGAAAAATA    TATTGCTAAC    ATATCGTTAT
2551    CAACTGAATT    ATCTAGTATA    TTAAATAATT
2581    TTATAAATTT    TATAAATTTT    AATAAAAAAT
2611    ACAATAACGA    CATAAAGATA    TTTAATCTTT
```

FIG. 20C

```
2641    AATTCTTGAT    CTGAAAAACA    CATCTATAAA
2671    ACTAGATAAA    AAGTTATTCG    ATAAAGATAA
2701    TAATGAATCG    AACGATGAAA    AATTGGAAAC
2731    AGAAGTTGAT    AAGCTAATTT    TTTTCATCTA
2761    AATAGTATTA    TTTTATTGAA    GTACGAAGTT
2791    TTACGTTAGA    TAAATAATAA    AGGTCGATTT
2821    TTACTTTGTT    AAATATCAAA    TATGTCATTA
2851    TCTGATAAAG    ATACAAAAAC    ACACGGTGAT
2881    TATCAACCAT    CTAACGAACA    GATATTACAA
2911    AAAATACGTC    GGACTATGGA    AAACGAAGCT
2941    GATAGCCTCA    ATAGAAGAAG    CATTAAAGAA
2971    ATTGTTGTAG    ATGTTATGAA    GAATTGGGAT
3001    CATCCTCAAC    GAAGAAATAG    ATAAAGTTCT
3031    AAACTGGAAA    AATGATACAT    TAAACGATTT
3061    AGATCATCTA    AATACAGATG    ATAATATTAA
3091    GGAAATCATA    CAATGTCTGA    TTAGAGAATT
3121    TGCGTTTAAA    AAGATCAATT    CTATTATGTA
3151    TAGTTATGCT    ATGGTAAAAC    TCAATTCAGA
3181    TAACGAACAT    TGAAAGATAA    AATTAAGGAT
3211    TATTTTATAG    AAACTATTCT    TAAAGACAAA
3241    CGTGGTTATA    AACAAAGCC     ATTACCCGGA
3271    TTGGAAACTA    AAATACTAGA    TAGTATTATA
3301    AGATTTTAAA    AACATAAAAT    TAATAGGTTT
3331    TTATAGATTG    ACTTATTATA    TACAATATGG
3361    ATAAAGATA     TATATCAACT    AGAAAGTTGA
3391    ATGACGGATT    CTTAATTTTA    TATTATGATT
3421    CAATAGAAAT    TATTGTCATG    TCGTGTAATC
2451    ATTTTATAAA    TATATCAGCG    TTACTAGCTA
3481    AGAAAACAA     GGACTTTAAT    GAATGGCTAA
3501    AGATAGAATC    ATTTAGAGAA    ATAATAGATA
3541    CTTTAGATAA    AATTAATTAC    GATCTAGGAC
3571    AACGATATTG    TGAAGAACTT    ACGGCGCATC
3601    ACATTCCAGT    GTAATTATTG    AGGTCAAAGC
3631    TAGTAACTTA    ATAGATGACA    GGACAGCTG
```

| | | | |
|---|---|---|---|
| 1 | TGTCTGGACT | AACTGATTTC | ATGGAACAAT |
| 31 | TTTCATCAAA | AATATCAGTT | ATACCTAGTT |
| 61 | CTACAAAGAC | AGAACTTTGA | TGTTATGTTT |
| 91 | GTGTTTGTAT | AGAAAATTTT | GGGATACTAA |
| 121 | CTGATATTTC | TGAATATTTC | TGAATATTTC |
| 151 | ATGTTACTTA | CTTACTCCTA | TCTTAGACGA |
| 181 | TAATAAAATT | CGAGGCGTAA | TATGTTTTTC |
| 211 | CAAATATTTG | AAATTCTTAT | ACGTATCGGC |
| 241 | GAAGAAAGT | AACATACTAT | AAGTGTTATG |
| 271 | CAAGTAAGGT | ATGTTAATGA | TATTGGATTT |
| 301 | AATTTCATTG | ACAATACATA | TGTCCAAACA |
| 331 | TTCCACTCGT | AATTATGTAC | GGAACGACTT |
| 361 | TAGTTAAATA | CTTAGTCACA | AAAAACTTAT |
| 391 | GACTGTCATT | ATCTGAAAAC | GGTGATTCCC |
| 421 | ATAAATCAGA | ATACTTAATA | TTAAATAGAA |
| 461 | TGCTCGCTTC | TGGAGGTTTC | CGGATACTAG |
| 481 | ATAACATATC | TTCTGTATTA | TAGTTTAATT |
| 511 | CACTCATTTT | ATTACATAAT | ACAGTAACAT |
| 541 | CTCCCGAAAC | CAATGATGTT | ATATTAGATT |
| 571 | TACTTACATA | CTTCTTGTAA | CTATCATGAA |
| 601 | TACGTTTGTT | ATGATCTATA | AAGAAGATGG |
| 631 | ATGTATATTC | TGTTCTAGAT | AGCAAGTTCT |
| 661 | TTAAGTTATT | CTTTGTCTGT | ATTACTATCA |
| 691 | TCGTCTTCAT | CATCGTCTAA | AGGTAGCATT |
| 721 | ATATAATAAA | TCTAATAGTT | GATTTCTCGA |
| 751 | TCTATCAGTA | CTCGCTTTCA | ATAACATTTT |
| 781 | TACTATAAGC | ATAATAGAAG | GCGGTGATAT |
| 811 | CACTATATTT | TTATCGGGTA | TTCTTTTAGT |
| 841 | AATTAGTTAG | TTCGTAGAAT | TTCGTAGAGA |
| 871 | TAAAAGCCAA | TTTGTTGTTG | ATACTGCTTA |
| 901 | CGTTACTCAT | GTTTCTTGTT | TCTGTTAATT |
| 931 | AACAGGTATA | CCCTTACAAT | AAGTTTAATT |
| 961 | AACTTTTAGG | TTTTTGTGAA | GAACTTTTAG |
| 991 | CTTCTAGTTC | CCTTATCCAT | AATTGGGTCT |
| 1021 | TAGATCTAGA | TTCTTCCCAT | GTATAAAGGG |
| 1051 | GGACATACCC | AAAATCTTTA | AATGCTTTGT |
| 1081 | CCGTTTCTAT | AGTAAATGTC | GTACATTCCT |
| 1111 | TAATCAAAGT | ATAAGGATTT | AGTAAAGGCG |
| 1141 | TGTAAGAACA | AATAGGTGAT | AGTAATACTC |
| 1171 | TTAAACCTTT | ATTAATATTA | GCGATAAACC |
| 1201 | TTAAACACCA | TAAGGAAGA | CATGTATTCC |
| 1231 | GTAGATCCAT | CCCTAATTGA | TTAAAGAAAT |
| 1261 | GCATGTTAAA | ATCATGATAA | TGTTCAGTAG |
| 1291 | GAGAGGTATC | GTAACAGTAA | TACACGTTAT |

FIG. 21B

| | | | |
|---|---|---|---|
| 1321 | TGCAGAGAGG | ACTATGTTGA | CCATTTTCTA |
| 1351 | TCATATTTCT | TGCTGCTAAA | ATATGCATCC |
| 1381 | AAGCTACGTT | TCCTGCATAG | ACTCTGCTAT |
| 1411 | GAAATACTTT | ATCATCCGCA | TATTTATACA |
| 1441 | TTTTCCTGCT | TTTATACGAT | CTTCTGTATA |
| 1471 | AAGTTTCTAG | TACTGGACAG | TATTCTCCGA |
| 1501 | AAACACCTAA | TGGGCGTAGC | GACAAGTGCA |
| 1531 | TAATCTAAGT | CCTATATTAG | ACATAGTACC |
| 1561 | GTTAGCTTCT | AGTATATATT | TCTCAGATAA |
| 1591 | CTTGTTTACT | AAGAGGATAA | GCCTCTTTAT |
| 1621 | GGTTAGATTG | ATAATACGTA | TTCTCGTTTC |
| 1651 | CTCTTATCAT | CGCATCTCCG | GAGAAAGTTA |
| 1681 | GGACCTACCG | CAGAATAACT | ACTCGTATAT |
| 1711 | ACTAAGACTC | TTACGCCGTT | ATACAGACAA |
| 1741 | GAATCTACTA | CGTTCTTCGT | TCCGTTGATA |
| 1771 | TTAACGTCCA | TTATAGAGTC | GTTAGTAAAC |
| 1801 | TTACCCGCTA | CATCATTTAT | CGAAGCAATA |
| 1831 | TGAATGACCA | CATCTGCTGA | TCTAAGCGCT |
| 1861 | TCGTCCAAAG | TACTTTTATT | TCTAACATCT |
| 1891 | CCAATCACGG | GAACTATCTT | TATTATATTA |
| 1921 | CATTTTTCTA | CAAGATCTAG | TAACCATTGG |
| 1951 | TCGATTCTAA | TATCGTAAAC | ACGAACTTCT |
| 1981 | TTTTAAAGAG | GATTCGAACA | AGATAAGATT |
| 2011 | ATTTATAATG | TGTCTACCTA | AAAATCCACA |
| 2041 | CCCTCCGGTT | ACCACGTATA | CTAGTGTACG |
| 2071 | CATTTGAGT | ATTAACTATA | TAAGACCAAA |
| 2101 | ATTATATTTT | CATTTCTGT | TATATTATAC |
| 2131 | TATATAATAA | AAACAAATAA | ATATACGAAT |
| 2161 | ATTATAAGAA | ATTTAGAACA | CGTTATTAAA |
| 2191 | GTATTGCCTT | TTTTATTAAC | GGCGTGTTCT |
| 2221 | TGTAATTGCC | GTTAGAATA | GTCTTTATTT |
| 2251 | ACTTTAGATA | ACTCTTCTAT | CATAACCGTC |
| 2281 | TCCTTATTCC | AATCTTCTTC | AGAAGTACAT |
| 2311 | GAGTACTTAC | CGAAGTTTAT | CATCATAGAG |
| 2341 | ATTATATATG | AAGAAA | |

FIG. 23

| FIG. 23A |
|---|
| FIG. 23B |
| FIG. 23C |
| FIG. 23D |
| FIG. 23E |
| FIG. 23F |
| FIG. 23G |
| FIG. 23H |
| FIG. 23I |
| FIG. 23J |
| FIG. 23K |
| FIG. 23L |

FIG. 23A pCHV37/vCP320

| | | | |
|---|---|---|---|
| AGTACAATAA<br>TCATGTTATT<br>―――――――<br>C6 flankin | AAAGTATTAA<br>TTTCATAATT<br>g arm    > | ATAAAAATAC<br>TATTTTTATG | 30 |
| TTACTTACGA<br>AATGAATGCT<br>C6 flankin | AAAAATGACT<br>TTTTTACTGA<br>g arm   > | AATTAGCTAT<br>TTAATCGATA | 60 |
| AAAAACCCGG<br>TTTTTGGGCC | GAAAGGATCC<br>CTTTCCTAGG | TGATCCTTTT<br>ACTAGGAAAA | 90 |
| TCTGGGTAAG<br>AGACCCATTC | TAATACGTCA<br>ATTATGCAGT | AGGAGAAAAC<br>TCCTCTTTTG | 120 |
| GAAACGATCT<br>CTTTGCTAGA | GTAGTTAGCG<br>CATCAATCGC | GCCAAACTCG<br>CGGTTTGAGC | 150 |
| AGGTCGACTG<br>TCCAGCTGAC | AGATAAAGTG<br>TCTATTTCAC | AAAATATATA<br>TTTTATATAT | 180 |
| TCATTATATT<br>AGTAATATAA<br>――――――― | ACAAAGTACA<br>TGTTTCATGT<br>I3L promot | ATTATTTAGG<br>TAATAAATCC<br>er―――――― | 210 |
| TTTAATCATG<br>AAATTAGTAC<br>____> M | TTTTCATTGT<br>AAAAGTAACA<br>F  S  L<br>__CHV gB__ | ATCTATATAT<br>TAGATATATA<br>Y  L  Y  I><br>      > | 240<br>8 |
| TTTTTTTATT<br>AAAAAAATAA<br>F  F  I | ATTTATACTT<br>TAAATATGAA<br>I  Y  T<br>__CHV gB__ | TAATAATATG<br>ATTATTATAC<br>L  I  I  C><br>      > | 270<br>18 |
| TGATCCAACA<br>ACTAGGTTGT<br>D  P  T<br>――――――― | ACACCGGAAA<br>TGTGGCCTTT<br>T  P  E<br>__CHV gB__ | GTACTATTAA<br>CATGATAATT<br>S  T  I  N><br>      > | 300<br>28 |

FIG. 23B

```
TCCATTAAAT   CATCACAATT   TATCAACACC        330
AGGTAATTTA   GTAGTGTTAA   ATAGTTGTGG
  P  L  N     H  H  N      L  S  T  P>       38
              _CHV gB__              >

TAAACCTACT   TCGGATGATA   TTCGTGAAAT        360
ATTTGGATGA   AGCCTACTAT   AAGCACTTTA
  K  P  T     S  D  D      I  R  E  I>       48
              _CHV gB__              >

TTTACGTGAA   TCCCAAATTG   AATCTGATGA        390
AAATGCACTT   AGGGTTTAAC   TTAGACTACT
  L  R  E     S  Q  I      E  S  D  D>       58
              _CHV gB__              >

TACATCAACA   TTTTACATGT   GCCCACCACC        420
ATGTAGTTGT   AAAATGTACA   CGGGTGGTGG
  T  S  T     F  Y  M      C  P  P  P>       68
              _CHV gB__              >

ATCGGGATCA   ACATTGGTGC   GTTTGGAGCC        450
TAGCCCTAGT   TGTAACCACG   CAAACCTCGG
  S  G  S     T  L  V      R  L  E  P>       78
              _CHV gB__              >

ACCTAGAGCA   TGTCCTAACT   ATAAACTTGG        480
TGGATCTCGT   ACAGGATTGA   TATTTGAACC
  P  R  A     C  P  N      Y  K  L  G>       88
              _CHV gB__              >

TAAAAATTTT   ACAGAAGGAA   TTGCTGTAAT        510
ATTTTTAAAA   TGTCTTCCTT   AACGACATTA
  K  N  F     T  E  G      I  A  V  I>       98
              _CHV gB__              >

ATTTAAGGAA   AATATTTCTC   CTTATAAATT        540
TAAATTCCTT   TTATAAGAG    GAATATTTAA
  F  K  E     N  I  S      P  Y  K  F>      108
              _CHV gB__              >
```

FIG. 23C

```
TAAAGCTAAT   ATATACTACA   AAAATATTAT           570
ATTTCGATTA   TATATGATGT   TTTTATAATA
  K  A  N      I  Y  Y     K  N  I  I>         118
             _CHV gB__                >

TATCACCACT   GTATGGTCTG   GAAGCACATA           600
ATAGTGGTGA   CATACCAGAC   CTTCGTGTAT
  I  T  T      V  W  S     G  S  T  Y>         128
             _CHV gB__                >

TGCAGTAATT   ACTAATAGAT   ATACAGATCG           630
ACGTCATTAA   TGATTATCTA   TATGTCTAGC
  A  V  I      T  N  R     Y  T  D  R>         138
             _CHV gB__                >

TGTACCTATA   GGTGTTCCTG   AAATTACAGA           660
ACATGGATAT   CCACAAGGAC   TTTAATGTCT
  V  P  I      G  V  P     E  I  T  E>         148
             _CHV gB__                >

GTTGATTGAT   AGAAGAGGTA   TGTGTTTATC           690
CAACTAACTA   TCTTCTCCAT   ACACAAATAG
  L  I  D      R  R  G     M  C  L  S>         158
             _CHV gB__                >

AAAAGCTGAT   TATATTCGTA   ATAATTATGA           720
TTTTCGACTA   ATATAAGCAT   TATTAATACT
  K  A  D      Y  I  R     N  N  Y  E>         168
             _CHV gB__                >

ATTTACCGCA   TTTGATAAGG   ATGAAGACCC           750
TAAATGGCGT   AAACTATTCC   TACTTCTGGG
  F  T  A      F  D  K     D  E  D  P>         178
             _CHV gB__                >

CAGAGAAGTT   CATTTAAAGC   CTTCAAAGTT           780
GTCTCTTCAA   GTAAATTTCG   GAAGTTTCAA
  R  E  V      H  L  K     P  S  K  F>         188
             _CHV gB__                >
```

FIG. 23D

| | | | |
|---|---|---|---|
| TAATACACCA<br>ATTATGTGGT<br>  N   T   P<br>─────────── | GGATCCCGTG<br>CCTAGGGCAC<br>  G   S   R<br>__CHV gB__ | GATGGCATAC<br>CTACCGTATG<br>  G   W   H   T><br>              > | 810<br><br>198 |
| AGTTAATGAT<br>TCAATTACTA<br>  V   N   D<br>─────────── | ACTTACACAA<br>TGAATGTGTT<br>  T   Y   T<br>__CHV gB__ | AAATTGGGGG<br>TTTAACCCCC<br>  K   I   G   G><br>              > | 840<br><br>208 |
| TTCTGGATTT<br>AAGACCTAAA<br>  S   G   F<br>─────────── | TATCATTCTG<br>ATAGTAAGAC<br>  Y   H   S<br>__CHV gB__ | GAACATCTGT<br>CTTGTAGACA<br>  G   T   S   V><br>              > | 870<br><br>218 |
| AAATTGTATA<br>TTTAACATAT<br>  N   C   I<br>─────────── | GTTGAAGAAG<br>CAACTTCTTC<br>  V   E   E<br>__CHV gB__ | TTGATGCCAG<br>AACTACGGTC<br>  V   D   A   R><br>              > | 900<br><br>228 |
| ATCTGTTTAT<br>TAGACAAATA<br>  S   V   Y<br>─────────── | CCATATGATT<br>GGTATACTAA<br>  P   Y   D<br>__CHV gB__ | CATTTGCTAT<br>GTAAACGATA<br>  S   F   A   I><br>              > | 930<br><br>238 |
| CTCCACCGGG<br>GAGGTGGCCC<br>  S   T   G<br>─────────── | GATATAATTC<br>CTATATTAAG<br>  D   I   I<br>__CHV gB__ | ATATGTCCCC<br>TATACAGGGG<br>  H   M   S   P><br>              > | 960<br><br>248 |
| TTTTTTTGGA<br>AAAAAAACCT<br>  F   F   G<br>─────────── | TTACGAGATG<br>AATGCTCTAC<br>  L   R   D<br>__CHV gB__ | GTGCTCATAC<br>CACGAGTATG<br>  G   A   H   T><br>              > | 990<br><br>258 |
| TGAATATATT<br>ACTTATATAA<br>  E   Y   I<br>─────────── | AGTTATTCAA<br>TCAATAAGTT<br>  S   Y   S<br>__CHV gB__ | CTGATAGATT<br>GACTATCTAA<br>  T   D   R   F><br>              > | 1020<br><br>268 |

FIG. 23E

| | | | |
|---|---|---|---|
| TCAACAAATA<br>AGTTGTTTAT<br>  Q  Q  I<br>_____ | GAAGGTTATT<br>CTTCCAATAA<br>  E  G  Y<br>\_\_CHV gB\_\_ | ATCCTATCGA<br>TAGGATAGCT<br> Y  P  I  D><br>          > | 1050<br><br>278 |
| CTTAGATACT<br>GAATCTATGA<br>  L  D  T<br>_____ | AGACTACAGC<br>TCTGATGTCG<br>  R  L  Q<br>\_\_CHV gB\_\_ | TTGGTGCACC<br>AACCACGTGG<br> L  G  A  P><br>          > | 1080<br><br>288 |
| AGTTTCTAGG<br>TCAAAGATCC<br>  V  S  R<br>_____ | AATTTTTTAA<br>TTAAAAAATT<br>  N  F  L<br>\_\_CHV gB\_\_ | CAACACAACA<br>GTTGTGTTGT<br> T  T  Q  H><br>          > | 1110<br><br>298 |
| CGTTACTGTT<br>GCAATGACAA<br>  V  T  V<br>_____ | GCTTGGAATT<br>CGAACCTTAA<br>  A  W  N<br>\_\_CHV gB\_\_ | GGGTTCCAAA<br>CCCAAGGTTT<br> W  V  P  K><br>          > | 1140<br><br>308 |
| AATTCGTGAA<br>TTAAGCACTT<br>  I  R  E<br>_____ | GTGTGTACTT<br>CACACATGAA<br>  V  C  T<br>\_\_CHV gB\_\_ | TGGCTAAATG<br>ACCGATTTAC<br> L  A  K  W><br>          > | 1170<br><br>318 |
| GCGTGAAATT<br>CGCACTTTAA<br>  R  E  I<br>_____ | GATGAAATTA<br>CTACTTTAAT<br>  D  E  I<br>\_\_CHV gB\_\_ | TTCGTGATGA<br>AAGCACTACT<br> I  R  D  E><br>          > | 1200<br><br>328 |
| GTATAAGGGA<br>CATATTCCCT<br>  Y  K  G<br>_____ | TCTTACAGAT<br>AGAATGTCTA<br>  S  Y  R<br>\_\_CHV gB\_\_ | TTACAGCAAA<br>AATGTCGTTT<br> F  T  A  K><br>          > | 1230<br><br>338 |
| ATCAATATCT<br>TAGTTATAGA<br>  S  I  S<br>_____ | GCAACATTTA<br>CGTTGTAAAT<br>  A  T  F<br>\_\_CHV gB\_\_ | TTTCTGATAC<br>AAAGACTATG<br> I  S  D  T><br>          > | 1260<br><br>348 |

FIG. 23F

```
TACTCAATTT  GATATTGATC  GTGTAAAGTT        1290
ATGAGTTAAA  CTATAACTAG  CACATTTCAA
  T  Q  F    D  I  D    R  V  K  L>       358
            __CHV gB__             >

AAGTGATTGT  GCCAAACGTG  AAGCCATAGA        1320
TTCACTAACA  CGGTTTGCAC  TTCGGTATCT
  S  D  C    A  K  R    E  A  I  E>       368
            __CHV gB__             >

AGCTATTGAT  AAGATCTACA  AAAAAAAATA        1350
TCGATAACTA  TTCTAGATGT  TTTTTTTTAT
  A  I  D    K  I  Y    K  K  K  Y>       378
            __CHV gB__             >

TAATAAAACT  CATATTCAAA  CAGGAGAATT        1380
ATTATTTTGA  GTATAAGTTT  GTCCTCTTAA
  N  K  T    H  I  Q    T  G  E  L>       388
            __CHV gB__             >

GGAAACATAC  TTGGCTAGAG  GGGGATTTAT        1410
CCTTTGTATG  AACCGATCTC  CCCCTAAATA
  E  T  Y    L  A  R    G  G  F  I>       398
            __CHV gB__             >

TATAGCATTT  AGACCAATGA  TTAGTAATGA        1440
ATATCGTAAA  TCTGGTTACT  AATCATTACT
  I  A  F    R  P  M    I  S  N  E>       408
            __CHV gB__             >

GTTAGCAAAA  TTGTATATAA  ATGAGTTAGT        1470
CAATCGTTTT  AACATATATT  TACTCAATCA
  L  A  K    L  Y  I    N  E  L  V>       418
            __CHV gB__             >

AAGATCTAAT  CGTACGGTTG  ATTTGAAATC        1500
TTCTAGATTA  GCATGCCAAC  TAAACTTTAG
  R  S  N    R  T  V    D  L  K  S>       428
            __CHV gB__             >
```

FIG. 23G

| | | | |
|---|---|---|---|
| TCTTTTAAAT<br>AGAAAATTTA<br>  L   L   N | CCATCTGTAA<br>GGTAGACATT<br>  P   S   V<br>__CHV gB__ | GAGGGGGGGC<br>CTCCCCCCCG<br>  R   G   A> | 1530<br><br>438 |
| TAGAAAGAGA<br>ATCTTTCTCT<br>  R   K   R | AGATCAGTAG<br>TCTAGTCATC<br>  R   S   V<br>__CHV gB__ | AGGAAAATAA<br>TCCTTTTATT<br>  E   E   N  K> | 1560<br><br>448 |
| AAGATCAAAA<br>TTCTAGTTTT<br>  R   S   K | CGTAATATTG<br>GCATTATAAC<br>  R   N   I<br>__CHV gB__ | AAGGTGGTAT<br>TTCCACCATA<br>  E   G   G  I> | 1590<br><br>458 |
| TGAAAATGTA<br>ACTTTTACAT<br>  E   N   V | AATAATTCAA<br>TTATTAAGTT<br>  N   N   S<br>__CHV gB__ | CAATAATTAA<br>GTTATTAATT<br>  T   I   I  K> | 1620<br><br>468 |
| GACAACTTCA<br>CTGTTGAAGT<br>  T   T   S | TCTGTTCATT<br>AGACAAGTAA<br>  S   V   H<br>__CHV gB__ | TTGCTATGCT<br>AACGATACGA<br>  F   A   M  L> | 1650<br><br>478 |
| TCAGTTTGCC<br>AGTCAAACGG<br>  Q   F   A | TATGATCATA<br>ATACTAGTAT<br>  Y   D   H<br>__CHV gB__ | TTCAATCACA<br>AAGTTAGTGT<br>  I   Q   S  H> | 1680<br><br>488 |
| TGTTAATGAA<br>ACAATTACTT<br>  V   N   E | ATGCTTAGTA<br>TACGAATCAT<br>  M   L   S<br>__CHV gB__ | GAATTGCAAC<br>CTTAACGTTG<br>  R   I   A  T> | 1710<br><br>498 |
| TGCATGGTGT<br>ACGTACCACA<br>  A   W   C | AATCTTCAAA<br>TTAGAAGTTT<br>  N   L   Q<br>__CHV gB__ | ATAAAGAGAG<br>TATTTCTCTC<br>  N   K   E  R> | 1740<br><br>508 |
| AACCCTTTGG<br>TTGGGAAACC<br>  T   L   W | AATGAAGTTA<br>TTACTTCAAT<br>  N   E   V<br>__CHV gB__ | TGAAACTTAA<br>ACTTTGAATT<br>  M   K   L  N> | 1770<br><br>518 |

FIG. 23H

```
TCCAACTAGT   GTGGCTTCGG   TTGCTATGGA    1800
AGGTTGATCA   CACCGAAGCC   AACGATACCT
   P  T  S     V  A  S      V  A  M  D>  528
               _CHV gB_              >

TCAAAGAGTT   TCAGCACGAA   TGTTAGGGGA    1830
AGTTTCTCAA   AGTCGTGCTT   ACAATCCCCT
   Q  R  V     S  A  R      M  L  G  D>  538
               _CHV gB_              >

TGTTCTTGCA   GTTACTCAAT   GTGTTAATAT    1860
ACAAGAACGT   CAATGAGTTA   CACAATTATA
   V  L  A     V  T  Q      C  V  N  I>  548
               _CHV gB_              >

ATCAGGTTCT   AGTGTTTTTA   TTCAAAATTC    1890
TAGTCCAAGA   TCACAAAAAT   AAGTTTTAAG
   S  G  S     S  V  F      I  Q  N  S>  558
               _CHV gB_              >

CATGCGTGTT   TTAGGGTCAA   CAACTACATG    1920
GTACGCACAA   AATCCCAGTT   GTTGATGTAC
   M  R  V     L  G  S      T  T  T  C>  568
               _CHV gB_              >

TTACAGTCGT   CCTCTTATAT   CATTTAAAGC    1950
AATGTCAGCA   GGAGAATATA   GTAAATTTCG
   Y  S  R     P  L  I      S  F  K  A>  578
               _CHV gB_              >

ACTAGAAAAC   TCAACTAACT   ATATTGAAGG    1980
TGATCTTTTG   AGTTGATTGA   TATAACTTCC
   L  E  N     S  T  N      Y  I  E  G>  588
               _CHV gB_              >

ACAACTTGGG   GAAAATAATG   AACTATTAGT    2010
TGTTGAACCC   CTTTTATTAC   TTGATAATCA
   Q  L  G     E  N  N      E  L  L  V>  598
               _CHV gB_              >

AGAACGAAAG   CTAATTGAAC   CATGTACAGC    2040
TCTTGCTTTC   GATTAACTTG   GTACATGTCG
   E  R  K     L  I  E      P  C  T  A>  608
               _CHV gB_              >
```

FIG. 231

```
TAACCATAAA   AGATATTTA   AATTTGGTGC        2070
ATTGGTATTT   TCTATAAAAT  TTAAACCACG
  N  H  K     R  Y  F     K  F  G  A>      618
              __CHV gB__            >

AGATTATGTA   TATTTTGAAA  ACTATGCATA        2100
TCTAATACAT   ATAAAACTTT  TGATACGTAT
  D  Y  V     Y  F  E     N  Y  A  Y>      628
              __CHV gB__            >

TGTTCGAAAG   GTACCTCTTA  ATGAAATTGA        2130
ACAAGCTTTC   CATGGAGAAT  TACTTTAACT
  V  R  K     V  P  L     N  E  I  E>      638
              __CHV gB__            >

AATGATCAGT   GCATATGTAG  ATCTTAATAT        2160
TTACTAGTCA   CGTATACATC  TAGAATTATA
  M  I  S     A  Y  V     D  L  N  I>      648
              __CHV gB__            >

TACATTACTT   GAGGATCGTG  AATTTTTACC        2190
ATGTAATGAA   CTCCTAGCAC  TTAAAAATGG
  T  L  L     E  D  R     E  F  L  P>      658
              __CHV gB__            >

ACTAGAGGTA   TATACTCGAG  CAGAGTTAGA        2220
TGATCTCCAT   ATATGAGCTC  GTCTCAATCT
  L  E  V     Y  T  R     A  E  L  E>      668
              __CHV gB__            >

AGATACAGGA   CTATTGGACT  ATAGTGAGAT        2250
TCTATGTCCT   GATAACCTGA  TATCACTCTA
  D  T  G     L  L  D     Y  S  E  I>      678
              __CHV gB__            >

TCAACGTAGA   AATCAACTAC  ATGCACTTAA        2280
AGTTGCATCT   TTAGTTGATG  TACGTGAATT
  Q  R  R     N  Q  L     H  A  L  K>      688
              __CHV gB__            >

GTTTTATGAT   ATTGACAGTG  TTGTAAAAGT        2310
CAAAATACTA   TAACTGTCAC  AACATTTTCA
  F  Y  D     I  D  S     V  V  K  V>      698
              __CHV gB__            >
```

FIG. 23J

| | | | |
|---|---|---|---|
| TGATAATAAT ACTATTATTA D  N  N | GTTGTAATTA CAACATTAAT V  V  I ‗‗CHV gB‗‗ | TGAGGGGCAT ACTCCCCGTA M  R  G  I> ‗‗‗‗‗‗‗‗‗‗> | 2340 708 |
| TGCAAATTTT ACGTTTAAAA A  N  F | TTCCAAGGAC AAGGTTCCTG F  Q  G ‗‗CHV gB‗‗ | TTGGAGATGT AACCTCTACA L  G  D  V> ‗‗‗‗‗‗‗‗‗‗> | 2370 718 |
| TGGAGCGGGA ACCTCGCCCT G  A  G | TTTGGAAAAG AAACCTTTTC F  G  K ‗‗CHV gB‗‗ | TTGTTTTGGG AACAAAACCC V  V  L  G> ‗‗‗‗‗‗‗‗‗‗> | 2400 728 |
| TGCTGCAAAT ACGACGTTTA A  A  N | GCTGTTATTG CGACAATAAC A  V  I ‗‗CHV gB‗‗ | CAACTGTTTC GTTGACAAAG A  T  V  S> ‗‗‗‗‗‗‗‗‗‗> | 2430 738 |
| TGGAGTGTCC ACCTCACAGG G  V  S | TCGTTTCTTA AGCAAAGAAT S  F  L ‗‗CHV gB‗‗ | ATAACCCATT TATTGGGTAA N  N  P  F> ‗‗‗‗‗‗‗‗‗‗> | 2460 748 |
| TGGGGCGCTA ACCCCGCGAT G  A  L | GCCGTTGGAT CGGCAACCTA A  V  G ‗‗CHV gB‗‗ | TGCTGATTTT ACGACTAAAA L  L  I  L> ‗‗‗‗‗‗‗‗‗‗> | 2490 758 |
| AGCTGGACTA TCGACCTGAT A  G  L | TTTGCAGCGT AAACGTCGCA F  A  A ‗‗CHV gB‗‗ | TTTTGGCTTA AAAACCGAAT F  L  A  Y> ‗‗‗‗‗‗‗‗‗‗> | 2520 768 |
| TAGATATGTT ATCTATACAA R  Y  V | TCTAAACTTA AGATTTGAAT S  K  L ‗‗CHV gB‗‗ | AGTCAAATCC TCAGTTTAGG K  S  N  P> ‗‗‗‗‗‗‗‗‗‗> | 2550 778 |
| AATGAAAGCA TTACTTTCGT M  K  A | CTATACCCAG GATATGGGTC L  Y  P ‗‗CHV gB‗‗ | TAACTACAAA ATTGATGTTT V  T  T  K> ‗‗‗‗‗‗‗‗‗‗> | 2580 788 |

FIG. 23K

| | | | |
|---|---|---|---|
| AAATTTAAAA<br>TTTAAATTTT<br>  N   L   K | GAAAGTGTTA<br>CTTTCACAAT<br>  E   S   V<br>\_\_CHV gB\_\_ | AGAATGGTAA<br>TCTTACCATT<br>  K   N   G  N><br>              > | 2610<br><br>798 |
| TTCTGGAAAT<br>AAGACCTTTA<br>  S   G   N | AATAGTGATG<br>TTATCACTAC<br>  N   S   D<br>\_\_CHV gB\_\_ | GAGAAGAAAA<br>CTCTTCTTTT<br>  G   E   E  N><br>              > | 2640<br><br>808 |
| TGATGATAAT<br>ACTACTATTA<br>  D   D   N | ATCGATGAAG<br>TAGCTACTTC<br>  I   D   E<br>\_\_CHV gB\_\_ | AAAAGCTTCA<br>TTTTCGAAGT<br>  E   K   L  Q><br>              > | 2670<br><br>818 |
| ACAAGCTAAA<br>TGTTCGATTT<br>  Q   A   K | GAAATGATTA<br>CTTTACTAAT<br>  E   M   I<br>\_\_CHV gB\_\_ | AATATATGTC<br>TTATATACAG<br>  K   Y   M  S><br>              > | 2700<br><br>828 |
| TCTAGTTTCT<br>AGATCAAAGA<br>  L   V   S | GCTATGGAAC<br>CGATACCTTG<br>  A   M   E<br>\_\_CHV gB\_\_ | AGCAGGAACA<br>TCGTCCTTGT<br>  Q   Q   E  H><br>              > | 2730<br><br>838 |
| TAAAGCTATT<br>ATTTCGATAA<br>  K   A   I | AAAAAAAATA<br>TTTTTTTTAT<br>  K   K   N<br>\_\_CHV gB\_\_ | GTGGCCCTGC<br>CACCGGGACG<br>  S   G   P  A><br>              > | 2760<br><br>848 |
| CCTTCTAGCA<br>GGAAGATCGT<br>  L   L   A | AGTCACATTA<br>TCAGTGTAAT<br>  S   H   I<br>\_\_CHV gB\_\_ | CAAACCTATC<br>GTTTGGATAG<br>  T   N   L  S><br>              > | 2790<br><br>858 |
| TCTTAAACAT<br>AGAATTTGTA<br>  L   K   H | CGTGGTCCAA<br>GCACCAGGTT<br>  R   G   P<br>\_\_CHV gB\_\_ | AATACAAACG<br>TTATGTTTGC<br>  K   Y   K  R><br>              > | 2820<br><br>868 |
| TTTGAAAAAT<br>AAACTTTTTA<br>  L   K   N | GTAAATGAAA<br>CATTTACTTT<br>  V   N   E<br>\_\_CHV gB\_\_ | ATGAAAGTAA<br>TACTTTCATT<br>  N   E   S  K><br>              > | 2850<br><br>878 |

FIG. 23L

```
AGTTTAACCC  GGGTACCGAG  CTCGAATTCT                2880
TCAAATTGGG  CCCATGGCTC  GAGCTTAAGA
    V>                                             879
____>

TTTTATTGAT  TAACTAGTCA  AATGAGTATA                2910
AAAATAACTA  ATTGATCAGT  TTACTCATAT
                  __         _____>

TATAATTGAA  AAAGTAAAAT  ATAAATCATA                2940
ATATTAACTT  TTTCATTTTA  TATTTAGTAT
_____  C6 flankin  g arm____>

TAATAATGAA  A                                     2951
ATTATTACTT  T
_____     _>
```

| | | | |
|---|---|---|---|
| GAGCTCGCGG | CCGCCTATCA | AAAGTCTTAA | 30 |
| CTCGAGCGCC | GGCGGATAGT | TTTCAGAATT | |
| _____C6 | flanking | arm_____> | |
| TGAGTTAGGT | GTAGATAGTA | TAGATATTAC | 60 |
| ACTCAATCCA | CATCTATCAT | ATCTATAATG | |
| _____C6 | flanking | arm_____> | |
| TACAAAGGTA | TTCATATTTC | CTATCAATTC | 90 |
| ATGTTTCCAT | AAGTATAAAG | GATAGTTAAG | |
| _____C6 | flanking | arm_____> | |
| TAAAGTAGAT | GATATTAATA | ACTCAAAGAT | 120 |
| ATTTCATCTA | CTATAATTAT | TGAGTTTCTA | |
| _____C6 | flanking | arm_____> | |
| GATGATAGTA | GATAATAGAT | ACGCTCATAT | 150 |
| CTACTATCAT | CTATTATCTA | TGCGAGTATA | |
| _____C6 | flanking | arm_____> | |
| AATGACTGCA | AATTTGGACG | GTTCACATTT | 180 |
| TTACTGACGT | TTAAACCTGC | CAAGTGTAAA | |
| _____C6 | flanking | arm_____> | |
| TAATCATCAC | GCGTTCATAA | GTTTCAACTG | 210 |
| ATTAGTAGTG | CGCAAGTATT | CAAAGTTGAC | |
| _____C6 | flanking | arm_____> | |
| CATAGATCAA | AATCTCACTA | AAAAGATAGC | 240 |
| GTATCTAGTT | TTAGAGTGAT | TTTTCTATCG | |
| _____C6 | flanking | arm_____> | |
| CGATGTATTT | GAGAGAGATT | GGACATCTAA | 270 |
| GCTACATAAA | CTCTCTCTAA | CCTGTAGATT | |
| _____C6 | flanking | arm_____> | |
| CTACGCTAAA | GAAATTACAG | TTATAAATAA | 300 |
| GATGCGATTT | CTTTAATGTC | AATATTTATT | |
| _____C6 | flanking | arm_____> | |
| TACATAATGG | ATTTTGTTAT | CATCAGTTAT | 330 |
| ATGTATTACC | TAAAACAATA | GTAGTCAATA | |
| _____C6 | flanking | arm_____> | |

FIG. 24B

```
ATTTAACATA  AGTACAATAA  AAAGTATTAA                360
TAAATTGTAT  TCATGTTATT  TTTCATAATT
_____C6   flanking    arm_____>

ATAAAAATAC  TTACTTACGA  AAAAATGACT                390
TATTTTTATG  AATGAATGCT  TTTTTACTGA
_____C6   flanking    arm____>
                                  >
                                __

AATTAGCTAT  AAAAACCCGG  GCTGCAGCTC                420
TTAATCGATA  TTTTTGGGCC  CGACGTCGAG
_____    __Cloning   sites____>

GAGGAATTCT  TTTTATTGAT  TAACTAGTCA                450
CTCCTTAAGA  AAAATAACTA  ATTGATCAGT
_____    __Cloning   sites__>
                                  >
                                __

AATGAGTATA  TATAATTGAA  AAAGTAAAAT                480
TTACTCATAT  ATATTAACTT  TTTCATTTTA
_____C6   flanking    arm_____>

ATAAATCATA  TAATAATGAA  ACGAAATATC                510
TATTTAGTAT  ATTATTACTT  TGCTTTATAG
_____C6   flanking    arm_____>

AGTAATAGAC  AGGAACTGGC  AGATTCTTCT                540
TCATTATCTG  TCCTTGACCG  TCTAAGAAGA
_____C6   flanking    arm_____>

TCTAATGAAG  TAAGTACTGC  TAAATCTCCA                570
AGATTACTTC  ATTCATGACG  ATTTAGAGGT
_____C6   flanking    arm_____>

AAATTAGATA  AAAATGATAC  AGCAAATACA                600
TTTAATCTAT  TTTTACTATG  TCGTTTATGT
_____C6   flanking    arm_____>

GCTTCATTCA  ACGAATTACC  TTTTAATTTT                630
CGAAGTAAGT  TGCTTAATGG  AAAATTAAAA
_____C6   flanking    arm_____>
```

FIG. 24C

| | | | |
|---|---|---|---|
| TTCAGACACA<br>AAGTCTGTGT<br>_____C6 | CCTTATTACA<br>GGAATAATGT<br>flanking | AACTAACTAA<br>TTGATTGATT<br>arm_____> | 660 |
| GTCAGATGAT<br>CAGTCTACTA<br>_____C6 | GAGAAAGTAA<br>CTCTTTCATT<br>flanking | ATATAAATTT<br>TATATTTAAA<br>arm_____> | 690 |
| AACTTATGGG<br>TTGAATACCC<br>_____C6 | TATAATATAA<br>ATATTATATT<br>flanking | TAAAGATTCA<br>ATTTCTAAGT<br>arm_____> | 720 |
| TGATATTAAT<br>ACTATAATTA<br>_____C6 | AATTTACTTA<br>TTAAATGAAT<br>flanking | ACGATGTTAA<br>TGCTACAATT<br>arm_____> | 750 |
| TAGACTTATT<br>ATCTGAATAA<br>_____C6 | CCATCAACCC<br>GGTAGTTGGG<br>flanking | CTTCAAACCT<br>GAAGTTTGGA<br>arm_____> | 780 |
| TTCTGGATAT<br>AAGACCTATA<br>_____C6 | TATAAAATAC<br>ATATTTTATG<br>flanking | CAGTTAATGA<br>GTCAATTACT<br>arm_____> | 810 |
| TATTAAAATA<br>ATAATTTAT<br>_____C6 | GATTGTTTAA<br>CTAACAAATT<br>flanking | GAGATGTAAA<br>CTCTACATTT<br>arm_____> | 840 |
| TAATTATTTG<br>ATTAATAAAC<br>_____C6 | GAGGTAAAGG<br>CTCCATTTCC<br>flanking | ATATAAAATT<br>TATATTTTAA<br>arm_____> | 870 |
| AGTCTATCTT<br>TCAGATAGAA<br>_____C6 | TCACATGGAA<br>AGTGTACCTT<br>flanking | ATGAATTACC<br>TACTTAATGG<br>arm_____> | 900 |
| TAATATTAAT<br>ATTATAATTA<br>_____C6 | AATTATGATA<br>TTAATACTAT<br>flanking | GGAATTTTTT<br>CCTTAAAAAA<br>arm_____> | 930 |
| AGGATTTACA<br>TCCTAAATGT<br>_____C6 | GCTGTTATAT<br>CGACAATATA<br>flanking | GTATCAACAA<br>CATAGTTGTT<br>arm_____> | 960 |

FIG. 24D

| | | | |
|---|---|---|---|
| TACAGGCAGA ATGTCCGTCT _____C6 | TCTATGGTTA AGATACCAAT flanking | TGGTAAAACA ACCATTTTGT arm_____> | 990 |
| CTGTAACGGG GACATTGCCC _____C6 | AAGCAGCATT TTCGTCGTAA flanking | CTATGGTAAC GATACCATTG arm_____> | 1020 |
| TGGCCTATGT ACCGGATACA _____C6 | TTAATAGCCA AATTATCGGT flanking | GATCATTTTA CTAGTAAAAT arm_____> | 1050 |
| CTCTATAAAC GAGATATTTG _____C6 | ATTTTACCAC TAAAATGGTG flanking | AAATAATAGG TTTATTATCC arm_____> | 1080 |
| ATCCTCTAGA TAGGAGATCT _____C6 | TATTTAATAT ATAAATTATA flanking | TATATCTAAC ATATAGATTG arm_____> | 1110 |
| AACAACAAAA TTGTTGTTTT _____C6 | AAATTTAACG TTTAAATTGC flanking | ATGTATGGCC TACATACCGG arm_____> | 1140 |
| AGAAGTATTT TCTTCATAAA _____C6 | TCTACTAATA AGATGATTAT flanking | AAGATAAAGA TTCTATTTCT arm_____> | 1170 |
| TAGTCTATCT ATCAGATAGA _____C6 | TATCTACAAG ATAGATGTTC flanking | ATATGAAAGA TATACTTTCT arm_____> | 1200 |
| AGATAATCAT TCTATTAGTA _____C6 | TTAGTAGTAG AATCATCATC flanking | CTACTAATAT GATGATTATA arm_____> | 1230 |
| GGAAAGAAAT CCTTTCTTTA _____C6 | GTATACAAAA CATATGTTTT flanking | ACGTGGAAGC TGCACCTTCG arm_____> | 1260 |
| TTTTATATTA AAAATATAAT _____C6 | AATAGCATAT TTATCGTATA flanking | TACTAGAAGA ATGATCTTCT arm_____> | 1290 |

FIG. 24E

| | | | |
|---|---|---|---|
| TTTAAAATCT | AGACTTAGTA | TAACAAAACA | 1320 |
| AAATTTTAGA | TCTGAATCAT | ATTGTTTTGT | |
| _____C6 | flanking | arm_____> | |
| GTTAAATGCC | AATATCGATT | CTATATTTCA | 1350 |
| CAATTTACGG | TTATAGCTAA | GATATAAAGT | |
| _____C6 | flanking | arm_____> | |
| TCATAACAGT | AGTACATTAA | TCAGTGATAT | 1380 |
| AGTATTGTCA | TCATGTAATT | AGTCACTATA | |
| _____C6 | flanking | arm_____> | |
| ACTGAAACGA | TCTACAGACT | CAACTATGCA | 1410 |
| TGACTTTGCT | AGATGTCTGA | GTTGATACGT | |
| _____C6 | flanking | arm_____> | |
| AGGAATAAGC | AATATGCCAA | TTATGTCTAA | 1440 |
| TCCTTATTCG | TTATACGGTT | AATACAGATT | |
| _____C6 | flanking | arm_____> | |
| TATTTTAACT | TTAGAACTAA | AACGTTCTAC | 1470 |
| ATAAAATTGA | AATCTTGATT | TTGCAAGATG | |
| _____C6 | flanking | arm_____> | |
| CAATACTAAA | AATAGGATAC | GTGATAGGCT | 1500 |
| GTTATGATTT | TTATCCTATG | CACTATCCGA | |
| _____C6 | flanking | arm_____> | |
| GTTAAAAGCT | GCAATAAATA | GTAAGGATGT | 1530 |
| CAATTTTCGA | CGTTATTTAT | CATTCCTACA | |
| _____C6 | flanking | arm_____> | |
| AGAAGAAATA | CTTTGTTCTA | TACCTTCGGA | 1560 |
| TCTTCTTTAT | GAAACAAGAT | ATGGAAGCCT | |
| _____C6 | flanking | arm_____> | |
| GGAAAGAACT | TTAGAACAAC | TTAAGTTTAA | 1590 |
| CCTTTCTTGA | AATCTTGTTG | AATTCAAATT | |
| _____C6 | flanking | arm_____> | |
| TCAAACTTGT | ATTTATGAAG | GTACC | 1615 |
| AGTTTGAACA | TAAATACTTC | CATGG | |
| _____C6 | flanking | arm__> | |

FIG. 26

| FIG. 26A |
| FIG. 26B |
| FIG. 26C |
| FIG. 26D |
| FIG. 26E |
| FIG. 26F |
| FIG. 26G |

FIG. 26A

```
AGTACAATAA  AAAGTATTAA  ATAAAAATAC              30
TCATGTTATT  TTTCATAATT  TATTTTTATG
_____C6  flanking    arm_____>

TTACTTACGA  AAAAATGACT  AATTAGCTAT              60
AATGAATGCT  TTTTTACTGA  TTAATCGATA
__C6 flank  ing arm__>

AAAAACCCGG  GAAAGGATCC  TGATCCTTTT              90
TTTTTGGGCC  CTTTCCTAGG  ACTAGGAAAA

TCTGGGTAAG  TAATACGTCA  AGGAGAAAAC             120
AGACCCATTC  ATTATGCAGT  TCCTCTTTTG

GAAACGATCT  GTAGTTAGCG  GCCAAACTCG             150
CTTTGCTAGA  CATCAATCGC  CGGTTTGAGC

AGGTCGACGG  TATCGATAAG  CTTGATTCTT             180
TCCAGCTGCC  ATAGCTATTC  GAACTAAGAA
                                    _____>

TATTCTATAC  TTAAAAGTG   AAAATAAATA             210
ATAAGATATG  AATTTTTCAC  TTTTATTTAT
_____H6  promoter__  _____>

CAAAGGTTCT  TGAGGGTTGT  GTTAAATTGA             240
GTTTCCAAGA  ACTCCCAACA  CAATTTAACT
_____H6  promoter__  _____>

AAGCGAGAAA  TAATCATAAA  TTATTTCATT             270
TTCGCTCTTT  ATTAGTATTT  AATAAAGTAA
_____H6  promoter__  _____>

ATCGCGATAT  CCGTTAAGTT  TGTATCGTAA             300
TAGCGCTATA  GGCAATTCAA  ACATAGCATT
_____H6  promoter__  _____>
                                    _____>

TGAGTTTTAA  AAATTTTTAT  CTAATATATG             330
ACTCAAAATT  TTTAAAAATA  GATTATATAC
 M  S  F  K   N  F  Y    L  I  Y>               10
                  _CHV gC__         _____>
```

FIG. 26B

```
TAATTATAAT    TTTTATAAAC    TCGATAATAA        360
ATTAATATTA    AAAATATTTG    AGCTATTATT
V   I   I   I     F   I   N     S   I   I>      20
              __CHV gC__      _____>

CTTCGGCATC    TACATCCAAA    CCTTCAACAC        390
GAAGCCGTAG    ATGTAGGTTT    GGAAGTTGTG
T   S   A   S     T   S   K     P   S   T>      30
              __CHV gC__      _____>

CTACCATAAT    TCCAACTTCA    GCAAATGAAT        420
GATGGTATTA    AGGTTGAAGT    CGTTTACTTA
P   T   I   I     P   T   S     A   N   E>      40
              __CHV gC__      _____>

CACCTGCTTC    CATAGATACA    ACTATAACAA        450
GTGGACGAAG    GTATCTATGT    TGATATTGTT
S   P   A   S     I   D   T     T   I   T>      50
              __CHV gC__      _____>

AACCTATATC    TACAGAGGCA    AATAATTTAA        480
TTGGATATAG    ATGTCTCCGT    TTATTAAATT
K   P   I   S     T   E   A     N   N   L>      60
              __CHV gC__      _____>

AATCAGTAAG    TACCTCAATT    AAACCACCTA        510
TTAGTCATTC    ATGGAGTTAA    TTTGGTGGAT
K   S   V   S     T   S   I     K   P   P>      70
              __CHV gC__      _____>

AAAACTTAAA    AAAAAAATTA    CTTAAATCTA        540
TTTTGAATTT    TTTTTTTAAT    GAATTTAGAT
K   N   L   K     K   K   L     L   K   S>      80
              __CHV gC__      _____>

AATGTAGAGA    TAATGTTATT    TATAGGCCAT        570
TTACATCTCT    ATTACAATAA    ATATCCGGTA
K   C   R   D     N   V   I     Y   R   P>      90
              __CHV gC__      _____>

ATTTTAGTCA    ATTAGAAATT    AACTGTACTA        600
TAAAATCAGT    TAATCTTTAA    TTGACATGAT
Y   F   S   Q     L   E   I     N   C   T>     100
              __CHV gC__      _____>
```

FIG. 26C

| | | | |
|---|---|---|---|
| TAACTAAAAA<br>ATTGATTTTT<br>I  T  K  K | GCAAAATTTA<br>CGTTTTAAAT<br>   Q  N  L<br>   _CHV gC_ | AGTAATCCTT<br>TCATTAGGAA<br>   S  N  P><br>         > | 630<br><br>110 |
| TAATTGAGTT<br>ATTAACTCAA<br>L  I  E  L | ATGGTTTAAA<br>TACCAAATTT<br>   W  F  K<br>   _CHV gC_ | GAACTTTCTA<br>CTTGAAAGAT<br>   E  L  S<br>         > | 660<br><br>120 |
| CATATAATAA<br>GTATATTATT<br>T  Y  N  K | AACCAATGAA<br>TTGGTTACTT<br>   T  N  E<br>   _CHV gC_ | AATGTTGAAA<br>TTACAACTTT<br>   N  V  E><br>         > | 690<br><br>130 |
| GTTTAAAAAC<br>CAAATTTTTG<br>S  L  K  T | AGATATATCA<br>TCTATATAGT<br>   D  I  S<br>   _CHV gC_ | AAAAATATTT<br>TTTTTATAAA<br>   K  N  I><br>         > | 720<br><br>140 |
| TATTATTTTC<br>ATAATAAAAG<br>L  L  F  S | GACAAAAAAT<br>CTGTTTTTTA<br>   T  K  N<br>   _CHV gC_ | AATAGTGATA<br>TTATCACTAT<br>   N  S  D><br>         > | 750<br><br>150 |
| ACTTTTATAA<br>TGAAAATATT<br>N  F  Y  N | TGATTTTTTA<br>ACTAAAAAAT<br>   D  F  L<br>   _CHV gC_ | TTAGGTATAC<br>AATCCATATG<br>   L  G  I><br>         > | 780<br><br>160 |
| AAAATCAACC<br>TTTTAGTTGG<br>Q  N  Q  P | AGTAAATTAT<br>TCATTTAATA<br>   V  N  Y<br>   _CHV gC_ | AAACTTTACG<br>TTTGAAATGC<br>   K  L  Y><br>         > | 810<br><br>170 |
| GTTCCCAATT<br>CAAGGGTTAA<br>G  S  Q  F | TTATGATAAT<br>AATACTATTA<br>   Y  D  N<br>   _CHV gC_ | GGAAACATAT<br>CCTTTGTATA<br>   G  N  I><br>         > | 840<br><br>180 |
| TACTAAATAT<br>ATGATTTATA<br>L  L  N  I | AAAGTCGGTT<br>TTTCAGCCAA<br>   K  S  V<br>   _CHV gC_ | GACTTTAAAA<br>CTGAAATTTT<br>   D  F  K><br>         > | 870<br><br>190 |

FIG. 26D

```
CCTCTGGAAT   ATATACTTGG   AAACTATATA         900
GGAGACCTTA   TATATGAACC   TTTGATATAT
 T  S  G  I    Y  T  W     K  L  Y>         200
              __CHV gC__              >

ATTCAAATAA   TGAAAGTATT   TTTGAAACTT         930
TAAGTTTATT   ACTTTCATAA   AAACTTTGAA
 N  S  N  N    E  S  I     F  E  T>         210
              __CHV gC__              >

TTAAAATTCA   AGTATATGCA   TATCATTCCC         960
AATTTTAAGT   TCATATACGT   ATAGTAAGGG
 F  K  I  Q    V  Y  A     Y  H  S>         220
              __CHV gC__              >

CAAATGTAAA   CTTAAAATCA   AACCCAAGTT         990
GTTTACATTT   GAATTTTAGT   TTGGGTTCAA
 P  N  V  N    L  K  S     N  P  S>         230
              __CHV gC__              >

TATATAATGA   AAACTACAGC   GCTATTTGTA        1020
ATATATTACT   TTTGATGTCG   CGATAAACAT
 L  Y  N  E    N  Y  S     A  I  C>         240
              __CHV gC__              >

CAATAGCAAA   TTACTTTCCA   TTGGAATCTA        1050
GTTATCGTTT   AATGAAAGGT   AACCTTAGAT
 T  I  A  N    Y  F  P     L  E  S>         250
              __CHV gC__              >

CGGAAATATT   TTGGTTTAAC   GATGGACAAC        1080
GCCTTTATAA   AACCAAATTG   CTACCTGTTG
 T  E  I  F    W  F  N     D  G  Q>         260
              __CHV gC__              >

CTATTGATAA   AAAATATATA   GATGAAACTT        1110
GATAACTATT   TTTTATATAT   CTACTTTGAA
 P  I  D  K    K  Y  I     D  E  T>         270
              __CHV gC__              >

ATAGTGTATG   GATTGACGGT   CTTATAACAC        1140
TATCACATAC   CTAACTGCCA   GAATATTGTG
 Y  S  V  W    I  D  G     L  I  T>         280
              __CHV gC__              >
```

FIG. 26E

```
GCACTTCAAT  ATTATCCTT   CCCTTTTCCG    1170
CGTGAAGTTA  TAATAGGGAA  GGGAAAAGGC
 R  T  S  I   L  S  L    P  F  S>     290
              _CHV gC_            >

AAGCCATGGA  AAGCCCCCCC  AATTTGCGAT    1200
TTCGGTACCT  TTCGGGGGGG  TTAAACGCTA
 E  A  M  E   S  P  P    N  L  R>     300
              _CHV gC_            >

GTAATGTTGA  ATGGTATAAA  AATTCAAGG     1230
CATTACAACT  TACCATATTT  TTAAGTTTCC
 C  N  V  E   W  Y  K    N  S  K>     310
              _CHV gC_            >

CATCAAAAAA  ATTTTCAAAT  ACCGTTATTC    1260
GTAGTTTTT   TAAAAGTTTA  TGGCAATAAG
 A  S  K  K   F  S  N    T  V  I>     320
              _CHV gC_            >

CAAAAGTTTA  CTATAAACCT  TTTATATCTA    1290
GTTTTCAAAT  GATATTTGGA  AAATATAGAT
 P  K  V  Y   Y  K  P    F  I  S>     330
              _CHV gC_            >

TAAAATTTGA  TAATGGTTTA  GCTATTGTG     1320
ATTTTAAACT  ATTACCAAAT  CGATAAACAC
 I  K  F  D   N  G  L    A  I  C>     340
              _CHV gC_            >

ATGCTAAATG  TGTTTCCCGT  GAAAATAATA    1350
TACGATTTAC  ACAAAGGGCA  CTTTTATTAT
 D  A  K  C   V  S  R    E  N  N>     350
              _CHV gC_            >

AATTACAATG  GTTAGTTAAA  GATATACCTA    1380
TTAATGTTAC  CAATCAATTT  CTATATGGAT
 K  L  Q  W   L  V  K    D  I  P>     360
              _CHV gC_            >

TAAATGGTGA  TGATATTATA  AGCGGCCCCT    1410
ATTTACCACT  ACTATAATAT  TCGCCGGGGA
 I  N  G  D   D  I  I    S  G  P>     370
              _CHV gC_            >
```

FIG. 26F

| | | | |
|---|---|---|---|
| GTTTAAACCA<br>CAAATTTGGT<br>C  L  N  H | CCCTGGTTTG<br>GGGACCAAAC<br>P  G  L<br>_CHV gC_ | GTCAATATTC<br>CAGTTATAAG<br>V  N  I> | 1440<br><br>380 |
| AAAATAAAAT<br>TTTTATTTTA<br>Q  N  K  I | AGATATATCG<br>TCTATATAGC<br>D  I  S<br>_CHV gC_ | GATTATGATG<br>CTAATACTAC<br>D  Y  D> | 1470<br><br>390 |
| AACCTGTTAC<br>TTGGACAATG<br>E  P  V  T | CTATAAATGT<br>GATATTTACA<br>Y  K  C<br>_CHV gC_ | TCAATTATTG<br>AGTTAATAAC<br>S  I  I> | 1500<br><br>400 |
| GTTATCCAAT<br>CAATAGGTTA<br>G  Y  P  I | AATTTTTCCC<br>TTAAAAAGGG<br>I  F  P<br>_CHV gC_ | AACTTTTATG<br>TTGAAAATAC<br>N  F  Y> | 1530<br><br>410 |
| ATGAAAAGGT<br>TACTTTTCCA<br>D  E  K  V | GTTTGATGCA<br>CAAACTACGT<br>F  D  A<br>_CHV gC_ | TCGGATGAAA<br>AGCCTACTTT<br>S  D  E> | 1560<br><br>420 |
| ATGTTAGTAA<br>TACAATCATT<br>N  V  S  K | ATCGATGTTA<br>TAGCTACAAT<br>S  M  L<br>_CHV gC_ | ATAAGTATTA<br>TATTCATAAT<br>I  S  I> | 1590<br><br>430 |
| CCACAATAAT<br>GGTGTTATTA<br>T  T  I  I | TGGTGGAGCC<br>ACCACCTCGG<br>G  G  A<br>_CHV gC_ | ATTTTTGTTA<br>TAAAAACAAT<br>I  F  V> | 1620<br><br>440 |
| TAGTATTGAT<br>ATCATAACTA<br>I  V  L  I | TTTTATAACA<br>AAAATATTGT<br>F  I  T<br>_CHV gC_ | GCTTTATGTT<br>CGAAATACAA<br>A  L  C> | 1650<br><br>450 |
| TTTATTGTTC<br>AAATAACAAG<br>F  Y  C  S | AAAAAATAAT<br>TTTTTTATTA<br>K  N  N<br>_CHV gC_ | AAGATCTAAC<br>TTCTAGATTG<br>K  I> | 1680<br><br>459 |

FIG. 26G

| | | | |
|---|---|---|---|
| TGCAAATTCT | TTTTATTGAT | TAACTAGTCA | 1710 |
| ACGTTTAAGA | AAAATAACTA | ATTGATCAGT | |
| | |       > | |
| AATGAGTATA | TATAATTGAA | AAAGTAAAAT | 1740 |
| TTACTCATAT | ATATTAACTT | TTTCATTTTA | |
|      C6 | flanking | arm    > | |
| ATAAATCATA | TAATAATGAA | A | 1761 |
| TATTTAGTAT | ATTATTACTT | T | |
|   C6 flank | ing arm | _> | |

FIG. 28A

```
AGTACAATAA  AAAGTATTAA  ATAAAAATAC              30
TCATGTTATT  TTTCATAATT  TATTTTTATG
_____C6  flanking    arm_____>

TTACTTACGA  AAAAATGACT  AATTAGCTAT              60
AATGAATGCT  TTTTTACTGA  TTAATCGATA
_C6 flank   ing arm_>

AAAAACCCGG  GAAAGGATCC  TGATCCTTTT              90
TTTTTGGGCC  CTTTCCTAGG  ACTAGGAAAA

TCTGGGTAAG  TAATACGTCA  AGGAGAAAAC             120
AGACCCATTC  ATTATGCAGT  TCCTCTTTTG

GAAACGATCT  GTAGTTAGCG  GCCAAACTCG             150
CTTTGCTAGA  CATCAATCGC  CGGTTTGAGC

AGGTCGACGG  TATCGATAAG  CTTGATTCTT             180
TCCAGCTGCC  ATAGCTATTC  GAACTAAGAA
                                    >

TATTCTATAC  TTAAAAGTG   AAAATAAATA             210
ATAAGATATG  AATTTTTCAC  TTTTATTTAT
_____H6  promoter__              >

CAAAGGTTCT  TGAGGGTTGT  GTTAAATTGA             240
GTTTCCAAGA  ACTCCCAACA  CAATTTAACT
_____H6  promoter__              >

AAGCGAGAAA  TAATCATAAA  TTATTTCATT             270
TTCGCTCTTT  ATTAGTATTT  AATAAAGTAA
_____H6  promoter__              >

ATCGCGATAT  CCGTTAAGTT  TGTATCGTAA             300
TAGCGCTATA  GGCAATTCAA  ACATAGCATT
_____H6  promoter__              >
                                    >

TGATTAAACT  TCTATTTATC  TTATTTATT              330
ACTAATTTGA  AGATAAATAG  AATAAATAA
M    I K L    L  F  I    L F Y>                 10
            _CHV gD__
_____
```

FIG. 28B

```
TTAACCCAAT   AACTGGATAT   AAATGGGTAG    360
AATTGGGTTA   TTGACCTATA   TTTACCCATC
 F   N   P   I    T   G   Y        K   W   V>    20
                __CHV gD__           _____>

ACCCTCCTCG   TAGGTATAAT   TACACCGTTT    390
TGGGAGGAGC   ATCCATATTA   ATGTGGCAAA
 D   P   P   R        R   Y   N        Y   T   V>    30
                __CHV gD__           _____>

TAAGAATGAT   TCCAGATATT   CCAAATCCAA    420
ATTCTTACTA   AGGTCTATAA   GGTTTAGGTT
 L   R   M   I        P   D   I        P   N   P>    40
                __CHV gD__           _____>

TGGATCCTTC   TAAAAACGCT   GAAGTTCGGT    450
ACCTAGGAAG   ATTTTTGCGA   CTTCAAGCCA
 M   D   P   S        K   N   A        E   V   R>    50
                __CHV gD__           _____>

ATGTAACTTC   TACTGACCCA   TGTGATATGG    480
TACATTGAAG   ATGACTGGGT   ACACTATACC
 Y   V   T   S        T   D   P        C   D   M>    60
                __CHV gD__           _____>

TTGCTTTGAT   TTCTAATCCA   AATATAGAAT    510
AACGAAACTA   AAGATTAGGT   TTATATCTTA
 V   A   L   I        S   N   P        N   I   E>    70
                __CHV gD__           _____>

CTACAATTAA   AACGATTCAA   TTTGTGCAAA    540
GATGTTAATT   TTGCTAAGTT   AAACACGTTT
 S   T   I   K        T   I   Q        F   V   Q>    80
                __CHV gD__           _____>

AGAAAAAATT   TTACAATGCA   TCTCTTAGTT    570
TCTTTTTTAA   AATGTTACGT   AGAGAATCAA
 K   K   K   F        Y   N   A        S   L   S>    90
                __CHV gD__           _____>

GGTTTAAAGT   TGGAGATGAT   TGTACATATC    600
CCAAATTTCA   ACCTCTACTA   ACATGTATAG
 W   F   K   V        G   D   D        C   T   Y>   100
                __CHV gD__           _____>
```

FIG. 28C

| | | | |
|---|---|---|---|
| CAATATATTT<br>GTTATATAAA<br>P  I  Y  L | AATTCAATAT<br>TTAAGTTATA<br>  I  Q  Y<br>__CHV gD__ | TTTGATTGTG<br>AAACTAACAC<br> F  D  C> | 630<br><br>110 |
| ATCCTCAAAG<br>TAGGAGTTTC<br>D  P  Q  R | AGAATTTGGC<br>TCTTAAACCG<br>  E  F  G<br>__CHV gD__ | ATATGTTTAA<br>TATACAAATT<br> I  C  L> | 660<br><br>120 |
| AAAGATCTCC<br>TTTCTAGAGG<br>K  R  S  P | AGATTTTGG<br>TCTAAAACC<br>  D  F  W<br>__CHV gD__ | AAACCATCGT<br>TTTGGTAGCA<br> K  P  S> | 690<br><br>130 |
| TAGTTGGTTA<br>ATCAACCAAT<br>L  V  G  Y | CACATTTTA<br>GTGTAAAAT<br>  T  F  L<br>__CHV gD__ | ACTGATGATG<br>TGACTACTAC<br> T  D  D> | 720<br><br>140 |
| AATTGGGATT<br>TTAACCCTAA<br>E  L  G  L | AGTTTAGCT<br>TCAAAATCGA<br>  V  L  A<br>__CHV gD__ | GCCCCCGCTC<br>CGGGGGCGAG<br> A  P  A> | 750<br><br>140 |
| CATTTAATCA<br>GTAAATTAGT<br>P  F  N  Q | AGGTCAATAT<br>TCCAGTTATA<br>  G  Q  Y<br>__CHV gD__ | AGACGGGTTA<br>TCTGCCCAAT<br> R  R  V> | 780<br><br>150 |
| TTCAAATTGA<br>AAGTTTAACT<br>I  Q  I  E | AAATGAAGTT<br>TTTACTTCAA<br>  N  E  V<br>__CHV gD__ | TTTTATACTG<br>AAAATATGAC<br> F  Y  T> | 810<br><br>160 |
| ATTTTATGGT<br>TAAAATACCA<br>D  F  M  V | TCAATTACCA<br>AGTTAATGGT<br>  Q  L  P<br>__CHV gD__ | CGAGAAACTT<br>GCTCTTTGAA<br> R  E  T> | 840<br><br>170 |
| GTTATTTTTC<br>CAATAAAAAG<br>C  Y  F  S | TAAAGAAGAT<br>ATTTCTTCTA<br>  K  E  D<br>__CHV gD__ | AAATTTGAAC<br>TTTAAACTTG<br> K  F  E> | 870<br><br>180 |

FIG. 28D

| | | | |
|---|---|---|---|
| CAACTTTTAT GTTGAAAATA P T F M | GGAATGGTGT CCTTACCACA E W C  CHV gD | AAGGAATCTA TTCCTTAGAT K E S> > | 900 190 |
| GATCTGTAGG CTAGACATCC R S V G | AGCATCAAAA TCGTAGTTTT A S K  CHV gD | GTTGACGATG CAACTGCTAC V D D> > | 930 200 |
| AACTTTTTTA TTGAAAAAAT E L F Y | TCTAAATAGA AGATTTATCT L N R  CHV gD | GCTGGTCCCC CGACCAGGGG A G P> > | 960 210 |
| AAACCCTGCT TTTGGGACGA Q T L L | TAAATATTAT ATTTATAATA K Y Y  CHV gD | GTTATTAAAG CAATAATTTC V I K> > | 990 220 |
| ATTTTTATAG TAAAAATATC D F Y R | ACTTAACGGT TGAATTGCCA L N G  CHV gD | AGAGAACCTC TCTCTTGGAG R E P> > | 1020 230 |
| CAATAAAATT GTTATTTTAA P I K F | TAAAGAAGCT ATTTCTTCGA K E A  CHV gD | CTTAGATACG GAATCTATGC L R Y> > | 1050 240 |
| ATATACCATA TATATGGTAT D I P Y | TAAAGTGAAT ATTTCACTTA K V N  CHV gD | GATAAATTTG CTATTTAAAC D K F> > | 1080 250 |
| ATGATGAATT TACTACTTAA D D E L | ACCATCGAGG TGGTAGCTCC P S R  CHV gD | CCACATATTA GGTGTATAAT P H I> > | 1110 260 |
| GTAATACTAT CATTATGATA S N T I | TAATAAAACT ATTATTTTGA N K T  CHV gD | ATTAAAGAAA TAATTTCTTT I K E> > | 1140 270 |

FIG. 28E

```
TTGTAAATCT   TGAAGATTAT   TTTAAAAATA        1170
AACATTTAGA   ACTTCTAATA   AAATTTTTAT
 I  V  N  L   E  D  Y      F  K  N>          280
              __CHV gD__             >

CAAATGTTAT   AGATACTACT   ACCCCAACAC        1200
GTTTACAATA   TCTATGATGA   TGGGGTTGTG
 T  N  V  I   D  T  T      T  P  T>          290
              __CHV gD__             >

CAATAAATAA   TACCCCAAAA   AATATAACCG        1230
GTTATTTATT   ATGGGGTTTT   TTATATTGGC
 P  I  N  N   T  P  K      N  I  T>          300
              __CHV gD__             >

TGGGAATTGT   TATAATTATA   TTAATAATAC        1260
ACCCTTAACA   ATATTAATAT   AATTATTATG
 V  G  I  V   I  I  I      L  I  I>          310
              __CHV gD__             >

TATTTATAAT   TGGATTTTTT   GTTTATAAAA        1290
ATAAATATTA   ACCTAAAAAA   CAAATATTTT
 L  F  I  I   G  F  F      V  Y  K>          320
              __CHV gD__             >

GACAAAAAAT   ATATAATAAT   TATAAAAAAT        1320
CTGTTTTTTA   TATATTATTA   ATATTTTTA
 R  Q  K  I   Y  N  N      Y  K  K>          330
              __CHV gD__             >

TAACAACAAA   TGTTTAGGAA   TTCTTTTTAT        1350
ATTGTTGTTT   ACAAATCCTT   AAGAAAAATA
 L  T  T  N   V>                             335
__CHV gD__    __>

TGATTAACTA   GTCAAATGAG   TATATATAAT        1380
ACTAATTGAT   CAGTTTACTC   ATATATATTA
              __C6 flank   ing arm___>

TGAAAAGTA    AAATATAAAT   CATATAATAA        1410
ACTTTTTCAT   TTTATATTTA   GTATATTATT
_____C6    flanking     arm_____>

TGAAA                                       1415
ACTTT
_____>
```

NUCLEOTIDE AND AMINO ACID SEQUENCES FOR CANINE HERPESVIRUS GB, GC AND GD AND USES THEREFOR

RELATED APPLICATIONS

This is application is a continuation-in-part of application Ser. No. 08/220,151, filed Mar. 30, 1994 now U.S. Pat. No. 5,529,780.

Reference is made to copending application Ser. No. 08/124,668, filed Sep. 21, 1993 as a divisional of copending application Ser. No. 07/502,834, filed Apr. 14, 1990, which in turn was a continuation-in-part of application Ser. No. 07/394,488, filed Aug. 16, 1989, which in turn is a continuation-in-part of application Ser. No. 07/339,004, filed Apr. 17, 1989. Reference is also made to copending application Ser. No. 08/105,483, filed Aug. 12, 1993 as a continuation of application Ser. No. 07/847,951, filed Mar. 6, 1992, which in turn was a continuation-in-part of application Ser. No. 07/713,967, filed Jun. 11, 1991 which in turn was a continuation-in-part of application Ser. No. 07/666,056, filed Mar. 7, 1991; and, reference is made to U.S. Pat. No. 5,364,773, issued Nov. 15, 1994.

Reference is also made to copending application of Ser. No. 07/847,977, filed Mar. 3, 1992 as a divisional of application Ser. No. 07/478,179 filed Feb. 14, 1990, now U.S. Pat. No. 5,224,336 (via U.S. Ser. No. 902,428, filed Jun. 23, 1992) which was a continuation-in-part of application Ser. No. 07/320,471 filed on Mar. 8, 1989 (now U.S. Pat. No. 5,155,020).

Reference is also made to U.S. Pat. No. 5,378,457 issued Jan. 3, 1995; and to Pat. No. 5,110,587 issued May 5, 1992 from U.S. application Ser. No. 537,882, filed May 4, 1992, which was a continuation of application Ser. No. 90,209 filed August 27, 1987, now abandoned, which was a divisional of U.S. application Ser. No. 622,135, filed Jun. 19, 1984, now U.S. Pat. No. 4,722,848 which was a continuation-in-part of U.S. application Ser. No. 446,825, filed Dec. 8, 1982 now U.S. Pat. No. 4,603,112 issued Jul. 29, 1986, which was a continuation-in-part of U.S. application Ser. No. 334,456, filed Dec. 24, 1981, now U.S. Pat. No. 4,769,330 issued Aug. 16, 1988. U.S. Pat. No. 5,174,993 issued Dec. 29, 1992, is also mentioned for reference.

Each of the above-mentioned patent and applications are hereby incorporated herein by reference.

FIELD OF THE INVENTION

This invention relates to canine herpesvirus (CHV), nucleotides or isolated nucleic acids encoding the CHV gB, gC and gD glycoproteins, and the amino acid sequences thereof, vectors, such as a recombinant poxvirus, e.g., vaccinia and avipox virus recombinants, containing the CHV gB, gC and/or gD coding or expressing the same, glycoproteins therefrom, vaccines, immunological or antigenic compositions from the nucleotide (such as from vectors, for instance, recombinant poxvirus, e.g., vaccinia or avipox virus recombinants containing the CHV, gB, gC and/or gD coding and expressing glycoprotein(s) therefrom), or, from the glycoproteins, for instance, from expression of the nucleotides in a vector system, and, to methods employing the nucleotides, glycoproteins, and compositions.

Several publications are cited in the following text, with full citation of each set forth in the section headed References. The publications cited throughout the text are hereby incorporated herein by reference.

BACKGROUND OF THE INVENTION

Canine herpesvirus (CHV) causes a fatal, hemorrhagic disease in neonatal puppies and a self-limiting, usually subclinical, upper respiratory tract infection in adult dogs (Appel, 1987). Little is known about the genomic structure of CHV. The genome has not been mapped and no nucleotide sequence has been published. In particular, genes encoding immunologically pertinent proteins have not been identified.

Herpesvirus glycoproteins mediate essential viral functions such as cellular attachment and penetration, cell to cell spread of the virus and, importantly, determine the pathogenicity profile of infection. Herpesvirus glycoproteins are critical components in the interaction with the host immune system (Spear, 1985a; Spear 1985b). Herpesvirus glycoproteins are antigens recognized by both the humoral and cellular immune systems and, have been shown to evoke protective immune responses in vaccinated hosts (Wachsman et al., 1987; Marchioli et al., 1987; Eberle et al., 1980; Papp-Vid et al., 1979).

During a herpesvirus infection, the majority of the immune response is directed against viral envelope glycoproteins. These antigens have been shown to elicit both humoral and cellular immune responses. Several reports have indicated that in other herpesvirus systems immunization with the herpesvirus gB, gC and/or gD glycoproteins can induce a protective immune response.

The well characterized glycoproteins of herpes simplex virus include gB, gC, gD, gE, gG, gH, gI, gJ, gK, gL and gM (Spear, 1985a; Spear 1985b; Ackermann et al., 1986; Frink et al. 1983; Frame et al., 1986; Longnecker et al., 1987; Richman et al., 1986; Swain et al., 1985; Zezulak, 1984; Roizman and Sears, 1990; Hutchinson et al., 1992a; Hutchinson et al., 1992b; Baines and Roizman, 1993). A number of studies have indicated the importance of herpes simplex virus glycoproteins in eliciting immune responses. Hence, it has been reported that gB and gD can elicit important immune responses (Berman et al., 1983; Cantin et al., 1987; Cremer et al., 1985; Lasky et al., 1984; Martin et al., 1987a; Martin et al., 1987b; Paoletti et al., 1984; Perkus et al., 1985; Rooney et al., 1988; Wachsman et al., 1987; Zarling et al., 1986a; Zarling et al., 1986b). gC can stimulate class I restricted cytotoxic lymphocytes (Glorioso et al., 1985; Rosenthal et al., 1987) whereas gD can stimulate class II cytotoxic T cell responses (Martin et al., 1987a; Martin et al,. 1987b; Wachsman et al., 1987; Zarling et al., 1986a; Zarling 1986b). gG was shown to be a target for complement-dependent antibody directed virus neutralization (Sullivan et al., 1987; Sullivan et al., 1988). A number of glycoproteins from other herpesviruses have also been shown to elicit important immune responses.

Both subtypes of equine herpesvirus (EHV) express six abundant glycoproteins (Allen et al., 1986; Allen et al., 1987). The genomic portions of the DNA sequences encoding gp2, gp10, gp13, gp14, gp17/18, and gp21/22a have been determined using lambda gt11 expression vectors and monoclonal antibodies (Allen et al., 1987). Glycoproteins gp 13 and gp14 were located in the same locations within the L component of the genome to which the gC and gB homologs, respectively, of herpes simplex virus map (Allen et al., 1987). The envelope glycoproteins are the principal immunogens of herpesviruses involved in eliciting both humoral and cellular host immune responses (Ben-Porat et al., 1986; Cantin et al., 1987; Glorioso et al., 1984; Wachsman et al., 1988; Wachsman et al., 1989) and so are of the highest interest for those attempting to design vaccines.

Recently, the nucleotide sequence of the Kentucky T431 strain of the EHV-1 transcriptional unit encoding gp13 has been reported (Allen et al., 1988). The glycoprotein was shown to be homologous to the herpes simplex virus (HSV) gC-1 and gC-2, to the pseudorabies virus (PRV) gIII and the varicella-zoster virus (VZV) gpV (Allen et al., 1988). EHV-1 gp13 is thus the structural homolog of the herpesvirus gC-like glycoproteins.

The nucleotide sequence of EHV-1 gp14 (Whalley et al., 1989; Riggio et al., 1989) has recently been reported. Analysis of the predicted amino acid sequence of gp14 glycoprotein revealed significant homology to the corresponding glycoprotein of HSV, gB.

Monoclonal antibodies directed against some EHV-1 glycoproteins have been shown to be neutralizing (Sinclair et al., 1989). Passive immunization experiments demonstrated that monoclonal antibodies directed against gp13 or gp 14 (Shimizu et al., 1989) or against gp13, gp14 or gp17/18 (Stokes et al., 1989) could protect hamsters against a lethal challenge. Other gB and gC glycoprotein analogs are also involved in protection against diseases caused by alphaherpesviruses (Cantin et al., 1987; Cranage et al., 1986; Glorioso et al., 1984).

Pseudorabies virus (PRV), an alphaherpesvirus, is the causative agent of Aujesky's disease. The PRV genome consists of a $90 \times 10^6$ dalton double stranded DNA (Rubenstein et al., 1975) separated by inverted repeat sequences into unique long ($U_L$) or unique short ($U_S$) segments (Stevely, 1977; Ben-Porat et al., 1979). The PRV genome encodes approximately 100 polypeptides whose expression is regulated in a cascade-like fashion similar to other herpesviruses (Ben-Porat et al., 1985; Hampl et al., 1984).

PRV glycoprotein gp50 is the Herpes simplex virus type 1 (HSV-1) gD analog (Wathen et al., 1984). The DNA open reading frame encodes 402 amino acids (Petrovskis et al., 1986). The mature glycosylated form (50–60 kDa) contains O-linked carbohydrate without N-linked glycosylation (Petrovskis et al., 1986). Swine serum is highly reactive with PRV gp50, suggesting its importance as an immunogen. Monoclonal antibodies to gp50 neutralize PRV in vitro with or without complement (Wathen et al., 1984; Wathen 1985; Eloit et al., 1988) and passively protect mice (Marchioli et al., 1988; Wathen et al., 1985; Eloit et al., 1988) and swine (Marchioli et al., 1988). Vaccinia virus recombinants expressing PRV gp50 induced serum neutralizing antibodies and protected both mice and swine against lethal PRV challenge (Kost et al., 1989; Marchioli et al., 1987; Ishii et al., 1988).

PRV gIII is the HSV-1 gC analog (Robbins et al., 1986). Functional replacement of PRV gIII by HSVgC was not observed (Whealy et al., 1989). Although PRV gIII is nonessential for replication in vitro (Wathen et al., 1986; Robbins et al., 1986), the mature glycosylated form (98 kDa) is an abundant constituent of the PRV envelope. Anti-gpIII monoclonal antibodies neutralize the virus in vitro with or without complement (Hampl et al., 1984; Eloit et al., 1988; Wathen et al., 1986) and can passively protect mice and swine (Marchioli et al., 1988). The PRV glycoprotein gIII can protect mice and swine from lethal PRV challenge after immunization with a Cro/gIII fusion protein expressed in *E. coli* (Robbins, A., R. Watson, L. Enquist, European Patent application 0162738A1) or when expressed in a vaccinia recombinant (Panicall, D., L. Gritz, G. Mazzara, European Patent application 0261940A2).

PRV gpII is the HSV-1 gB homolog (Robbins et al., 1987). Monoclonal antibodies directed against PRV gpII have been shown to neutralize the virus in vitro (Ben-Porat et al., 1986) with or without complement (Wittmann et al., 1989). Moreover, passive immunization studies demonstrated that neutralizing monoclonal antibodies partially protected swine (Marchioli et al., 1988). Immunization with NYVAC (highly attenuated vaccinia virus)-based recombinants expressing pseudorabies virus (PRV) gII (gB) or gp50 (gD) has been shown to protect swine against a virulent PRV challenge (Brockmeier et al., 1993). Furthermore, vaccinia recombinants expressing PRV gII and gp50, or gII, gIII (gC) and gp50 have been shown to elicit a higher level of protection than recombinants expressing gII or gp50 alone, suggesting a potential synergistic effect with these glycoproteins (Riviere et al., 1992).

The herpes simplex virus type 1 (HSV1) genome encodes at least eleven antigenically distinct glycoproteins: gB, gC, gD, gE, gG, gH, gI, gJ, gK, gL and gM (Roizman et al., 1990). Mice immunized with purified HSV1 gB, gC or gD are protected against lethal HSV1 challenge (Chan, 1983). Mice have also been protected against lethal HSV1 or HSV2 challenge by passive immunization with antibodies to total MSV1 (Davis et al., 1979) or HSV2 (Oakes et al., 1978) virus and with antibodies to the individual HSV2 gB, gC, gD or gE glycoproteins (Balachandran et al., 1982).

Vaccinia virus vectors expressing HSV1 gB (McLaughlin-Taylor et al., 1988) and HSV1 gC (Rosenthal et al., 1987) have been shown to induce cytotoxic T-cell responses. In addition, it has been shown that mice immunized with recombinant vaccinia virus expressing either HSV1 gB (Cantin et al., 1987), HSV1 gC (Weir et al., 1989) or HSV1 gD (Paoletti et al., 1984) are protected against a lethal challenge of HSV1. A recombinant vaccinia virus expressing HSV1 gD has also been shown to be protective against HSV2 in a guinea pig model system (Wachsman et al., 1987).

Bovine herpesvirus 1 (BHV1) specifies more than 30 structural polypeptides, 11 of which are glycosylated (Misra et al., 1981). Three of these glycoproteins, gI, gIII and gIV, have been characterized and found to be homologous to the herpes simplex virus (HSV) glycoproteins gB, gC and gD (Lawrence et al., 1986; Zamb, 1987). Immunization with purified bovine herpesvirus type 1 (BHV1) gI (gB), gIII (gC) and/or gIV (gD) has been shown to protect cattle against a BHV1/*Pasteurella haemolytica* challenge (Babiuk et al., 1987).

Feline herpesvirus type-1 (FHV-1) has been shown to contain at least 23 different proteins (Meas et al., 1984; Fargeaud et al., 1984). Of these, at least five are glycosylated (Fargeaud et al., 1984; Compton, 1989) with reported molecular masses ranging from 120 kDa to 60 kDa. The FHV-1 glycoproteins have been shown to be immunogenic (Meas et al., 1984; Compton, 1989). Like several other alphaherpesviruses, FHV-1 appears to have a homolog of glycoprotein B (gB) of HSV-1 (Maeda et al., 1992). The FHV-1 gB glycoprotein is a 134 kDa complex which is dissociated with B-mercaptoethanol into two glycoproteins of 66 kDa and 60 kDa. The FHV-1 DNA genome is approximately 134 Kb in size (Rota et al., 1986).

Epstein Barr Virus (EBV), a human B lymphotropic herpesvirus, is a member of the genus lymphocryptovirus which belongs to the subfamily gammaherpesvirus (Roizman et al., 1990). Since the EBV genome was completely sequenced (Baer et al., 1984) as the genomes of VZV (Davison et al., 1986), HSV1 (McGeoch et al., 1988), MCHV (Chee et al., 1990) and EHV1 (Telford et al., 1992) numerous homologies between these different herpesviruses have been described (Kieff et al., 1990).

Human cytomegalovirus (HCMV) is a member of the betaherpesvirinae subfamily (family Herpesviridae). Three immunologically distinct families of glycoproteins associated with the HCMV envelope have been described (Gretch et al., 1988): gCI (gp55 and gp93–130); gCII (gp47–52); and gCIII (gp85–p145). The gene coding for gCI is homologous to HSVI gB.

In addition, immunization with a fowlpox recombinant expressing Marek's disease virus (MDV) gB has been shown to protect chickens against a virulent MDV challenge (Nazarian et al., 1992).

The results of these studies indicate that an immune response against gB, gC and/or gD glycoproteins can protect target species animals against a herpesvirus challenge and, that the provision of nucleotides for CHV gB, gC and gD glycoproteins is a valuable advance over the current state of the art as it allows for the provision of the glycoproteins and, antigenic, immunological or vaccine compositions from the vector systems or from the glycoproteins. Further, the glycoproteins from expression of the nucleotides can be used to elicit antibodies which can be further used in antibody binding diagnostic assays, kits or tests for ascertaining the presence or absence in a sample such as sera of the glycoprotein(s) and therefore the presence or absence of CHV or of an immune or antigenic response (to either CHV or to the glycoproteins). Thus, many utilities flow from the provision of the nucleotides for CHV gB, gC and gD glycoproteins.

Various vector systems exist for the expression of exogenous DNA, such as the phage, e.g., lambda, and *E. coli* systems (Allen et al., 1987; Robbins, EPA 0162738A1; Panicall, EPA 0261940A2, each of which is expressly incorporated herein by reference).

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (Piccini et al., 1987).

Specifically, the recombinant poxviruses are constructed in two steps known in the art and analogous to the methods for creating synthetic recombinants of poxviruses such as the vaccinia virus and avipox virus described in U.S. Pat. Nos. 4,769,330, 4,772,848, 4,603,112, 5,100,587, and 5,179,993, the disclosures of which are incorporated herein by reference.

First, the DNA gene sequence to be inserted into the virus, particularly an open reading frame from a non-pox source, is placed into an *E. coli* plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within *E. coli* bacteria (Clewell, 1972) and isolated (Clewell et al., 1969; Maniatis et al., 1982).

Second, the isolated plasmid containing the DNA gene sequence to be inserted is transfected into a cell culture, e.g. chick embryo fibroblasts, along with the poxvirus. Recombination between homologous pox DNA in the plasmid and the vital genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new vital genomes within the infected host cell. Thus, genetic recombination between viral genes may occur during the vital replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome. Additional strategies have recently been reported for generating recombinant vaccinia virus.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

Vaccinia virus has been used successfully to immunize against smallpox, culminating in the worldwide eradication of smallpox in 1980. In the course of its history, many strains of vaccinia have arisen. These different strains demonstrate varying immunogenicity and are implicated to varying degrees with potential complications, the most serious of which are post-vaccinial encephalitis and generalized vaccinia (Behbehani, 1983).

With the eradication of smallpox, a new role for vaccinia became important, that of a genetically engineered vector for the expression of foreign genes. Genes encoding a vast number of heterologous antigens have been expressed in vaccinia, often resulting in protective immunity against challenge by the corresponding pathogen (reviewed in Tartaglia et al., 1990a).

The genetic background of the vaccinia vector has been shown to affect the protective efficacy of the expressed foreign immunogen. For example, expression of Epstein Barr Virus (EBV) gp340 in the Wyeth vaccine strain of vaccinia virus did not protect cottontop tamarins against EBV virus induced lymphoma, while expression of the same gene in the WR laboratory strain of vaccinia virus was protective (Morgan et al., 1988).

A fine balance between the efficacy and the safety of a vaccinia virus-based recombinant vaccine candidate is extremely important. The recombinant virus must present the immunogen(s) in a manner that elicits a protective immune response in the vaccinated animal but lacks any significant pathogenic properties. Therefore attenuation of the vector strain would be a highly desirable advance over the current state of technology.

A number of vaccinia genes have been identified which are non-essential for growth of the virus in tissue culture and whose deletion or inactivation reduces virulence in a variety of animal systems.

The gene encoding the vaccinia virus thymidine kinase (TK) has been mapped (Hruby et al., 1982) and sequenced (Hruby et al., 1983; Weir et al., 1983). Inactivation or complete deletion of the thymidine kinase gene does not prevent growth of vaccinia virus in a wide variety of cells in tissue culture. TK⁻ vaccinia virus is also capable of replication in vivo at the site of inoculation in a variety of hosts by a variety of routes.

It has been shown for herpes simplex virus type 2 that intravaginal inoculation of guinea pigs with TK⁻ virus resulted in significantly lower virus titers in the spinal cord than did inoculation with TK⁺ virus (Stanberry et al., 1985). It has been demonstrated that herpesvirus encoded TK activity in vitro was not important for virus growth in actively metabolizing cells, but was required for virus growth in quiescent cells (Jamieson et al., 1974).

Attenuation of TK⁻ vaccinia has been shown in mice inoculated by the intracerebral and intraperitoneal routes (Buller et al., 1985). Attenuation was observed both for the WR neurovirulent laboratory strain and for the Wyeth vaccine strain. In mice inoculated by the intradermal route, TK⁻ recombinant vaccinia generated equivalent anti-vaccinia neutralizing antibodies as compared with the parental TK⁺ vaccinia virus, indicating that in this test system the loss of TK function does not significantly decrease immunogenicity of the vaccinia virus vector. Following intranasal inoculation of mice with TK⁻ and TK⁺ recombinant vaccinia virus (WR strain), significantly less dissemination of virus to other locations, including the brain, has been found (Taylor et al., 1991a).

Another enzyme involved with nucleotide metabolism is ribonucleotide reductase. Loss of virally encoded ribonucleotide reductase activity in herpes simplex virus (HSV) by deletion of the gene encoding the large subunit was shown to have no effect on viral growth and DNA synthesis in dividing cells in vitro, but severely compromised the ability of the virus to grow on serum starved cells (Goldstein et al., 1988). Using a mouse model for acute HSV infection of the eye and reactivatable latent infection in the trigeminal ganglia, reduced virulence was demonstrated for HSV deleted of the large subunit of ribonucleotide reductase, compared to the virulence exhibited by wild type HSV (Jacobson et al., 1989).

Both the small (Slabaugh et al., 1988) and large (Schmitt et al., 1988) subunits of ribonucleotide reductase have been identified in vaccinia virus. Insertional inactivation of the large subunit of ribonucleotide reductase in the WR strain of vaccinia virus leads to attenuation of the virus as measured by intracranial inoculation of mice (Child et al., 1990).

The vaccinia virus hemagglutinin gene (HA) has been mapped and sequenced (Shida, 1986). The HA gene of vaccinia virus is nonessential for growth in tissue culture (Ichihashi et al., 1971). Inactivation of the HA gene of vaccinia virus results in reduced neurovirulence in rabbits inoculated by the intracranial route and smaller lesions in rabbits at the site of intradermal inoculation (Shida et al., 1988). The HA locus was used for the insertion of foreign genes in the WR strain (Shida et al., 1987), derivatives of the Lister strain (Shida et al., 1988) and the Copenhagen strain (Guo et al., 1989) of vaccinia virus. Recombinant HA⁻ vaccinia virus expressing foreign genes have been shown to be immunogenic (Guo et al., 1989; Itamura et al., 1990; Shida et al., 1988; Shida et al., 1987) and protective against challenge by the relevant pathogen (Guo et al., 1989; Shida et al., 1987).

Cowpox virus (Brighton red strain) produces red (hemorrhagic) pocks on the chorioallantoic membrane of chicken eggs. Spontaneous deletions within the cowpox genome generate mutants which produce white pocks (Pickup et al., 1984). The hemorrhagic function (u) maps to a 38 kDa protein encoded by an early gene (Pickup et al., 1986). This gene, which has homology to serine protease inhibitors, has been shown to inhibit the host inflammatory response to cowpox virus (Palumbo et al., 1989) and is an inhibitor of blood coagulation.

The u gene is present in WR strain of vaccinia virus (Kotwal et al., 1989b). Mice inoculated with a WR vaccinia virus recombinant in which the u region has been inactivated by insertion of a foreign gene produce higher antibody levels to the foreign gene product compared to mice inoculated with a similar recombinant vaccinia virus in which the u gene is intact (Zhou et al., 1990). The u region is present in a defective nonfunctional form in Copenhagen strain of vaccinia virus (open reading frames B13 and B14 by the terminology reported in Goebel et al., 1990a,b).

Cowpox virus is localized in infected cells in cytoplasmic A type inclusion bodies (ATI) (Kato et al., 1959). The function of ATI is thought to be the protection of cowpox virus virions during dissemination from animal to animal (Bergoin et al., 1971). The ATI region of the cowpox genome encodes a 160 kDa protein which forms the matrix of the ATI bodies (Funahashi et al., 1988; Patel et al., 1987). Vaccinia virus, though containing a homologous region in its genome, generally does not produce ATI. In WR strain of vaccinia, the ATI region of the genome is translated as a 94 kDa protein (Patel et al., 1988). In Copenhagen strain of vaccinia virus, most of the DNA sequences corresponding to the ATI region are deleted, with the remaining 3' end of the region fused with sequences upstream from the ATI region to form open reading frame (ORF) A26L (Goebel et al., 1990a,b).

A variety of spontaneous (Altenburger et al., 1989; Drillien et al., 1981; Lai et al., 1989; Moss et al., 1981; Paez et al., 1985; Panicall et al., 1981) and engineered (Perkus et al., 1991; Perkus et al., 1989; Perkus et al., 1986) deletions have been reported near the left end of the vaccinia virus genome. A WR strain of vaccinia virus with a 10 kb spontaneous deletion (Moss et al., 1981; Panicali et al., 1981) was shown to be attenuated by intracranial inoculation in mice (Buller et al., 1985). This deletion was later shown to include 17 potential ORFs (Kotwal et al., 1988b). Specific genes within the deleted region include the virokine N1L and a 35 kDa protein (C3L, by the terminology reported in Goebel et al., 1990a,b). Insertional inactivation of N1 reduces virulence by intracranial inoculation for both normal and nude mice (Kotwal et al., 1989a). The 35 kDa protein is secreted like N1 into the medium of vaccinia virus infected cells. The protein contains homology to the family of complement control proteins, particularly the complement 4B binding protein (C4bp) (Kotwal et al., 1988a). Like the cellular C4bp, the vaccinia 35 kDa protein binds the fourth component of complement and inhibits the classical complement cascade (Kotwal et al., 1990). Thus the vaccinia 35 kDa protein appears to be involved in aiding the virus in evading host defense mechanisms.

The left end of the vaccinia genome includes two genes which have been identified as host range genes, K1L (Gillard et al., 1986) and C7L (Perkus et al., 1990). Deletion of both of these genes reduces the ability of vaccinia virus to grow on a variety of human cell lines (Perkus et al., 1990).

Two additional vaccine vector systems involve the use of naturally host-restricted poxviruses, avipoxviruses. Both fowlpoxvirus (FPV) and canarypoxvirus (CPV) have been engineered to express foreign gene products. Fowlpox virus (FPV) is the prototypic virus of the Avipox genus of the Poxvirus family. The virus causes an economically important disease of poultry which has been well controlled since the 1920's by the use of live attenuated vaccines. Replication of the avipox viruses is limited to avian species (Matthews, 1982b) and there are no reports in the literature of avipoxvirus causing a productive infection in any nonavian species including man. This host restriction provides an inherent safety barrier to transmission of the virus to other species and makes use of avipoxvirus based vaccine vectors in veterinary and human applications an attractive proposition.

FPV has been used advantageously as a vector expressing antigens from poultry pathogens. The hemagglutinin protein of a virulent avian influenza virus was expressed in an FPV recombinant (Taylor et al., 1988a). After inoculation of the recombinant into chickens and turkeys, an immune response was induced which was protective against either a homologous or a heterologous virulent influenza virus challenge (Taylor et al., 1988a). FPV recombinants expressing the surface glycoproteins of Newcastle Disease Virus have also been developed (Taylor et al., 1990; Edbauer et al., 1990).

Despite the host-restriction for replication of FPV and CPV to avian systems, recombinants derived from these viruses were found to express extrinsic proteins in cells of nonavian origin. Further, such recombinant viruses were shown to elicit immunological responses directed towards the foreign gene product and where appropriate were shown to afford protection from challenge against the corresponding pathogen (Tartaglia et al., 1993 a,b; Taylor et al., 1992; 1991b; 1988b).

Thus, heretofore, the nucleotide and amino acid sequences for the CHV gB, gC and gD glycoproteins, have not been taught or suggested and, providing these sequences would be of great value. Further, vaccine, antigenic or immunological compositions from the nucleotides for the CHV gB, gC and gD glycoproteins (such as from vector systems containing such nucleotides) as well as from the glycoproteins themselves (such as from expression by the vector systems) have not heretofore been taught or suggested and, these nucleotides, vector systems, glycoproteins and compositions would be of great value.

OBJECTS AND SUMMARY OF THE INVENTION

It is therefore an object of the invention to provide nucleotides or isolated nucleic acids coding for CHV gB, gC and gD.

It is a further object of the invention to provide vectors containing nucleotides or isolated nucleic acids coding for CHV gB, gC and/or gD.

It is another object of the invention to provide CHV gB, gC and/or gD glycoproteins, especially from expression of nucleotides or isolated nucleic acids therefor in a vector system.

It is an additional object of the invention to provide antigenic, vaccine or immunological compositions from the CHV gB, gC and/or gD nucleotides or isolated nucleic acids or a vector containing them or, from the glycoproteins themselves, such as by way of expression by the vector.

It is yet another object of this invention to provide modified recombinant viruses, which viruses have enhanced safety, and to provide a method of making such recombinant viruses.

It is an additional object of this invention to provide a recombinant poxvirus antigenic, vaccine or immunological composition having an increased level of safety compared to known recombinant poxvirus antigenic, vaccine or immunological compositions.

It is a further object of this invention to provide a modified vector for expressing a gene product in a host, wherein the vector is modified so that it has attenuated virulence in the host.

It is another object of this invention to provide a method for expressing a gene product, such as CHV gB, gC and/or gD, in a cell cultured in vitro using a modified recombinant virus or modified vector having an increased level of safety.

These and other objects and advantages of the present invention will become more readily apparent after consideration of the following.

The present invention involves the elucidation of the CHV gB, gC and gD nucleotides, glycoproteins therefrom and, antigenic, vaccine or immunological compositions employing the nucleotide sequences and the glycoproteins.

Accordingly, the present invention provides a nucleotide or isolated nucleic acid coding for canine herpesvirus gB glycoprotein.

The present invention provides a nucleotide or isolated nucleic acid coding for canine herpesvirus gC glycoprotein.

The present invention provides a nucleotide or isolated nucleic acid coding for canine herpesvirus gD glycoprotein.

The nucleotides are preferably DNA. The nucleotides or isolated nucleic acids preferably have the DNA sequences as set forth in FIGS. 1, 4 and 7.

The present invention also provides canine herpesvirus glycoprotein gB.

The present invention provides canine herpesvirus glycoprotein gC.

The present invention provides canine herpesvirus glycoprotein gD.

The present invention further provides a vector containing the nucleotide or isolated nucleic acid for canine herpesvirus gB, gC and/or gD. Preferably the vector is a recombinant poxvirus such as a recombinant vaccinia or avipox virus, more preferably the vaccinia or avipox virus is attenuated such as NYVAC, ALVAC or TROVAC.

Thus, in one preferred aspect, the present invention relates to a modified recombinant virus having inactivated virus-encoded genetic functions so that the recombinant virus has attenuated virulence and enhanced safety. The functions can be non-essential, or associated with virulence. The virus is advantageously a poxvirus, particularly a vaccinia virus or an avipox virus, such as fowlpox virus and canarypox virus. The modified recombinant virus can include, within a nonessential region of the virus genome, a heterologous DNA sequence which encodes a CHV antigenic protein, e.g., CHV gC, gB, and gD or any combination thereof.

In a still further preferred aspect, the present invention relates to a modified recombinant virus having nonessential virus-encoded genetic functions inactivated therein so that the virus has attenuated virulence, and wherein the modified recombinant virus further contains DNA from a heterologous source in a nonessential region of the virus genome. The DNA can code for a CHV gB, gC and gD, or any combination thereof. In particular, the genetic functions are inactivated by deleting an open reading frame encoding a virulence factor or by utilizing naturally host restricted viruses. The virus used according to the present invention is advantageously a poxvirus, particularly a vaccinia virus or an avipox virus, such as fowlpox virus and canarypox virus. Advantageously, the open reading frame is selected from the group consisting of J2R, B13R+B14R, A26L, A56R, C7L-K1L, and I4L (by the terminology reported in Goebel et al., 1990a,b); and, the combination thereof. In this respect, the open reading frame comprises a thymidine kinase gene, a hemorrhagic region, an A type inclusion body region, a hemagglutinin gene, a host range gene region or a large subunit, ribonucleotide reductase; or, the combination thereof. The modified Copenhagen strain of vaccinia virus is identified as NYVAC (Tartaglia et al., 1992).

The present invention still further provides an antigenic, vaccine or immunological composition for inducing an antigenic or immunological response in a host, such as a canine, comprising a suitable vector containing the nucleotide(s) or isolated nucleic acid(s) for canine herpesvirus gB, gC and/or gD and a suitable carrier; or, canine herpesvirus gB, gC and/or gD glycoprotein(s), such as from expression thereof in a vector containing the nucleotide(s) of the invention, and a suitable carrier.

The present invention yet further provides methods employing the inventive nucleotide(s) or isolated nucleic acid(s), glycoprotein(s), composition(s).

Thus, the invention provides a method for preparing canine herpesvirus gB, gC and/or gD comprising inserting the nucleotide(s) or isolated nucleic acid(s) therefor into a suitable vector, cultivating the vector, and, collecting the glycoprotein from the vector. The vector can be a poxvirus, such as vaccinia or avipox virus, a phage such as lambda, or E. coli or any other suitable virus or bacterial vector. The cultivating can be infecting cells susceptible to viral infection by the virus vector or, growing colonies of the bacterial vector system, such as by plate or broth methods. And, collecting can be by separating the glycoprotein(s) from the viral-infected cells or from the bacterial cells.

Thus, in a preferred aspect, the present invention relates to a method for expressing a gene product in a cell cultured in vitro by introducing into the cell a modified recombinant virus having attenuated virulence and enhanced safety. The modified recombinant virus can include, within a non-essential region of the virus genome, a heterologous DNA sequence which encodes an antigenic protein, e.g., CHV gB, gC and gD, or any combination thereof.

Likewise, the invention provides a method for inoculating or for stimulating an antigenic or immunological response in a host such as a canine against canine herpesvirus comprising administering the inventive antigenic, vaccine or immunological composition to the host, e.g., canine. Additionally, the invention includes an antibody elicited by the expression of the inventive nucleotide(s). The antibody can be generated into a monoclonal antibody by known techniques and, the antibody or the monoclonal antibody can be employed in a binding diagnostic assay, test or kit to determine the presence or absence of CHV gB, gC and/or gD in a sample such as sera and therefore the presence or absence of CHV or, of an antibody or immune response to CHV or to glycoproteins thereof.

These and other embodiments within the present invention are described or are obvious from the following detailed description.

BRIEF DESCRIPTION OF DRAWINGS

The following detailed description, given by way of example, but not intended to limit the invention solely to the specific embodiments described, may best be understood in conjunction with the accompanying drawings, in which:

FIG. 1 shows the nucleotide sequence and predicted amino acid sequence of the CHV gB homologue (SEQ ID NOS:1, 2);

FIG. 3 show the amino acid homology of 8 gB homologues (SEQ ID NOS:3–10);

FIG. 4 shows the nucleotide sequence and predicted amino acid sequence of the CHV gC homologue and ORF2 (SEQ ID NOS:11–13);

FIG. 6 shows the amino acid homology of 4 gC homologues (SEQ ID NOS:14–17);

FIG. 7 shows the nucleotide sequence and predicted amino acid sequence of the CHV gD homologue; SEQ ID NOS:18–20);

FIG. 9 shows amino acid homology of 4 gD homologues (SEQ ID NOS:20–23);

FIG. 17 shows the DNA sequence (SEQ ID NO:62) of a canarypox PvuII fragment containing the C5 ORF.

FIG. 20 shows the nucleotide sequence (SEQ ID NO:72) of a fragment of TROVAC DNA containing an F8 RF;

FIG. 21 shows the DNA sequence (SEQ ID NO:75) of a 2356 base pair fragment of TROVAC DNA containing the F7ORF;

FIG. 23 shows the nucleotide sequence of the I3L-promoted CHV gB gene contained in pCHV37 and vCP320;

FIG. 24 shows the nucleotide sequence of the ALVAC C6 flanking arms;

FIG. 26 shows the nucleotide sequence of the H6-promoted CHV gC gene contained in pCHV40 and vCP322;

FIG. 28 shows the nucleotide sequence of the H6-promoted CHV gD gene contained in pCHV26 and vCP294.

DETAILED DESCRIPTION

Figure 2:
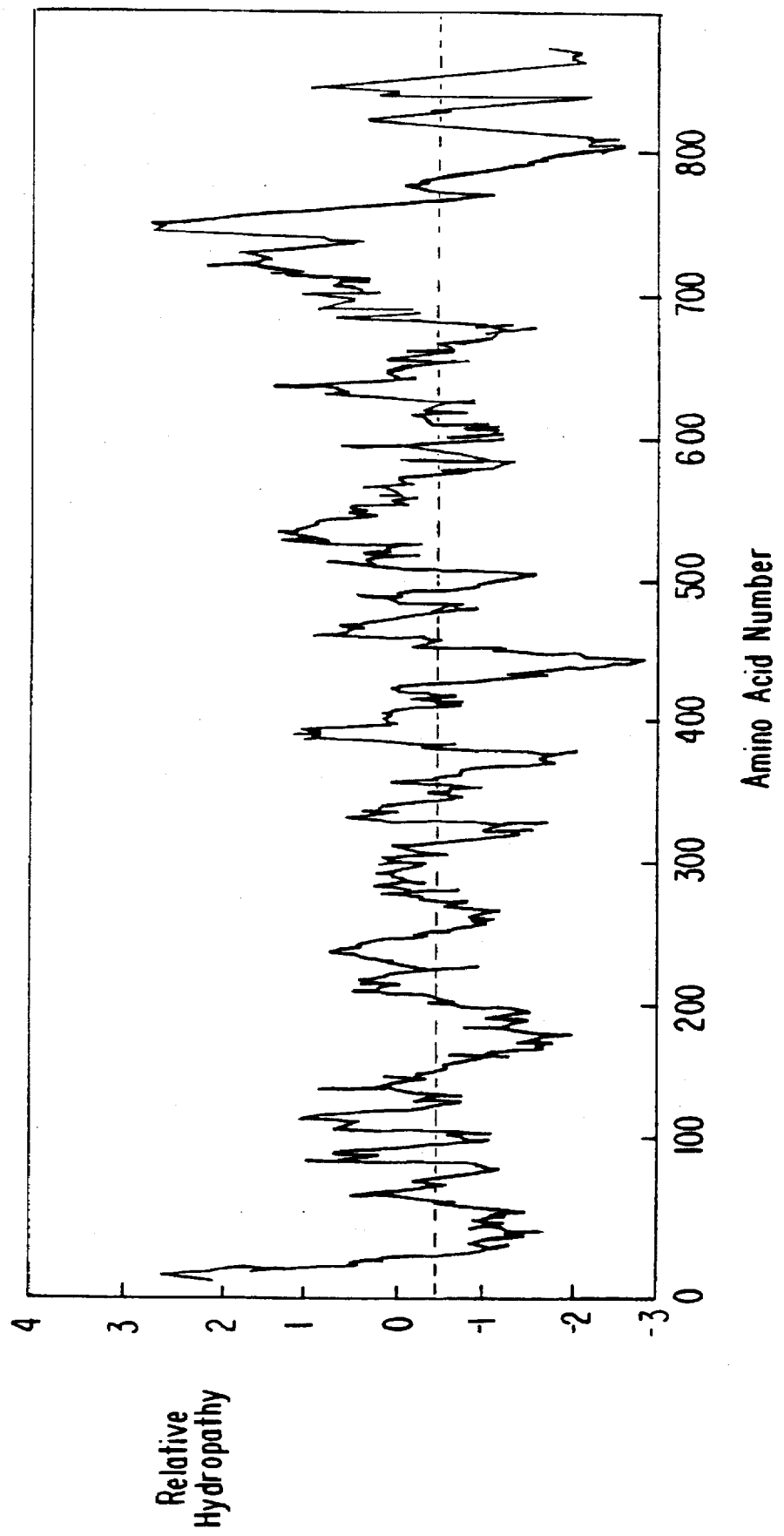
FIG. 2 shows the hydropathicity analysis of the CHV gB homologue.

This invention provides nucleotides coding for the CHV gB, gC and gD genes. These genes encode polypeptides of 879, 459 and 345 amino acids, respectively. Comparison of the predicted amino acid sequence of these glycoproteins with the gB, gC and gD amino acid sequences of other herpesviruses indicates that CHV is an alpha-herpesvirus; a conclusion that is consistent with the previous classification of this virus according to biological properties. This analysis also revealed that the homology among gB homologues is greater than the homology among gC or gD homologues, suggesting that the structural and functional constraints on gB may be greater than those on gC or gD.

Alignment of homologous gB, gC and gD polypeptides revealed that the vast majority of cysteine residues are perfectly conserved. These results suggest that these cysteine residues, due to their ability to form disulfide bonds, are important in maintaining the structural and functional integrity of the gB, gC and gD glycoproteins. In fact, in HSV1 gD, it has been shown that cysteine 1 forms a disulfide bond with cysteine 5, cysteine 2 forms a disulfide bond with cysteine 6 and cysteine 3 forms a disulfide bond with cysteine 4 (Long et al., 1992). Furthermore, it has been shown that a mutation of any of these residues has a profound effect on the conformation, processing and function of the resulting glycoprotein (Wilcox et al., 1988; Long et al., 1990). Therefore, the conservation of cysteine residues in the glycoproteins of the invention may also have structural significance.

The high degree of homology among the gC, gD and, in particular, gB homologues also suggests that these glycoproteins have common functions. In fact, it has been shown that the BHV1 gB homologue can rescue a gB$^-$ PRV virus, indicating that these 2 glycoproteins are functionally equivalent (Kopp & Mettenleiter, 1992).

Alignment of the gB, gC and gD amino acid sequences also revealed that potential N-linked glycosylation sites are somewhat conserved. N-linked glycosylation is thought to play a role in a variety of functions, such as maintenance of protein conformation and protection against proteolytic degradation. The biological significance of N-linked carbohydrates on herpesvirus glycoproteins, however, is not completely understood. For example, tunicamycin treatment of HSV1 infected cells has been shown to inhibit the production of infectious virions (Pizer et al., 1980). In addition, endoglycosidase treatment of HSV1 virions has been shown to decrease infectivity (Kuhn et al., 1988). On the other hand, N-linked glycosylation of HSV1 gD does not appear to be absolutely essential, since mutagenesis of the glycosylation sites on this glycoprotein does not affect infectivity (Sodora et al., 1991). Therefore, although the glycosylation sites on the gB, gC and gD glycoproteins are relatively well conserved, proper glycosylation of each of these polypeptides may not be absolutely essential.

The G+C content of herpesviruses varies from 33%–75% (Roizman, 1982). It has been suggested that this extensive variability is due to a nonselective mutational bias based on the presence (or absence) of virally encoded or induced enzymes involved in nucleotide metabolism (Honess, 1984). For example, VZV and herpesvirus saimiri (HVS) both have relatively low G+C contents (46% and 46%, respectively) and both encode an enzyme, thymidylate synthetase, which is involved in TTP synthesis (Davison & Scott, 1986; Honess et al., 1986). HSV1, HCMV and EBV, on the other hand, have relatively high G+C contents (68%, 57% and 60%, respectively) and do not appear to encode a thymidylate synthetase (Honess et al., 1986). CHV has been determined by DNA density analysis to have the lowest G+C content of any herpesvirus, 33% (Plummer et al., 1969; Roizman, 1982); a value which is consistent with the relatively low G+C content of the nucleotides of the invention (29%). Without wishing it to be bound by the theory that CHV does not encode an enzyme involved in nucleotide metabolism, from the present invention the ORF located immediately downstream from the CHV gC gene is not homologous to VZV thymidylate synthetase. Therefore, if CHV contains a thymidylate synthetase gene, it is not found at the same genomic location as VZV.

Newborn pups exposed to CHV usually die without forming CHV-specific neutralizing antibodies. Also, the maternal antibodies or treatment with immune serum from seropositive dogs can protect pups from a fatal CHV infection (Carmichael, 1970). Therefore, serum neutralizing antibodies can protect pups against a fatal CHV infection. Likewise, serum neutralizing antibodies can protect adult dogs from the self-limiting subclinical, upper respiratory tract infection.

Three CHV glycoproteins, gp145/112, gp80 and gp47, are known to elicit CHV neutralizing antibodies (Xuan et al., 1991). The genes encoding these glycoproteins have not been identified. Without wishing to be bound by any one theory, it is possible, however, that these antigens are encoded by the gB, gC and gD genes of this invention. Since several reports have indicated that an immune response against gB, gC and/or gD can provide protection of target species animals against a herpesvirus challenge (Babiuk et al., 1987; Nazarian et al., 1992; Riviere et al., 1992; Brockmeier et al., 1993), the CHV gB, gC and gD genes of this invention provide efficacious CHV glycoproteins, immunological or vaccine compositions and methods of using the same.

In particular, the nucleotides of this invention can be inserted into any suitable vector system for expression. For instance, the nucleotide(s) can be inserted into any suitable bacterial vector system such as the E. coli system, employing known methods (see, e.g., Robbins, EPA 0162738A1; Panicali, EPA 0261940A2).

The nucleotide(s) can be inserted into any suitable phage or vital vector system such as lambda, poxvirus, herpesvirus (see Roizman, U.S. Pat. No. 4,769,331, incorporated herein by reference), baculovirus, polio virus (see Kitson et al., J. Virol. 65, 3068–3075, 1991, incorporated herein by reference), and adenovirus (see Grunhaus et al., 1992, "Adenovirus as cloning vectors," Seminars in Virology (Vol. 3) p. 237–52, 1993; Ballay et al., EMBO Journal, vol. 4, p. 3861–65; Graham, Tibtech 8, 85–87, April, 1990; Prevec et al., J. Gen. Virol. 70, 429–434, each of which is incorporated herein by reference) systems employing known methods.

The preferred vector system is a poxvirus vector system, especially an avipox vaccinia virus system wherein recombination is as in U.S. Pat. Nos. 4,769,330, 4,772,848, 4,603,112, 5,100,587 and 5,179,993. However, an attenuated poxvirus system is even more preferred.

To develop a new vaccinia vaccine strain, NYVAC (vP866), the Copenhagen vaccine strain of vaccinia virus was modified by the deletion of six nonessential regions of the genome encoding known or potential virulence factors. The sequential deletions are detailed below. All designations of vaccinia restriction fragments, open reading frames and nucleotide positions are based on the terminology reported in Goebel et al., 1990a,b.

The deletion loci were also engineered as recipient loci for the insertion of foreign genes.

The regions deleted in NYVAC are listed below. Also listed are the abbreviations and open reading frame designations for the deleted regions (Goebel et al., 1990a,b) and the designation of the vaccinia recombinant (vP) containing all deletions through the deletion specified:

(1) thymidine kinase gene (TK; J2R) vP410;

(2) hemorrhagic region (u; B13R +B14R) vP553;

(3) A type inclusion body region (ATI; A26L) vP618;

(4) hemagglutinin gene (HA; A56R) vP723;

(5) host range gene region (C7L - K1L) vP804; and (6) large subunit, ribonucleotide reductase (I4L) vP866 (NYVAC).

NYVAC is a genetically engineered vaccinia virus strain that was generated by the specific deletion of eighteen open reading frames encoding gene products associated with virulence and host range. NYVAC is highly attenuated by a number of criteria including i) decreased virulence after intracerebral inoculation in newborn mice, ii) inocuity in genetically ($nu^+/nu^+$) or chemically (cyclophosphamide) immunocompromised mice, iii) failure to cause disseminated infection in immunocompromised mice, iv) lack of significant induration and ulceration on rabbit skin, v) rapid clearance from the site of inoculation, and vi) greatly reduced replication competency on a number of tissue culture cell lines including those of human origin. Nevertheless, NYVAC based vectors induce excellent responses to extrinsic immunogens and provided protective immunity.

TROVAC refers to an attenuated fowlpox that was a plaque-cloned isolate derived from the FP-1 vaccine strain of fowlpoxvirus which is licensed for vaccination of 1 day old chicks. ALVAC is an attenuated canarypox virus-based vector that was a plaque-cloned derivative of the licensed canarypox vaccine, Kanapox (Tartaglia et al., 1992). ALVAC has some general properties which are the same as some general properties of Kanapox. ALVAC-based recombinant viruses expressing extrinsic immunogens have also been demonstrated efficacious as vaccine vectors (Tartaglia et al., 1993 a,b). This avipox vector is restricted to avian species for productive replication. On human cell cultures, canarypox virus replication is aborted early in the viral replication cycle prior to viral DNA synthesis. Nevertheless, when engineered to express extrinsic immunogens, authentic expression and processing is observed in vitro in mammalian cells and inoculation into numerous mammalian species induces antibody and cellular immune responses to the extrinsic immunogen and provides protection against challenge with the cognate pathogen (Taylor et al., 1992; Taylor et al., 1991). Recent Phase I clinical trials in both Europe and the United States of a canarypox/rabies glycoprotein recombinant (ALVAC-RG) demonstrated that the experimental vaccine was well tolerated and induced protective levels of rabiesvirus neutralizing antibody titers (Cadoz et al., 1992; Fries et al., 1992). Additionally, peripheral blood mononuclear cells (PBMCs) derived from the ALVAC-RG vaccinates demonstrated significant levels of lymphocyte proliferation when stimulated with purified rabies virus (Fries et al., 1992).

NYVAC, ALVAC and TROVAC have also been recognized as unique among all poxviruses in that the National Institutes of Health ("NIH")(U.S. Public Health Service), Recombinant DNA Advisory Committee, which issues guidelines for the physical containment of genetic material such as viruses and vectors, i.e., guidelines for safety procedures for the use of such viruses and vectors which are based upon the pathogenicity of the particular virus or vector, granted a reduction in physical containment level: from BSL2 to BSL1. No other poxvirus has a BSL1 physical containment level. Even the Copenhagen strain of vaccinia virus—the common smallpox vaccine—has a higher physical containment level; namely, BSL2. Accordingly, the art has recognized that NYVAC, ALVAC and TROVAC have a lower pathogenicity than any other poxvirus.

Clearly based on the attenuation profiles of the NYVAC, ALVAC, and TROVAC vectors and their demonstrated ability to elicit both humoral and cellular immunological responses to extrinsic immunogens (Tartaglia et al., 1993a,b; Taylor et al., 1992; Konishi et al., 1992) such recombinant viruses offer a distinct advantage over previously described vaccinia-based recombinant viruses.

After growing the bacteria or infecting cells with the recombinant virus, the glycoprotein(s) are collected by known techniques such as chromatography (see Robbins, EPA 0162738A1; Panicali, EPA 0261940A2).

The collected glycoprotein(s) can then be employed in a vaccine, antigenic or immunological composition which also contains a suitable carrier. Accordingly, the inventive nucleotides are quite useful.

Alternatively, the viral vector system, especially the preferred poxvirus vector system, can be employed in a vaccine, antigenic or immunological composition which also contains a suitable carrier. The CHV recombinant poxvirus in the composition expresses the CHV glycoprotein in vivo after administration or inoculation.

The antigenic, immunlogical or vaccine composition of the invention (either containing glycoprotein(s) expressed from a vector system containing the inventive nucleotide(s) or containing a suitable vector system such as the CHV recombinant poxvirus) is administered to pups in the same fashion as maternal antibodies or immune serum from seropositive dogs (Carmichael, 1970). Seronegative dogs are administered the composition in the same fashion as other antigenic, vaccine or immunological compositions are administered. One skilled in the veterinary arts can determine dosage from this disclosure without undue experimentation, taking into consideration such factors as the age, weight, breed, sex and general health of the particular dog or pup.

Additionally, the inventive recombinant poxvirus and the expression products therefrom stimulate an immune or antibody response in animals. From those antibodies, by techniques well-known in the art, monoclonal antibodies can be prepared and, those monoclonal antibodies or the antigens expressed from the inventive nucleotides, can be employed in well known antibody binding assays, diagnostic kits or tests to determine the presence or absence of particular CHV gB, gC and/or gD antigen(s)or antibodies thereto and therefrom the presence or absence of the virus or, to determine whether an immune response to the virus or antigen(s) has simply been stimulated.

Monoclonal antibodies are immunoglobulins produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H., U.S. Pat. No. 4,376,110, issued Mar. 8, 1983, incorporated herein by reference.

Monoclonal antibodies have also been used to recover materials by immunoadsorption chromatography, e.g. Milstein, C., 1980, Scientific American 243:66, 70, incorporated herein by reference.

Additionally, the inventive nucleotides can be used as probes to ascertain the presence of CHV DNA in samples, as well as in the generation of PCR primers for replicating or cloning CHV DNA. Methods for using DNA as probes or for preparing PCR primers are known in the art.

Thus, the inventive nucleotides and expression products of the inventive nucleotides (and therefore the nucleotides) are quite useful.

The following non-limiting Examples are given by way of illustration only and are not to be considered a limitation of this invention.

EXAMPLES

METHODS AND MATERIALS

Preparation of genomic CHV DNA. CHV (obtained from L. Carmichael, Cornell University) was propagated on Madin-Darby canine kidney (MDCK) cells (ATCC CCL34). Viral DNA was isolated by standard methodology (Tartaglia et al., 1990).

DNA hybridization. CHV genomic DNA was digested with restriction enzymes, run on agarose gels and transferred to Gene-Screen membranes (New England Nuclear) under conditions recommended by the manufacturers. Hybridizations were performed at 44° C., 53° C. or 59° C. in 1M NaCl, 1% SDS and 10% dextran sulfate. The hybridization probe included a 1800 bp BamHI-XbaI fragment, containing an internal segment of the feline herpesvirus (FHV) gB gene, a 950 bp BamHI-EcoRI fragment, containing the 3'-end of the FHV gC gene and a 970 bp BamHI-HindIII fragment, containing the 3'-end of the FHV gD gene (Audonnet, unpublished results).

Cloning and DNA sequencing. CHV genomic fragments were subcloned into pBluescriptSK (Stratagene). Plasmid DNA was prepared and manipulated using standard techniques. Nucleotide sequencing was performed on double-stranded plasmid templates, using the modified T7 enzyme, Sequenase (U.S. Biochemical Corporation), and standard protocols recommended by the manufacturer. M13 forward and reverse primers were used to obtain initial sequence, and custom primers, prepared with a Biosearch 8700 or an Applied Biosystems 380B oligonucleotide synthesizer, were used for subsequent reactions. DNA and amino acid sequence analyses. DNA and amino acid sequence analyses were performed with PC/GENE (IntelliGenetics, Incorporated), ALIGN Plus (Scientific and Educational Software) and IBI-Pustell (International Biotechnologies, Incorporated) software packages. Homology searches were conducted on the SWISS-PROT (Release 20 or 23) (IntelliGenetics, Incorporated) database, using the FASTA program (Pearson & Lipman, 1988).

DNA Cloning and Synthesis. Plasmids were constructed, screened and grown by standard procedures (Maniatis et al., 1982; Perkus et al., 1985; Piccini et al., 1987). Restriction endonucleases were obtained from Bethesda Research Laboratories, Gaithersburg, Md., New England Biolabs, Beverly, Mass.; and Boehringer Mannheim Biochemicals, Indianapolis, Ind. Klenow fragment of E. coli polymerase was obtained from Boehringer Mannheim Biochemicals. BAL-31 exonuclease and phage T4 DNA ligase were obtained from New England Biolabs. The reagents were used as specified by the various suppliers.

Synthetic oligodeoxyribonucleotides were prepared on a Biosearch 8750 or Applied Biosystems 380B DNA synthesizer as previously described (Perkus et al., 1989). DNA sequencing was performed by the dideoxy-chain termination method (Sanger et al., 1977) using Sequenase (Tabor et al., 1987) as previously described (Guo et al., 1989). DNA amplification by polymerase chain reaction (PCR) for sequence verification (Engelke et al., 1988) was performed using custom synthesized oligonucleotide primers and GeneAmp DNA amplification Reagent Kit (Perkin Elmer Cetus, Norwalk, Conn.) in an automated Perkin Elmer Cetus DNA Thermal Cycler. Excess DNA sequences were deleted from plasmids by restriction endonuclease digestion followed by limited digestion by BAL-31 exonuclease and mutagenesis (Mandecki, 1986) using synthetic oligonucleotides.

Cells, Virus, and Transfection. The origins and conditions of cultivation of the Copenhagen strain of vaccinia virus has been previously described (Guo et al., 1989). Generation of recombinant virus by recombination, in situ hybridization of nitrocellulose filters and screening for B-galactosidase activity are as previously described (Piccini et al., 1987).

The origins and conditions of cultivation of the Copenhagen strain of vaccinia virus and NYVAC has been previously described (Guo et al., 1989; Tartaglia et al., 1992). Generation of recombinant virus by recombination, in situ hybridization of nitrocellulose filters and screening for B-galactosidase activity are as previously described (Panicali et al., 1982; Perkus et al., 1989).

The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC.

The strain of fowlpox virus (FPV) designated FP-1 has been described previously (Taylor et al., 1988a). It is an attenuated vaccine strain useful in vaccination of day old chickens. The parental virus strain Duvette was obtained in France as a fowlpox scale from a chicken. The virus was attenuated by approximately 50 serial passages in chicken embryonated eggs followed by 25 passages on chicken embryo fibroblast cells. The virus was subjected to four successive plaque purifications. One plaque isolate was further amplified in primary CEF cells and a stock virus, designated as TROVAC, established.

NYVAC, ALVAC and TROVAC viral vectors and their derivatives were propagated as described previously (Piccini et al., 1987; Taylor et al., 1988a,b). Vero cells and chick embryo fibroblasts (CEF) were propagated as described previously (Taylor et al., 1988a,b).

Example 1

IDENTIFICATION AND SEQUENCING OF THE CHV gB GENE

Hybridization of CHV genomic DNA at relatively low stringency with a radiolabelled probe containing the feline herpesvirus (FHV) gB, gC and gD genes (Audonnet, unpublished results).identified one complimentary sequence. A 6 kb xbaI fragment containing this sequence was cloned and the nucleotide sequence of the hybridizing region was determined. The sequence of the nucleotide coding the CHV gB gene is shown in FIG. 1 together with the predicted amino acid expression (gB glycoprotein) therefrom. The putative transmembrane regions and potential TATA, CAAT and polyadenylation signal sequences are underlined. Nucleotides and predicted amino acid residues are numbered to the right of the sequence.

An open reading frame (ORF) starting at position 201 and ending at position 2840 was identified. The translation product (predicted) of this ORF is 879 amino acids long. Comparison of this amino acid sequence with the SWISS-PROT (Release 20) database revealed significant homology with the gB glycoprotein of numerous herpesviruses. Additional analyses revealed that the CHV gene product (predicted) was more homologous to the gB glycoprotein of alpha-herpesviruses, such as herpes simplex virus type 1 (HSV1), than beta- or gamma-herpesviruses, such as human cytomegalovirus (HCMV) or Epstein-Bart virus (EBV). These analyses and the results thereof are shown in Table 1 below. These results indicate that CHV should be classified as an alpha-herpesvirus; a conclusion that is consistent with the previous classification of this virus according to biological properties (Carmichael et al., 1965; Roizman, 1982).

TABLE 1

HOMOLOGY BETWEEN THE PREDICTED AMINO ACID SEQUENCES OF 10 HERPESVIRUS gB GLYCOPROTEINS

| | FHV | EHV1 | PRV | BHV1 | VZV | MDV | HSV1 | HCMV | EBV |
|---|---|---|---|---|---|---|---|---|---|
| CHV | 78 | 61 | 61 | 59 | 55 | 52 | 50 | 29 | 27 |
| PHV | | 57 | 59 | 58 | 51 | 48 | 48 | 27 | 27 |
| EHV1 | | | 52 | 52 | 47 | 45 | 44 | 27 | 26 |
| PRV | | | | 63 | 52 | 48 | 50 | 29 | 29 |
| BHV1 | | | | | 52 | 46 | 48 | 28 | 28 |
| VZV | | | | | | 49 | 48 | 30 | 28 |
| MDV | | | | | | | 48 | 30 | 29 |
| HSV1 | | | | | | | | 28 | 29 |
| HCMV | | | | | | | | | 32 |

Values in Table 1 were obtained using the ALIGN Plus program and are expressed as percent homology. The entire gB amino acid sequence was used. The alignment parameters were: mismatch penalty=2, open gap penalty=4, extended gap penalty=1. References: FHV (Maeda et al., 1992), EHV1 (Whalley et al., 1989), PRV (Robbins et al., 1987), BHV1 (Whitbeck et al., 1988), VZV (Keller et al., 1986), MDV (Ross et al., 1989), HSV1 (Bzik et al., 1984), HCMV (Kouzarides et al., 1987) and EBV (Pellett et al., 1985).

Example 2

ANALYSIS OF THE CHV gB NUCLEOTIDE SEQUENCE

The 5'- and 3'-noncoding regions of the CHV gB gene contain numerous RNA polymerase II regulatory sequence motifs, such as TATA box, CAAT box and polyadenylation signal sequences (Corden et al., 1980; Proudfoot & Brownlee, 1976) (FIG. 1). Potential TATA box sequences are found at positions 34, 36, 119 and 148, approximately 165 bp, 160 bp, 80 bp and 50 bp upstream from the CHV gB initiation codon. Potential CAAT box sequences (ATTG) are found at positions 89, 97 and 165, approximately 110 bp, 100 bp and 35 bp upstream from the gB initiation codon. Potential polyadenylation signal sequences (AATAAA) are found at positions 2839 and 2961, approximately 0 bp and 120 bp downstream from the CHV gB termination codon.

The nucleotide sequence surrounding the initiation codon has been shown to affect the efficiency of translation initiation (Kozak, 1986). In particular, the sequence, [A/G] NNATGG, has been found to be most efficient. Therefore, relative to Kozak's rules, the nucleotide sequence surrounding the CHV gB initiation codon (AGTATGT) is favorable at position −3, but not at position +4 (FIG. 1). The fact that the CHV gB gene does not follow Kozak's rules is not unusual. The FHV (Maeda et al., 1992), PRV (Robbins et al., 1987), varicella-zoster virus (VZV) (Keller et al., 1986), MDV (Ross et al., 1989) and HSV1 (Bzik et al., 1984) gB genes also contain a pyrimidine at position +4.

Example 3

ANALYSIS OF THE PREDICTED CHV gB AMINO ACID SEQUENCE

The deduced amino acid sequence of the CHV gB homologue is presented in FIG. 1. Hydropathicity analysis of this amino acid sequence is shown in FIG. 2. The profile was obtained with the PC/GENE SOAP program, using the method of Kyte & Doolittle (1982) and an interval of 13 amino acids. The vertical axis represents relative hydropathicity, where positive values are hydrophobic and negative values are hydrophilic. The horizontal axis represents the amino acid number of the CHV gB homologue.

Hydropathicity analysis of this amino acid sequence revealed the presence of 2 prominent hydrophobic peaks. The first peak, located at the N-terminus, without wishing to be bound by any one theory, represents a potential signal sequence. N-terminal signal sequences initiate transport across the endoplasmic reticulum membrane and can be critical for the proper post-translational modification and targeting of glycoproteins (Blobel, 1980). Signal sequences vary in length from about 15–30 residues and usually consist of a basic N-terminal region, a central hydrophobic region and a short, relatively polar C-terminal region. In addition, the cleavage site usually conforms to the −3, −1 rule, where the residue at position −1 is small (Ala, Ser, Gly, Cys, Thr or Gln) and the residue at position −3 is not aromatic (Phe, His, Tyr or Trp), charged (Asp, Glu, Lys or Arg) or large and polar (Asn or Gln), and residues −3 through +1 are not Pro (yon Heijne, 1986). Although analysis with PSIGNAL, a PC/GENE program designed to detect eukaryotic signal sequences, does not identify the N-terminal end of CHV gB as a potential signal sequence, this region does have elements consistent with typical signal sequences; namely a hydrophobic core (residues 2–17) and a relatively polar C-terminal region (FIG. 1). The fact that PSIGNAL does not detect a signal sequence in the N-terminal region of CHV gB is not unique. This algorithm also does not detect a signal sequence in the N-terminal region of the VZV gB homologue.

The second, very broad, hydrophobic peak(s) (FIG. 2), with predicted membrane-spanning segments between amino acid residues 725 and 741 and 746–750 and 766–772 (using the method of Klein et al. (1985)), without wishing to be bound by any one theory, functions as a membrane anchor region. It has been hypothesized that the transmembrane domain of HSV1 gB, as well as other gB homologues, transverses the membrane 3 times (Pellett et al., 1985). Hydropathicity analysis of CHV gB reveals the presence of at least 2 distinct hydrophobic peaks. Therefore, CHV gB and HSV1 gB have similar transmembrane structures.

Alignment of the CHV gB amino acid sequence with similar sequences from other herpesviruses revealed extensive homology throughout the entire sequence, with the exception of the N-terminus, a region surrounding the putative cleavage site (see below) and a region near the C-terminus. FIG. 3 show the amino acid homology of 8 gB homologues. The amino acid sequences of the CHV, FHV, EHV1, PRV, HSV1, VZV, HCMV and EBV gB homologues (for references from which the sequences were obtained, see text below Table 1) were aligned using the PC/GENE CLUSTAL program. Gaps, indicated by dashes, were introduced to maximize homology. Aligned residues which are identical in all 8 sequences are indicated by an asterisk (*). Aligned residues which are identical in the majority of sequences are indicated by a period (.). Conserved cysteine residues are boxed. Potential N-linked glycosylation sites are shaded. Putative proteolytic cleavage sites are underlined.

This alignment also revealed that the vast majority of cysteine residues are perfectly conserved. For example, CHV gB contains 11 cysteine residues, 10 of which are perfectly conserved in all alpha-, beta- and gamma-herpesviruses. In fact, the only cysteine residue in CHV gB that is not conserved is found near the N-terminus and may be located in the putative signal sequence. These results show that the gB glycoproteins have relatively similar tertiary structures.

Alignment of the gB amino acid sequences also revealed that the potential N-linked glycosylation sites are relatively well conserved (FIG. 3). N-linked oligosaccharides can be added to Asn residues that have the sequence Asn-X-Ser or Asn-X-Thr, where X is not Pro (Bause, 1983). CHV gB contains 13 potential N-linked glycosylation sites. Three of these sites, however, are situated in the putative cytoplasmic domain and, therefore, may not be glycosylated. The location of the potential N-linked glycosylation sites is relatively well conserved in the majority of gB glycoproteins (FIG. 3).

The gB glycoprotein of most herpesviruses is cleaved internally during maturation, with the subsequent peptides being held together by disulfide bonds. The VZV gB homologue (gpII), for example, is cleaved between Arg and Ser residues, resulting in 2 glycoproteins of approximately 60 kd (Keller et al., 1986). The gB glycoproteins of FHV (Maeda et al., 1992), equine herpesvirus type 1 (EHV1) (Whalley et al., 19989), PRV (Robbins et al., 1987), BHV1 (Whitbeck et al., 1988), MDV (Ross et al., 1989) and HCMV (Kouzarides et al., 1987) are also cleaved. Furthermore, a sequence, Arg-X-Arg-Arg/Lys-Ser/Ala, similar to the sequence at the VZV cleavage site, Arg-Thr-Arg-Arg-Ser, is present at virtually the same location in each of these gB glycoproteins. Conversely, this sequence is not found in the HSV1 (Bzik et al., 1984) and EBV (Pellett et al., 1985) gB glycoproteins, which are not cleaved. The significance of this cleavage event is unknown. It does not appear, however, to be essential for replication, in vitro, since strains of BHV1 (Blewett & Misra, 1991) and HCMV (Spaete et al., 1990) that have been mutated at the cleavage site, and therefore encode an uncleaved gB glycoprotein, are still infectious. Without wishing to be bound by the theory that CHV gB is cleaved internally, proteolytically, the sequence, Arg-Lys-Arg-Arg-Ser, is present at the same location in CHV as in VZV, FHV, EHV1, PRV, BHV1, MDV and HCMV.

Example 4

IDENTIFICATION AND SEQUENCING OF THE CHV gC GENE

CHV genomic fragments were randomly cloned into pBluescriptSK. The nucleotide sequence of the termini of these fragments was determined and the predicted amino acid sequence of potential ORFs were analyzed for homology against the SWISS-PROT (Release 20) amino acid database. Using this methodology, a 12 kb XbaI fragment encoding an ORF with homology to herpesvirus gC glycoproteins was identified. The nucleotide sequence of this ORF is presented in FIG. 4. FIG. 4 shows the nucleotide sequence and predicted amino acid sequence of the CHV gC homologue and ORF2. The putative transmembrane region and potential TATA, CAAT and polyadenylation signal sequences are underlined. Nucleotides and predicted amino acid residues are numbered to the right of the sequence. The putative CHV gC gene starts at position 201 and ends at position 1580. The predicted translation product is 459 amino acids long. Comparison of this amino acid sequence with the sequence of gC glycoproteins from other herpesviruses is shown in Table 2, below, and revealed extensive homology, indicating that this ORF encodes the CHV gC homologue (Table 2).

TABLE 2

HOMOLOGY BETWEEN THE PREDICTED AMINO ACID SEQUENCES OF 9 HERPESVIRUS gC GLYCOPROTEINS

|      | FHV | EHV1 | EHV4 | PRV | BHV1 | VZV | MDV | HSV1 |
|------|-----|------|------|-----|------|-----|-----|------|
| CHV  | 44  | 32   | 34   | 27  | 27   | 29  | 27  | 25   |
| FHV  |     | 32   | 33   | 29  | 31   | 28  | 25  | 23   |
| EHV1 |     |      | 81   | 31  | 32   | 30  | 27  | 27   |
| EHV4 |     |      |      | 32  | 31   | 31  | 25  | 27   |
| PRV  |     |      |      |     | 37   | 27  | 25  | 29   |
| BHV1 |     |      |      |     |      | 29  | 25  | 27   |
| VZV  |     |      |      |     |      |     | 22  | 22   |
| MDV  |     |      |      |     |      |     |     | 23   |

Values in Table 2 were obtained using the ALIGN Plus program and are expressed as percent homology. The entire gC amino acid sequence was used. See Table 1 for alignment parameters. References: FHV (Audonnet, unpublished results), EHV1 (Allen & Coogle, 1988), EHV4 (Nicolson & Onions, 1990), PRV (Robbins et al., 1986), BHV1 (Fitzpatrick et al., 1989), VZV (Davison & Scott, 1986), MDV (Ihara et al., 1989) and HSV1 (McGeoch et al., 1988).

Example 5
ANALYSIS OF THE CHV gC NUCLEOTIDE SEQUENCE

Potential TATA box sequences (TATA) are found at positions 22 and 81, approximately 180 bp and 120 bp upstream from the CHV gC initiation codon (FIG. 4). An additional TATA sequence is found at position 175. Due to its proximity to the gC initiation codon, however, this sequence may not be a potential TATA box sequence. Potential CAAT box sequences (CAAT and ATTG) are found at positions 13, 59 and 119, approximately 190 bp, 140 bp and 80 bp upstream from the gC initiation codon. A potential polyadenylation signal sequence (AATAAA) is found at position 1744, approximately 165 bp downstream from the CHV gC termination codon and 45 bp within ORF2 (see below). Other potential polyadenylation signal-like sequences are also found in the gC 3'-noncoding region.

Like the CHV gB gene, the nucleotide sequence surrounding the CHV gC initiation codon (AAAATGA) is favorable with respect to Kozak's rules at position −3, but not at position +4 (FIG. 4). The FHV (Audonnet, unpublished results), EHV1 (Allen & Coogle, 1988) and VZV (Davison & Scott, 1986) gC genes also contain an unfavorable nucleotide at position +4.

Example 6
ANALYSIS OF THE CHV gC AMINO ACID SEQUENCE PREDICTED

Figure 5:
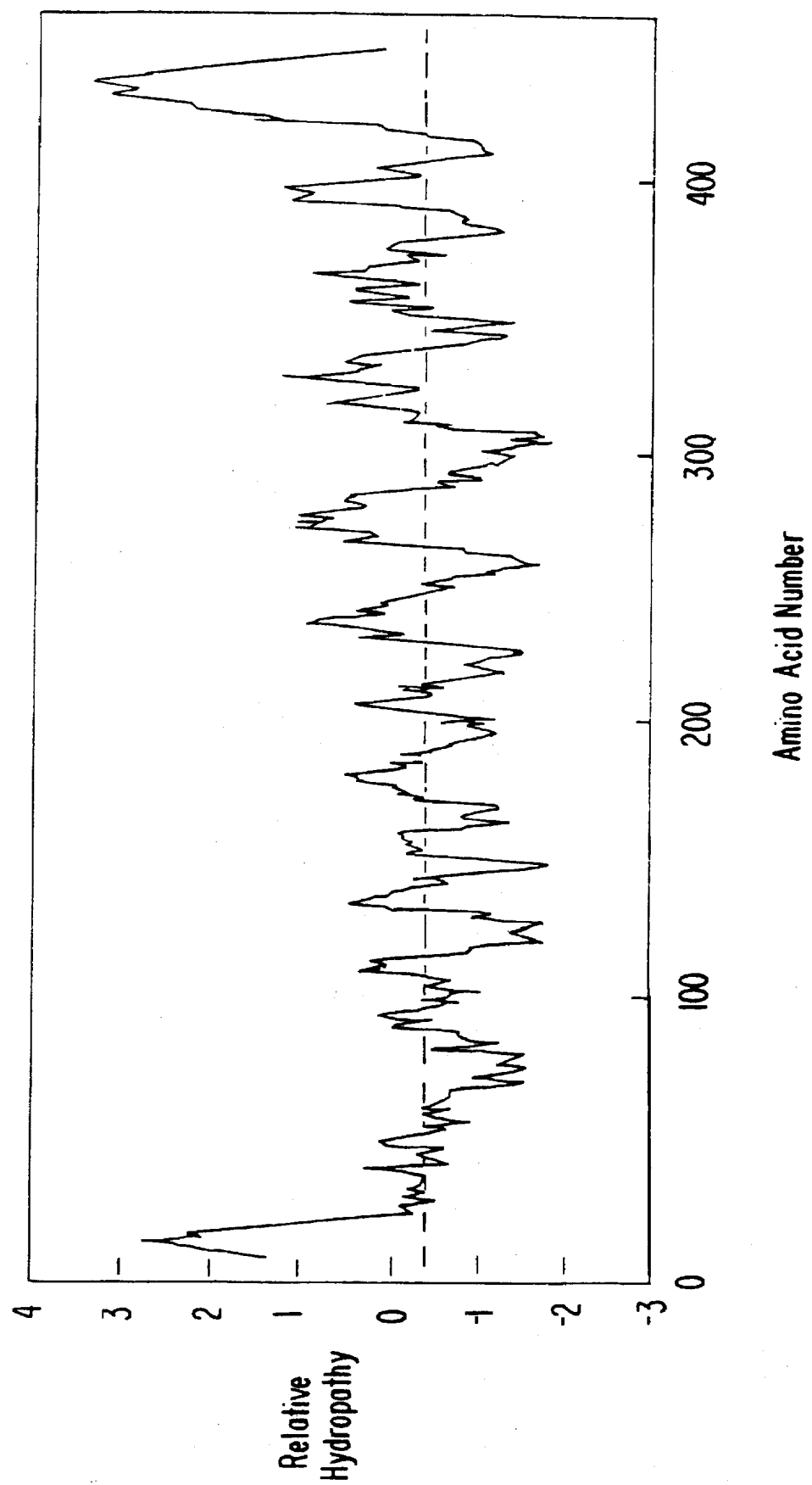
FIG. 5 shows the hydropathicity analysis of the CHV gC homologue.

The deduced amino acid sequence of the CHV gC homologue is presented in FIG. 4. FIG. 5 shows the hydropathicity analysis of the CHV gC homologue. The profile was obtained with the PC/GENE SOAP program, using the method of Kyte & Doolittle (1982) and an interval of 13 amino acids. The vertical axis represents relative hydropathicity, where positive values are hydrophobic and negative values are hydrophilic. The horizontal axis represents the amino acid number of the CHV gC homologue.

Figure 6B:
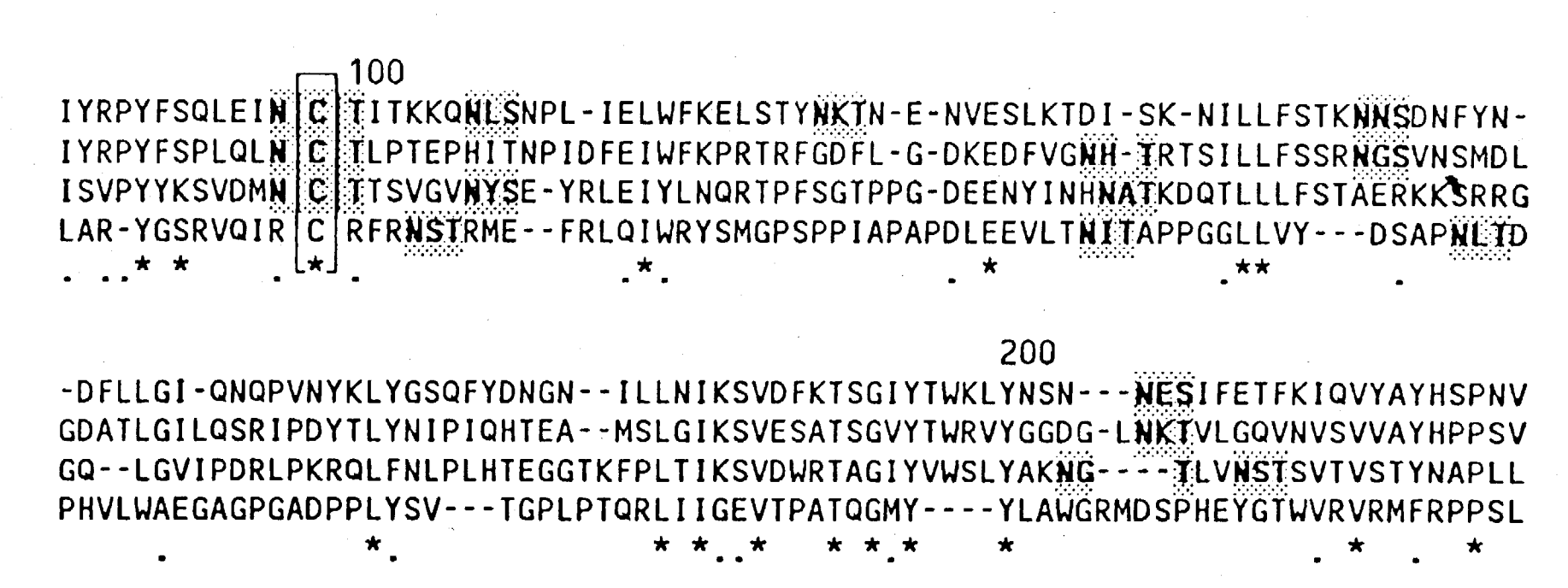

Hydropathicity analysis of the predicted CHV gC amino acid sequence revealed the presence of 2 prominent hydrophobic peaks (FIG. 5). The first peak, located at the N-terminus, without wishing to be bound by any one theory, represents a potential signal sequence. Although analysis with PSIGNAL does not identify the N-terminal end of this polypeptide as a potential signal sequence, this region does have a basic N-terminal region, a hydrophobic core (residues 6–20) and a relatively polar C-terminal region (FIG. 4). The second hydrophobic peak, with a predicted membrane-spanning segment between residues 424–433 and 449–456 (using the method of Klein et al. (1985)), without wishing to be bound by any one theory, functions as a membrane anchor region. FIG. 6 shows the amino acid homology of 4 gC homologues. The amino acid sequences of the CHV, FHV, EHV1 and HSV1 gC homologues (for references see Table 2) were aligned using the PC/GENE CLUSTAL program. Gaps, indicated by dashes, were introduced to maximize homology. Aligned residues which are identical in all 4 sequences are indicated by an asterisk (*). Aligned residues which are identical in the majority of sequences are indicated by a period (.). Conserved cysteine residues are boxed. Potential N-linked glycosylation sites are shaded.

Alignment of the CHV gC amino acid sequence with homologous sequences from other herpesviruses revealed a moderate level of homology throughout the entire sequence, with the exception of the N-terminus (FIG. 6). This alignment also revealed that the majority of cysteine residues are perfectly conserved. For example, CHV gC contains 10 cysteine residues, 8 of which are perfectly conserved in all alpha-herpesviruses. In fact, the only cysteine residues in CHV gC that are not conserved are located in the putative transmembrane or intracellular domains. These results show that the gC glycoproteins have relatively similar tertiary structures. Alignment with other gC sequences also revealed the relative conservation of potential N-linked glycosylation sites.

Example 7
IDENTIFICATION AND SEQUENCING OF ORF2

Nucleotide sequence analysis of the region downstream from the CHV gC gene revealed the presence of a second ORF (FIG. 4). This ORF (ORF2) starts at position 1699 and ends at position 2226. The predicted translation product is 175 amino acids long. Table 3, below, shows the comparison of this amino acid sequence with the SWISS-PROT (Release 23) database revealed significant homology with the ORFs located downstream from other alpha-herpesvirus gC genes. The homology scores for the ORF2 homologues shows that in CHV, FHV, EHV1, equine herpesvirus type 4 (EHV4), MDV, herpesvirus of turkey (HVT) and possibly HSV1, the ORF located downstream from the gC gene represents a highly divergent, but evolutionarily related, gene family. Conversely, the ORF (gene 13) located next to the VZV gC gene does not exhibit significant homology with any of the other comparably positioned ORFs. Furthermore, gene 13 is oriented on the genome in the opposite direction relative to all the other ORF2-like genes (Davison & Scott, 1986). These results are consistent with the proposed functions of the proteins encoded by these 2 groups of genes; VZV gene 13 encodes a thymidylate synthetase (Davison and Scott, 1986), whereas the HSV1 ORF2-like gene (UL45) encodes a putative virion protein (Telford et al., 1992). Therefore, the ORFs located next to the gC gene in CHV, FHV, EHV1, EHV4, MDV, HVT and possibly HSV1 encode proteins that are structurally and functionally unrelated to the Protein encoded downstream from the VZV gC homologue.

TABLE 3

HOMOLOGY BETWEEN THE PREDICTED AMINO ACID SEQUENCES OF THE ORFS LOCATED ADJACENT TO THE gC GENE IN 8 HERPESVIRUSES

|      | FHV     | EHV1    | EHV4    | MDV    | HTV     | HSV1   | VZV   |
| ---- | ------- | ------- | ------- | ------ | ------- | ------ | ----- |
| CHV  | 197(22) | 211(22) | 219(21) | 62(4)  | 105(13) | 53(4)  | 31(0) |
| FHV  |         | 177(24) | 167(18) | 69(4)  | 66(4)   | 40(1)  | 52(1) |
| EHV1 |         |         | 470(50) | 95(8)  | 104(9)  | 79(7)  | 58(3) |
| EHV4 |         |         |         | 132(8) | 130(11) | 60(5)  | 30(0) |
| MDV  |         |         |         |        | 767(75) | 83(6)  | 28(0) |
| HTV  |         |         |         |        |         | 91(7)  | 33(0) |
| HSV1 |         |         |         |        |         |        | 49(2) |

Values in Table 3 were obtained using the FASTA and RDF2 programs (Pearson & Lipman, 1988). A ktup of 1 was used. Values in parentheses represent the number of standard deviations between the FASTA score and the mean of the scores obtained from 100 randomly permutated versions of the potentially related sequence. References: FHV (Audonnet, unpublished results), EHV1 (Telford et al., 1992), EHV4 (Nicolson & Onions, 1990), MDV (Ihara et al., 1989), HVT (Kato et al., 1989), HSV1 (McGeoch et al., 1988) and VZV (Davison & Scott, 1986).

Example 8

ANALYSIS OF THE CHV ORF2 NUCLEOTIDE SEQUENCE

Potential TATA box sequences (TATA) are found at positions 1604, 1606, 1635 and 1662, approximately 95, 93, 65 and 35 bp upstream from the ORF2 initiation codon and approximately 24, 26, 55 and 80 bp downstream from the gC gene termination codon (FIG. 4). A potential CAAT box sequence (CAAT) is found at position 1584, approximately 115 bp upstream from the initiation codon. Potential polyadenylation signal sequences (AATAAA) are found at overlapping positions 2225, 2229, 2234 and 2238, approximately 0–15 bp downstream from the ORF2 termination codon. The nucleotide sequence surrounding the ORF2 initiation codon (AATATGG) is favorable with respect to Kozak's rules at positions −3 and +4.

Example 9

IDENTIFICATION AND SEQUENCING OF THE CHV gD GENE

Employing the same methodology used to map the CHV gC homologue, a 7 kb PstI fragment encoding an ORF with homology to herpesvirus gD glycoproteins was identified. FIG. 7 shows the nucleotide sequence and predicted amino acid sequence of the CHV gD homologue. The putative signal sequence, transmembrane region and potential polyadenylation signal sequences are underlined. Nucleotides and predicted amino acid residues are numbered to the right of the sequence. The CHV gD gene starts at position 201 and ends at position 1238. The translation product (predicted) is 345 amino acids long. Table 4, below, provides comparison of this amino acid sequence with the sequence of other gD glycoproteins and, revealed extensive homology, indicating that this ORF encodes the CHV gD homologue.

TABLE 4

| Homology between the predicted amino acid sequences of 6 herpesvirus gD glycoproteins | | | | | |
| --- | --- | --- | --- | --- | --- |
|      | FHV | EHV1 | PRV | BHV1 | HSV1 |
| CHV  | 45  | 35   | 27  | 34   | 21   |
| FHV  |     | 31   | 30  | 34   | 24   |
| EHV1 |     |      | 26  | 27   | 21   |
| PRV  |     |      |     | 37   | 27   |
| BHV1 |     |      |     |      | 24   |

Values in Table 4 were obtained using the ALIGN Plus program and are expressed as percent homology. The entire gD amino acid sequence was used. See Table 1 for alignment parameters. References: FHV (Audonnet, unpublished results), EHV1 (Flowers et al., 1991), PRV (Petrovskis et al., 1986), BHV1 (Tikoo et al., 1990) and HSV1 (Lasky & Dowbenko, 1984).

Example 10

ANALYSIS OF THE CHV gD NUCLEOTIDE SEQUENCE

No TATA or CAAT/ATTG sequences were identified immediately upstream from the CHV gD gene (FIG. 7). Numerous potential TATA box-like sequences, however, were found. Potential polyadenylation signal sequences (AATAAA) were found at positions 1260 and 1287, approximately 25 bp and 50 bp downstream from the CHV gD termination codon. Like the CHV gB and gC genes, the nucleotide sequence surrounding the CHV gD initiation codon (AAAATGA) is favorable with respect to Kozak's rules at position −3, but not at position +4 (FIG. 7). The FHV (Audonnet, unpublished results), EHV1 (Audonnet et al., 1990; Flowers et al., 1991), PRV (Petrovskis et al., 1986) and BHV1 (Tikoo et al., 1990) gD genes also contain an unfavorable nucleotide at position +4.

Example 11

ANALYSIS OF THE PREDICTED CHV gD AMINO ACID SEQUENCE

Figure 8:
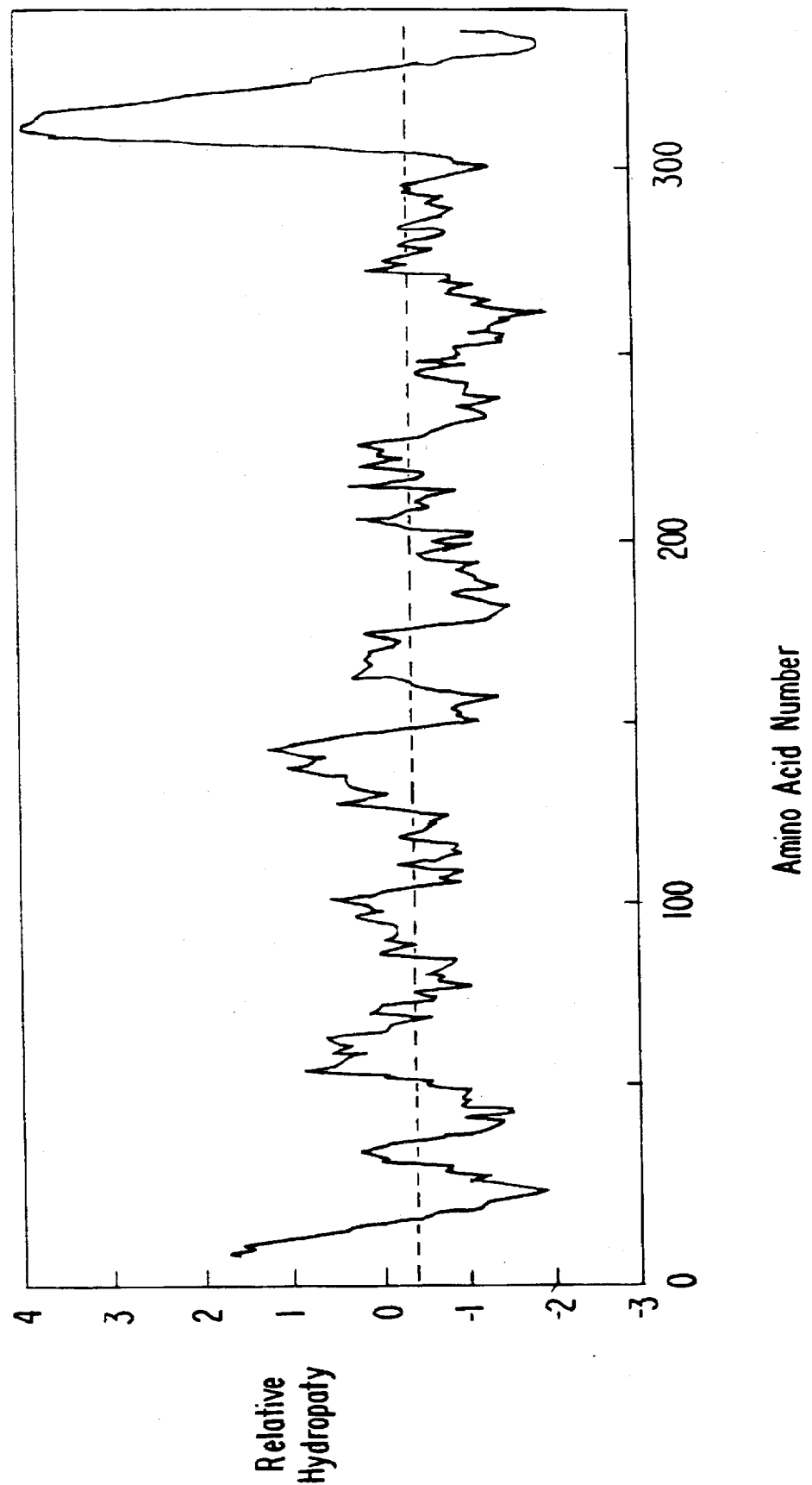
FIG. 8 shows the hydropathicity analysis of the CHV gD homologue.

The deduced amino acid sequence of the CPV gD homologue is presented in FIG. 7. FIG. 8 shows the hydropathicity analysis of the CHV gD homologue. The profile was obtained with the PC/GENE SOAP program, using the method of Kyte & Doolittle (1982) and an interval of 11 amino acids. The vertical axis represents relative hydropathicity, where positive values are hydrophobic and negative values are hydrophilic. The horizontal axis represents the amino acid number of the CHV gD homologue.

Hydropathicity analysis of the predicted CHV gD amino acid sequence revealed the presence of 2 prominent hydrophobic peaks (FIG. 8). The first peak, located at the N-terminus, without wishing to be bound by any one theory, represents a potential signal sequence. In fact, PSIGNAL identified a potential cleavage site between positions 16 and 17. The second hydrophobic peak, with a predicted membrane-spanning segment between residues 304–311 and 327–332 (using the method of Klein et al. (1985)), without wishing to be bound by any one theory, functions as a membrane anchor region.

FIG. 9 shows amino acid homology of 4 gD homologues. The amino acid sequences of the CHV, FHV, EHV1 and HSV1 gD homologues (for references see Table 4) were aligned using the PC/GENE CLUSTAL program. Gaps, indicated by dashes, were introduced to maximize homology. Aligned residues which are identical in all 4 sequences are indicated by an asterisk (*). Aligned residues which are identical in the majority of sequences are indicated by a period (.). Conserved cysteine residues are boxed. Potential N-linked glycosylation sites are shaded. Alignment of the CHV gD amino acid sequence with homologous sequences from other herpesviruses revealed a moderate level of homology throughout the entire sequence, with the exception of the N-terminus (FIG. 9). This alignment also revealed that the vast majority of cysteine residues are perfectly conserved. For example, CHV gD contains 6 cysteine residues, all of which are perfectly conserved in all alpha-herpesviruses. These results show that the gD glycoproteins have relatively similar tertiary structures. This alignment also revealed that the potential N-linked glycosylation sites are well conserved. Without wishing to be bound by any theory that the CHV gD glycosylation sites are utilized, it is known that all of the potential HSV1 gD glycosylation sites are used (Sodora et al., 1991).

Example 12

GENOMIC ORGANIZATION

The gB, gC and gD genes were not mapped to specific locations on the CHV genome. Nucleotide sequence analyses of the regions flanking these genes, however, indicates that the genomic organization of CHV is similar to other alpha-herpesviruses. For example, the ORF located immediately upstream from the CHV gB gene has homology with gene 30 of VZV (Davison & Scott, 1986) and UL28 of HSV1 (McGeoch et al., 1988), both of which are located immediately upstream from the gB homologue in those viruses. ORF2, located immediately downstream from the CHV gC gene, has homology with the ORFs located immediately downstream from the gC homologue in FHV (Audonnet, unpublished results), EHV1 (Telford et al., 1992), EHV4 (Nicolson & Onions, 1990), HVT (Karo et al., 1988) and perhaps HSV1 (McGeoch et al., 1988. Additionally, the ORF located immediately downstream from the CHV gD gene has homology to the gI gene of EHV1 (Audonnet et al., 1990) and the gp63 gene of PRV (Petrovskis et al., 1986), both of which are located immediately downstream from the gD homologue in those viruses (data not shown).

Example 13

CONSTRUCTION OF PLASMID pSD460 FOR DELETION OF THYMIDINE KINASE GENE (J2R)

Figure 10:
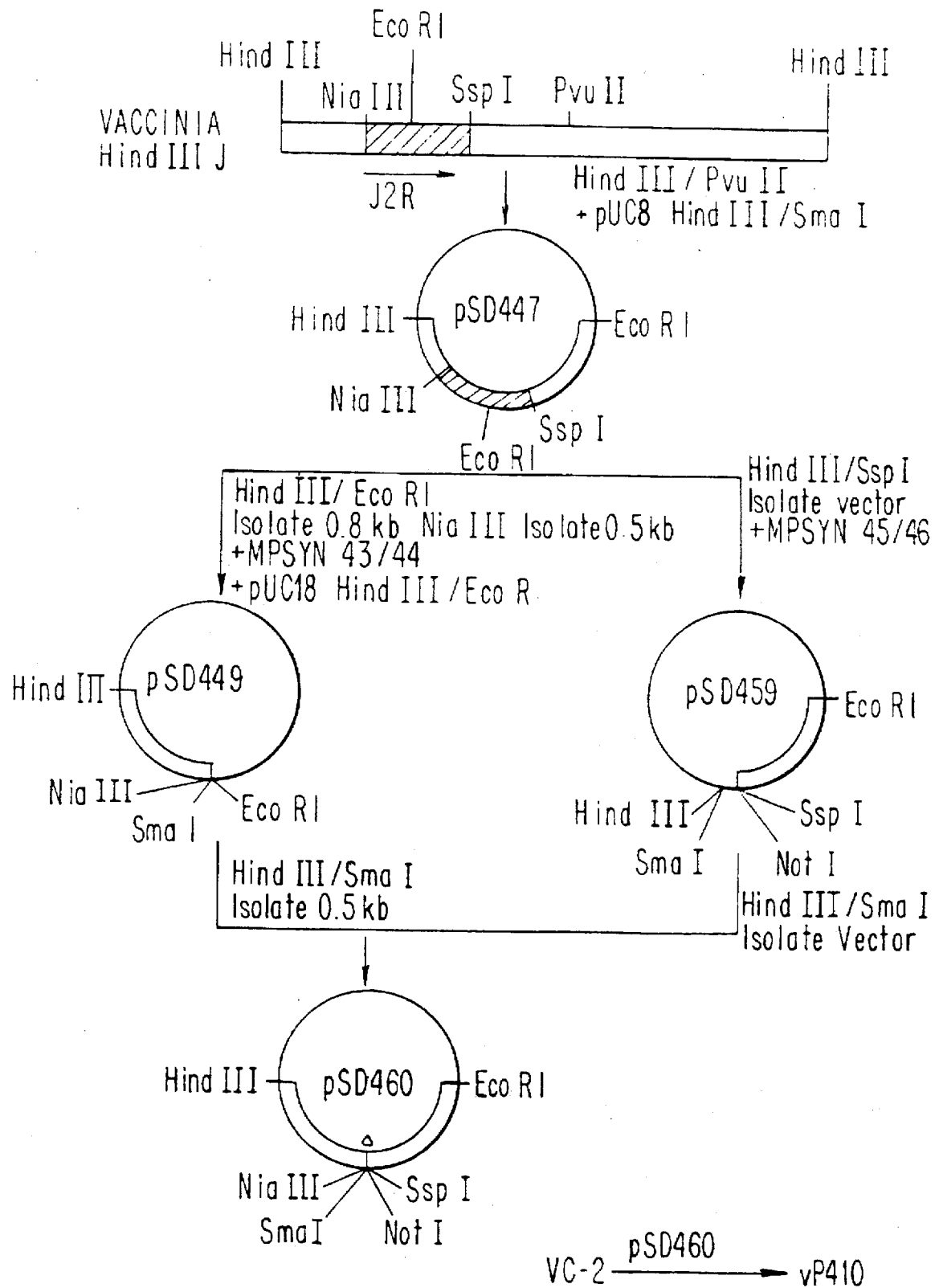
FIG. 10 schematically shows a method for the construction of plasmid pSD460 for deletion of thymidine kinase gene and generation of recombinant vaccinia virus vP410.

Referring now to FIG. 10, plasmid pSD406 contains vaccinia HindIII J (pos. 83359–88377) cloned into pUC8. pSD406 was cut with HindIII and PvuII, and the 1.7 kb fragment from the left side of HindIII J cloned into pUC8 cut with HindIII/SmaI, forming pSD447. pSD447 contains the entire gene for J2R (pos. 83855–84385). The initiation codon is contained within an NlaIII site and the termination codon is contained within an SspI site. Direction of transcription is indicated by an arrow in FIG. 10.

To obtain a left flanking arm, a 0.8 kb HindIII/EcoRI fragment was isolated from pSD447, then digested with NlaIII and a 0.5 kb HindIII/NlaIII fragment isolated. Annealed synthetic oligonucleotides MPSYN43/MPSYN44 (SEQ ID NO:24/SEQ ID NO:25)

were ligated with the 0.5 kb HindIII/NlaIII fragment into pUC18 vector plasmid cut with HindIII/EcoRI, generating plasmid pSD449.

To obtain a restriction fragment containing a vaccinia right flanking arm and pUC vector sequences, pSD447 was cut with SspI (partial) within vaccinia sequences and HindIII at the pUC/vaccinia junction, and a 2.9 kb vector fragment isolated. This vector fragment was ligated with annealed synthetic oligonucleotides MPSYN45/MPSYN46 (SEQ ID NO:26/SEQ ID NO:27)

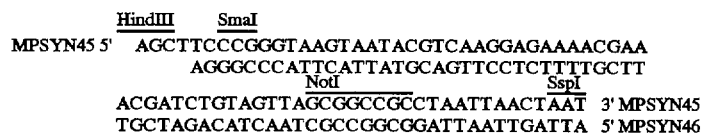

generating pSD459.

To combine the left and right flanking arms into one plasmid, a 0.5 kb HindIII/SmaI fragment was isolated from pSD449 and ligated with pSD459 vector plasmid cut with HindIII/SmaI, generating plasmid pSD460. pSD460 was used as donor plasmid for recombination with wild type parental vaccinia virus Copenhagen strain VC-2. $^{32}$P labelled probe was synthesized by primer extension using MPSYN45 (SEQ ID NO:26) as template and the complementary 20mer oligonucleotide MPSYN47 (SEQ ID NO:28) (5' TTAGTTAATTAGGCGGCCGC 3') as primer. Recombinant virus vP410 was identified by plaque hybridization.

Example 4
CONSTRUCTION OF PLASMID pSD486 FOR DELETION OF HEMORRHAGIC REGION (B13R+B14R)

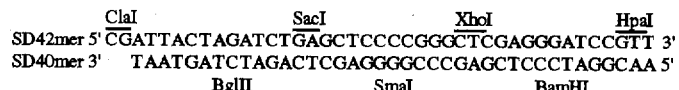

Figure 11:
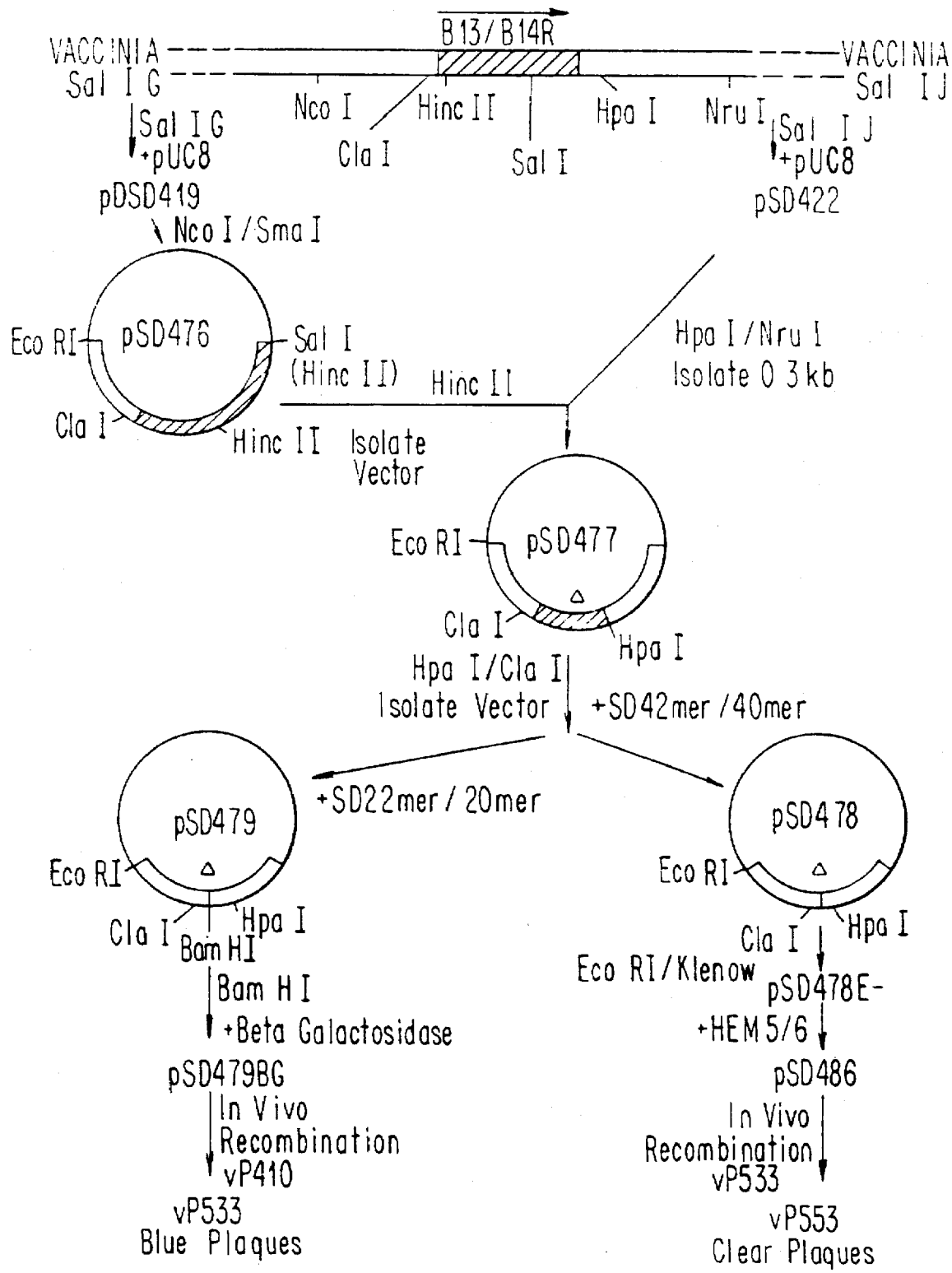
FIG. 11 schematically shows a method for the construction of plasmid pSD486 for deletion of hemorrhagic region and generation of recombinant vaccinia virus vP553.

Referring now to FIG. 11, plasmid pSD419 contains vaccinia SalI G (pos. 160,744–173,351) cloned into pUC8. pSD422 contains the contiguous vaccinia SalI fragment to the right, SalI J (pos. 173,351–182,746) cloned into pUC8. To construct a plasmid deleted for the hemorrhagic region, u, B13R–B14R (pos. 172,549–173,552), pSD419 was used as the source for the left flanking arm and pSD422 was used as the source of the right flanking arm. The direction of transcription for the u region is indicated by an arrow in FIG. 11.

To remove unwanted sequences from pSD419, sequences to the left of the NcoI site (pos. 172,253) were removed by digestion of pSD419 with NcoI/SmaI followed by blunt ending with Klenow fragment of *E. coli* polymerase and ligation generating plasmid pSD476. A vaccinia right flanking arm was obtained by digestion of pSD422 with HpaI at the termination codon of B14R and by digestion with NruI 0.3 kb to the right. This 0.3 kb fragment was isolated and ligated with a 3.4 kb HincII vector fragment isolated from pSD476, generating plasmid pSD477. The location of the partial deletion of the vaccinia u region in pSD477 is indicated by a triangle. The remaining B13R coding sequences in pSD477 were removed by digestion with ClaI/HpaI, and the resulting vector fragment was ligated with annealed synthetic oligonucleotides SD22mer/SD20mer (SEQ ID NO:29/SEQ ID NO:30)

generating pSD479. pSD479 contains an initiation codon (underlined) followed by a BamHI site. To place *E. coli* Beta-galactosidase in the B13–B14 (u) deletion locus under the control of the u promoter, a 3.2 kb BamHI fragment containing the Beta-galactosidase gene (Shapira et al., 1983) was inserted into the BamHI site of pSD479, generating pSD479BG. pSD479BG was used as donor plasmid for recombination with vaccinia virus vP410. Recombinant vaccinia virus vP533 was isolated as a blue plaque in the presence of chromogenic substrate X-gal. In vP533 the B13R–B14R region is deleted and is replaced by Beta-galactosidase.

To remove Beta-galactosidase sequences from vP533, plasmid pSD486, a derivative of pSD477 containing a polylinker region but no initiation codon at the u deletion junction, was utilized. First the ClaI/HpaI vector fragment from pSD477 referred to above was ligated with annealed synthetic oligonucleotides SD42mer/SD40mer (SEQ ID NO:31/SEQ ID NO:32)

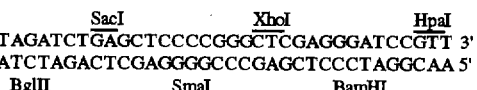

generating plasmid pSD478. Next the EcoRI site at the pUC/vaccinia junction was destroyed by digestion of pSD478 with EcoRI followed by blunt ending with Klenow fragment of *E. coli* polymerase and ligation, generating plasmid pSD478E⁻. pSD478E⁻ was digested with BamHI and HpaI and ligated with annealed synthetic oligonucleotides HEM5/HEM6 (SEQ ID NO:33/SEQ ID NO:34)

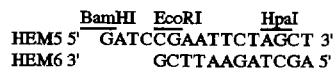

generating plasmid pSD486. pSD486 was used as donor plasmid for recombination with recombinant vaccinia virus vP533, generating vP553, which was isolated as a clear plaque in the presence of X-gal.

Example 15
CONSTRUCTION OF PLASMID pMP494Δ FOR DELETION OF ATI REGION (A26L)

Figure 12:
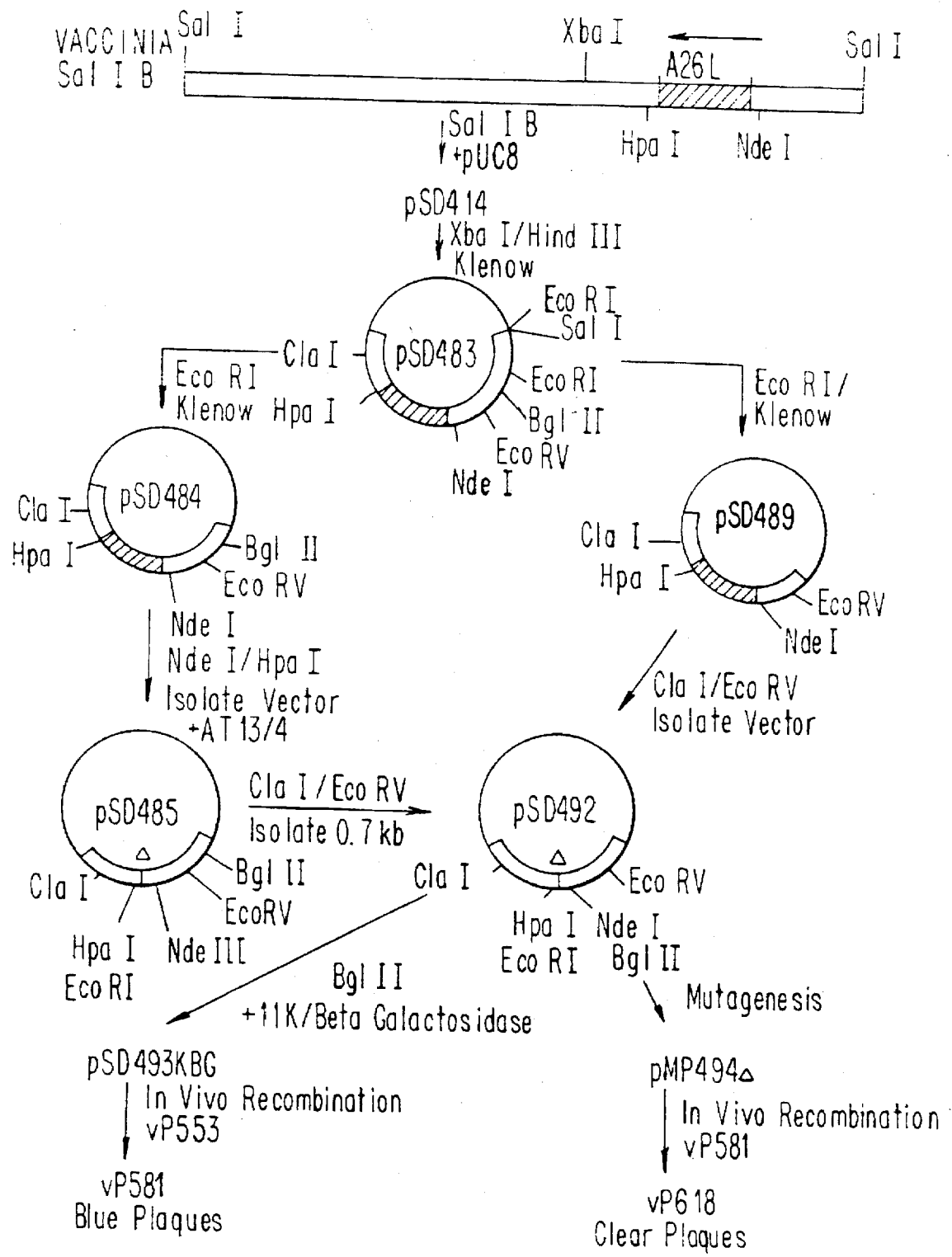
FIG. 12 schematically shows a method for the construction of plasmid pMP494Δ for deletion of ATI region and generation of recombinant vaccinia virus vP618.

Referring now to FIG. 12, pSD414 contains SalI B cloned into pUC8. To remove unwanted DNA sequences to the left of the A26L region, pSD414 was cut with ubaI within vaccinia sequences (pos. 137,079) and with HindIII at the pUC/vaccinia junction, then blunt ended with Klenow fragment of *E. coli* polymerase and ligated, resulting in plasmid pSD483. To remove unwanted vaccinia DNA sequences to the right of the A26L region, pSD483 was cut with EcoRI (pos. 140,665 and at the pUC/vaccinia junction) and ligated, forming plasmid pSD484. To remove the A26L coding region, pSD484 was cut with NdeI (partial) slightly upstream from the A26L ORF (pos. 139,004) and with HpaI (pos. 137,889) slightly downstream from the A26L ORF. The 5.2 kb vector fragment was isolated and ligated with annealed synthetic oligonucleotides ATI3/ATI4 (SEQ ID NO:35/SEQ ID NO:36)

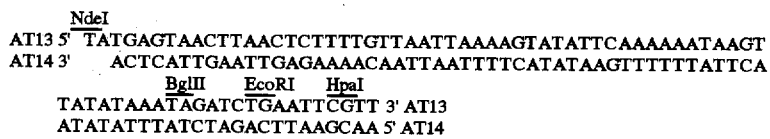

reconstructing the region upstream from A26L and replacing the A26L ORF with a short polylinker region containing the restriction sites BglII, EcoRI and HpaI, as indicated above. The resulting plasmid was designated pSD485. Since the BglII and EcoRI sites in the polylinker region of pSD485 are not unique, unwanted BglII and EcoRI sites were removed from plasmid pSD483 (described above) by digestion with BglII (pos. 140,136) and with EcoRI at the pUC/vaccinia junction, followed by blunt ending with Klenow fragment of *E. coli* polymerase and ligation. The resulting plasmid was designated pSD489. The 1.8 kb ClaI (pos. 137,198)/EcoRV (pos. 139,048) fragment from pSD489 containing the A26L ORF was replaced with the corresponding 0.7 kb polylinker-containing ClaI/EcoRV fragment from pSD485, generating pSD492. The ulII and EcoRI sites in the polylinker region of pSD492 are unique.

A 3.3 kb BglII cassette containing the *E. coli* Beta-galactosidase gene (Shapira et al., 1983) under the control of the vaccinia 11 kDa promoter (Bertholet et al., 1985; Perkus et al., 1990) was inserted into the BglII site of pSD492, forming pSD493KBG. Plasmid pSD493KBG was used in recombination with rescuing virus vP553. Recombinant vaccinia virus, vP581, containing Beta-galactosidase in the A26L deletion region, was isolated as a blue plaque in the presence of X-gal.

To generate a plasmid for the removal of Beta-galactosidase sequences from vaccinia recombinant virus vP581, the polylinker region of plasmid pSD492 was deleted by mutagenesis (Mandecki, 1986) using synthetic oligonucleotide MPSYN177 (SEQ ID NO:37) (5' AAAATGGGCGTGGATTGTTAACTT-TATATAACTTATTTTTTGAATATAC 3'). In the resulting plasmid, pMP494A, vaccinia DNA encompassing positions [137,889–138,937], including the entire A26L ORF is deleted. Recombination between the pMP494Δ and the Beta-galactosidase containing vaccinia recombinant, vP581, resulted in vaccinia deletion mutant vP618, which was isolated as a clear plaque in the presence of X-gal.

Example 16

CONSTRUCTION OF PLASMID pSD467 FOR DELETION OF HEMAGGLUTININ GENE (A56R)

Figure 13:
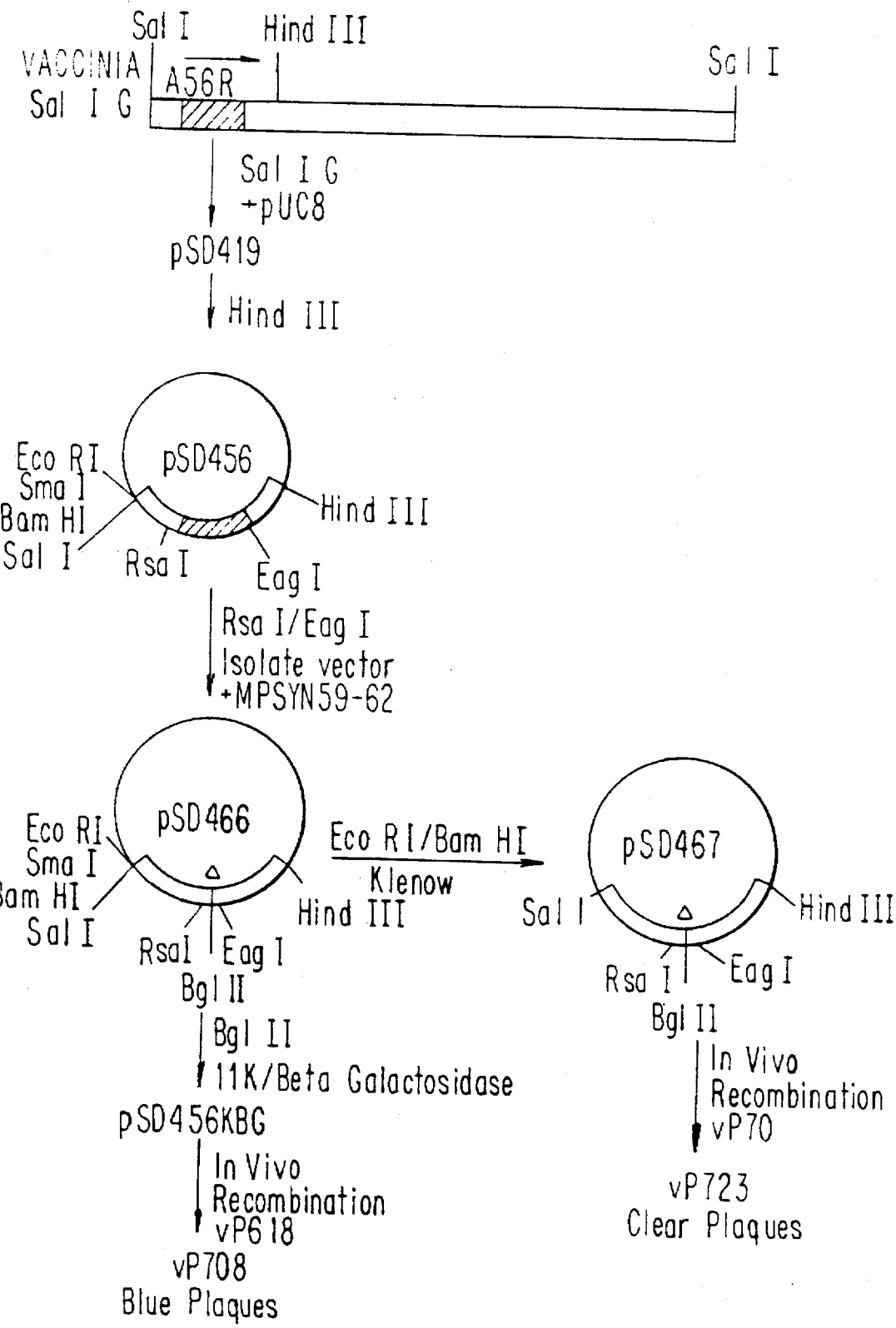
FIG. 13 schematically shows a method for the construction of plasmid pSD467 for deletion of hemagglutinin gene and generation of recombinant vaccinia virus vP723.

Referring now to FIG. 13, vaccinia SalI G restriction fragment (pos. 160,744–173,351) crosses the HindIII A/B junction (pos. 162,539). pSD419 contains vaccinia SalI G cloned into pUC8. The direction of transcription for the hemagglutinin (HA) gene is indicated by an arrow in FIG. 13. Vaccinia sequences derived from HindIII B were removed by digestion of pSD419 with HindIII within vaccinia sequences and at the pUC/vaccinia junction followed by ligation. The resulting plasmid, pSD456, contains the HA gene, A56R, flanked by 0.4 kb of vaccinia sequences to the left and 0.4 kb of vaccinia sequences to the right. A56R coding sequences were removed by cutting pSD456 with RsaI (partial; pos. 161,090) upstream from A56R coding sequences, and with EagI (pos. 162,054) near the end of the gene. The 3.6 kb RsaI/EagI vector fragment from pSD456 was isolated and ligated with annealed synthetic oligonucleotides MPSYN59 (SEQ ID NO:38), MPSYN62 (SEQ ID NO:39), MPSYN60 (SEQ ID NO:40), and MPSYN61 (SEQ ID NO:41)

reconstructing the DNA sequences upstream from the A56R ORF and replacing the A56R ORF with a polylinker region as indicated above. The resulting plasmid is pSD466. The vaccinia deletion in pSD466 encompasses positions [161,185–162,053]. The site of the deletion in pSD466 is indicated by a triangle in FIG. 13.

A 3.2 kb BuII/BamHI (partial) cassette containing the *E. coli* Beta-galactosidase gene (Shapira et al., 1983) under the control of the vaccinia 11 kDa promoter (Bertholet et al., 1985; Guo et al., 1989) was inserted into the BglII site of pSD466, forming pSD466KBG. Plasmid pSD466KBG was used in recombination with rescuing virus vP618. Recombinant vaccinia virus, vP708, containing Beta-galactosidase in the A56R deletion, was isolated as a blue plaque in the presence of X-gal.

Beta-galactosidase sequences were deleted from vP708 using donor plasmid pSD467. pSD467 is identical to pSD466, except that EcoRI, SmaI and BamHI sites were removed from the pUC/vaccinia junction by digestion of pSD466 with EcoRI/BamHI followed by blunt ending with Klenow fragment of *E. coli* polymerase and ligation. Recombination between vP708 and pSD467 resulted in recombinant vaccinia deletion mutant, vP723, which was isolated as a clear plaque in the presence of X-gal.

Example 17

CONSTRUCTION OF PLASMID pMPCSK1Δ FOR DELETION OF OPEN READING FRAMES [C7LT-K1L]

Figure 14:
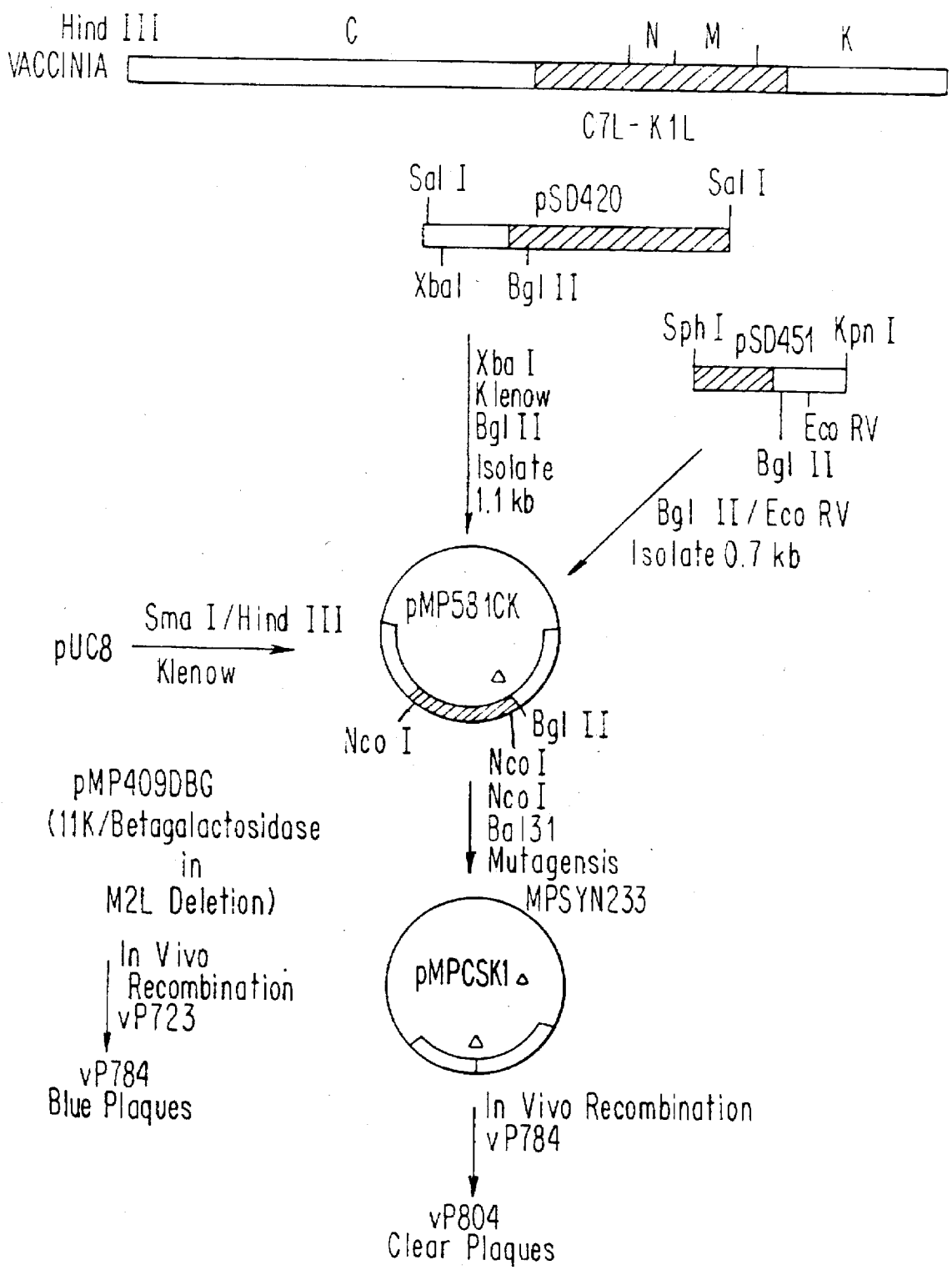
FIG. 14 schematically shows a method for the construction of plasmid pMPCK1Δ for deletion of gene cluster [C7L–K1L] and generation of recombinant vaccinia virus vP804.

Referring now to FIG. 14, the following vaccinia clones were utilized in the construction of pMPCSK1Δ. pSD420 is SalI H cloned into pUC8. pSD435 is KpnI F cloned into pUC18. pSD435 was cut with SphI and religated, forming pSD451. In pSD451, DNA sequences to the left of the SphI site (pos. 27,416) in HindIII M are removed (Perkus et al., 1990). pSD409 is HindIII M cloned into pUC8.

To provide a substrate for the deletion of the [C7L–K1L] gene cluster from vaccinia, *E. coli* Beta-galactosidase was first inserted into the vaccinia M2L deletion locus (Guo et al., 1990) as follows. To eliminate the BglII site in pSD409, the plasmid was cut with BglII in vaccinia sequences (pos. 28,212) and with BamHI at the pUC/vaccinia junction, then ligated to form plasmid pMP409B. pMP409B was cut at the unique SphI site (pos. 27,416). M2L coding sequences were removed by mutagenesis (Guo et al., 1990; Mandecki, 1986) using synthetic oligonucleotide

```
              RsaI
MPSYN59 5' ACACGAATGATTTTCTAAAGTATTTGGAAAGTTTTATAGGT —
MPSYN62 3' TGTGCTTACTAAAAGATTTCATAAACCTTTCAAAATATCCA —
MPSYN59    AGTTGATAGAACAAAATACATAATTT 3'
           TCAACTATCT 5'
MPSYN60 5'                          TGTAAAAATAAATCACTTTTTATA —
MPSYN61 3' TGTTTTATGTATTAAAACATTTTTATTTAGTGAAAAATAT —
            BglII   SmaI    PstI   EagI
MPSYN60 CTAAGATCTCCCGGGCTGCAGC         3'
MPSYN61 GATTCTAGAGGGCCCGACGTCGCCGG 5'
```

```
                                    BglII
MPSYN82 (SEQ ID NO:42)  5'  TTTCTGTATATTTGCACCAATTTAGATCTT —
                            ACTCAAAATATGTAACAATA 3'
```

The resulting plasmid, pMP409D, contains a unique BglII site inserted into the M2L deletion locus as indicated above. A 3.2 kb BamHI (partial)/BglII cassette containing the E. coli Beta-galactosidase gene (Shapira et al., 1983) under the control of the 11 kDa promoter (Bertholet et al., 1985) was inserted into pMP409D cut with BglII. The resulting plasmid, pMP409DBG (Guo et al., 1990), was used as donor plasmid for recombination with rescuing vaccinia virus vP723. Recombinant vaccinia Virus, vP784, containing Beta-galactosidase inserted into the M2L deletion locus, was isolated as a blue plaque in the presence of X-gal.

A plasmid deleted for vaccinia genes [C7L–K1L] was assembled in pUC8 cut with SmaI, HindIII and blunt ended with Klenow fragment of E. coli polymerase. The left flanking arm consisting of vaccinia HindIII C sequences was obtained by digestion of pSD420 with XbaI (pos. 18,628) followed by blunt ending with Klenow fragment of E. coli polymerase and digestion with BglII (pos. 19,706). The right flanking arm consisting of vaccinia HindIII K sequences was obtained by digestion of pSD451 with BglII (pos. 29,062) and EcoRV (pos. 29,778). The resulting plasmid, pMP581CK is deleted for vaccinia sequences between the BglII site (pos. 19,706) in HindIII C and the BglII site (pos. 29,062) in HindIII K. The site of the deletion of vaccinia sequences in plasmid pMP581CK is indicated by a triangle in FIG. 14.

To remove excess DNA at the vaccinia deletion junction, plasmid pMP581CK, was cut at the NcoI sites within vaccinia sequences (pos. 18,811; 19,655), treated with Bal-31 exonuclease and subjected to mutagenesis (Mandecki, 1986) using synthetic oligonucleotide MPSYN233 (SEQ ID NO:43) 5'-TGTCATTTAACACTATACTCATATTAAT AAAAATAATATTTATT-3'. The resulting plasmid, pMPCSK1Δ, is deleted for vaccinia sequences positions 18,805–29,108, encompassing 12 vaccinia open reading frames [C7L–K1L]. Recombination between pMPCSK1Δ and the Beta-galactosidase containing vaccinia recombinant, vP784, resulted in vaccinia deletion mutant, vP804, which was isolated as a clear plaque in the presence of X-gal.

Example 18

CONSTRUCTION OF PLASMID pSD548 FOR DELETION OF LARGE SUBUNIT, RIBONUCLEOTIDE REDUCTASE (I4L)

Figure 15:
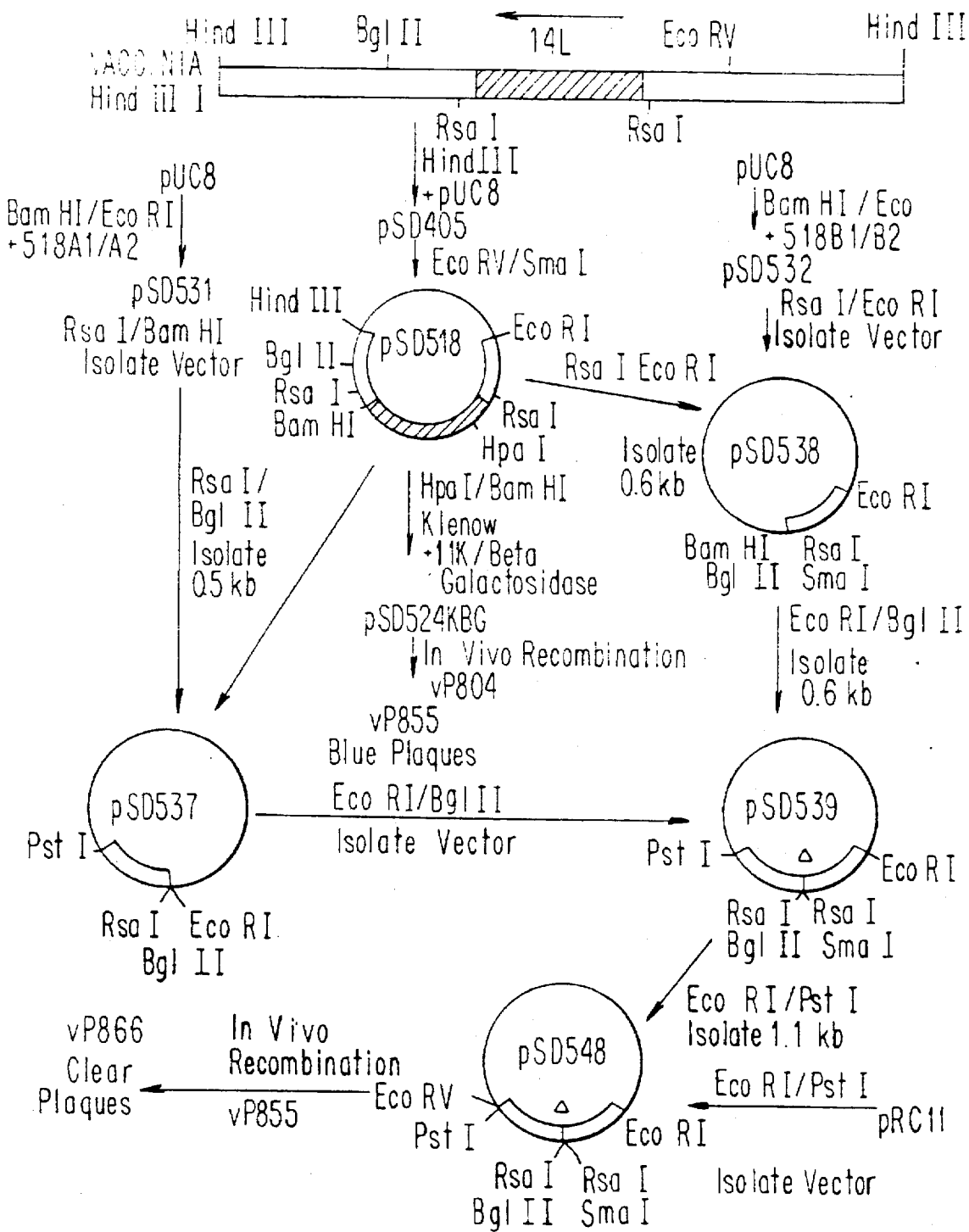
FIG. 15 schematically shows a method for the construction of plasmid pSD548 for deletion of large subunit, ribonucleotide reductase and generation of recombinant vaccinia virus vpS866 (NYVAC)

Referring now to FIG. 15, plasmid pSD405 contains vaccinia HindIII I (pos. 63,875–70,367) cloned in pUC8. pSD405 was digested with EuoRV within vaccinia sequences (pos. 67,933) and with SmaI at the pUC/vaccinia junction, and ligated, forming plasmid pSD518. pSD518 was used as the source of all the vaccinia restriction fragments used in the construction of pSD548.

The vaccinia I4L gene extends from position 67,371–65,059. Direction of transcription for I4L is indicated by an arrow in FIG. 15. To obtain a vector plasmid fragment deleted for a portion of the I4L coding sequences, pSD518 was digested with BamHI (pos. 65,381) and HpaI (pos. 67,001) and blunt ended using Klenow fragment of E. coli polymerase. This 4.8 kb vector fragment was ligated with a 3.2 kb SmaI cassette containing the E. coli Beta-galactosidase gene (Shapira et al., 1983) under the control of the vaccinia 11 kDa promoter (Bertholet et al., 1985; Perkus et al., 1990), resulting in plasmid pSD524KBG. pSD524KBG was used as donor plasmid for recombination with vaccinia virus vP804. Recombinant vaccinia virus, vP855, containing Beta-galactosidase in a partial deletion of the I4L gene, was isolated as a blue plaque in the presence of X-gal.

To delete Beta-galactosidase and the remainder of the I4L ORF from vP855, deletion plasmid pSD548 was constructed. The left and right vaccinia flanking arms were assembled separately in pUC8 as detailed below and presented schematically in FIG. 15.

To construct a vector plasmid to accept the left vaccinia flanking arm, pUC8 was cut with BamHI/EcoRI and ligated with annealed synthetic oligonucleotides 518A1/518A2 (SEQ ID NO:44/SEQ ID NO:45)

```
              BamHI    RsaI
518A1 5' GATCCTGAGTACTTTGTAATATAATGATATATATTTTCACTTTATCTCAT
518A2 3'      GACTCATGAAACATTATATTACTATATATAAAAGTGAAATAGAGTA
               BglII    EcoRI
         TTGAGAATAAAAAGATCTTAGG      3' 518A1
``` forming plasmid pSD531. pSD531 was cut with RsaI (partial) and BamHI and a 2.7 kb vector fragment isolated. pSD518 was cut with BulII (pos. 64,459)/RsaI (pos. 64,994) and a 0.5 kb fragment isolated. The two fragments were ligated together, forming pSD537, which contains the complete vaccinia flanking arm left of the I4L coding sequences.

To construct a vector plasmid to accept the right vaccinia flanking arm, pUC8 was cut with BamHI/EcoRI and ligated with annealed synthetic oligonucleotides 518B1/518B2 (SEQ ID NO:46/SEQ ID NO:47)

```
         BamHI   BglII   SmaI
518B1    GATCCGATCTCCCGGGAAAAAAATTATTTAACTTTTCATTAATAG—
518B2         GCTAGAGGGCCCTTTTTTAATAAATTGAAAAGTAATTATC—
                                  RsaI      EcoRI
         GGATTTGACGTATGTAGGTACTAGG         3' 518B1
         CCTAAACTGCATACTACGCATGATCCTTAA 5' 518B2
``` forming plasmid pSD532. pSD532 was cut with RsaI (partial)/EcoRI and a 2.7 kb vector fragment isolated. pSD518 was cut with RsaI within vaccinia sequences (pos. 67,436) and EcoRI at the vaccinia/pUC junction, and a 0.6 kb fragment isolated. The two fragments were ligated together, forming pSD538, which contains the complete vaccinia flanking arm to the right of I4L coding sequences.

The right vaccinia flanking arm was isolated as a 0.6 kb EcoRI/BglII fragment from pSD538 and ligated into pSD537 vector plasmid cut with EcoRI/BglII. In the resulting plasmid, pSD539, the I4L ORF (pos. 65,047–67,386) is replaced by a polylinker region, which is flanked by 0.6 kb vaccinia DNA to the left and 0.6 kb vaccinia DNA to the right, all in a pUC background. The site of deletion within vaccinia sequences is indicated by a triangle in FIG. 15. To avoid possible recombination of Beta-galactosidase sequences in the pUC-derived portion of pSD539 with Beta-galactosidase sequences in recombinant vaccinia virus vP855, the vaccinia I4L deletion cassette was moved from pSD539 into pRC11, a pUC derivative from which all Beta-galactosidase sequences have been removed and replaced with a polylinker region (Colinas et al., 1990). pSD539 was cut with EcoRI/PstI and the 1.2 kb fragment isolated. This fragment was ligated into pRC11 cut with EcoRI/PstI (2.35 kb), forming pSD548. Recombination between pSD548 and the Beta-galactosidase containing vaccinia recombinant, vP855, resulted in vaccinia deletion mutant vP866, which was isolated as a clear plaque in the presence of X-gal.

DNA from recombinant vaccinia virus vP866 was analyzed by restriction digests followed by electrophoresis on an agarose gel. The restriction patterns were as expected. Polymerase chain reactions (PCR) (Engelke et al., 1988) using vP866 as template and primers flanking the six deletion loci detailed above produced DNA fragments of the expected sizes. Sequence analysis of the PCR generated fragments around the areas of the deletion junctions confirmed that the junctions were as expected. Recombinant vaccinia virus vP866, containing the six engineered deletions as described above, was designated vaccinia vaccine strain "NYVAC."

Example 19

INSERTION OF A RABIES GLYCOPROTEIN G GENE INTO NYVAC

The gene encoding rabies glycoprotein G under the control of the vaccinia H6 promoter (Taylor et al., 1988a,b) was inserted into TK deletion plasmid pSD513. pSD513 is identical to plasmid pSD460 (FIG. 10) except for the presence of a polylinker region.

Figure 16:
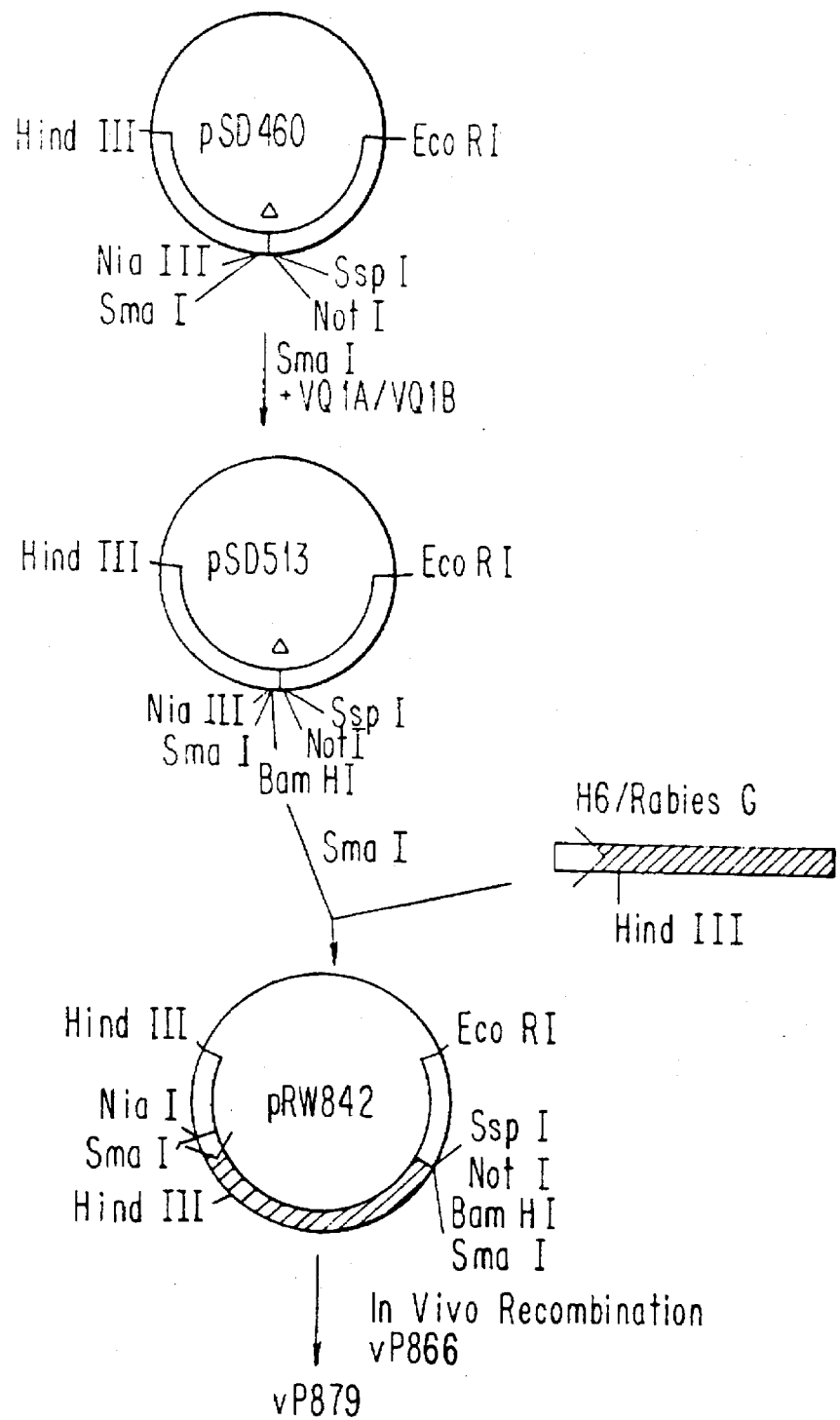
FIG. 16 schematically shows a method for the construction of plasmid pRW842 for insertion of rabies glycoprotein G gene into the TK deletion locus and generation of recombinant vaccinia virus vP879.

Referring now to FIG. 16, the polylinker region was inserted by cutting pSD460 with SmaI and ligating the plasmid vector with annealed synthetic oligonucleotides VQ1A/VQ1B (SEQ ID NO:48/SEQ ID NO:49)

rescuing virus (vP866). Recombinant vaccinia virus vP879 was identified by plaque hybridization using $^{32}$P-labelled DNA probe to rabies glycoprotein G coding sequences.

The modified recombinant viruses of the present invention provide advantages as recombinant vaccine vectors. The attenuated virulence of the vector advantageously reduces the opportunity for the possibility of a runaway infection due to vaccination in the vaccinated individual and also diminishes transmission from vaccinated to unvaccinated individuals or contamination of the environment.

The modified recombinant viruses are also advantageously used in a method for expressing a gene product in a cell cultured in vitro by introducing into the cell the modified recombinant virus having foreign DNA which codes for and expresses gene products in the cell.

Example 20

CONSTRUCTION OF TROVAC-NDV EXPRESSING THE FUSION AND HEMAGGLUTININ-NEURAMINIDASE GLYCOPROTEINS OF NEWCASTLE DISEASE VIRUS

This example describes the development of TROVAC, a fowlpox virus vector and, of a fowlpox Newcastle Disease Virus recombinant designated TROVAC-NDV and its safety and efficacy. A fowlpox virus (FPV) vector expressing both F and HN genes of the virulent NDV strain Texas was constructed. The recombinant produced was designated TROVAC-NDV. TROVAC-NDV expresses authentically processed NDV glycoproteins in avian cells infected with the recombinant virus and inoculation of day old chicks protects against subsequent virulent NDV challenge.

Cells and Viruses. The Texas strain of NDV is a velogenic strain. Preparation of cDNA clones of the F and HN genes has been previously described (Taylor et al., 1990; Edbauer et al., 1990). The strain of FPV designated FP-1 has been described previously (Taylor et al., 1988a). It is a vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chicken embryo fibroblast cells. The virus was subjected to four successive plaque purifications. One plaque isolate was further amplified in primary CEF cells and a stock virus, designated as TROVAC, established. The stock virus used in the in vitro recombination test to produce TROVAC-NDV had been subjected to twelve passages in primary CEF cells from the plaque isolate.

Construction of a cassette for NDV-F. A 1.8 kbp BamHI fragment containing all but 22 nucleotides from the 5' end of the F protein coding sequence was excised from pNDV81 (Taylor et al., 1990) and inserted at the BamHI site of pUC18 to form pCE13. The vaccinia virus H6 promoter previously described (Taylor et al., 1988a,b; Guo et al.,

```
        SmaI   BglII   XhoI   PstI   NarI   BamHI
VQ1A  5'  GGGAGATCTCTCGAGCTGCAGGGCGCCGGATCCTTTTTCT   3'
VQ1B  3'    CCCTCTAGAGAGCTCGACGTCCCGCGGCCTAGGAAAAAGA  5'
``` to form vector plasmid pSD513. pSD513 was cut with SmaI and ligated with a SmaI ended 1.8 kb cassette containing the gene encoding the rabies glycoprotein G gene under the control of the vaccinia H6 promoter (Taylor et al., 1988a,b). The resulting plasmid was designated pRW842. pRW842 was used as donor plasmid for recombination with NYVAC 1989; Perkus et al., 1989) was inserted into pCE13 by digesting pCE13 with SalI, filling in the sticky ends with Klenow fragment of E. coli DNA polymerase and digesting with HindIII. A HindIII-EcoRV fragment containing the H6 promoter sequence was then inserted into pCE13 to form pCE38. A perfect 5' end was generated by digesting pCE38 with KpnI and NruI and inserting the annealed and kinased oligonucleotides CE75 (SEQ ID NO:50) and CE76 (SEQ ID NO:51) to generate pCE47.

CE75: CGATATCCGTTAAGTTTGTATCGTAATGGGCTCCAGATCTTCTACCAGGATCCCGGTAC

CE76: CGGGATCCTGGTAGAAGATCTGGAGCCCATTACGATACAAACTTAACGGATATCG.

In order to remove non-coding sequence from the 3' end of the NDV-F a SmaI to PstI fragment from pCE13 was inserted into the SmaI and PstI sites of pUC18 to form pCE23. The non-coding sequences were removed by sequential digestion of pCE23 with SacI, BamHI, Exonuclease III, SI nuclease and EcoRI. The annealed and kinased oligonucleotides CE42 (SEQ ID NO:52) and CE43 (SEQ ID NO:53) were then inserted to form pCE29.

CE42: AATTCGAGCTCCCCGGG

CE43: CCCGGGGAGCTCG

The 3' end of the NDV-F sequence was then inserted into plasmid pCE20 already containing the 5' end of NDV-F by cloning a PstI-SacI fragment from pCE29 into the PstI and SacI sites of pCE20 to form pCE32. Generation of pCE20 has previously been described in Taylor et al., 1990.

In order to align the H6 promoter and NDV-F 5' sequences contained in pCE47 with the 3' NDV-F sequences contained in pCE32, a HindIII-PstI fragment of pCE47 was inserted into the HindIII and PstI sites of pCE32 to form pCE49. The H6 promoted NDV-F sequences were then transferred to the de-ORFed F8 locus (described below) by cloning a HindIII-NruI fragment from pCE49 into the HindIII and SmaI sites of pJCA002 (described below) to form pCE54. Transcription stop signals were inserted into pCE54 by digesting pCE54 with SacI, partially digesting with BamHI and inserting the annealed and kinased oligonucleotides CE166 (SEQ ID NO:54) and CE167 (SEQ ID NO:55) to generate pCE58.

CE166: CTTTTTATAAAAAGTTAACTACGTAG

CE167: GATCCTACGTAGTTAACTTTTTATAAAAAGAGCT

A perfect 3' end for NDV-F was obtained by using the polymerase chain reaction (PCR) with pCE54 as template and oligonucleotides CE182 (SEQ ID NO:56) and CE183 (SEQ ID NO:57) as primers.

CE182: CTTAACTCAGCTGACTATCC

CE183: TACGTAGTTAACTTTTTATAAAAATCATATTTTTGTAGTGGCTC

The PCR fragment was digested with PvuII and HpaI and cloned into pCE58 that had been digested with HpaI and partially digested with PvuII. The resulting plasmid was designated pCE64. Translation stop signals were inserted by cloning a HindIII-HpaI fragment which contains the complete H6 promoter and F coding sequence from pCE64 into the HindIII and HpaI sites of pRW846 to generate pCE71, the final cassette for NDV-F. Plasmid pRW846 is essentially equivalent to plasmid pJCA002 (described below) but containing the H6 promoter and transcription and translation stop signals. Digestion of pRW846 with HindIII and HpaI eliminates the H6 promoter but leaves the stop signals intact.

Construction of Cassette for NDV-HN. Construction of plasmid pRW802 was previously described in Edbauer et al., 1990. This plasmid contains the NDV-HN sequences linked to the 3' end of the vaccinia virus H6 promoter in a pUC9 vector. A HindIII-EcoRV fragment encompassing the 5' end of the vaccinia virus H6 promoter was inserted into the HindIII and EcoRV sites of pRW802 to form pRW830. A perfect 3' end for NDV-HN was obtained by inserting the annealed and kinased oligonucleotides CE162 (SEQ ID NO:58) and CE163 (SEQ ID NO:59) into the EcoRI site of pRW830 to form pCE59, the final cassette for NDV-HN.

CE162:

AATTCAGGATCGTTCCTTTACTAGTTGAGATTCTCAAGGATGATGGGATTTAATTTTTAT

AAGCTTG

CE163:

AATTCAAGCTTATAAAAATTAAATCCCATCATCCTTGAGAATCTCAACTAGTAAAGGAAC

GATCCTG

Construction of FPV Insertion Vector. Plasmid pRW731 15 contains a 10kb PvuII-PvuII fragment cloned from genomic DNA. The nucleotide sequence was determined on both strands for a 3660 bp PvuII-EcoRV fragment. The limits of an open reading frame designated here as F8 were determined. Plasmid pRW761 is a sub-clone of pRW731-15 containing a 2430 bp EcoRV-EcoRV fragment. The F8ORF was entirely contained between an XbaI site and an SspI site in pRW761. In order to create an insertion plasmid which on recombination with TROVAC genomic DNA would eliminate the F8 ORF, the following steps were followed. Plasmid pRW761 was completely digested with XbaI and partially digested with SspI. A 3700 bp XbaI-SspI band was isolated from the gel and ligated with the annealed double-stranded oligonucleotides JCA017 (SEQ ID NO:60) and JCA018 (SEQ ID NO:61).

JCA017:5'

CTAGACACTTTATGTTTTTTAATATCCGGTCTTAAAAGCTTCCCGGGGATCCTTATACGG

GGAATAAT

JCA018:5'

ATTATTCCCCGTATAAGGATCCCCCGGGAAGCTTTTAAGACCGGATATTAAAAAACATAA

AGTGT

The plasmid resulting from this ligation was designated pJCA002.

Construction of Double Insertion vector for NDV F and HN. The H6 promoted NDV-HN sequence was inserted into the H6 promoted NDV-F cassette by cloning a HindIII fragment from pCE59 that had been filled in with Klenow fragment of E. coli DNA polymerase into the HpaI site of pCE71 to form pCE80. Plasmid pCE80 was completely digested with NdeI and partially digested with BglII to generate an NdeI-BglII 4760 bp fragment containing the NDV F and HN genes both driven by the H6 promoter and linked to F8 flanking arms. Plasmid pJCA021 was obtained by inserting a 4900 bp PvuII-HindII fragment from pRW731-15 into the SmaI and HindII sites of pBSSK+. Plasmid pJCA021 was then digested with NdeI and. BglII and ligated to the 4760 bp NdeI-BglII fragment of pCE80 to form pJCA024. Plasmid pJCA024 therefore contains the NDV-F and HN genes inserted in opposite orientation with 3' ends adjacent between FPV flanking arms. Both genes are linked to the vaccinia virus H6 promoter. The right flanking arm adjacent to the NDV-F sequence consists of 2350 bp of FPV sequence. The left flanking arm adjacent to the NDV-HN sequence consists of 1700 bp of FPV sequence.

Development of TROVAC-NDV. Plasmid pJCA024 was transfected into TROVAC infected primary CEF cells by using the calcium phosphate precipitation method previously described (Panicali et al., 1982; Piccini et al., 1987). Positive plaques were selected on the basis of hybridization to specific NDV-F and HN radiolabelled probes and subjected to five sequential rounds of plaque purification until a pure population was achieved. One representative plaque was then amplified and the resulting TROVAC recombinant was designated TROVAC-NDV (vFP96).

Immunofluorescence. Indirect immunofluorescence was performed as described (Taylor et al., 1990) using a polyclonal anti-NDV serum and, as mono-specific reagents, sera produced in rabbits against vaccinia virus recombinants expressing NDV-F or NDV-HN.

Immunoprecipitation. Immunoprecipitation reactions were performed as described (Taylor et al., 1990) using a polyclonal anti-NDV serum obtained from SPAFAS Inc., Storrs, CT.

The stock virus was screened by in situ plaque hybridization to confirm that the F8ORF was deleted. The correct insertion of the NDV genes into the TROVAC genome and the deletion of the F8ORF was also confirmed by Southern blot hybridization.

In NDV-infected cells, the F glycoprotein is anchored in the membrane via a hydrophobic transmembrane region near the carboxyl terminus and requires post-translational cleavage of a precursor, $F_0$, into two disulfide linked polypeptides $F_1$ and $F_2$. Cleavage of $F_0$ is important in determining the pathogenicity of a given NDV strain (Homma and Ohuchi, 1973; Nagai et al., 1976; Nagai et al., 1980), and the sequence of amino acids at the cleavage site is therefore critical in determining viral virulence. It has been determined that amino acids at the cleavage site in the NDV-F sequence inserted into FPV to form recombinant vFP29 had the sequence Arg-Arg-Gln-Arg-Arg (SEQ ID NO:42) (Taylor et al., 1990) which conforms to the sequence found to be a requirement for virulent NDV strains (Chambers et al., 1986; Espion et al., 1987; Le et al., 1988; McGinnes and Morrison, 1986; Toyoda et al., 1987). The HN glycoprotein synthesized in cells infected with virulent strains of NDV is an uncleaved glycoprotein of 74 kDa. Extremely avirulent strains such as Ulster and Queensland encode an HN precursor (HNo) which requires cleavage for activation (Garten et al., 1980).

The expression of F and HN genes in TROVAC-NDV was analyzed to confirm that the gene products were authentically processed and presented. Indirect-immunofluorescence using a polyclonal anti-NDV chicken serum confirmed that immunoreactive proteins were presented on the infected cell surface. To determine that both proteins were presented on the plasma membrane, mono-specific rabbit sera were produced against vaccinia recombinants expressing either the F or HN glycoproteins. Indirect immunofluorescence using these sera confirmed the surface presentation of both proteins.

Immunoprecipitation experiments were performed by using ($^{35}$S) methionine labeled lysates of CEF cells infected with parental and recombinant viruses. The expected values of apparent molecular weights of the glycosylated forms of $F_1$ and $F_2$ are 54.7 and 10.3 kDa respectively (Chambers et al., 1986). In the immunoprecipitation experiments using a polyclonal anti-NDV serum, fusion specific products of the appropriate size were detected from the NDV-F single recombinant vFP29 (Taylor et al., 1990) and the TROVAC-NDV double recombinant vFP96. The HN glycoprotein of appropriate size was also detected from the NDV-HN single recombinant VFP-47 (Edbauer et al., 1990) and TROVAC-NDV. No NDV specific products were detected from uninfected and parental TROVAC infected CEF cells.

In CEF cells, the F and HN glycoproteins are appropriately presented on the infected cell surface where they are recognized by NDV immune serum. Immunoprecipitation analysis indicated that the $F_0$ protein is authentically cleaved to the $F_1$ and $F_2$ components required in virulent strains. Similarly, the HN glycoprotein was authentically processed in CEF cells infected with recombinant TROVAC-NDV.

Previous reports (Taylor et al., 1990; Edbauer et al., 1990; Boursnell et al., 1990a,b,c; Ogawa et al., 1990) would indicate that expression of either HN or F alone is sufficient to elicit protective immunity against NDV challenge. Work on other paramyxoviruses has indicated, however, that antibody to both proteins may be required for full protective immunity. It has been demonstrated that SV5 virus could spread in tissue culture in the presence of antibody to the HN glycoprotein but not to the F glycoprotein (Merz et al., 1980). In addition, it has been suggested that vaccine failures with killed measles virus vaccines were due to inactivation of the fusion component (Norrby et al., 1975).

Since both NDV glycoproteins have been shown to be responsible for eliciting virus neutralizing antibody (Avery et al., 1979) and both glycoproteins, when expressed individually in a fowlpox vector are able to induce a protective immune response, it can be appreciated that the most efficacious NDV vaccine should express both glycoproteins.

Example 21

CONSTRUCTION OF ALVAC RECOMBINANTS EXPRESSING RABIES VIRUS GLYCOPROTEIN G

This example describes the development of ALVAC, a canarypox virus vector and, of a canarypox-rabies recombinant designated as ALVAC-RG (vCP65) and its safety and efficacy.

Cells and Viruses. The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC.

Construction of a Canarypox Insertion Vector. An 880 bp canarypox PvuII fragment was cloned between the PvuII sites of pUC9 to form pRW764.5. The sequence of this fragment is shown in FIG. 17 (SEQ ID NO:62) between positions 1372 and 2251. The limits of an open reading frame designated as C5 were defined. It was determined that the open reading frame was initiated at position 166 within the fragment and terminated at position 487. The C5 deletion was made without interruption of open reading frames. Bases from position 167 through position 455 were replaced with the sequence (SEQ ID NO:63) GCTTCCCGGGAAT-TCTAGCTAGCTAGTTT. This replacement sequence contains HindIII, SmaI and EcoRI insertion sites followed by translation stops and a transcription termination signal recognized by vaccinia virus RNA polymerase (Yuen et al., 1987). Deletion of the C5ORF was performed as described below. Plasmid pRW764.5 was partially cut with RsaI and the linear product was isolated. The RsaI linear fragment was recut with BglII and the pRW764.5 fragment now with a RsaI to BglII deletion from position 156 to position 462 was isolated and used as a vector for the following synthetic oligonucleotides:

Construction of Insertion Vector Containing the Rabies G Gene. Construction of pRW838 is illustrated below. Oligonucleotides A through E, which overlap the translation initiation codon of the H6 promoter with the ATG of rabies G, were cloned into pUC9 as pRW737. Oligonucleotides A through E contain the H6 promoter, starting at NruI, through the HindIII site of rabies G followed by BglII. Sequences of oligonucleotides A through E ((SEQ ID NO:66)–(SEQ ID NO:70)) are:

RW145 (SEQ ID NO:64): ACTCTCAAAAGCTTCCCGGGAATTCTAGCTAGCTAGTTTTTATAAA

RW146 (SEQ ID NO:65): GATCTTTATAAAAACTAGCTAGCTAGAATTCCCGGGAAGCTTTTGAGAGT

Oligonucleotides RW145 and RW146 were annealed and inserted into the pRW 764.5 RsaI and BglII vector described above. The resulting plasmid is designated pRW831.

A (SEQ ID NO:66): CTGAAATTATTTCATTATCGCGATATCCGTTAA

GTTTGTATCGTAATGGTTCCTCAGGCTCTCCTGTTTGT

B (SEQ ID NO:67): CATTACGATACAAACTTAACGGATATCGCGATAA TGAAATAATTTCAG

C (SEQ ID NO:68): ACCCCTTCTGGTTTTTCCGTTGTGTTTTGGGAAA

TTCCCTATTTACACGATCCCAGACAAGCTTAGATCTCAG

D (SEQ ID NO:69): CTGAGATCTAAGCTTGTCTGGGATCGTGTAAATA GGGAATTTCCCAAAACA

E (SEQ ID NO:70): CAACGGAAAAACCAGAAGGGGTACAAACAGGAGA GCCTGAGGAAC

The diagram of annealed oligonucleotides A through E is as follows:

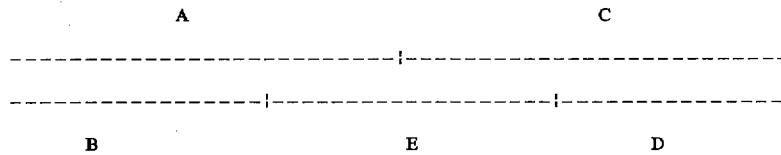

Oligonucleotides A through E were kinased, annealed (95° C. for 5 minutes, then cooled to room temperature), and inserted between the PvuII sites of pUC9. The resulting plasmid, pRW737, was cut with HindIII and BglII and used as a vector for the 1.6 kbp HindIII-BglII fragment of ptg155PRO (Kieny et al., 1984) generating pRW739. The ptg155PRO HindIII site is 86 bp downstream of the rabies G translation initiation codon. BglII is downstream of the rabies G translation stop codon in ptg155PRO. pRW739 was partially cut with NruI, completely cut with BglII, and a 1.7 kbp NruI-BalII fragment, containing the 3' end of the H6 promoter previously described (Taylor et al., 1988a,b; Guo et al., 1989; Perkus et al., 1989) through the entire rabies G gene, was inserted between the NruI and BamHI sites of pRW824. The resulting plasmid is designated pRW832. Insertion into pRW824 added the H6 promoter 5' of NruI. The pRW824 sequence of BamHI followed by SmaI is (SEQ ID NO:77): GGATCCCCGGG. pRW824 is a plasmid that contains a nonpertinent gene linked precisely to the vaccinia virus H6 promoter. Digestion with NruI and BamHI completely excised this nonpertinent gene. The 1.8 kbp pRW832 SmaI fragment, containing H6 promoted rabies G, was inserted into the SmaI of pRW831, to form plasmid pRW838.

Development of ALVAC-RG. Plasmid pRW838 was transfected into ALVAC infected primary CEF cells by using the calcium phosphate precipitation method previously described (Panicali et al., 1982; Piccini et al., 1987). Positive plaques were selected on the basis of hybridization to a specific rabies G probe and subjected to 6 sequential rounds of plaque purification until a pure population was achieved. One representative plaque was then amplified and the resulting ALVAC recombinant was designated ALVAC-RG (vCP65) (see also FIGS. 18A and 18B). The correct insertion of the rabies G gene into the ALVAC genome without subsequent mutation was confirmed by sequence analysis.

Immunofluorescence. During the final stages of assembly of mature rabies virus particles, the glycoprotein component is transported from the golgi apparatus to the plasma membrane where it accumulates with the carboxy terminus extending into the cytoplasm and the bulk of the protein on the external surface of the cell membrane. In order to confirm that the rabies glycoprotein expressed in ALVAC-RG was correctly presented, immunofluorescence was performed on primary CEF cells infected with ALVAC or ALVAC-RG. Immunofluorescence was performed as previously described (Taylor et al., 1990) using a rabies G monoclonal antibody. Strong surface fluorescence was detected on CEF cells infected with ALVAC-RG but not with the parental ALVAC.

Immunoprecipitation. Preformed monolayers of primary CEF, Vero (a line of African Green monkey kidney cells ATCC #CCL81) and MRC-5 cells (a fibroblast-like cell line derived from normal human fetal lung tissue ATCC #CCL171) were inoculated at 10 pfu per cell with parental virus ALVAC and recombinant virus ALVAC-RG in the presence of radiolabelled $^{35}$S-methionine and treated as previously described (Taylor et al., 1990). Immunoprecipitation reactions were performed using a rabies G specific monoclonal antibody. Efficient expression of a rabies. specific glycoprotein with a molecular weight of approximately 67 kDa was detected with the recombinant ALVAC-RG. No rabies specific products were detected in uninfected cells or cells infected with the parental ALVAC virus.

Sequential Passaging Experiment. In studies with ALVAC virus in a range of non-avian species no proliferative infection or overt disease was observed (Taylor et al., 1991b). However, in order to establish that neither the parental nor recombinant virus could be adapted to grow in non-avian cells, a sequential passaging experiment was performed.

The two viruses, ALVAC and ALVAC-RG, were inoculated in 10 sequential blind passages in three cell lines:

(1) Primary chick embryo fibroblast (CEF) cells produced from 11 day old white leghorn embryos;
(2) Vero cells—a continuous line of African Green monkey kidney cells (ATCC #CCL81); and
(3) MRC-5 cells—a diploid cell line derived from human fetal lung tissue (ATCC #CCL171).

The initial inoculation was performed at an m.o.i. of 0.1 pfu per cell using three 60mm dishes of each cell line containing 2×10$^6$ cells per dish. One dish was inoculated in the presence of 40µg/ml of Cytosine arabinoside (Ara C), an inhibitor of DNA replication. After an absorption period of 1 hour at 37° C., the inoculum was removed and the monolayer washed to remove unabsorbed virus. At this time the medium was replaced with 5 ml of EMEM+2% NBCS on two dishes (samples t0 and t7) and 5 ml of EMEM+2% NBCS containing 40 µg/ml Ara C on the third (sample t7A). Sample t0 was frozen at −70° C. to provide an indication of the residual input virus. Samples t7 and t7A were incubated at 37° C. for 7 days, after which time the contents were harvested and the cells disrupted by indirect sonication.

One ml of sample t7 of each cell line was inoculated undiluted onto three dishes of the same cell line (to provide samples t0, t7 and t7A) and onto one dish of primary CEF cells. Samples t0, t7 and t7A were treated as for passage one. The additional inoculation on CEF cells was included to provide an amplification step for more sensitive detection of virus which might be present in the non-avian cells.

This procedure was repeated for 10 (CEF and MRC-5) or 8 (Vero) sequential blind passages. Samples were then frozen and thawed three times and assayed by titration on primary CEF monolayers.

Virus yield in each sample was then determined by plaque titration on CEF monolayers under agarose. Summarized results of the experiment are shown in Tables 5 and 6.

The results indicate that both the parental ALVAC and the recombinant ALVAC-RG are capable of sustained replication on CEF monolayers with no loss of titer. In Vero cells, levels of virus fell below the level of detection after 2 passages for ALVAC and 1 passage for ALVAC-RG. In MRC-5 cells, a similar result was evident, and no virus was detected after 1 passage. Although the results for only four passages are shown in Tables 5 and 6 the series was continued for 8 (Vero) and 10 (MRC-5) passages with no detectable adaptation of either virus to growth in the non-avian cells.

In passage 1 relatively high levels of virus were present in the t7 sample in MRC-5 and Vero cells. However this level of virus was equivalent to that seen in the t0 sample and the t7A sample incubated in the presence of Cytosine arabinoside in which no viral replication can occur. This demonstrated that the levels of virus seen at 7 days in non-avian cells represented residual virus and not newly replicated virus.

In order to make the assay more sensitive, a portion of the 7 day harvest from each cell line was inoculated onto a permissive CEF monolayer and harvested at cytopathic effect (CPE) or at 7 days if no CPE was evident. The results of this experiment are shown in Table 7. Even after amplification through a permissive cell line, virus was only detected in MRC-5 and Vero cells for two additional passages. These results indicated that under the conditions used, there was no adaptation of either virus to growth in Vero or MRC-5 cells.

Inoculation of Macaques. Four HIV seropositive macagues were initially inoculated with ALVAC-RG as described in Table 8. After 100 days these animals were re-inoculated to determine a booster effect, and an additional seven animals were inoculated with a range of doses. Blood was drawn at appropriate intervals and sera analyzed, after heat inactivation at 56° C. for 30 minutes, for the presence of anti-rabies antibody using the Rapid Fluorescent Focus Inhibition Assay (Smith et al., 1973).

Inoculation of Chimpanzees. Two adult male chimpanzees (50 to 65 kg weight range) were inoculated intramuscularly or subcutaneously with $1 \times 10^7$ pfu of vCP65. Animals were monitored for reactions and bled at regular intervals for analysis for the presence of anti-rabies antibody with the RFFI test (Smith et al., 1973). Animals were re-inoculated with an equivalent dose 13 weeks after the initial inoculation.

Inoculation of Mice. Groups of mice were inoculated with 50 to 100 µl of a range of dilutions of different batches of vCP65. Mice were inoculated in the footpad. On day 14, mice were challenged by intracranial inoculation of from 15 to 43 mouse $LD_{50}$ of the virulent CVS strain of rabies virus. Survival of mice was monitored and a protective dose 50% ($PD_{50}$) calculated at 28 days post-inoculation.

Inoculation Of Dogs and Cats. Ten beagle dogs, 5 months old, and 10 cats, 4 months old, were inoculated subcutaneously with either 6.7 or 7.7 $\log_{10}$ $TCID_{50}$ of ALVAC-RG. Four dogs and four cats were not inoculated. Animals were bled at 14 and 28 days post-inoculation and anti-rabies antibody assessed in an RFFI test. The animals receiving 6.7 $\log_{10}$ $TCID_{50}$ of ALVAC-RG were challenged at 29 days post-vaccination with 3.7 $\log_{10}$ mouse $LD_{50}$ (dogs) or 4.3 $\log_{10}$ mouse $LD_{50}$ (cats) of the NYGS rabies virus challenge strain.

Inoculation of Squirrel Monkeys. Three groups of four squirrel monkeys (*Saimiri sciureus*) were inoculated with one of three viruses (a) ALVAC, the parental canarypox virus, (b) ALVAC-RG, the recombinant expressing the rabies G glycoprotein or (c) vCP37, a canarypox recombinant expressing the envelope glycoprotein of feline leukemia virus. Inoculations were performed under ketamine anaesthesia. Each animal received at the same time: (1) 20 µl instilled on the surface of the right eye without scarification; (2) 100 µl as several droplets in the mouth; (3) 100 µl in each of two intradermal injection sites in the shaven skin of the external face of the right arm; and (4) 100 µl in the anterior muscle of the right thigh.

Four monkeys were inoculated with each virus, two with a total of 5.0 $\log_{10}$ pfu and two with a total of 7.0 $\log_{10}$ pfu. Animals were bled at regular intervals and sera analyzed for the presence of antirabies antibody using an RFFI test (Smith et al., 1973). Animals were monitored daily for reactions to vaccination. Six months after the initial inoculation the four monkeys receiving ALVAC-RG, two monkeys initially receiving vCP37, and two monkeys initially receiving ALVAC, as well as one naive monkey were inoculated with 6.5 $\log_{10}$ pfu of ALVAC-RG subcutaneously. Sera were monitored for the presence of rabies neutralizing antibody in an RFFI test (Smith et al., 1973).

Inoculation of Human Cell Lines with ALVAC-RG. In order to determine whether efficient expression of a foreign gene could be obtained in non-avian cells in which the virus does not productively replicate, five cell types, one avian and four non-avian, were analyzed for virus yield, expression of the foreign rabies G gene and viral specific DNA accumulation. The cells inoculated were:

(a) Vero, African Green monkey kidney cells, ATCC #CCL81;

(b) MRC-5, human embryonic lung, ATCC #CCL 171;

(c) WISH human amnion, ATCC #CCL 25;

(d) Detroit-532, human foreskin, Downs's syndrome, ATCC #CCL 54; and (e) Primary CEF cells.

Chicken embryo fibroblast cells produced from 11 day old white leghorn embryos were included as a positive control. All inoculations were performed on preformed monolayers of $2 \times 10^6$ cells as discussed below.

A. Methods for DNA analysis

Three dishes of each cell line were inoculated at 5 pfu/cell of the virus under test, allowing one extra dish of each cell line un-inoculated. One dish was incubated in the presence of 40 µg/ml of cytosine arabinoside (Ara C). After an adsorption period of 60 minutes at 37° C., the inoculum was removed and the monolayer washed twice to remove unadsorbed virus. Medium (with or without Ara C) was then replaced. Cells from one dish (without Ara C) were harvested as a time zero sample. The remaining dishes were incubated at 37° C. for 72 hours, at which time the cells were harvested and used to analyze DNA accumulation. Each sample of $2 \times 10^6$ cells was resuspended in 0.5 ml phosphate buffered saline (PBS) containing 40 mM EDTA and incubated for 5 minutes at 37° C. An equal volume of 1.5% agarose prewarmed at 42° C. and containing 120 mM EDTA was added to the cell suspension and gently mixed. The suspension was transferred to an agarose plug mold and allowed to harden for at least 15 min. The agarose plugs were then removed and incubated for 12–16 hours at 50° C. in a volume of lysis buffer (1% sarkosyl, 100 µg/ml proteinase K, 10 mM Tris HCl pH 7.5, 200 mM EDTA) that completely covers the plug. The lysis buffer was then replaced with 5.0 ml sterile 0.5× TBE (44.5 mM Tris-borate, 44.5 mM boric acid, 0.5 mM EDTA) and equilibrated at 4°

C. for 6 hours with 3 changes of TBE buffer. The viral DNA within the plug was fractionated from cellular RNA and DNA using a pulse field electrophoresis system. Electrophoresis was performed for 20 hours at 180 V with a ramp of 50–90 sec at 15° C. in 0.5× TBE. The DNA was run with lambda DNA molecular weight Standards. After electrophoresis the vital DNA band was visualized by staining with ethidium bromide. The DNA was then transferred to a nitrocellulose membrane and probed with a radiolabelled probe prepared from purified ALVAC genomic DNA.

B. Estimation of virus yield

Dishes were inoculated exactly as described above, with the exception that input multiplicity was 0.1 pfu/cell. At 72 hours post infection, cells were lysed by three successive cycles of freezing and thawing. Virus yield was assessed by plaque titration on CEF monolayers.

C. Analysis of expression of Rabies G gene Dishes were inoculated with recombinant or parental virus at a multiplicity of 10 pfu/cell, allowing an additional dish as an uninfected virus control. After a one hour absorption period, the medium was removed and replaced with methionine free medium. After a 30 minute period, this medium was replaced with methionine-free medium containing 25 uCi/ml of $^{35}$S-Methionine. Infected cells were labelled overnight (approximately 16 hours), then lysed by the addition of buffer A lysis buffer. Immunoprecipitation was performed as previously described (Taylor et al., 1990) using a rabies G specific monoclonal antibody.

Results: Estimation of Viral Yield. The results of titration for yield at 72 hours after inoculation at 0.1 pfu per cell are shown in Table 9. The results indicate that while a productive infection can be attained in the avian cells, no increase in virus yield can be detected by this method in the four non-avian cell systems.

Analysis of Viral DNA Accumulation. In order to determine whether the block to productive viral replication in the non-avian cells occurred before or after DNA replication, DNA from the cell lysates was fractionated by electrophoresis, transferred to nitrocellulose and probed for the presence of viral specific DNA. DNA from uninfected CEF cells, ALVAC-RG infected CEF cells at time zero, ALVAC-RG infected CEF cells at 72 hours post-infection and ALVAC-RG infected CEF cells at 72 hours post-infection in the presence of 40 µg/ml of cytosine arabinoside all showed some background activity, probably due to contaminating CEF cellular DNA in the radiolabelled ALVAC DNA probe preparation. However, ALVAC-RG infected CEF cells at 72 hours post-infection exhibited a strong band in the region of approximately 350 kbp representing ALVAC-specific viral DNA accumulation. No such band is detectable when the culture is incubated in the presence of the DNA synthesis inhibitor, cytosine arabinoside. Equivalent samples produced in Vero cells showed a very faint band at approximately 350 kbp in the ALVAC-RG infected Vero cells at time zero. This level represented residual virus. The intensity of the band was amplified at 72 hours post-infection indicating that some level of viral specific DNA replication had occurred in Vero cells which had not resulted in an increase in viral progeny. Equivalent samples produced in MRC-5 cells indicated that no viral specific DNA accumulation was detected under these conditions in this cell line. This experiment was then extended to include additional human cell lines, specifically WISH and Detroit-532 cells. ALVAC infected CEF cells served as a positive control. No viral specific DNA accumulation was detected in either WISH or Detroit cells inoculated with ALVAC-RG. It should be noted that the limits of detection of this method have not been fully ascertained and vital DNA accumulation may be occurring, but at a level below the sensitivity of the method. Other experiments in which viral DNA replication was measured by $^3$H-thymidine incorporation support the results obtained with Vero and MRC-5 cells.

Analysis of Rabies Gene Expression. To determine if any vital gene expression, particularly that of the inserted foreign gene, was occurring in the human cell lines even in the absence of viral DNA replication, immunoprecipitation experiments were performed on $^{35}$S-methionine labelled lysates of avian and non-avian cells infected with ALVAC and ALVAC-RG. The results of immunoprecipitation using a rabies G specific monoclonal antibody illustrated specific immunoprecipitation of a 67 kDa glycoprotein in CEF, Vero and MRC-5, WISH and Detroit cells infected with ALVAC-RG. No such specific rabies gene products were detected in any of the uninfected and parentally infected cell lysates.

The results of this experiment indicated that in the human cell lines analyzed, although the ALVAC-RG recombinant was able to initiate an infection and express a foreign gene product under the transcriptional control of the H6 early/late vaccinia virus promoter, the replication did not proceed through DNA replication, nor was there any detectable vital progeny produced. In the Vero cells, although some level of ALVAC-RG specific DNA accumulation was observed, no viral progeny was detected by these methods. These results would indicate that in the human cell lines analyzed the block to viral replication occurs prior to the onset of DNA replication, while in Vero cells, the block occurs following the onset of viral DNA replication.

In order to determine whether the rabies glycoprotein expressed in ALVAC-RG was immunogenic, a number of animal species were tested by inoculation of the recombinant. The efficacy of current rabies vaccines is evaluated in a mouse model system. A similar test was therefore performed using ALVAC-RG. Nine different preparations of virus (including one vaccine batch (J) produced after 10 serial tissue culture passages of the seed virus) with infectious titers ranging from 6.7 to 8.4 $\log_{10}$ TCID$_{50}$ per ml were serially diluted and 50 to 100 µl of dilutions inoculated into the footpad of four to six week old mice. Mice were challenged 14 days later by the intracranial route with 300 µl of the CVS strain of rabies virus containing from 15 to 43 mouse LD$_{50}$ as determined by lethality titration in a control group of mice. Potency, expressed as the PD$_{50}$ (Protective dose 50%), was calculated at 14 days post-challenge. The results of the experiment are shown in Table 10. The results indicated that ALVAC-RG was consistently able to protect mice against rabies virus challenge with a PD$_{50}$ value ranging from 3.33 to 4.56 with a mean value of 3.73 (STD 0.48). As an extension of this study, male mice were inoculated intracranially with 50 µl of virus containing 6.0 $\log_{10}$ TCID$_{50}$ of ALVAC-RG or with an equivalent volume of an uninfected cell suspension. Mice were sacrificed on days 1, 3 and 6 post-inoculation and their brains removed, fixed and sectioned. Histopathological examination showed no evidence for neurovirulence of ALVAC-RG in mice.

In order to evaluate the safety and efficacy of ALVAC-RG for dogs and cats, a group of 14, 5 month old beagles and 14, 4 month old cats were analyzed. Four animals in each species were not vaccinated. Five animals received 6.7 $\log_{10}$ TCID$_{50}$ subcutaneously and five animals received 7.7 $\log_{10}$ TCID$_{50}$ by the same route. Animals were bled for analysis for anti-rabies antibody. Animals receiving no inoculation or 6.7 $\log_{10}$ TCID$_{50}$ of ALVAC-RG were challenged at 29 days post-vaccination with 3.7 $\log_{10}$ mouse LD$_{50}$ (dogs, in the temporal muscle) or 4.3 log₁₀ mouse LD₅₀ (cats, in the neck) of the NYGS rabies virus challenge strain. The results of the experiment are shown in Table 11.

No adverse reactions to inoculation were seen in either cats or dogs with either dose of inoculum virus. Four of 5 dogs immunized with 6.7 log₁₀ TCID₅₀ had antibody titers on day 14 post-vaccination and all dogs had titers at 29 days. All dogs were protected from a challenge which killed three out of four controls. In cats, three of five cats receiving 6.7 log₁₀ TCID₅₀ had specific antibody titers on day 14 and all cats were positive on day 29 although the mean antibody titer was low at 2.9 IU. Three of five cats survived a challenge which killed all controls. All cats immunized with 7.7 log₁₀ TCID₅₀ had antibody titers on day 14 and at day 29 the Geometric Mean Titer was calculated as 8.1 International Units.

The immune response of squirrel monkeys (*Saimiri sciureus*) to inoculation with ALVAC, ALVAC-RG and an unrelated canarypox virus recombinant was examined. Groups of monkeys were inoculated as described above and sera analyzed for the presence of rabies specific antibody. Apart from minor typical skin reactions to inoculation by the intradermal route, no adverse reactivity was seen in any of the monkeys. Small amounts of residual virus were isolated from skin lesions after intradermal inoculation on days two and four post-inoculation only. All specimens were negative on day seven and later. There was no local reaction to intra-muscular injection. All four monkeys inoculated with ALVAC-RG developed anti-rabies serum neutralizing antibodies as measured in an RFFI test. Approximately six months after the initial inoculation all monkeys and one additional naive monkey were re-inoculated by the subcutaneous route on the external face of the left thigh with 6.5 log₁₀ TCID₅₀ of ALVAC-RG. Sera were analyzed for the presence of anti-rabies antibody. The results are shown in Table 12.

Four of the five monkeys naive to rabies developed a serological response by seven days post-inoculation with ALVAC-RG. All five monkeys had detectable antibody by 11 days post-inoculation. Of the four monkeys with previous exposure to the rabies glycoprotein, all showed a significant increase in serum neutralization titer between days 3 and 7 post-vaccination. The results indicate that vaccination of squirrel monkeys with ALVAC-RG does not produce adverse side-effects and a primary neutralizing antibody response can be induced. An amnanestic response is also induced on re-vaccination. Prior exposure to ALVAC or to a canarypox recombinant expressing an unrelated foreign gene does not interfere with induction of an anti-rabies immune response upon re-vaccination.

The immunological response of HIV-2 seropositive macaques to inoculation with ALVAC-RG was assessed. Animals were inoculated as described above and the presence of anti-rabies serum neutralizing antibody assessed in an RFFI test. The results, shown in Table 13, indicated that HIV-2 positive animals inoculated by the subcutaneous route developed anti-rabies antibody by 11 days after one inoculation. An amnanestic response was detected after a booster inoculation given approximately three months after the first inoculation. No response was detected in animals receiving the recombinant by the oral route. In addition, a series of six animals were inoculated with decreasing doses of ALVAC-RG given by either the intra-muscular or subcutaneous routes. Five of the six animals inoculated responded by 14 days post-vaccination with no significant difference in antibody titer.

Two chimpanzees with prior exposure to HIV were inoculated with 7.0 log₁₀ pfu of ALVAC-RG by the subcutaneous or intra-muscular route. At 3 months post-inoculations both animals were re-vaccinated in an identical fashion. The results are shown in Table 14.

No adverse reactivity to inoculation was noted by either intramuscular or subcutaneous routes. Both chimpanzees responded to primary inoculation by 14 days and a strongly rising response was detected following re-vaccination.

TABLE 5

Sequential Passage of ALVAC in Avian and non-Avian Cells.

| | CEF | Vero | MRC-5 |
|---|---|---|---|
| Pass 1 | | | |
| Sample t0[a] | 2.4 | 3.0 | 2.6 |
| t7[b] | 7.0 | 1.4 | 0.4 |
| t7A[c] | 1.2 | 1.2 | 0.4 |
| Pass 2 | | | |
| Sample t0 | 5.0 | 0.4 | N.D.[d] |
| t7 | 7.3 | 0.4 | N.D. |
| t7A | 3.9 | N.D. | N.D. |
| Pass 3 | | | |
| Sample t0 | 5.4 | 0.4 | N.D. |
| t7 | 7.4 | N.D. | N.D. |
| t7A | 3.8 | N.D. | N.D. |
| Pass 4 | | | |
| Sample t0 | 5.2 | N.D. | N.D. |
| t7 | 7.1 | N.D. | N.D. |
| t7A | 3.9 | N.D. | N.D. |

[a]This sample was harvested at zero time and represents the residual input virus. The titer is expressed as log₁₀ pfu per ml.
[b]This sample was harvested at 7 days post-infection.
[c]This sample was inoculated in the presence of 40 µg/ml of Cytosine arabinoside and harvested at 7 days post infection.
[d]Not detectable

TABLE 6

Sequential Passage of ALVAC-RG in Avian and non-Avian Cells

| | CEF | Vero | MRC-5 |
|---|---|---|---|
| Pass 1 | | | |
| Sample t0[a] | 3.0 | 2.9 | 2.9 |
| t7[b] | 7.1 | 1.0 | 1.4 |
| t7A[c] | 1.8 | 1.4 | 1.2 |
| Pass 2 | | | |
| Sample t0 | 5.1 | 0.4 | 0.4 |
| t7 | 7.1 | N.D.[d] | N.D. |
| t7A | 3.8 | N.D. | N.D. |
| Pass 3 | | | |
| Sample t0 | 5.1 | 0.4 | N.D. |
| t7 | 7.2 | N.D. | N.D. |
| t7A | 3.6 | N.D. | N.D. |
| Pass 4 | | | |
| Sample t0 | 5.1 | N.D. | N.D. |
| t7 | 7.0 | N.D. | N.D. |
| t7A | 4.0 | N.D. | N.D |

[a]This sample was harvested at zero time and represents the residual input virus. The titer is expressed as log₁₀ pfu per ml.
[b]This sample was harvested at 7 days post-infection.
[c]This sample was inoculated in the presence of 40 µg/ml of Cytosine arabinoside and harvested at 7 days post-infection.
[d]Not detectable.

TABLE 7

Amplification of residual virus by passage in CEF cells

| CEF | Vero | MRC-5 |
|---|---|---|
| a) ALVAC | | |
| Pass 2[a] | 7.0[b] | 6.0 | 5.2 |
| 3 | 7.5 | 4.1 | 4.9 |
| 4 | 7.5 | N.D.[c] | N.D. |
| 5 | 7.1 | N.D. | N.D. |
| b) ALVAC-RG | | |
| Pass 2[a] | 7.2 | 5.5 | 5.5 |
| 3 | 7.2 | 5.0 | 5.1 |
| 4 | 7.2 | N.D. | N.D. |
| 5 | 7.2 | N.D. | N.D. |

[a]Pass 2 represents the amplification in CEF cells of the 7 day sample from Pass 1.
[b]Titer expressed as $\log_{10}$ pfu per ml
[c]Not Detectable

TABLE 8

Schedule of inoculation of rhesus macaques with ALVAC-RG (vCP65)

| Animal | | Inoculation |
|---|---|---|
| 176L | Primary: | $1 \times 10^8$ pfu of vCP65 orally in TANG |
| | Secondary: | $1 \times 10^7$ pfu of vCP65 plus $1 \times 10^7$ pfu of vCP82[a] by SC route |
| 185L | Primary: | $1 \times 10^8$ pfu of vCP65 orally in Tang |
| | Secondary: | $1 \times 10^7$ pfu of vCP65 plus $1 \times 10^7$ pfu of vCP82 by SC route |
| 177L | Primary: | $5 \times 10^7$ pfu SC of vCP65 by SC route |
| | Secondary: | $1 \times 10^7$ pfu of vCP65 plus $1 \times 10^7$ pfu of vCP82 by SC route |
| 186L | Primary: | $5 \times 10^7$ pfu of vCP65 by SC route |
| | Secondary: | $1 \times 10^7$ pfu of vCP65 plus $1 \times 10^7$ pfu of vCP82 by SC route |
| 178L | Primary: | $1 \times 10^7$ pfu of vCP65 by SC route |
| 182L | Primary: | $1 \times 10^1$ pfu of vCP65 by IM route |
| 179L | Primary: | $1 \times 10^6$ pfu of vCP65 by SC route |
| 183L | Primary: | $1 \times 10^6$ pfu of vCP65 by IM route |
| 180L | Primary: | $1 \times 10^6$ pfu of vCP65 by SC route |
| 184L | Primary: | $1 \times 10^5$ pfu of vCP65 by IM route |
| 187L | Primary | $1 \times 10^7$ pfu of vCP65 orally |

[a]vCP82 is a canarypox virus recombinant expressing the measles virus fusion and hemagglutinin genes.

TABLE 9

Analysis of yield in avian and non-avian cells inoculated with ALVAC-RG

| Sample Time Cell Type | t0 | t72 | t72A[b] |
|---|---|---|---|
| Expt 1 | | | |
| CEF | 3.3[a] | 7.4 | 1.7 |
| Vero | 3.0 | 1.4 | 1.7 |
| MRC-5 | 3.4 | 2.0 | 1.7 |
| Expt 2 | | | |
| CEF | 2.9 | 7.5 | <1.7 |
| WISH | 3.3 | 2.2 | 2.0 |
| Detroit-532 | 2.8 | 1.7 | <1.7 |

[a]Titer expressed as $\log_{10}$ pfu per ml
[b]Culture incubated in the presence of 40 μg/ml of Cytosine arabinoside

TABLE 10

Potency of ALVAC-RG as tested in mice

| Test | Challenge Dose[a] | PD$_{50}$[b] |
|---|---|---|
| Initial seed | 4.3 | 4.56 |
| Primary seed | 2.3 | 3.34 |
| Vaccine Batch H | 2.3 | 4.52 |
| Vaccine Batch I | 2.3 | 3.33 |
| Vaccine Batch K | 1.5 | 3.64 |
| Vaccine Batch L | 1.5 | 4.03 |
| Vaccine Batch M | 1.5 | 3.32 |
| Vaccine Batch N | 1.5 | 3.39 |
| Vaccine Batch J | 2.3 | 3.42 |

[a]Expressed as mouse LD$_{50}$
[b]Expressed as $\log_{10}$ TCID$_{50}$

TABLE 11

Efficacy of ALVAC-RG in dogs and cats

| Dose | Dogs Antibody[a] | Survival[b] | Cats Antibody | Survival |
|---|---|---|---|---|
| 6.7 | 11.9 | 5/5 | 2.9 | 3/5 |
| 7.7 | 10.1 | N.T. | 8.1 | |
| N.T. | | | | |

[a]Antibody at day 29 post inoculation expressed as the geometric mean titer in International Units.
[b]Expressed as a ratio of survivors over animals challenged

TABLE 12

Anti-rabies serological response of Squirrel monkeys inoculated with canarypox recombinants

| Monkey # | Previous Exposure | Rabies serum-neutralizing antibody[a] | | | | | |
|---|---|---|---|---|---|---|---|
| | | −196[b] | 0 | 3 | 7 | 11 | 21 | 28 |
| 22 | ALVAC[c] | NT[g] | <1.2 | <1.2 | <1.2 | 2.1 | 2.3 | 2.2 |
| 51 | ALVAC[c] | NT | <1.2 | <1.2 | 1.7 | 2.2 | 2.2 | 2.2 |
| 39 | vCp37[d] | NT | <1.2 | <1.2 | 1.7 | 2.1 | 2.2 | N.T.[g] |
| 55 | vCp37[d] | NT | <1.2 | <1.2 | 1.7 | 2.2 | 2.1 | N.T. |
| 37 | ALVAC-RG[e] | 2.2 | <1.2 | <1.2 | 3.2 | 3.5 | 3.5 | 3.2 |
| 53 | ALVAC-RG[e] | 2.2 | <1.2 | <1.2 | 3.6 | 3.6 | 3.6 | 3.4 |
| 38 | ALVAC-RG[f] | 2.7 | <1.7 | <1.7 | 3.2 | 3.8 | 3.6 | N.T. |
| 54 | ALVAC-RG[f] | 3.2 | <1.7 | <1.5 | 3.6 | 4.2 | 4.0 | 3.6 |
| 57 | None | NT | <1.2 | <1.2 | 1.7 | 2.7 | 2.7 | 2.3 |

[a]As determined by RFFI test on days indicated and expressed in International Units
[b]Day-196 represents serum from day 28 after primary vaccination
[c]Animals received 5.0 $\log_{10}$ TCID$_{50}$ of ALVAC
[d]Animals received 5.0 $\log_{10}$ TCID$_{50}$ of vCP37
[e]Animals received 5.0 $\log_{10}$ TCID$_{50}$ of ALVAC-RG
[f]Animals received 7.0 $\log_{10}$ TCID$_{50}$ of ALVAC-RG
[g]Not tested.

TABLE 13

Inoculation of rhesus macaques with ALVAC-RG[a]

| | | | | | Route of Primary Inoculation | | | | | |
|---|---|---|---|---|---|---|---|---|---|---|
| Days post- | or/Tang | | SC | SC | SC | IM | SC | IM | SC | IM | OR |
| Inoculation | 176L[b] | 185L | 177L | 186L | 178L | 182L | 179L | 183L | 180L | 184L | 187L[b] |
| −84 | — | — | | | — | | | | | | |
| −9 | — | — | — | — | — | — | | | | | |
| 3 | — | — | — | — | | | | | | | |
| 6 | — | — | ± | ± | | | | | | | |
| 11 | — | — | 16[d] | 128 | | | | | | | |
| 19 | — | — | 32 | 128 | — | | — | | | | |
| 35 | — | — | 32 | 512 | | | | | | | |
| 59 | — | — | 64 | 256 | | | | | | | |
| 75 | — | — | 64 | 128 | — | | — | | | | |
| 99[c] | — | — | 64 | 256 | — | — | — | — | — | — | — |
| 2 | — | — | 32 | 256 | — | — | — | — | — | — | — |
| 6 | — | — | 512 | 512 | — | — | — | — | — | — | — |
| 15 | 16 | 16 | 512 | 512 | 64 | 32 | 64 | 128 | 32 | — | — |
| 29 | 16 | 32 | 256 | 256 | 64 | 64 | 32 | 128 | 32 | — | — |
| 55 | | 32 | | | | 32 | | 32 | 16 | — | |
| 57 | 16 | | 128 | 128 | 16 | | 16 | | | | — |

[a]See Table 9 for schedule of inoculations.
[b]Animals 176L and 185L received 8.0 log$_{10}$ pfu by the oral route in 5 ml Tang. Animal 187L received 7.0 log$_{10}$ pfu by oral route not in Tang.
[c]Day of re-vaccination for animals 176L, 185L, 177L and 186L by S.C. route, and primary vaccination for animals 178L, 182L, 179L, 183L, 180L, 184L and 187L.
[d]Titers expressed as reciprocal of last dilution showing inhibition of fluorescence in an RFFI test.

TABLE 14

Inoculation of chimpanzees with ALVAC-RG

| Weeks post-Inoculation | Animal 431 I.M. | Animal 457 S.C. |
|---|---|---|
| 0 | <8[a] | <8 |
| 1 | <8 | <8 |
| 2 | 8 | 32 |
| 4 | 16 | 32 |
| 8 | 16 | 32 |
| 12[b]/0 | 16 | 8 |
| 13/1 | 128 | 128 |
| 15/3 | 256 | 512 |
| 20/8 | 64 | 128 |
| 26/12 | 32 | 128 |

[a]Titer expressed as reciprocal of last dilution showing inhibition of fluorescence in an RFFI test
[b]Day of re-inoculation Example 22

IMMUNIZATION OF HUMANS USING CANARYPOX EXPRESSING RABIES GLYCOPROTEIN (ALVAC-RG; vCP65)

Figure 18A:
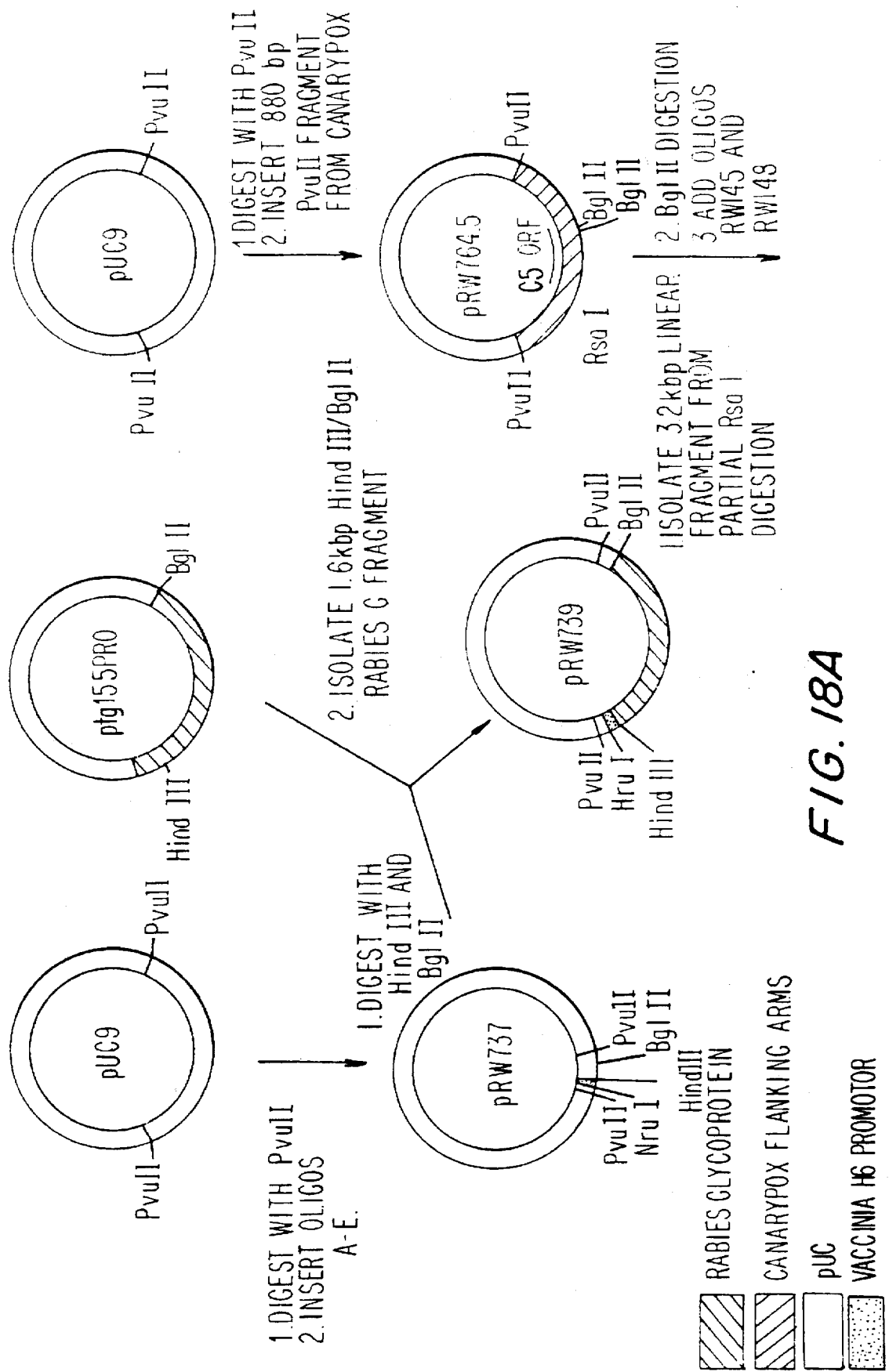
FIGS. 18A and 18B schematically show a method for the construction of recombinant canarypox virus vCP65 (ALVAC-RG)
Figure 18B:
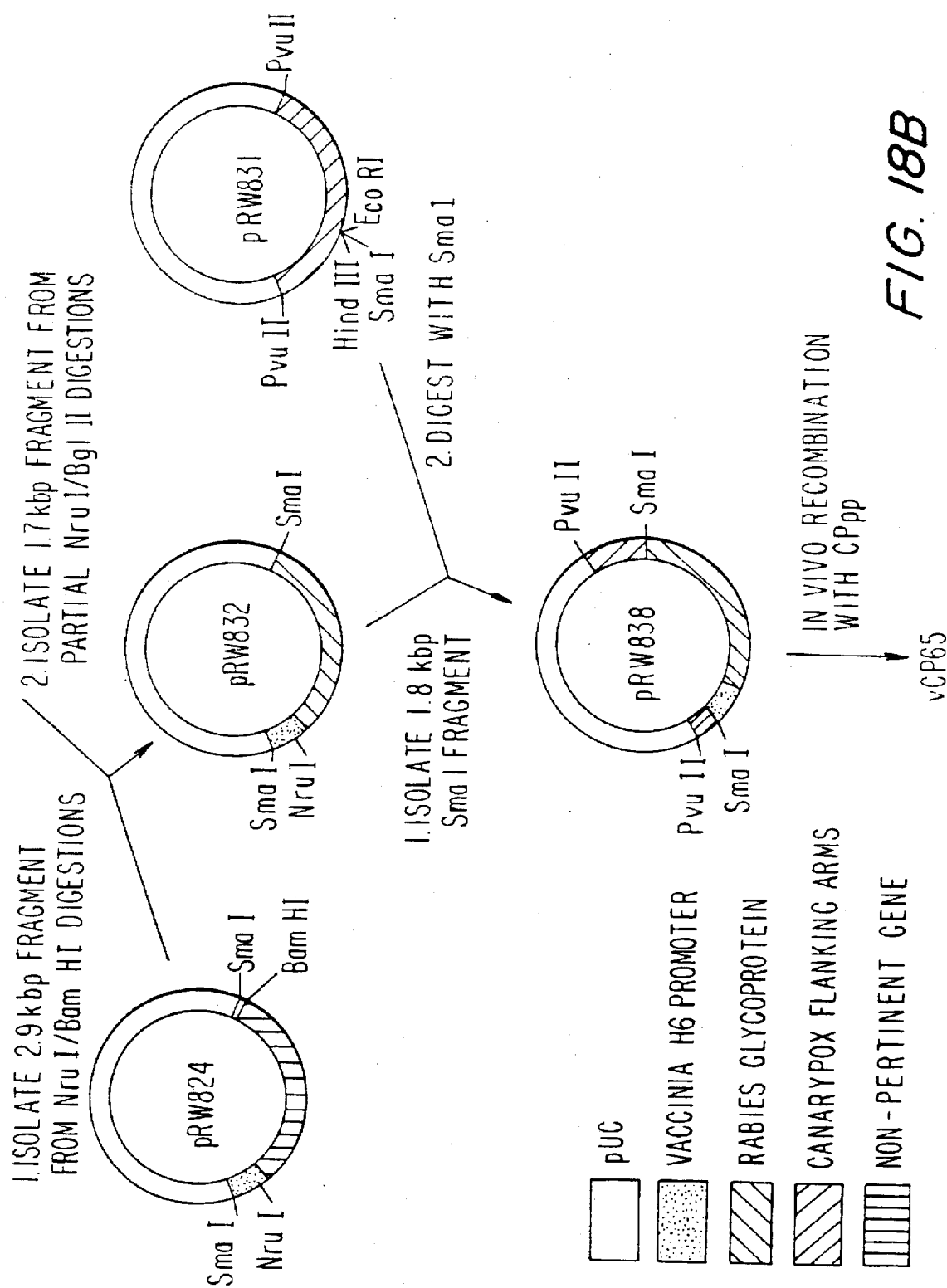

ALVAC-RG (vCP65) was generated as described in Example 21 and FIGS. 18A and 18B. For scaling-up and vaccine manufacturing ALVAC-RG (vCP65) was grown in primary CEF derived from specified pathogen free eggs. Cells were infected at a multiplicity of 0.01 and incubated at 37° C. for three days.

The vaccine virus suspension was obtained by ultrasonic disruption in serum free medium of the infected cells; cell debris were then removed by centrifugation and filtration. The resulting clarified suspension was supplemented with lyophilization stabilizer (mixture of amino-acids), dispensed in single dose vials and freeze dried. Three batches of decreasing titer were prepared by ten-fold serial dilutions of the virus suspension in a mixture of serum free medium and lyophilization stabilizer, prior to lyophilization.

Quality control tests were applied to the cell substrates, media and virus seeds and final product with emphasis on the search for adventitious agents and innocuity in laboratory rodents. No undesirable trait was found.

Preclinical data. Studies in vitro indicated that VERO or MRC-5 cells do not support the growth of ALVAC-RG (vCP65); a series of eight (VERO) and 10 (MRC) blind serial passages caused no detectable adaptation of the virus to grow in these non avian lines. Analyses of human cell lines (MRC-5, WISH, Detroit 532, HEL, HNK or EBV-transformed lymphoblastoid cells) infected or inoculated with ALVAC-RG (vCP65) showed no accumulation of virus specific DNA suggesting that in these cells the block in replication occurs prior to DNA synthesis. Significantly, however, the expression of the rabies virus glycoprotein gene in all cell lines tested indicating that the abortive step in the canarypox replication cycle occurs prior to viral DNA replication.

The safety and efficacy of ALVAC-RG (vCP65) were documented in a series of experiments in animals. A number of species including canaries, chickens, ducks, geese, laboratory rodents (suckling and adult mice), hamsters, guinea-pigs, rabbits, cats and dogs, squirrel monkeys, rhesus macagues and chimpanzees, were inoculated with doses ranging from $10^5$ to $10^8$ pfu. A variety of routes were used, most commonly subcutaneous, intramuscular and intradermal but also oral (monkeys and mice) and intracerebral (mice).

In canaries, ALVAC-RG (vCP65) caused a "take" lesion at the site of scarification with no indication of disease or death. Intradermal inoculation of rabbits resulted in a typical poxvirus inoculation reaction which did not spread and healed in seven to ten days. There was no adverse side effects due to canarypox in any of the animal tests. Immunogenicity was documented by the development of anti-rabies antibodies following inoculation of ALVAC-RG (vCP65) in rodents, dogs, cats, and primates, as measured by Rapid Fluorescent Focus Inhibition Test (RFFIT). Protection was also demonstrated by rabies virus challenge experiments in mice, dogs, and cats immunized with ALVAC-RG (vCP65).

Volunteers. Twenty-five healthy adults aged 20–45 with no previous history of rabies immunization were enrolled. Their health status was assessed by complete medical histories, physical examinations, hematological and blood chemistry analyses. Exclusion criteria included pregnancy, allergies, immune depression of any kind, chronic debilitating disease, cancer, injection of immune globins in the past three months, and seropositivity to human immunodeficiency virus (HIV) or to hepatitis B virus surface antigen.

Study design. Participants were randomly allocated to receive either standard Human Diploid Cell Rabies Vaccine (HDC) batch no E0751 (Pasteur Merieux Serums & Vaccine, Lyon, France) or the study vaccine ALVAC-RG (vCP65).

The trial was designated as a dose escalation study. Three batches of experimental ALVAC-RG (vCP65) vaccine were used sequentially in three groups of volunteers (Groups A, B and C) with two week intervals between each step. The concentration of the three batches was $10^{3.5}$, $10^{4.5}$, $10^{5.5}$ Tissue Culture Infectious Dose ($TCID_{50}$) per dose, respectively.

Each volunteer received two doses of the same vaccine subcutaneously in the deltoid region at an interval of four weeks. The nature of the injected vaccine was not known by the participants at the time of the first injection but was known by the investigator.

In order to minimize the risk of immediate hypersensitivity at the time of the second injection, the volunteers of Group B allocated to the medium dose of experimental vaccine were injected 1 h previously with the lower dose and those allocated to the higher dose (Group C) received successively the lower and the medium dose at hourly intervals.

Six months later, the recipients of the highest dosage of ALVAC-RG (vCP65) (Group C) and HDC vaccine were offered a third dose of vaccine; they were then randomized to receive either the same vaccine as previously or the alternate vaccine. As a result, four groups were formed corresponding to the following immunization scheme:1. HDC, HDC-HDC; 2. HDC, HDC-ALVAC-RG (vCP65); 3. ALVAC-RG (vCP65), ALVAC-RG (vCP65)-HDC; 4. ALVAC-RG (vCP65), ALVAC-RG (vCP65), ALVAC-RG (vCP65).

Monitoring of Side Effects. All subjects were monitored for 1 h after injection and re-examined every day for the next five days. They were asked to record local and systemic reactions for the next three weeks and were questioned by telephone two times a week.

Laboratory Investigators. Blood specimens were obtained before enrollment and two, four and six days after each injection. Analysis included complete blood cell count, liver enzymes and creatine kinase assays.

Antibody assays. Antibody assays were performed seven days prior to the first injection and at days 7, 28, 35, 56, 173, 187 and 208 of the study.

The levels of neutralizing antibodies to rabies were determined using the Rapid Fluorescent Focus Inhibition test (RFFIT) (Smith & Yaeger, In Laboratory Techniques on Rabies). Canarypox antibodies were measured by direct ELISA. The antigen, a suspension of purified canarypox virus disrupted with 0.1% Triton X100, was coated in microplates. Fixed dilutions of the sera were reacted for two hours at room temperature and reacting antibodies were revealed with a peroxidase labelled anti-human IgG goat serum. The results are expressed as the optical density read at 490nm.

Analysis. Twenty-five subjects were enrolled and completed the study. There were 10 males and 15 females and the mean age was 31.9 (21 to 48). All but three subjects had evidence of previous smallpox vaccination; the three remaining subjects had no typical scar and vaccination history. Three subjects received each of the lower doses of experimental vaccine ($10^{3.5}$ and $10^{4.5}$ $TCID_{50}$), nine subjects received $10^{5.5}$ $TCID_{50}$ and ten received the HDC vaccine.

Safety (Table 14). During the primary series of immunization, fever greater than 37.7° C was noted within 24 hours after injection in one HDC recipient (37.8° C.) and in one vCP65 $10^{5.5}$ $TCID_{50}$ recipient (38° C.). No other systemic reaction attributable to vaccination was observed in any participant.

Local reactions were noted in 9/10 recipients of HDC vaccine injected subcutaneously and in 0/3, 1/3 and 9/9 recipients of vCP65 $10^{3.5}$, $10^{4.5}$, $10^{5.5}$ $TCID^{50}$, respectively.

Tenderness was the most common symptoms and was always mild. Other local symptoms included redness and induration which were also mild and transient. All symptoms usually subsided within 24 hours and never lasted more than 72 hours.

There was no significant change in blood cell counts, liver enzymes or creatine kinase values.

Immune Responses: Neutralizing Antibodies to Rabies (Table 16 ). Twenty eight days after the first injection all the HDC recipients had protective titers ($\geq 0.5$ IU/ml). By contrast none in groups A and B ($10^{3.5}$ and $10^{4.5}$ $TCID_{50}$) and only 2/9 in group C ($10^{5.5}$ $TCID_{50}$) ALVAC-RG (vCP65) recipients reached this protective titer.

At day 56 (i.e. 28 days after the second injection) protective titers were achieved in 0/3 of Group A, 2/3 of Group B and 9/9 of Group C recipients of ALVAC-RG (vCP65) vaccine and persisted in all 10 HDC recipients.

At day 56 the geometric mean titers were 0.05, 0.47, 4.4 and 11.5 IU/ml in groups A, B, C and HDC respectively.

At day 180, the rabies antibody titers had substantially decreased in all subjects but remained above the minimum protective titer of 0.5 IU/ml in 5/10 HCD recipients and in 5/9 ALVAC-RG (vCP65) recipients; the geometric mean titers were 0.51 and 0.45 IU/ml in groups HCD and C, respectively.

Antibodies to the Canarypox virus (Table 17). The pre-immune titers observed varied widely with titers varying from 0.22 to 1.23 O.D. units despite the absence of any previous contact with canary birds in those subjects with the highest titers. When defined as a greater than two-fold increase between preimmunization and post second injection titers, a seroconversion was obtained in 1/3 subjects in group B and in 9/9 subjects in group C whereas no subject seroconverted in groups A or HDC.

Booster Injection. The vaccine was similarly well tolerated six months later, at the time of the booster injection: fever was noted in 2/9 HDC booster recipients and in 1/10 ALVAC-RG (vCP65) booster recipients. Local reactions were present in 5/9 recipients of HDC booster and in 6/10 recipients of the ALVAC-RG (vCP65) booster.

Observations. FIGS. 22A–22D shows graphs of rabies neutralizing antibody titers (Rapid Fluorescent Focus Inhibition Test or RFFIT, IU/ml): Booster effect of HDC and vCP65 ($10^{5.5}$ $TCID_{50}$) in volunteers previously immunized with either the same or the alternate vaccine. Vaccines were given at days 0, 28 and 180. Antibody titers were measured at days 0, 7, 28, 35, 56, 173, and 187 and 208.

As shown in FIGS. 22A–22D, the booster dose given resulted in a further increase in rabies antibody titers in every subject whatever the immunization scheme. However, the ALVAC-RG (vCP65) booster globally elicited lower immune responses than the HDC booster and the ALVAC-RG (vCP65), ALVAC-RG (vCP65)-ALVAC-RG (vCP65) group had significantly lower titers than the three other groups. Similarly, the ALVAC-RG (vCP65) booster injection resulted in an increase in canarypox antibody titers in 3/5 subjects who had previously received the HDC vaccine and in all five subjects previously immunized with ALVAC-RG (vCP65).

In general, none of the local side effects from administration of vCP65 was indicative of a local replication of the virus. In particular, lesions of the skin such as those observed after injection of vaccine were absent. In spite of the apparent absence of replication of the virus, the injection resulted in the volunteers generating significant amounts of antibodies to both the canarypox vector and to the expressed rabies glycoprotein.

Rabies neutralizing antibodies were assayed with the Rapid Fluorescent Focus Inhibition Test (RFFIT) which is known to correlate well with the sero neutralization test in mice. Of 9 recipients of $10^{5.5}$ TCID50, five had low level responses after the first dose. Protective titers of rabies antibodies were obtained after the second injection in all recipients of the highest dose tested and even in 2 of the 3 recipients of the medium dose. In this study, both vaccines were given subcutaneously as usually recommended for live vaccines, but not for the inactivated HDC vaccine. This route of injection was selected as it best allowed a careful examination of the injection site, but this could explain the late appearance of antibodies in HDC recipients: indeed, none of the HDC recipients had an antibody increase at day 7, whereas, in most studies where HDC vaccine is give intramuscularly a significant proportion of subjects do (Klietmann et al., Int'l Green Cross—Geneva, 1981; Kuwert et al., Int'l Green Cross—Geneva, 1981). However, this invention is not necessarily limited to the subcutaneous route of administration.

The GMT (geometric mean titers) of rabies neutralizing antibodies was lower with the investigational vaccine than with the HDC control vaccine, but still well above the minimum titer required for protection. The clear dose effect response obtained with the three dosages used in this study suggest that a higher dosage might induce a stronger response. Certainly from this disclosure the skilled artisan can select an appropriate dosage for a given patient.

The ability to boost the antibody response is another important result of this Example; indeed, an increase in rabies antibody titers was obtained in every subject after the 6 month dose whatever the immunization scheme, showing that preexisting immunity elicited by either the canarypox vector or the rabies glycoprotein had no blocking effect on the booster with the recombinant vaccine candidate or the conventional HDC rabies vaccine. This contrasts findings of others with vaccinia recombinants in humans that immune response may be blocked by pre-existing immunity (Cooney et al., Lancet 1991, 337:567–72; Etinger et al., Vaccine 9:470–72, 1991).

Thus, this Example clearly demonstrates that a nonreplicating poxvirus can serve as an immunizing vector in animals or humans, with all of the advantages that replicating agents confer on the immune response, but without the safety problem created by a fully permissive virus.

TABLE 15

Reactions in the 5 days following vaccination

| vCP65 dosage (TCID50) | $10^{3.5}$ | | $10^{4.5}$ | | $10^{5.5}$ | | HDC control | |
|---|---|---|---|---|---|---|---|---|
| Injection | 1st | 2nd | 1st | 2nd | 1st | 2nd | 1st | 2nd |
| No. vaccinees | 3 | 3 | 3 | 3 | 9 | 9 | 10 | 10 |
| temp >37.7° C. | 0 | 0 | 0 | 0 | 0 | 1 | 1 | 0 |
| soreness | 0 | 0 | 1 | 1 | 6 | 8 | 8 | 6 |
| redness | 0 | 0 | 0 | 0 | 0 | 4 | 5 | 4 |
| induration | 0 | 0 | 0 | 0 | 0 | 4 | 5 | 4 |

TABLE 16

Rabies neutralizing antibodies (REFIT; IU/ml) Individual titers and geometric mean titers GMT)

| | | Days | | | | |
|---|---|---|---|---|---|---|
| No. | TCID50/dose | 0 | 7 | 28 | 35 | 56 |
| 1 | $10^{3.5}$ | <0.1 | <0.1 | <0.1 | <0.1 | 0.2 |
| 3 | $10^{3.5}$ | <0.1 | <0.1 | <0.1 | <0.1 | <0.1 |
| 4 | $10^{3.5}$ | <0.1 | <0.1 | <0.1 | <0.1 | <0.1 |
| | G.M.T. | <0.1 | <0.1 | <0.1 | <0.1 | <0.1 |
| 6 | $10^{4.5}$ | <0.1 | <0.1 | <0.1 | <0.1 | <0.1 |
| 7 | $10^{4.5}$ | <0.1 | <0.1 | <0.1 | 2.4 | 1.9 |
| 10 | $10^{4.5}$ | <0.1 | <0.1 | <0.1 | 1.6 | 1.1 |
| | G.M.T. | <0.1 | <0.1 | 0.1 | 0.58 | 0.47 |
| 11 | $10^{5.5}$ | <0.1 | <0.1 | 1.0 | 3.2 | 4.3 |
| 13 | $10^{5.5}$ | <0.1 | <0.1 | 0.3 | 6.0 | 8.8 |
| 14 | $10^{5.5}$ | <0.1 | <0.1 | 0.2 | 2.1 | 9.4 |
| 17 | $10^{5.5}$ | <0.1 | <0.1 | <0.1 | 1.2 | 2.5 |
| 18 | $10^{5.5}$ | <0.1 | <0.1 | 0.7 | 8.3 | 12.5 |
| 20 | $10^{5.5}$ | <0.1 | <0.1 | <0.1 | 0.3 | 3.7 |
| 21 | $10^{5.5}$ | <0.1 | <0.1 | 0.2 | 2.6 | 3.9 |
| 23 | $10^{5.5}$ | <0.1 | <0.1 | <0.1 | 1.7 | 4.2 |
| 25 | $10^{5.5}$ | <0.1 | <0.1 | <0.1 | 0.6 | 0.9 |
| | G.M.T. | <0.1 | <0.1 | 0.16 | 1.9 | 4.4* |
| 2 | HDC | <0.1 | <0.1 | 0.8 | 7.1 | 7.2 |
| 5 | HDC | <0.1 | <0.1 | 9.9 | 12.8 | 18.7 |
| 8 | HDC | <0.1 | <0.1 | 12.7 | 21.1 | 16.5 |
| 9 | HDC | <0.1 | <0.1 | 6.0 | 9.9 | 14.3 |
| 12 | HDC | <0.1 | <0.1 | 5.0 | 9.2 | 25.3 |
| 15 | HDC | <0.1 | <0.1 | 2.2 | 5.2 | 8.6 |
| 16 | HDC | <0.1 | <0.1 | 2.7 | 7.7 | 20.7 |
| 19 | HDC | <0.1 | <0.1 | 2.6 | 9.9 | 9.1 |
| 22 | HDC | <0.1 | <0.1 | 1.4 | 8.6 | 6.6 |
| 24 | HDC | <0.1 | <0.1 | 0.8 | 5.8 | 4.7 |
| | G.M.T. | <0.1 | <0.1 | 2.96 | 9.0 | 11.5* |

*p = 0.007 student t test

TABLE 17

Canarypox antibodies: ELISA Geometric Mean Titers*

| | Days | | | | |
|---|---|---|---|---|---|
| vCP65 dosage TCID50/dose | 0 | 7 | 28 | 35 | 56 |
| $10^{3.5}$ | 0.69 | ND | 0.76 | ND | 0.68 |
| $10^{4.5}$ | 0.49 | 0.45 | 0.56 | 0.63 | 0.87 |
| $10^{5.5}$ | 0.38 | 0.38 | 0.77 | 1.42 | 1.63 |
| HDC control | 0.45 | 0.39 | 0.40 | 0.35 | 0.39 |

* optical density at 1/25 dilution

Example 23

COMPARISON OF THE LD$_{50}$ OF ALVAC AND NYVAC WITH VARIOUS VACCINIA VIRUS STRAINS

Mice. Male outbred Swiss Webster mice were purchased from Taconic Farms (Germantown, N.Y.) and maintained on mouse chow and water ad libitum until use at 3 weeks of age ("normal" mice). Newborn outbred Swiss Webster mice were of both sexes and were obtained following timed pregnancies performed by Taconic Farms. All newborn mice used were delivered within a two day period.

Viruses. ALVAC was derived by plaque purification of a canarypox virus population and was prepared in primary chick embryo fibroblast cells (CEF). Following purification by centrifugation over sucrose density gradients, ALVAC was enumerated for plaque forming units in CEF cells. The WR(L) variant of vaccinia virus was derived by selection of large plaque phenotypes of WR (Panicali et al., 1981). The Wyeth New York State Board of Health vaccine strain of vaccinia virus was obtained from Pharmaceuticals Calf Lymph Type vaccine Dryvax, control number 302001B. Copenhagen strain vaccinia virus VC-2 was obtained from Institut Merieux, France. Vaccinia virus strain NYVAC was derived from Copenhagen VC-2. All vaccinia virus strains except the Wyeth strain were cultivated in Vero African green monkey kidney cells, purified by sucrose gradient density centrifugation and enumerated for plaque forming units on Vero cells. The Wyeth strain was grown in CEF cells and enumerated in CEF cells.

Inoculations. Groups of 10 normal mice were inoculated intracranially (ic) with 0.05 ml of one of several dilutions of virus prepared by 10-fold serially diluting the stock preparations in sterile phosphate-buffered saline. In some instances, undiluted stock virus preparation was used for inoculation.

Groups of 10 newborn mice, 1 to 2 days old, were inoculated ic similarly to the normal mice except that an injection volume of 0.03 ml was used.

All mice were observed daily for mortality for a period of 14 days (newborn mice) or 21 days (normal mice) after inoculation. Mice found dead the morning following inoculation were excluded due to potential death by trauma.

The lethal dose required to produce mortality for 50% of the experimental population (LD$_{50}$) was determined by the proportional method of Reed and Muench.

Comparison of the LD$_{50}$ of ALVAC and NYVAC with Various Vaccinia Virus Strains for Normal, Young Outbred Mice by the ic Route. In young, normal mice, the virulence of NYVAC and ALVAC were several orders of magnitude lower than the other vaccinia virus strains tested (Table 18). NYVAC and ALVAC were found to be over 3,000 times less virulent in normal mice than the Wyeth strain; over 12,500 times less virulent than the parental VC-2 strain; and over 63,000,000 times less virulent than the WR(L) variant. These results would suggest that NYVAC is highly attenuated compared to other vaccinia strains, and that ALVAC is generally nonvirulent for young mice when administered intracranially, although both may cause mortality in mice at extremely high doses (3.85×10$^8$ PFUs, ALVAC and 3×10$^8$ PFUs, NYVAC) by an undetermined mechanism by this route of inoculation.

Comparison of the LD$_{50}$ of ALVAC and NYVAC with various Vaccinia Virus Strains for Newborn Outbred Mice by the ic Route. The relative virulence of 5 poxvirus strains for normal, newborn mice was tested by titration in an intracranial (ic) challenge model system (Table 19). With mortality as the endpoint, LD$_{50}$ values indicated that ALVAC is over 100,000 times less virulent than the Wyeth vaccine strain of vaccinia virus; over 200,000 times less virulent than the Copenhagen VC-2 strain of vaccinia virus; and over 25,000,000 times less virulent than the WR-L variant of vaccinia virus. Nonetheless, at the highest dose tested, 6.3×10$^7$ PFUs, 100% mortality resulted. Mortality rates of 33.3% were observed at 6.3×10$^6$ PFUs. The cause of death, while not actually determined, was not likely of toxicological or traumatic nature since the mean survival time (MST) of mice of the highest dosage group (approximately 6.3 LD$_{50}$) was 6.7±1.5 days. When compared to WR(L) at a challenge dose of 5 LD$_{50}$, wherein MST is 4.8±0.6 days, the MST of ALVAC challenged mice was significantly longer (P=0.001).

Relative to NYVAC, Wyeth was found to be over 15,000 times more virulent; VC-2, greater than 35,000 times more virulent; and WR(L), over 3,000,000 times more virulent. Similar to ALVAC, the two highest doses of NYVAC, 6×10$^8$ and 6×10$^7$ PFUs, caused 100% mortality. However, the MST of mice challenged with the highest dose, corresponding to 380 LD$_{50}$, was only 2 days (9 deaths on day 2 and 1 on day 4). In contrast, all mice challenged with the highest dose of WR-L, equivalent to 500 LD$_{50}$, survived to day 4.

TABLE 18

Calculated 50% Lethal Dose for mice by various vaccinia virus strains and for canarypox virus (ALVAC) by the ic route.

| POXVIRUS STRAIN | CALCULATED LD$_{50}$ (PFUs) |
| --- | --- |
| WR(L) | 2.5 |
| VC-2 | 1.26 × 10$^4$ |
| WYETH | 5.00 × 10$^4$ |
| NYVAC | 1.58 × 10$^8$ |
| ALVAC | 1.58 × 10$^8$ |

TABLE 19

Calculated 50% Lethal Dose for newborn mice by various vaccinia virus strains and for canarypox virus (ALVAC) by the ic route.

| POXVIRUS STRAIN | CALCULATED LD$_{50}$ (PFUs) |
| --- | --- |
| WR(L) | 0.4 |
| VC-2 | 0.1 |
| WYETH | 1.6 |
| NYVAC | 1.58 × 10$^6$ |
| ALVAC | 1.00 × 10$^7$ |

Example 24

EVALUATION OF NYVAC (vP866) AND NYVAC-RG (VP879)

Immunoprecipitations. Preformed monolayers of avian or non-avian cells were inoculated with 10 pfu per cell of parental NYVAC (vP866) or NYVAC-RG (vP879) virus. The inoculation was performed in EMEM free of methionine and supplemented with 2% dialyzed fetal bovine serum. After a one hour incubation, the inoculum was removed and the medium replaced with EMEM (methionine free) containing 20 μCi/ml of $^{35}$S-methionine. After an overnight incubation of approximately 16 hours, cells were lysed by the addition of Buffer A (1% Nonidet P-40, 10 mM Tris pH7.4, 150 mM NaCl, 1 mM EDTA, 0.01% sodium azide, 500 units per ml of aprotinin, and 0.02% phenyl methyl sulfonyl fluoride). Immunoprecipitation was performed using a rabies glycoprotein specific monoclonal antibody designated 24-3F10 supplied by Dr. C. Trimarchi, Griffith Laboratories, New York State Department of Health, Albany, N.Y., and a rat anti-mouse conjugate obtained from Boehringer Mannheim Corporation (Cat. #605-500). Protein A Sepharose CL-48 obtained from Pharmacia LKB Biotechnology Inc., Piscataway, N.J., was used as a support matrix. Immunoprecipitates were fractionated on 10% polyacrylamide gels according to the method of Dreyfuss et. al. (1984). Gels were fixed, treated for fluorography with 1M Na-salicylate for one hour, and exposed to Kodak XAR-2 film to visualize the immunoprecipitated protein species.

Sources of Animals. New Zealand White rabbits were obtained from Hare-Marland (Hewitt, N.J.). Three week old male Swiss Webster outbred mice, timed pregnant female Swiss Webster outbred mice, and four week old Swiss Webster nude ($nu^+nu^+$) mice were obtained from Taconic Farms, Inc. (Germantown, N.Y.). All animals were maintained according to NIH guidelines. All animal protocols were approved by the institutional IACUC. When deemed necessary, mice which were obviously terminally ill were euthanized.

Evaluation of Lesions in Rabbits. Each of two rabbits was inoculated intradermally at multiple sites with 0.1 ml of PBS containing $10^4$, $10^5$, $10^6$, $10^7$, or $10^8$ pfu of each test virus or with PBS alone. The rabbits were observed daily from day 4 until lesion resolution. Indurations and ulcerations were measured and recorded.

Virus Recovery from Inoculation Sites. A single rabbit was inoculated intradermally at multiple sites of 0/1 u ml of PBS containing $10^6$, $10^7$, or $10^8$ pfu of each test virus or with PBS alone. After 11 days, the rabbit was euthanized and skin biopsy specimens taken from each of the inoculation sites were aseptically prepared by mechanical disruption and indirect sonication for virus recovery. Infectious virus was assayed by plaque titration on CEF monolayers.

Virulence in Mice. Groups of ten mice, or five in the nude mice experiment, were inoculated ip with one of several dilutions of virus in 0.5 ml of sterile PBS. Reference is also made to Example 23.

Cyclophosphamide (CY) Treatment. Mice were injected by the ip route with 4 mg (0.02 ml) of CY (SIGMA) on day −2, followed by virus injection on day 0. On the following days post infection, mice were injected ip with CY:4 mg on day 1; 2 mg on days 4, 7 and 11; 3 mg on days 14, 18, 21, 25 and 28. Immunosuppression was indirectly monitored by enumerating white blood cells with a Coulter Counter on day 11. The average white blood cell count was 13,500 cells per µl for untreated mice (n=4) and 4,220 cells per µl for CY-treated control mice (n=5).

Calculation of $LD_{50}$. The lethal dose required to produce 50% mortality ($LD_{50}$) was determined by the proportional method of Reed and Muench (Reed and Muench 1938).

Potency Testing of NYVAC-RG in Mice. Four to six week old mice were inoculated in the footpad with 50 to 100 µl of a range of dilutions (2.0–8.0 $log_{10}$ tissue culture infective dose 50% ($TCID_{50}$)) of either VV-RG (Kieny et al., 1984), ALVAC-RG (Taylor et al., 1991b), or the NYVAC-RG. Each group consisted of eight mice. At 14 days post-vaccination, the mice were challenged by intracranial inoculation with 15 $LD_{50}$ of the rabies virus CVS strain (0.03 ml). On day 28, surviving mice were counted and protective does 50% ($PD_{50}$) calculated.

Figure 19:
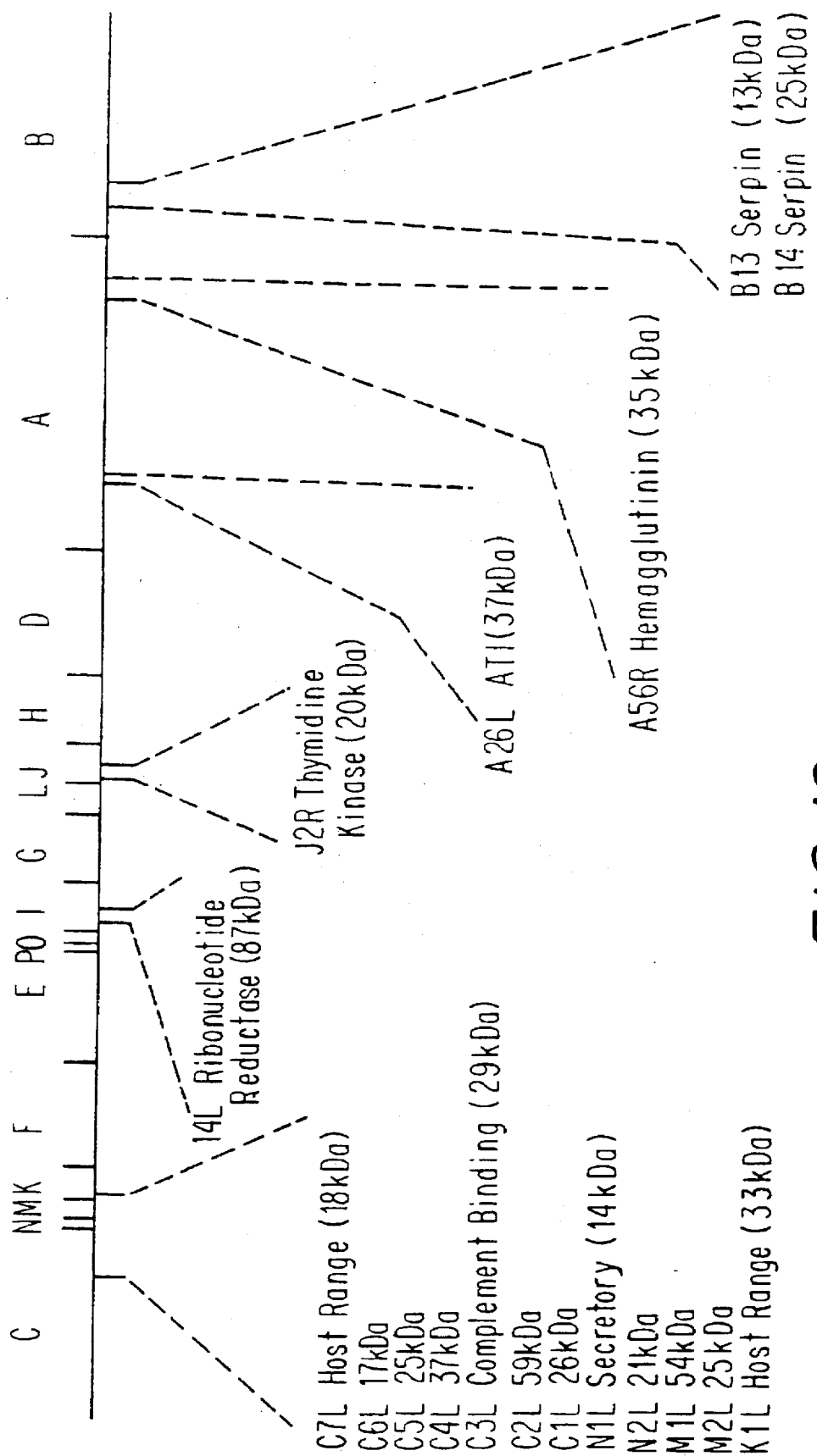
FIG. 19 shows schematically the ORFs deleted to generate NYVAC.
Figure 22A:
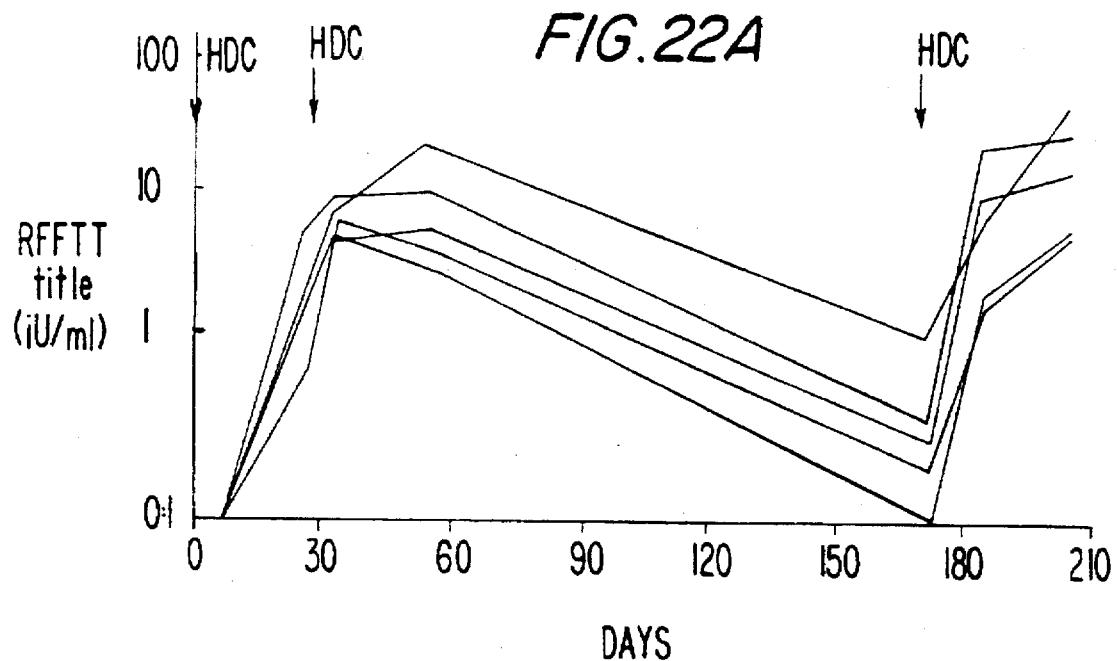
FIGS. 22A to 22D show graphs of rabies neutralizing antibody titers (RFFIT, IU/ml), booster effect of HDC and vCP65 ($10^{5.5}$ TCID50) in volunteers previously immunized with either the same or the alternate vaccine (vaccines given at days 0, 28 and 180, antibody titers measured at days 0, 7, 28, 35, 56, 173, 187 and 208)
Figure 22C:
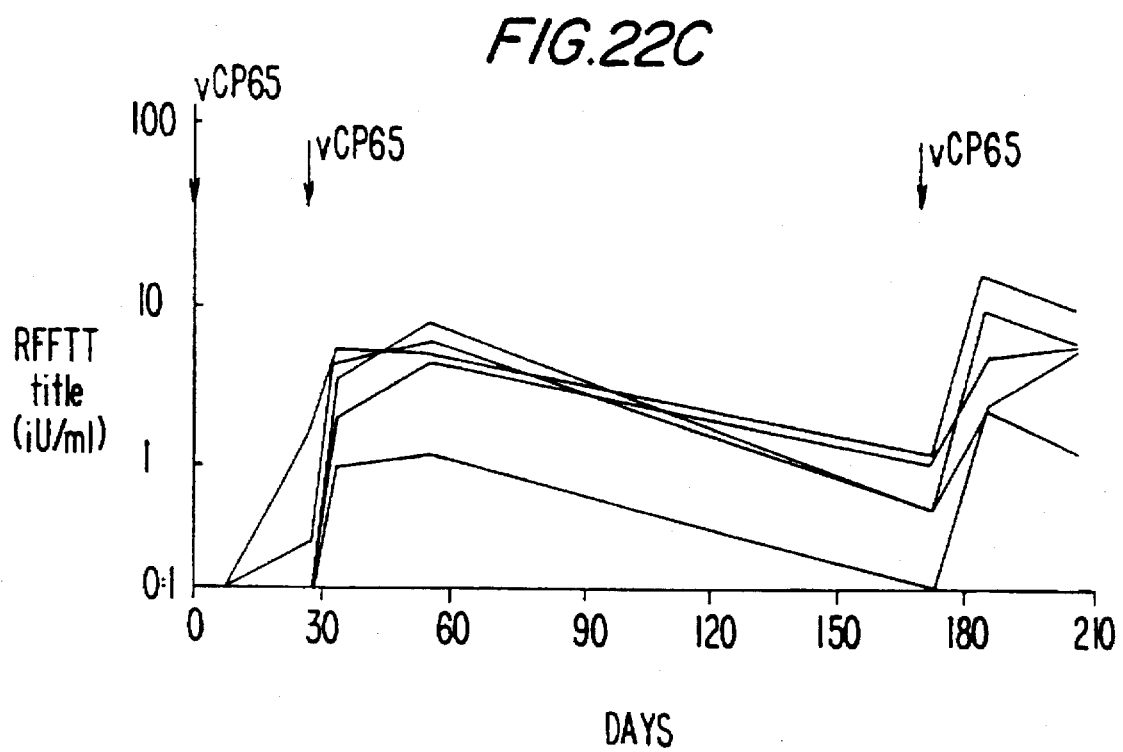
Figure 22B:
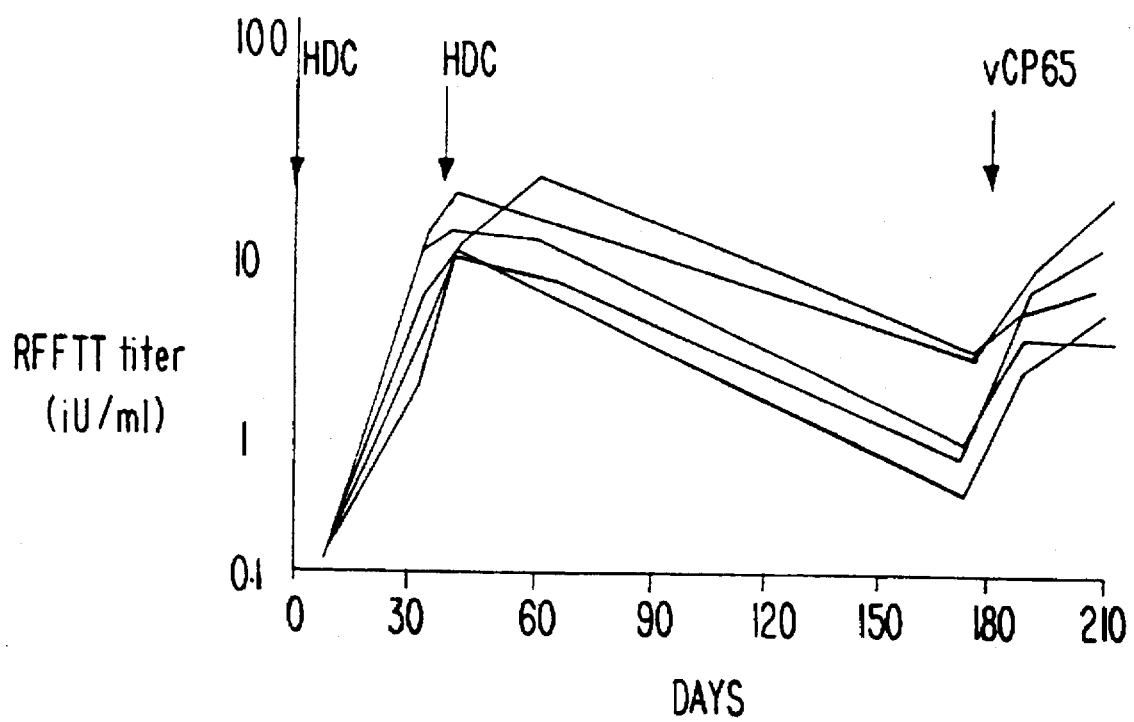
Figure 22D:
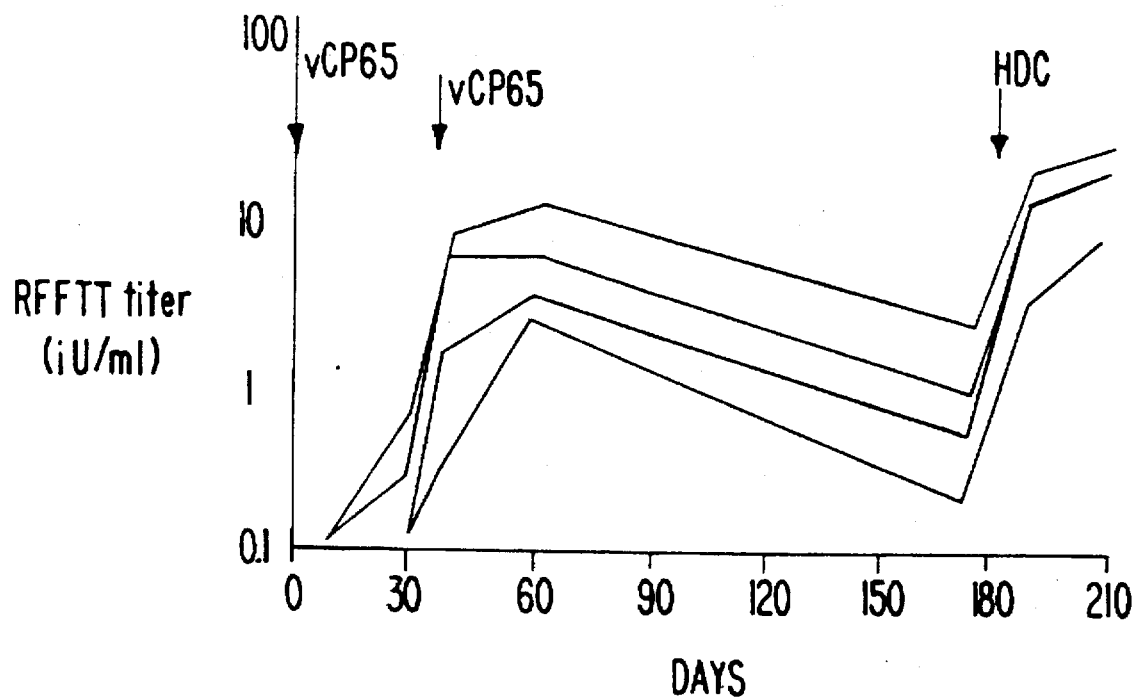

Derivation of NYVAC (vP866). The NYVAC strain of vaccinia virus was generated from VC-2, a plaque cloned isolate of the COPENHAGEN vaccine strain. To generate NYVAC from VC-2, eighteen vaccinia ORFs, including a number of vital functions associated with virulence, were precisely deleted in a series of sequential manipulations as described earlier in this disclosure. These deletions were constructed in a manner designed to prevent the appearance of novel unwanted open reading frames. FIG. 19 schematically depicts the ORFs deleted to generate NYVAC. At the top of FIG. 19 is depicted the HindIII restriction map of the vaccinia virus genome (VC-2 plaque isolate, COPENHAGEN strain). Expanded are the six regions of VC-2 that were sequentially deleted in the generation of NYVAC. The deletions were described earlier in this disclosure (Examples 13 through 18). Below such deletion locus is listed the ORFs which were deleted from that locus, along with the functions or homologies and molecular weight of their gene products.

Replication Studies of NYVAC and ALVAC on Human Tissue Cell Lines. In order to determine the level of replication of NYVAC strain of vaccinia virus (vP866) in cells of human origin, six cell lines were inoculated at an input multiplicity of 0.1 pfu per cell under liquid culture and incubated for 72 hours. The COPENHAGEN parental clone (VC-2) was inoculated in parallel. Primary chick embryo fibroblast (CEF) cells (obtained from 10–11 day old embryonated eggs of SPF origin, Spafas, Inc., Storrs, Conn.) were included to represent a permissive cell substrate for all viruses. Cultures were analyzed on the basis of two criteria: the occurrence of productive viral replication and expression of an extrinsic antigen.

The replication potential of NYVAC in a number of human derived cells are shown in Table 20. Both VC-2 and NYVAC are capable of productive replication in CEF cells, although NYVAC with slightly reduced yields. VC-2 is also capable of productive replication in the six human derived cell lines tested with comparable yields except in the EBV transformed lymphoblastoid cell line JT-1 (human lymphoblastoid cell line transformed with Epstein-Barr virus, see Rickinson et al., 1984). In contract, NYVAC is highly attenuated in its ability to productively replicate in any of the human derived cell lines tested. Small increases of infectious virus above residual virus levels were obtained from NYVAC-infected MRC-5 (ATCC #CCL171, human embryonic lung origin), DETROIT 532 (ATCC #CCL54, human foreskin, Downs Syndrome), HEL 299 (ATCC #CCL137, human embryonic lung cells) and HNK (human neonatal kidney cells, Whittiker Bioproducts, Inc. Walkersville, Md., Cat #70-151) cells. Replication on these cell lines was significantly reduced when compared to virus yields obtained from NYVAC-infected CEF cells or with parental VC-2 (Table 20). It should be noted that the yields at 24 hours in CEF cells for both NYVAC and VC-2 is equivalent to the 72-hour yield. Allowing the human cell line cultures to incubate an additional 48 hours (another two viral growth cycles) may, therefore, have amplified the relative virus yield obtained.

Consistent with the low levels of virus yields obtained in the human-derived cell lines, MRC-5 and DETROIT 532, detectable but reduced levels of NYVAC-specific DNA accumulation were noted. The level of DNA accumulation in the MRC-5 and DETROIT 532 NYVAC-infected cell lines relative to that observed in NYVAC-infected CEF cells paralleled the relative virus yields. NYVAC-specific viral DNA accumulation was not observed in any of the other human-derived cells.

An equivalent experiment was also performed using the avipox virus, ALVAC. The results of virus replication are also shown in Table 20. No progeny virus was detectable in any of the human cell lines consistent with the host range restriction of canarypox virus to avian species. Also consistent with a lack of productive replication of ALVAC in these human-derived cells is the observation that no ALVAC-specific DNA accumulation was detectable in any of the human-derived cell lines.

Expression of Rabies Glycoprotein by NYVAC-RG (vP879) in Human Cells. In order to determine whether efficient expression of a foreign gene could be obtained in the absence of significant levels of productive viral replication, the same cell lines were inoculated with the NYVAC recombinant expressing the rabies virus glycoprotein (vP879, Example 19) in the presence of $^{35}$S-methionine. Immunoprecipitation of the rabies glycoprotein was performed from the radiolabelled culture lysate using a monoclonal antibody specific for the rabies glycoprotein. Immunoprecipitation of a 67kDa protein was detected consistent with a fully glycosylated form of the rabies glycoprotein. No serologically crossreactive product was detected in uninfected or parental NYVAC infected cell lysates. Equivalent results were obtained with all other human cells analyzed.

Inoculations on the Rabbit Skin. The induction and nature of skin lesions on rabbits following intradermal (id) inoculations has been previously used as a measure of pathogenicity of vaccinia virus strains (Bullet et al., 1988; Child et al., 1990; Fenner, 1958, Flexner et al., 1987; Ghendon and Chernos 1964). Therefore, the nature of lesions associated with id inoculations with the vaccinia strains WR (ATCC #VR119 plaque purified on CV-1 cells, ATCC #CCL70, and a plaque isolate designated L variant, ATCC #VR2035 selected, as described in Panicali et al., 1981)), WYETH (ATCC #VR325 marketed as DRYVAC by Wyeth Laboratories, Marietta, Pa.), COPENHAGEN (VC-2), and NYVAC was evaluated by inoculation of two rabbits (A069 and A128). The two rabbits displayed different overall sensitivities to the viruses, with rabbit A128 displaying less severe reactions than rabbit A069. In rabbit A128, lesions were relatively small and resolved by 27 days post-inoculation. On rabbit A069, lesions were intense, especially for the WR inoculation sites, and resolved only after 49 days. Intensity of the lesions was also dependent on the location of the inoculation sites relative to the lymph drainage network. In particular, all sites located above the back-spine displayed more intense lesions and required longer times to resolve the lesions located on the flanks. All lesions were measured daily from day 4 to the disappearance of the last lesion, and the means of maximum lesion size and days to resolution were calculated (Table 21). No local reactions were observed from sites injected with the control PBS. Ulcerative lesions were observed at sites injected with WR, VC-2 and WYETH vaccinia virus strains. Significantly, no induration or ulcerative lesions were observed at sites of inoculation with NYVAC.

Persistence of Infectious Virus at the Site of Inoculation. To assess the relative persistence of these viruses at the site of inoculation, a rabbit was inoculated intradermally at multiple sites with 0.1 ml PBS containing $10^6$, $10^7$ or $10^8$ pfu of VC-2, WR, WYETH or NYVAC. For each virus, the $10^7$ pfu dose was located above the backspine, flanked by the $10^6$ and $10^8$ doses. Sites of inoculation were observed daily for 11 days. WR elicited the most intense response, followed by VC-2 and WYETH (Table 22). Ulceration was first observed at day 9 for WR and WYETH and day 10 for VC-2. Sites inoculated with NYVAC or control PBS displayed no induration or ulceration. At day 11 after inoculation, skin samples from the sites of inoculation were excised, mechanically disrupted, and virus was titrated on CEF cells.

The results are shown in Table 22. un no case was more virus recovered at this timepoint than was administered. Recovery of vaccinia strain, WR, was approximately $10^6$ pfu of virus at each site irrespective of amount of virus administered. Recovery of vaccinia strains WYETH and VC-2 was $10^3$ to $10^4$ pfu regardless of amount administered. No infectious virus was recovered from sites inoculated with NYVAC.

Inoculation of Genetically or Chemically Immune Deficient Mice. Intraperitoneal inoculation of high doses of NYVAC ($5\times10^8$ pfu) or ALVAC ($10^9$ pfu) into nude mice caused no deaths, no lesions, and no apparent disease through the 100 day observation period. In contrast, mice inoculated with WR ($10^3$ to $10^4$ pfu), WYETH ($5\times10^7$ or $5\times10^8$ pfu) or VC-2 ($10^4$ to $10^9$ pfu) displayed disseminated lesions typical of poxviruses first on the toes, then on the tail, followed by severe orchitis in some animals. In mice infected with WR or WYETH, the appearance of disseminated lesions generally led to eventual death, whereas most mice infected with VC-2 eventually recovered. Calculated $LD_{50}$ values are given in Table 23.

In particular, mice inoculated with VC-2 began to display lesions on their toes (red papules) and 1 to 2 days later on the tail. These lesions occurred between 11 and 13 days post-inoculation (pi) in mice given the highest doses ($10^9$, $10^8$, $10^7$ and $10^6$ pfu), on day 16 pi in mice given $10^5$ pfu and on day 21 pi in mice given $10^4$ pfu. No lesions were observed in mice inoculated with $10^3$ and $10^2$ pfu during the 100 day observation period. Orchitis was noticed on day 23 pi in mice given $10^9$ and $10^8$ pfu, and approximately 7 days later in the other groups ($10^7$ to $10_4$ pfu). Orchitis was especially intense in the $10^9$ and $10^8$ pfu groups and, although receding, was observed until the end of the 100 day observation period. Some pox-like lesions were noticed on the skin of a few mice, occurring around 30–35 days pi. Most pox lesions healed normally between 60–90 days pi. Only one mouse died in the group inoculated with $10^9$ pfu (Day 34 pi) and one mouse died in the group inoculated with $10^8$ pfu (Day 94 pi). No other deaths were observed in the VC-2 inoculated mice.

Mice inoculated with $10^4$ pfu of the WR strain of vaccinia started to display pox lesions on Day 17 pi. These lesions appeared identical to the lesions displayed by the VC-2 injected mice (swollen toes, tail). Mice inoculated with $10^3$ pfu of the WR strain did not develop lesions until 34 days pi. Orchitis was noticed only in the mice inoculated with the highest dose of WR ($10^4$ pfu). During the latter stages of the observation period, lesions appeared around the mouth and the mice stopped eating. All mice inoculated with $10^4$ pfu of WR died or were euthanized when deemed necessary between 21 days and 31 days pi. Four out of the 5 mice injected with $10^3$ pfu of WR died or were euthanized when deemed necessary between 35 days and 57 days pi. No deaths were observed in mice inoculated with lower doses of WR (1 to 100 pfu).

Mice inoculated with the WYETH strain of vaccinia virus at higher doses $5\times10^7$ and $5\times10^8$ pfu) showed lesions on toes and tails, developed orchitis, and died. Mice injected with $5\times10^6$ pfu or less of WYETH showed no signs of disease or lesions.

As shown in Table 23, CY-treated mice provided a more sensitive model for assaying poxvirus virulence than did nude mice. $LD_{50}$ values for the WR, WYETH, and VC-2 vaccinia virus strains were significantly lower in this model system than in the nude mouse model. Additionally, lesions developed in mice injected with WYETH, WR and VC-2 vaccinia viruses, as noted below, with higher doses of each virus resulting in more rapid formation of lesions. As was seen with nude mice, CY-treated mice injected with NYVAC or ALVAC did not develop lesions. However, unlike nude mice, some deaths were observed in CY-treated mice challenged with NYVAC or ALVAC, regardless of the dose. These random incidences are suspect as to the cause of death.

Mice injected with all doses of WYETH ($9.5 \times 10^4$ to $9.5 \times 10^8$ pfu) displayed pox lesions on their tail and/or on their toes between 7 and 15 days pi. In addition, the tails and toes were swollen. Evolution of lesions on the tail was typical of pox lesions with formation of a papule, ulceration and finally formation of a scab. Mice inoculated with all doses of VC-2 ($1.65 \times 10^5$ to $1.65 \times 10^9$) also developed pox lesions on their tails and/or their toes analogous to those of WYETH injected mice. These lesions were observed between 7-12 days post inoculation. No lesions were observed on mice injected with lower doses of WR virus, although deaths occurred in these groups.

Potency Testing of NYVAC-RG. In order to determine that attenuation of the COPENHAGEN strain of vaccinia virus had been effected without significantly altering the ability of the resulting NYVAC strain to be a useful vector, comparative potency tests were performed. In order to monitor the immunogenic potential of the vector during the sequential genetic manipulations performed to attenuate the virus, a rabiesvirus glycoprotein was used as a reporter extrinsic antigen. The protective efficacy of the vectors expressing the rabies glycoprotein gene was evaluated in the standard NIH mouse potency test for rabies (Seligmann, 1973). Table 24 demonstrates that the $PD_{50}$ values obtained with the highly attenuated NYVAC vector are identical to those obtained using a COPENHAGEN-based recombinant containing the rabies glycoprotein gene in the tk locus (Kieny et al., 1984) and similar to $PD_{50}$ values obtained with ALVAC-RG, a canarypox based vector restricted to replication to avian species.

Observations. NYVAC, deleted of known virulence genes and having restricted in vitro growth characteristics, was analyzed in animal model systems to assess its attenuation characteristics. These studies were performed in comparison with the neurovirulent vaccinia virus laboratory strain, WR, two vaccinia virus vaccine strains, WYETH (New York City Board of Health) and COPENHAGEN (VC-2), as well as with a canarypox virus strain, ALVAC (See also Example 23). Together, these viruses provided a spectrum of relative pathogenic potentials in the mouse challenge model and the rabbit skin model, with WR being the most virulent strain, WYETH and COPENHAGEN (VC-2) providing previously utilized attenuated vaccine strains with documented characteristics, and ALVAC providing an example of a poxvirus whose replication is restricted to avian species. Results from these in vivo analyses clearly demonstrate the highly attenuated properties of NYVAC relative to the vaccinia virus strains, WR, WYETH and COPENHAGEN (VC-2) (Tables 18–24). Significantly, the $LD_{50}$ values for NYVAC were comparable to those observed with the avian host restricted avipoxvirus, ALVAC. Deaths due to NYVAC, as well as ALVAC, were observed only when extremely high doses of virus were administered via the intracranial route (Example 23, Tables 18, 19, 23). It has not yet been established whether these deaths were due to nonspecific consequences of inoculation of a high protein mass. Results from analyses in immunocompromised mouse models (nude and CY-treated) also demonstrate the relatively high attenuation characteristics of NYVAC, as compared to WR, WYETH and COPENHAGEN strains (Tables 21 and 22). Significantly, no evidence of disseminated vaccinia infection or vaccinial disease was observed in NYVAC-inoculated animals or ALVAC-inoculated animals over the observation period. The deletion of multiple virulence-associated genes in NYVAC shows a synergistic effect with respect to pathogenicity. Another measure of the innocuity of NYVAC was provided by the intradermal administration on rabbit skin (Tables 21 and 22). Considering the results with ALVAC, a virus unable to replicate in nonavian species, the ability to replicate at the site of inoculation is not the sole correlate with reactivity, since intradermal inoculation of ALVAC caused areas of induration in a dose dependent manner. Therefore, it is likely that factors other than the replicative capacity of the virus contribute to the formation of the lesions. Deletion of genes in NYVAC prevents lesion occurrence.

Together, the results in this Example and in foregoing Examples, including Example 23, demonstrate the highly attenuated nature of NYVAC relative to WR, and the previously utilized vaccinia virus vaccine strains, WYETH and COPENHAGEN. In fact, the pathogenic profile of NYVAC, in the animal model systems tested, was similar to that of ALVAC, a poxvirus known to productively replicate only in avian species. The apparently restricted capacity of NYVAC to productively replicate on cells derived from humans (Table 20) and other species, including the mouse, swine, dog and horse, provides a considerable barrier that limits or prevents potential transmission to unvaccinated contacts or to the general environment in addition to providing a vector with reduced probability of dissemination within the vaccinated individual.

Significantly, NYVAC-based vaccine candidates have been shown to be efficacious. NYVAC recombinants expressing foreign gene products from a number of pathogene have elicited immunological responses towards the foreign gene products in several animal species, including primates. In particular, a NYVAC-based recombinant expressing the rabies glycoprotein was able to protect mice against a lethal rabies challenge. The potency of the NYVAC-based rabies glycoprotein recombinant was comparable to the $PD_{50}$ value for a COPENHAGEN-based recombinant containing the rabies glycoprotein in the tk locus (Table 24). NYVAC-based recombinants have also been shown to elicit measles virus neutralizing antibodies in rabbits and protection against pseudorabies virus and Japanese encephalitis virus challenge in swine. The highly attenuated NYVAC strain confers safety advantages with human and veterinary applications (Tartaglia et al., 1990). Furthermore, the use of NYVAC as a general laboratory expression vector system may greatly reduce the biological hazards associated with using vaccinia virus.

By the following criteria, the results of this Example and the Examples herein, including Example 23, show NYVAC to be highly attenuated: a) no detectable induration or ulceration at site of inoculation (rabbit skin); b) rapid clearance of infectious virus from intradermal site of inoculation (rabbit skin); c) absence of testicular inflammation (nude mice); d) greatly reduced virulence (intracranial challenge, both three-week old and newborn mice); e) greatly reduced pathogenicity and failure to disseminate in immunodeficient subjects (nude and cyclophosphamide treated mice); and f) dramatically reduced ability to replicate on a variety of human tissue culture cells. Yet, in spite of being highly attenuated, NYVAC, as a vector, retains the ability to induce strong immune responses to extrinsic antigens.

TABLE 20

Replication of COPENHAGEN (VC-2), NYVAC and ALVAC in avian or human derived cell lines

| Cells | Hours post-infection | Yield[a] VC-2 | NYVAC | ALVAC | % Yield |
|---|---|---|---|---|---|
| CEF | 0 | 3.8[b] | 3.7 | 4.5 | |
| | 24 | 8.3 | 7.8 | 6.6 | |
| | 48 | 8.6 | 7.9 | 7.7 | |
| | 72 | 8.3 | 7.7 | 7.5 | 25 |
| | 72A[c] | <1.4 | 1.8 | 3.1 | |
| MRC-5 | 0 | 3.8 | 3.8 | 4.7 | |
| | 72 | 7.2 | 4.6 | 3.8 | 0.25 |
| | 72A | 2.2 | 2.2 | 3.7 | |
| WISH* | 0 | 3.4 | 3.4 | 4.3 | |
| | 72 | 7.6 | 2.2 | 3.1 | 0.0004 |
| | 72A | —[d] | 1.9 | 2.9 | |
| DETROIT | 0 | 3.8 | 3.7 | 4.4 | |
| | 72 | 7.2 | 5.4 | 3.4 | 1.6 |
| | 72A | 1.7 | 1.7 | 2.9 | |
| HEL | 0 | 3.8 | 3.5 | 4.3 | |
| | 72 | 7.5 | 4.6 | 3.3 | 0.125 |
| | 72A | 2.5 | 2.1 | 3.6 | |
| JT-1 | 0 | 3.1 | 3.1 | 4.1 | |
| | 72 | 6.5 | 3.1 | 4.2 | 0.039 |
| | 72A | 2.4 | 2.1 | 4.4 | |
| HNK | 0 | 3.8 | 3.7 | 4.7 | |
| | 72 | 7.6 | 4.5 | 3.6 | 0.079 |
| | 72A | 3.1 | 2.7 | 3.7 | |

[a]: Yield of NYVAC at 72 hours post-infection expressed as a percentage of yield of VAC-2 after 72 hours on the same cell line.
[b]: Titer expressed as $LOG_{50}$ pfu per ml.
[c]: Sample was incubated in the presence of 40 μg/ml of cytosine arabinoside.
[d]: Not determined.
*: ATCC #CCL25 Human amnionic cells.

TABLE 21

Induration and ulceration at the site of intradermal inoculation of the rabbit skin

| VIRUS STRAIN | DOSE[a] | INDURATION Size[b] | Days[c] | ULCERATION Size | Days |
|---|---|---|---|---|---|
| WR | $10^4$ | 386 | 30 | 88 | 30 |
| | $10^5$ | 622 | 35 | 149 | 32 |
| | $10^6$ | 1057 | 34 | 271 | 34 |
| | $10^7$ | 877 | 35 | 204 | 35 |
| | $10^8$ | 581 | 25 | 88 | 26 |
| WYETH | $10^4$ | 32 | 5 | —[d] | — |
| | $10^5$ | 116 | 15 | — | — |
| | $10^6$ | 267 | 17 | 3 | 15 |
| | $10^7$ | 202 | 17 | 3 | 24 |
| | $10^8$ | 240 | 29 | 12 | 31 |
| VC-2 | $10^4$ | 64 | 7 | — | — |
| | $10^5$ | 86 | 8 | — | — |
| | $10^6$ | 136 | 17 | — | — |
| | $10^7$ | 167 | 21 | 6 | 10 |
| | $10^8$ | 155 | 32 | 6 | 8 |
| NYVAC | $10^4$ | — | — | — | — |
| | $10^5$ | — | — | — | — |
| | $10^6$ | — | — | — | — |
| | $10^7$ | — | — | — | — |
| | $10^8$ | — | — | — | — |

[a] pfu of indicated vaccinia virus in 0.1 ml PBS inoculated intradermally into one site.
[b] mean maximum size of lesions ($mm^2$)
[c] mean time after inoculation for complete healing of lesion.
[d] no lesions discernable.

TABLE 22

Persistence of poxviruses at the site of intradermal inoculation

| Virus | Inoculum Dose | Total Virus Recovered |
|---|---|---|
| WR | 8.0[a] | 6.14 |
| | 7.0 | 6.26 |
| | 6.0 | 6.21 |
| WYETH | 8.0 | 3.66 |
| | 7.0 | 4.10 |
| | 6.0 | 3.59 |
| VC-2 | 8.0 | 4.47 |
| | 7.0 | 4.74 |
| | 6.0 | 3.97 |
| NYVAC | 8.0 | 0 |
| | 7.0 | 0 |
| | 6.0 | 0 | a: expressed as $log_{10}$ pfu.

TABLE 23

Virulence studies in immunocompromised mice

| Poxvirus Strain | $LD_{50}$[a] Nude mice | Cyclophosphamide treated mice |
|---|---|---|
| WR | 422 | 42 |
| VC-2 | $>10^9$ | $<1.65 \times 10^5$ |
| WYETH | $1.58 \times 10^7$ | $1.83 \times 10^6$ |
| NYVAC | $>5.50 \times 10^8$ | $7.23 \times 10^8$ |
| ALVAC | $>10^9$ | $\geq 5.00 \times 10^{8b}$ |

[a]: Calculated 50% lethal dose (pfu) for nude or cyclophosphamide treated mice by the indicated vaccinia viruses and for ALVAC by intraperitoneal route.
[b]: 5 out of 10 mice died at the highest dose of $5 \times 10^8$ pfu.

TABLE 24

Comparative efficacy of NYVAC-RG and ALVAC-RG in mice

| Recombinant | $PD_{50}$[a] |
|---|---|
| VV-RG | 3.74 |
| ALVAC-RG | 3.86 |
| NYVAC-RG | 3.70 |

[a]: Four to six week old mice were inoculated in the footpad with 50–100 μl of a range of dilutions (2.0–8.0 $log_{10}$ tissue culture infection dose 50% ($TCID_{50}$) of either the VV-RG (Kieny et al., 1984), ALVAC-RG (vCP65) or NYVAC-RG (vP879). At day 14, mice of each group were challenged by intracranial inoculation of 30 μl of a live CVS strain rabies virus corresponding to 15 lethal dose 50% ($LD_{50}$) per mouse. At day 28, surviving mice were counted and a protective dose 50% ($PD_{50}$) was calculated.

Example 25

CONSTRUCTION OF TROVAC RECOMBINANTS EXPRESSING THE HEMAGGLUTININ GLYCOPROTEINS OF AVIAN INFLUENZA VIRUSES

This Example describes the development of fowlpox virus recombinants expressing the hemagglutinin genes of three serotypes of avian influenza virus.

Cells and Viruses. Plasmids containing cDNA clones of the H4, H5 and H7 hemagglutinin genes were obtained from Dr. Robert Webster, St. Jude Children's Research Hospital, Memphis, Tenn. The strain of FPV designated FP-1 has been described previously (Taylor et al., 1988a, b). It is a vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chick embryo fibroblast (CEF) cells. This virus was obtained in September 1980 by Rhone Merieux, Lyon, France, and a master viral seed established. The virus was received by Virogenetics in September 1989, where it was subjected to four successive plaque purifications. One plaque isolate was further amplified in primary CEF cells and a stock virus, designated as TROVAC, was established. The stock virus used in the in vitro recombination test to produce TROVAC-AIH5 (vFP89) and TROVAC-AIH4 (vFP92) had been further amplified though 8 passages in primary CEF cells. The stock virus used to produce TROVAC-AIH7 (vFP100) had been further amplified through 12 passages in primary CEF cells.

Consturction of Fowlpox Insertion Plasmid at F8 Locus. Plasmid pRW731.15 contains a 10 kbp PvuII-PvuII fragment cloned from TROVAC genomic DNA. The nucleotide sequence was determined on both strands for a 3659 bp PvuII-EcoRV fragment. This sequence is shown in FIG. 20 (SEQ ID NO:72). The limits of an open reading frame designated in this laboratory as F8 were determined within this sequence. The open reading frame is initiated at position 495 and terminates at position 1887. A deletion was made from position 779 to position 1926, as described below.

Plasmid pRW761 is a sub-clone of pRW731.15 containing a 2430 bp EcoRV-EcoRV fragment. Plasmid pRW761 was completely digested with XbaI and partially digested with SspI. A 3700 bp XbaI-SspI band was isolated and ligated with the annealed double-stranded oligonucleotides JCA017 (SEQ ID NO:60) and JCA018 (SEQ ID NO:61).

Plasmid pRW846 therefore contains the H6 promoter 5' of EcoRV in the de-ORFed F8 locus. The HincII site 3' of the H6 promoter in pRW846 is followed by translation stop codons, a transcriptional stop sequence recognized by vaccinia virus early promoters (Yuen et al., 1987) and a SmaI site.

Construction of Fowlpox Insertion Plasmid at F7 Locus. The original F7 non-de-ORFed insertion plasmid, pRW731.13, contained a 5.5 kb FP genomic PvuII fragment in the PvuII site of pUC9. The insertion site was a unique HincII site within these sequences. The nucleotide sequence shown in FIG. 21 (SEQ ID NO:75) was determined for a 2356 bp region encompassing the unique HincII site. Analysis of this sequence revealed that the unique HincII site (FIG. 21, underlined) was situated within an ORF encoding a polypeptide of 90 amino acids. The ORF begins with an ATG at position 1531 and terminates at position 898 (positions marked by arrows in FIG. 21).

The arms for the de-ORFed insertion plasmid were derived by PCR using pRW731.13 as template. A 596 bp arm (designated as HB) corresponding to the region upstream from the ORF was amplified with oligonucleotides F73PH2 (SEQ ID NO:76) (5'-GACAATCTAAGTCCTATATTAGAC-3') and F73PB (SEQ ID NO:77) (5'-GGTTTTTAGGTAGACAC-3'). A 270 bp arm (designated as EH) corresponding to the region downstream from the ORF was amplified using oligonucleotides F75PE (SEQ ID NO:78) (5'-TCATCGTCTTCATCATCG-3') and F73PH1 (SEQ ID NO:79) (5'-GTCTTAAACTTATTGTAAGGGTATACCTG-3').

JCA017 (SEQ ID NO:60)  5'  CTAGACACTTTATGTTTTTAATATCCGGTCTT

AAAAGCTTCCCGGGGATCCTTATACGGGGAATAAT  3'

JCA018 (SEQ ID NO:61)  5'  ATTATTCCCCGTATAAGGATCCCCCGGGAA

GCTTTTAAGACCGGATATTAAAAAACATAAAGTGT  3'

The plasmid resulting from this ligation was designated pJCA002. Plasmid pJCA004 contains a non-pertinent gene linked to the vaccinia virus H6 promoter in plasmid pJCA002. The sequence of the vaccinia virus H6 promoter has been previously described (Taylor et al., 1988a, b; Guo et al. 1989; Perkus et al., 1989). Plasmid pJCA004 was digested with EcoRV and BamHI which deletes the non-pertinent gene and a portion of the 3' end of the H6 promoter. Annealed oligonucleotides RW178 (SEQ ID NO:73) and RW179 (SEQ ID NO:74) were cut with EcoRV and BamHI and inserted between the EcoRV and BamHI sites of JCA004 to form pRW846.

Fragment EH was digested with EcoRV to generate a 126 bp fragment. The EcoRV site is at the 3'-end and the 5'-end was formed, by PCR, to contain the 3' end of a HincII site. This fragment was inserted into pBS-SK (Stratagene, La. Jolla, Calif.) digested with HincII to form plasmid pF7D1. The sequence was confirmed by dideoxynucleotide sequence analysis. The plasmid pF7D1 was linearized with ApaI, blunt-ended using T4 DNA polymerase, and ligated to the 596 bp HB fragment. The resultant plasmid was designated as pF7D2. The entire sequence and orientation were confirmed by nucleotide sequence analysis.

The plasmid pF7D2 was digested with EcoRV and BglII to generate a 600 bp fragment. This fragment was inserted into pBS-SK that was digested with ApaI, blunt-ended with

RW178 (SEQ ID NO:73):  5'  TCATTATCGCGATATCCGTGTTAACTAGCTA

GCTAATTTTTATTCCCGGGATCCTTATCA  3'

RW179 (SEQ ID NO:74):  5'  GTATAAGGATCCCGGGAATAAAAATTAGCT

AGCTAGTTAACACGGATATCGCGATAATGA  3'

T4 DNA polymerase, and subsequently digested with BamHI. The resultant plasmid was designated as pF7D3. This plasmid contains an HB arm of 404 bp and a EH arm of 126 bp.

The plasmid pF7D3 was linearized with XhoI and blunt-ended with the Klenow fragment of the *E. coli* DNA polymerase in the presence of 2mM dNTPs. This linearized plasmid was ligated with annealed oligonucleotides F7MCSB (SEQ ID NO:80) (5'-AACGATTAGTTAGTTACTAAAAGCTTGCTGCAG-CCCGGGTTTTTTATTAGTTTAGTTAGTC-3') and F7MCSA (SEQ ID NO:81) (5'-GACTAACTAACTAATAAAAAACCCGGGCTGCAGC- Construction of Insertion Plasmid for H5 Hemagglutinin at the F8 Locus. A cDNA clone of avian influenza H5 derived from A/Turkey/Ireland/1378/83 was received in plasmid pTH29 from Dr. R. Webster. Synthetic oligonucleotides RW10 (SEQ ID NO:84) through RW13 (SEQ ID NO:87) were designed to overlap the translation initiation codon of the previously described vaccinia virus H6 promoter with the ATG of the H5 gene. The sequence continues through the 5' SalI site of the H5 gene and begins again at the 3' H5 DraI site containing the H5 stop codon.

RW10 (SEQ ID NO:84): 5'  GAAAAATTTAAAGTCGACCTGTTTTGTTGAGT
                         TGTTTGCGTGGTAACCAATGCAAATCTGGTC
                         ACT 3'

RW11 (SEQ ID NO:85): 5'  TCTAGCAAGACTGACTATTGCAAAAAGAAGCA
                         CTATTTCCTCCATTACGATACAAACTTAACG
                         GAT 3'

RW12 (SEQ ID NO:86): 5'  ATCCGTTAAGTTTGTATCGTAATGGAGGAAA
                         TAGTGCTTCTTTTTGCAATAGTCAGTCTTGCTAGAAGTGACCAGATTT
                         GCATTGGT 3'

RW13 (SEQ ID NO:87): 5'  TACCACGCAAACAACTCAACAAAACAGGTCG
                         ACTTTAAATTTTTCTGCA 3'

AAGCTTTTTGTAACTAACTAATCGTT-3'). This was performed to insert a multiple cloning region containing the restriction sites for HindIII, PstI and SmaI between the EH and HB arms. The resultant plasmid was designated as pF7DO.

Construction of Insertion Plasmid for the H4 Hemagglutinin at the F8 Locus. A cDNA copy encoding the avian influenza H4 derived from A/Ty/Min/833/80 was obtained from Dr. R. Webster in plasmid pTM4H833. The plasmid was digested with HindIII and NruI and blunt-ended using the Klenow fragment of DNA polymerase in the presence of dNTPs. The blunt-ended 2.5 kbp HindIII-NruI fragment containing the H4 coding region was inserted into the HincII site of pIBI25 (International Biotechnologies, Inc., New Haven, Conn.). The resulting plasmid pRW828 was partially cut with BanII, the linear product isolated and recur with HindIII. Plasmid pRW828 now with a 100 bp HindIII-BanII deletion was used as a vector for the synthetic oligonucleotides RW152 (SEQ ID NO:79) and RW153 (SEQ ID NO:80). These oligonucleotides represent the 3' portion of the H6 promoter from the EcoRV site and align the ATG of the promoter with the ATG of the H4 cDNA.

The oligonucleotides were annealed at 95° C. for three minutes followed by slow cooling at room temperature. This results in the following double strand structure with the indicated ends.

```
EcoRV                                              PstI
|           RW12        |            RW13          |
       RW11        |           RW10
```

Cloning of oligonucleotides between the EcoRV and PstI sites of pRW742B resulted in pRW744. Plasmid pRW742B contains the vaccinia virus H6 promoter linked to a non-pertinent gene inserted at the HincII site of pRW731.15 described previously. Digestion with PstI and EcoRV eliminates the non-pertinent gene and the 3'-end of the H6 promoter. Plasmid pRW744 now contains the 3' portion of the H6 promoter overlapping the ATG of avian influenza H5. The plasmid also contains the H5 sequence through the 5' SalI site and the 3' sequence from the H5 stop codon (containing a DraI site). Use of the DraI site removes the H5

RW152 (SEQ ID NO:82): 5'  GCACGGAACAAAGCTTATCGCGATATCCGTTA
                          AGTTTGTATCGTAATGCTATCAATCACGATTCTGTTCCTGCTCATAGC
                          AGAGGGCTCATCTCAGAAT 3'

RW153 (SEQ ID NO:83): 5'  ATTCTGAGATGAGCCCTCTGCTATGAGCAGGA
                          ACAGAATCGTGATTGATAGCATTACGATACAAACTTAACGGATATCGC
                          GATAAGCTTTGTTCCGTGC 3'

The oligonucleotides were annealed, cut with BanII and HindIII and inserted into the HindIII-BanII deleted pRW828 vector described above. The resulting plasmid pRW844 was cut with EcoRV and DraI and the 1.7 kbp fragment containing the 3' H6 promoted H4 coding sequence was inserted between the EcoRV and HincII sites of pRW846 (described previously) forming plasmid pRW848. Plasmid pRW848 therefore contains the H4 coding sequence linked to the vaccinia virus H6 promoter in the de-ORFed F8 locus of fowlpox virus.

3' non-coding end. The oligonucleotides add a transcription termination signal recognized by early vaccinia virus RNA polymerase (Yuen et al., 1987). To complete the H6 promoted H5 construct, the H5 coding region was isolated as a 1.6 kpb SalI-DraI fragment from pTH29. Plasmid pRW744 was partially digested with DraI, the linear fragment isolated, recur with SalI and the plasmid now with eight bases deleted between SalI and DraI was used as a vector for the 1.6 kpb pTH29 SalI and DraI fragment. The resulting plasmid pRW759 was cut with EcoRV and DraI. The 1.7 kbp PRW759 EcoRV-DraI fragment containing the 3' H6 promoter and the H5 gene was inserted between the EcoRV and HincII sites of pRW846 (previously described). The resulting plasmid pRW849 contains the H6 promoted avian influenza virus H5 gene in the de-ORFed F8 locus.

Construction of Insertion Vector for H7 Hemagglutinin at the F7 Locus. Plasmid pCVH71 containing the H7 hemagglutinin from A/CK/VIC/1/85 was received from Dr. R. Webster. An EcoRI-BamHI fragment containing the H7 gene was blunt-ended with the Klenow fragment of DNA polymerase and inserted into the HincII site of pIBI25 as PRW827. Synthetic oligonucleotides RW165 (SEQ ID NO:88) and RW166 (SEQ ID NO:89) were annealed, cut with HincII and StyI and inserted between the ECoRV and StyI sites of pRW827 to generate pRW845.

RW165 (SEQ ID NO:88): 5' GTACAGGTCGACAAGCTTCCCGGGTATCGCG
ATATCCGTTAAGTTTGTATCGTAATGAATACTCAAATTCTAATACTCA
CTCTTGTGGCAGCCATTCACACAAATGCAGACAAAATCTGCCTTGGAC
ATCAT 3'

RW166 (SEQ ID NO:89): 5' ATGATGTCCAAGGCAGATTTTGTCTGCATTTG
TGTGAATGGCTGCCACAAGAGTGAGTATTAGAATTTGAGTATTCATTA
CGATACAAACTTAACGGATATCGCGATACCCGGGAAGCTTGTCGACCT
GTAC 3'

Oligonucleotides RW165 (SEQ ID NO:88) and RW166 (SEQ ID NO:89) link the 3' portion of the H6 promoter to the H7 gene. The 3' non-coding end of the H7 gene was removed by isolating the linear product of an ApaLI digestion of pRW845, recutting it with EcoRI, isolating the largest fragment and annealing with synthetic oligonucleotides RW227 (SEQ ID NO:90) and RW228 (SEQ ID NO:91). The resulting plasmid was pRW854.

RW227 (SEQ ID NO:90):

5' ATAACATGCGGTGCACCATTTGTATAT
AAGTTAACGAATTCCAAGTCAAGC 3'

RW228 (SEQ ID NO:91):

5' GCTTGACTTGGAATTCGTTAACTTATA
TACAAATGGTGCACCGCATGTTAT 3'

The stop codon of H7 in PRW854 is followed by an HpaI site. The intermediate H6 promoted H7 construct in the de-ORFed F7 locus (described below) was generated by moving the pRW854 EcoRV-HpaI fragment into pRW858 which had been cut with EcoRV and blunt-ended at its PstI site. Plasmid pRW858 (described below) contains the H6 promoter in an F7 de-ORFed insertion plasmid.

The plasmid pRW858 was constructed by insertion of an 850 bp SmaI/HpaI fragment, containing the H6 promoter linked to a non-pertinent gene, into the smaI site of pF7DO described previously. The non-pertinent sequences were excised by digestion of pRW858 with EcoRV (site 24 bp upstream of the 3'-end of the H6 promoter) and PstI. The 3.5 kb resultant fragment was isolated and blunt-ended using the Klenow fragment of the *E. coli* DNA polymerase in the presence of 2mM dNTPs. This blunt-ended fragment was ligated to a 1700 bp EcoRV/HpaI fragment derived from pRW854 (described previously). This EcoRV/HpaI fragment contains the entire AIV HA (H7) gene juxtaposed 3' to the 3'-most 24 bp of the VV H6 promoter. The resultant plasmid was designated pRW861.

The 126 bp EH arm (defined previously) was lengthened in pRW861 to increase the recombination frequency with genomic TROVAC DNA. To accomplish this, a 575 bp AccI/SnaBI fragment was derived from pRW 731.13 (defined previously). The fragment was isolated and inserted between the AccI and NaeI sites of pRW861. The resultant plasmid, containing an EH arm of 725 bp and a HB arm of 404 bp flanking the AIV H7 gene, was designated as pRW869. Plasmid pRW869 therefore consists of the H7 coding sequence linked at its 5' end to the vaccinia virus H6 promoter. The left flanking arm consists of 404 bp of TROVAC sequence and the right flanking arm of 725 bp of TROVAC sequence which directs insertion to the de-ORFed F7 locus.

Development of TROVAC-Avian Influenza Virus Recombinants. Insertion plasmids containing the avian influenza virus HA coding sequences were individually transfected into TROVAC infected primary CEF cells by using the calcium phosphate precipitation method previously described (Panicali et al., 1982; Piccini et al., 1987). Positive plaques were selected on the basis of hybridization to HA specific radiolabelled probes and subjected to sequential rounds of plaque purification until a pure population was achieved. One representative plaque was then amplified to produce a stock virus. Plasmid pRW849 was used in an in vitro recombination test to produce recombinant TROVAC-AIH5 (vFP89) expressing the H5 hemagglutinin. Plasmid pRW848 was used to produce recombinant TROVAC-AIH4 (vFP92) expressing the H4 hemagglutinin. Plasmid pRW869 was used to produce recombinant TROVAC-AIH7 (vFP100) expressing the H7 hemagglutinin.

Immunofluorescence. In influenza virus infected cells, the HA molecule is synthesized and glycosylated as a precursor molecule at the rough endoplasmic reticulum. During passage to the plasma membrane it undergoes extensive post-translational modification culminating in proteolytic cleavage into the disulphide linked $HA_1$ and $HA_2$ subunits and insertion into the host cell membrane where it is subsequently incorporated into mature viral envelopes. To determine whether the HA molecules produced in cells infected with the TROVAC-AIV recombinant viruses were expressed on the cell surface, immunofluorescence studies were performed. Indirect immunofluorescence was performed as described (Taylor et al., 1990). Surface expression of the H5 hemagglutinin in TROVAC-AIH5, H4 hemagglutinin in TROVAC-AIH4 and H7 hemagglutinin in TROVAC-AIH7 was confirmed by indirect immunofluorescence. Expression of the H5 hemagglutinin was detected using a pool of monoclonal antibodies specific for the H5HA. Expression of the H4HA was analyzed using a goat monospecific anti-H4 serum. Expression of the H7HA was analyzed using a H7 specific monoclonal antibody preparation.

Immunoprecipitation. It has been determined that the sequence at and around the cleavage site of the hemagglutinin molecule plays an important role in determining viral virulence since cleavage of the hemagglutinin polypeptide is necessary for virus particles to be infectious. The hemagglutinin proteins of the virulent H5 and H7 viruses possess more than one basic amino acid at the carboxy terminus of HA1. It is thought that this allows cellular proteases which recognize a series of basic amino acids to cleave the hemagglutinin and allow the infectious virus to spread both in vitro and in vivo. The hemagglutinin molecules of H4 avirulent strains are not cleaved in tissue culture unless exogenous trypsin is added.

In order to determine that the hemagglutinin molecules expressed by the TROVAC recombinants were authentically processed, immunoprecipitation experiments were performed as described (Taylor et al., 1990) using the specific reagents described above.

Immunoprecipitation analysis of the H5 hemagglutinin expressed by TROVAC-AIH5 (vFP89) showed that the glycoprotein is evident as the two cleavage products $HA_1$ and $HA_2$ with approximate molecular weights of 44 and 23 kDa, respectively. No such proteins were precipitated from uninfected cells or cells infected with parental TROVAC. Similarly immunoprecipitation analysis of the hemagglutinin expressed by TROVAC-AIH7 (vFP100) showed specific precipitation of the HA2 cleavage product. The $HA_1$ cleavage product was not recognized. No proteins were specifically precipitated from uninfected CEF cells or TROVAC infected CEF cells. In contrast, immunoprecipitation analysis of the expression product of TROVAC-AIH4 (vFP92) showed expression of only the precursor protein $HA_O$. This is in agreement with the lack of cleavage of the hemagglutinins of avirulent subtypes in tissue culture. No H4 specific proteins were detected in uninfected CEF cells or cells infected with TROVAC. Generation of recombinant virus by recombination, in situ hybridization of nitrocellulose filters and screening for B-galactosidase activity are as previously described (Panicali et al., 1982; Perkus et al., 1989).

Example 26

CHV gB, gC AND gD NUCLEOTIDES IN VECTOR SYSTEM, EXPRESSION THEREFROM AND USE OF VECTOR SYSTEM AND EXPRESSION PRODUCT

Expression of the CHV gB glycoprotein is accomplished by putting the CHV gB homolog gene under the control of the vaccinia virus I3L promoter. Expression of the CHV gC glycoprotein is accomplished by putting the CHV gC homolog gene under the control of the vaccinia virus H6 promoter. Expression of the CHV gD glycoprotein is accomplished by putting the CHV gD homolog gene under the control of the entomopox virus 42K gene promoter. The gB and gC coding is in the ATI locus and, the gD coding is in the HA locus.

Generation of Donor Plasmid. The CHV gB coding sequence is PCR-derived. The CHV gB fragment is fused to a PCR-derived fragment containing the I3L promoter element in a plasmid containing the cassette I3L-CHV gB in the ATI deorfed locus. The CHV gC coding is PCR-derived and is fused in the HA deorfed locus in a plasmid.

A donor plasmid is used to insert the I3L-CHV gB-H6-CHV gC double construction in the NYVAC ATI deorfed locus.

In vitro recombination is performed on Vero cells using the donor plasmid and vP866 (NYVAC) as the rescuing virus. Standard protocols were used to identify and purify the recombinant virus (Piccini et al., 1987). The NYVAC-based recombinant containing the CHV gB and gC genes in the ATI deorfed locus is designated NYVAC-CHVgBgC.

Generation of Donor Plasmid. The CHV gD coding sequence is fused to the 42K promoter and a resulting plasmid therefrom generated for insertion with the NYVAC HA deorfed locus.

In vitro recombination is performed on Vero cells using the CHVgD-42K donor plasmid and recombinant vaccinia virus NYVAC-CHVgBgC (NYVAC background) as the rescuing virus. This is performed with standard procedures (Piccini et al., 1987). The NYVAC-based recombinant containing the CHV gB and gC genes in the ATI deorfed locus and the CHV gD gene in the HA deorfed locus is designated NYVAC-CHVgBgCgD.

Generation of ALVAC donor plasmid. A plasmid donor plasmid to insert the I3L-CHV gB-H6-CHV gC-42K-CHV gD triple construction in the ALVAC C3 deorfed locus is constructed from the above plasmids.

In vitro recombination is performed on primary chick embryo fibroblasts using the donor plasmid and CPpp (ALVAC) as the rescuing virus. Standard procedures are followed to identify and purify the generated recombinant (Piccini et al., 1987). The ALVAC-based recombinant contains the CHV gB, gC and gD genes in the C3 deorfed locus and is designated ALVAC-CHVgBgCgD.

Analysis confirms expression of the glycoproteins by the recombinants and, the glycoproteins are substantially within the predicted sequences.

Example 27

GENERATION OF vCP320; AN ALVAC RECOMBINANT EXPRESSING CHV gB vCP320, an ALVAC recombinant expressing CHV gB, was generated by the following procedure. A 6 kb XbaI fragment, containing the CHV gB gene, was isolated from genomic CHV DNA and cloned into the XbaI site of pBSK+. The plasmid generated by this manipulation is called pCHV2.

The CHV gB gene was then cloned between canarypox flanking arms. This was accomplished by cloning the 3,700 bp SacI-EcoRV fragment of pCHV2, containing the CHV gB gene, into the 5,800 bp SacI-NaeI fragment of pBHVC16. (pBHVC16 contains a copy of the BHV1 gC gene cloned between C5 flanking arms.) The plasmid generated by this manipulation is called pCHV14.

Extraneous 3'-noncoding sequence was then eliminated. This was accomplished by cloning a 210 bp SmaI-CuaI-digested PCR fragment, containing the 3'-end of the gB gene, into the 5,500 bp partial SmaI-ClaI fragment of pCHV14. (This PCR fragment was generated from the plasmid, pCHV2, with the primers, CHVP39 (SEQ ID NO:92; 5'-TAAGAATGGTAATTCT-3') and CHVP40 (SEQ ID NO:93; 5'-TTCCCGGGTTAAACTTTACTTTCATTTTC-3').) The plasmid generated by this manipulation is called pCHV15.

The I3L promoter was then cloned upstream from the gB initiation codon. In addition, 3 $T_5NT$ early transcription termination signal sequences located in the 5'-end of the gB gene were modified. This was accomplished by cloning a 140 bp ScaI-SalI-digested PCR fragment, containing the I3L promoter and the $T_5NT$-modified 5'-end of the gB gene, into the 6,300 bp ScaI-SalI fragment of pCHV15. (This PCR fragment was generated from the plasmid, pCHV2, with the primers, CHVP42 (SEQ ID NO:94; 5'-TTGTCGACTGAGATAAAGTGAAAATATATATCA-TTATATTACAAAGTACAATTATTTAGG TTTAATCATGTTTTCATTGTATCTATAT-3') and CHVP78 (SEQ ID NO:95; 5'-TTAGTA-CTTTCCGGTGTTGTTGGATCACATATTATTAAAGTAT-AAATAATAAAGAA-3').) The plasmid generated by this manipulation is called pCHV27.

An error in the sequence flanking the ScaI-SalI fragment of pCHV27 was then corrected. This was accomplished by cloning the 180 bp ScaI-SalI fragment of pCHV27, containing the I3L promoter and the $T_5NT$-modified 5'-end of the gB gene, into the 6,300 bp ScaI-SalI fragment of pCHV15. The plasmid generated by this manipulation is called pCHV28.

An early transcription termination signal sequence near the 3'-end of the CHV gB gene was then modified. This was accomplished by cloning a 330 bp SpeI-Asp718-digested PCR fragment, containing the $T_5NT$-modified region of the CHV gB gene, into the 5,450 bp SpeI-Asp718 fragment of pCHV28. (This PCR fragment was generated from a 150 bp PCR fragment, a 280 bp PCR fragment and the primers, CHVP89 (SEQ ID NO:96; 5'-TGGAATGAAGTTATGAAACT-3') and CHVP92 (SEQ ID NO:97; 5'-TGCACTGATCATTTCAATTTC-3'). The 150 bp PCR fragment was generated from the plasmid, pCHV2, with the primers, CHVP89 (SEQ ID NO:96; 5'-TGGAATGAAGTTATGAAACT-3') and CHVP90 (SEQ ID NO:98; 5'-TGGAATTTTGAATGAAAACACTAGAACC-3'). The 280 bp PCR fragment was generated from the plasmid, pCHV2, with the primers, CHVP91 (SEQ ID NO:99; 5'-TTCTAGTGTTTTCATTCAAAATTCCAT-3,) and CHVP92 (SEQ ID NO:97; 5'-TGCACTGATCATTTCAATTTC-3').) The plasmid generated by this manipulation is called pCHV31.

An early transcription termination signal sequence in the middle of the CHV gB gene was then modified. This was accomplished by cloning a 480 bp BamHI-BsaBI-digested PCR fragment, containing the $T_5NT$-modified region of the gB gene, into the 5,000 bp BamHI-BsaBI fragment of pCHV31. (This PCR fragment was generated from a 380 bp PCR fragment, a 210 bp PCR fragment and the primers, CHVP87 (SEQ ID NO:100; 5'-CCTTCAAAGTTTAATACACC-3,) and CHVP94 (SEQ ID NO:101; 5'-TATGGCTTCACGTTTGGCAC-3,). The 380 bp PCR fragment was generated from the plasmid, pCHV2, with the primers, CHVP93 (SEQ ID NO:102; 5'-CACCGGGGATATAATTCATATGTCCCCTTTCTTT-GGATTACGAGATGGT-3') and CHVP94 (SEQ ID NO:101; 5'-TATGGCTTCACGTTTGGCAC-3'). The 210 bp PCR fragment was generated from the plasmid, pCHV2, with the primers, CHVP87 (SEQ ID NO:100; 5'-CCTTCAAAGTTTAATACACC-3') and CHVP88 (SEQ ID NO:103; 5'-CCATCTCGTAATCCAAAGAAA-GGGGACATATGAAT-3').) The plasmid generated by this manipulation is called pCHV32.

A portion of the gB gene removed in the previous manipulation was then cloned back into pCHV32. This was accomplished by cloning the 2,000 bp partial BsaBI-PstI fragment of pCHV31, containing the 3'-end of the gB gene removed in the previous manipulation, into the 5,450 bp BsaBI-PstI fragment of pCHV32. The plasmid generated by this manipulation is called pCHV36.

The I3L-promoted gB gene was then cloned between C6 flanking arms. This was accomplished by cloning the 2,750 bp SalI-SmaI fragment of pCHV36, containing the I3L-promoted gB gene, into the 4,350 bp SalI-SmaI fragment of pHIV34. (pHIV34 contains a copy of the H6-promoted HIV2 gp120 (+TM) gene cloned between C6 flanking arms.) The plasmid generated by this manipulation is called pCHV37. The DNA sequence of the I3L-promoted gB gene in pCHV37 (SEQ ID NOS:104, 105, 106) is shown in FIG. 23. The DNA sequence of the ALVAC C6 flanking arms (SEQ ID NOS:107, 108) is shown in FIG. 24.

pCHV37 was used in in vitro recombination experiments with ALVAC as the rescuing virus to yield vCP320.

Figure 25:
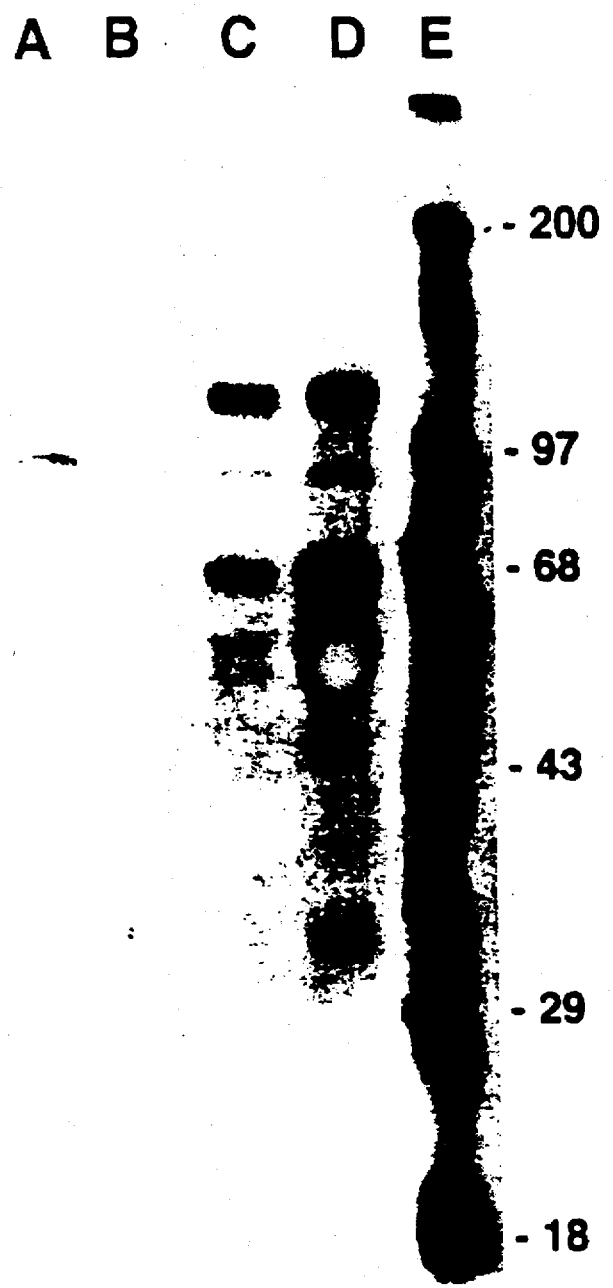
FIG. 25 shows the immunoprecipitation analysis of vCP320-infected cells (Lysates from $^{35}$S-labeled mock-infected cells (lane A), ALVAC-infected cells (lane B), vCP320-infected cells (lane C) and CHV-infected cells (lane D) were immunoprecipitated with a CHV gB-specific monoclonal antibody, 1125B2 (obtained from Rhone Merieux, Lyon, France), and resolved on an SDS-polyacrylamide gel. Molecular weight standards are resolved in lane E)

Immunoprecipitation analysis was performed to determine whether vCP320 expresses CHV gB. MDCK cell monolayers were either mock infected or infected with the parental virus (ALVAC) (m.o.i.=15 PFU/cell), vCP320 (m.o.i.=15 PFU/cell) or CHV (m.o.i.=10 PFU/cell). Following an hour adsorption period, the inoculum was removed and the cells were overlayed with 2 mls of modified Eagle's medium (minus cysteine) containing 2% dialyzed fetal bovine serum and [$^{35}$S]-cysteine (50 µCi/ml). The lysates were harvested at 18 hrs post-infection in 1 ml 3× buffer A (450 mM NaCl, 3% NP-40, 30 mM Tris (pH=7.4),.3 mM EDTA, 0.03% Na-Azide and 0.6 mg/ml PMSF) and analyzed for CHV gB expression using a 1:100 dilution of a gB-specific monoclonal antibody, 1125B2 (obtained from Dr. Michel Riviere, Rhone Merieux, Lyon, France). Lysates, precleared with normal mouse sera and a goat anti-mouse-protein A-sepharose complex, were incubated overnight at 4° C. with a monoclonal antibody-goat anti-mouse-protein A-sepharose complex and washed 4× with 1× buffer A and 2× with a $LiCl_2$ urea buffer. Precipitated proteins were dissociated from the immune complexes by the addition of 2× Laemmli's buffer (125 mM Tris (pH =6.8), 4% SDS, 20% glycerol, 10% 2-mercaptoethanol) and boiling for 5 min. Proteins were fractionated on an SDS-polyacrylamide gel, fixed and treated with 1M Na-salicylate for fluorography. Proteins of the appropriate size were precipitated from CHV-infected cells (lane D) and vCP320-infected cells (lane C), but were not precipitated from mock-infected cells (lane A) or ALVAC-infected cells (lane B) (FIG. 25). These results indicate that vCP320 expresses CHV gB.

Example 28

GENERATION OF VCP322; AN ALVAC RECOMBINANT EXPRESSING CHV gC

VCP322, an ALVAC recombinant expressing CHV gC, was generated by the following procedure. A 2.2 kb EcoRI fragment, containing the CHV gC gene, was isolated from genomic CHV DNA and cloned into the EcoRI site of pVQH6CP3LSA. (pVQH6CP3LSA contains a copy of the H6 promoter cloned between C3 flanking arms.) This manipulation positions the gC gene downstream from the H6 promoter and between C3 flanking arms. The plasmid generated by this manipulation is called pCHV17.

Extraneous 3'-noncoding sequence was then eliminated and 3 $T_5NT$ early transcription termination signal sequences located near the 3'-end of the gC gene were modified. This was accomplished by cloning the oligonucleotides, CHVL66 (SEQ ID NO:109; 5'-CGATGTTAATAAGTATTACCACAATAATTGGTGG-AGCCATTTTCGTTATAGTATTGATTT TCATAACAGCTTTATGTTTCTATTGTTCAAAAAAT-AATAAGATCTAACTGCA-3') and CHVL67 (SEQ ID NO:110; 5'-GTTAGATCTTATTATTTTTTGAACAATA-GAAACATAAAGCTGTTATGAAAATCAATACTA TAACGAAAATGGCTCCACCAATTATTGTGGTAATA-CTTATTAACAT-3'), into the 8,400 bp partial ClaI-PstI fragment of pCHV17. The plasmid generated by this manipulation is called pCHV20.

The initiation codon of the gC gene was then aligned with the initiation codon of the H6 promoter. In addition, 2 early transcription termination signal sequences were modified. This was accomplished by cloning a 740 bp NruI-BsrGI-digested PCR fragment, containing the 3'-end of the H6 promoter and the 5'-end of the $T_5NT$-modified gC gene, into the 7,900 bp NruI-BsrGI fragment of pCHV20. (This PCR fragment was generated from a 500 bp PCR fragment, a 300 bp PCR fragment and the oligonucleotides, CHVP96 (SEQ ID NO:111; 5'-CGTAGATTCCAATGGAAAGT-3') and CHVP97 (SEQ ID NO:112; 5'-TTTTCGCGATATCCGTTAAGT-3'). The 500 bp PCR fragment was generated from the plasmid, pCHV13, with the oligonucleotides, CHVP68 (SEQ ID NO:113; 5'-TTTTCGCGATATCCGTTAAGTTTGTATCGTAATG-AGTTTTAAAAATTTCTATCTAATATA TGTAATTATAATTTTCATAAACTCGATAATAAC-3') and CHVP69 (SEQ ID NO:114; 5'-TTTGTATACCTAATAAGAAATCATTATAAAAGT-3'). The 300 bp PCR fragment was generated from the plasmid, pCHV13, with the oligonucleotides, CHVP95 (SEQ ID NO:115; 5'-CTTTTATAATGATTTCTTATTAGGT-ATACAAAATC-3') and CHVP96 (SEQ ID NO:111; 5'-CGTAGATTCCAATGGAAAGT-3'). pCHV13 was obtained by cloning the 2.2 kb EcoRI CHV genomic fragment, containing the gC gene, into the EcoRI site of pBSK+.) The plasmid generated by this manipulation is called pCHV38.

Figures 26, 26A, 26B, 26C, 26D, 26E, 26F, 26G:
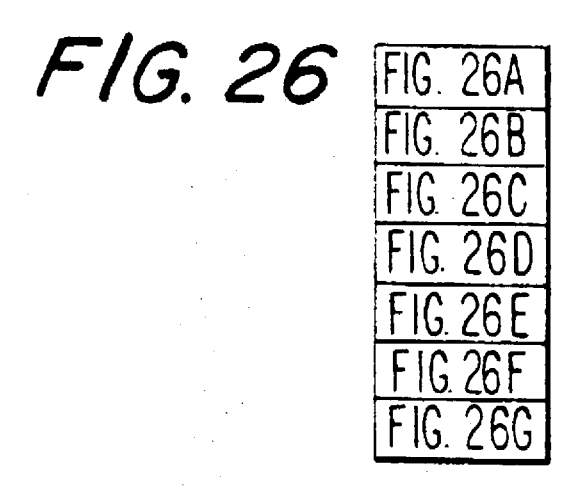

The H6-promoted gC gene was then cloned between C6 flanking arms. This was accomplished by cloning the 1,400 bp NruI-PstI fragment of pCHV38, containing the H6-promoted gC gene, and the oligonucleotide, CHVL98 (SEQ ID NO:116; 5'-AATTTGCA-3'), into the 4,500 bp NruI-EcoRI fragment of pHIV34. (pHIV34 contains a copy of the H6-promoted HIV2 gp120 (+TM) gene cloned between C6 flanking arms.) The plasmid generated by this manipulation is called pCHV40. The DNA sequence of the H6-promoted gC gene in pCHV40 (SEQ ID NOS:117, 118, 119) is shown in FIG. 26. The DNA sequence of the ALVAC C6 flanking arms (SEQ ID NOS:107, 108) is shown in FIG. 24.

pCHV40 was used in in vitro recombination experiments with ALVAC as the rescuing virus to yield vCP322.

Figure 27:
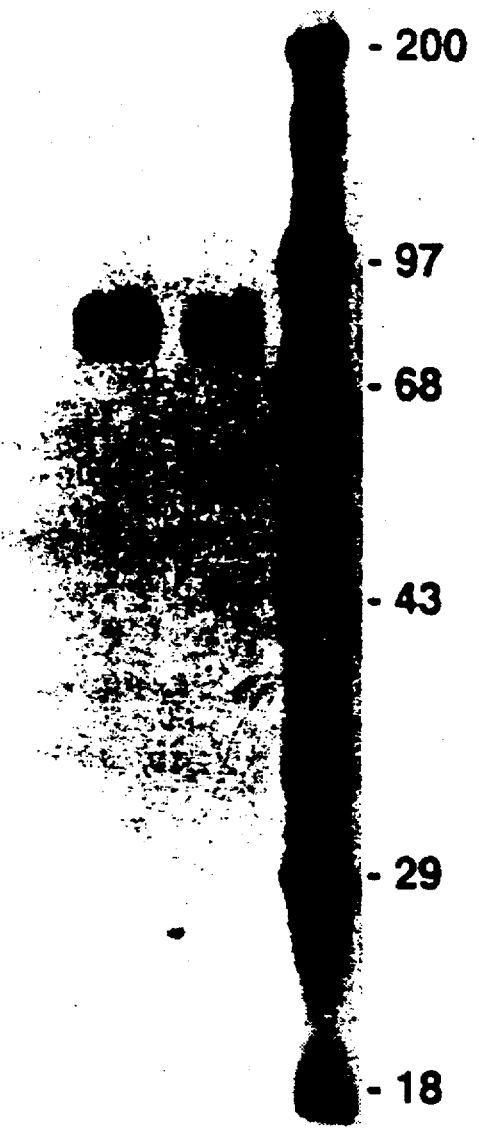
FIG. 27 shows the immunoprecipitation analysis of vCP322-infected cells (Lysates from $^{35}$S-labeled mock-infected cells (lane A), ALVAC-infected cells (lane B), vCP322-infected cells (lane. C) and CHV-infected cells (lane D) were immunoprecipitated with a CHV gC-specific monoclonal antibody, 2011A9 (obtained from Rhone Merieux, Lyon, France), and resolved on an SDS-polyacrylamide gel. Molecular weight standards are resolved in lane E)

Immunoprecipitation analysis was performed to determine whether vCP322 expresses CHV gC. MDCK cell monolayers were either mock infected or infected with the parental virus (ALVAC) (m.o.i.=15 PFU/cell), vCP322 (m.o.i.=15 PFU/cell) or CHV (m.o.i.=10 PFU/cell). Following an hour adsorption period, the inoculum was removed and the cells were overlayed with 2 mls of modified Eagle's medium (minus cysteine) containing 2% dialyzed fetal bovine serum and [$^{35}$S]-cysteine (50 µCi/ml). The lysates were harvested at 18 hrs post-infection in 1 ml 3× buffer A (450 mM NaCl, 3% NP-40, 30 mM Tris (pH =7.4), 3 mM EDTA, 0.03% Na-Azide and 0.6 mg/ml PMSF) and analyzed for CHV gC expression using a 1:100 dilution of a gC-specific monoclonal antibody, 2011A9 (obtained from Dr. Michel Riviere, Rhone Merieux, Lyon, France). Lysates, precleared with normal mouse sera and a goat anti-mouse-protein A-sepharose complex, were incubated overnight at 4° C. with a monoclonal antibody-goat anti-mouse-protein A-sepharose complex and washed 4× with 1× buffer A and 2X with a LiCl$_2$/urea buffer. Precipitated proteins were dissociated from the immune complexes by the addition of 2× Laemmli's buffer (125 mM Tris (pH=6.8), 4% SDS, 20% glycerol, 10% 2-mercaptoethanol) and boiling for 5 min. Proteins were fractionated on an SDS-polyacrylamide gel, fixed and treated with 1M Na-salicylate for fluorography. Proteins of the appropriate size were precipitated from CHV-infected cells (lane D) and vCP322-infected cells (lane C), but were not precipitated from mock-infected cells (lane A) or ALVAC-infected cells (lane B) (FIG. 27). These results indicate that vCP322 expresses CHV gC.

Example 29

GENERATION OF vCP294; AN ALVAC RECOMBINANT EXPRESSING CHV gD vCP294, an ALVAC recombinant expressing CHV gD, was generated by the following procedure. A 7 kb PstI fragment, containing the CHV gD gene, was isolated from genomic CHV DNA and cloned into the PstI site of pBSK+. The plasmid generated by this manipulation is called pCHV11.

The CHV gD gene was then cloned between canarypox flanking arms. This was accomplished by cloning the 1,475 bp PstI-SnaBI fragment of pCHV11, containing the CHVgD gene, into the 5,600 bp PstI-SmaI fragment of pHIV34. (pHIV34 contains a copy of the H6-promoted HIV2 gp120 (+TM) gene cloned between C6 flanking arms.) This places the CHV gD gene between C6 flanking arms and downstream from the H6 promoter. The plasmid generated by this manipulation is called pCHV18.

The initiation codon of the H6 promoter was then aligned with the initiation codon of the CHV gD gene. This was accomplished by cloning the oligonucleotides, CHVL81 (SEQ ID NO:120; 5'-CGATATCCGTT- AAGTTTGTATCG-TAATGATTAAACTTCTATTTATCTTATTTTATTTTAA CCCAATAA-3') and CHVL82 (SEQ ID NO:121; 5'-TTGGGTTAAAATAAAATAAGATAAATAGAAGTTT-AATCATTACGATACAAACTTAACGGA TATCG-3'), into the 5,600 bp NruI-PflMI fragment of pCHV18. The plasmid generated by this manipulation is called pCHV21.

Three early transcription termination signal sequences at the 3'-end of the CHVgD gene were then modified. This was accomplished by cloning the 1,400 bp BglII-Asp718 fragment of pCHV22, containing the "$T_5$NT-modified" 3'-end of the CHV gD gene and C3 flanking arm, into the 3,700 bp BglII-Asp718 fragment of pCHV21. (pCHV22 was generated by cloning a 430 bp BglII-EcoRI-digested PCR fragment, containing the "$T_5$NT-modified" 3'-end of the CHV gD gene, into the 3,900 bp BglII-EcoRI fragment of pHIV43 (pHIV43 contains a copy of the H6-promoted HIV1 gp120-murine IL-2 fusion gene cloned between C3 flanking arms). (This PCR fragment was generated from the plasmid, pCHV18, with the oligonucleotides, CHVP79 (SEQ ID NO:122; 5'-TTGAATTCCTAAACATTTGTTG-TTAATTTTTTATAATTATTATATATTTTTTGTC TTTTATAAACAAAGAAT-3') and CHVP80 (SEQ ID NO:123; 5'-TTAGATCTGTAGGAGCATCAAAA-GTTGACGATGAACTTTTCTATCTAAATAGAGC TGGTCCCCAAACCCTGCTTAAATATTATGTTATTAA-AGATTTCTAT-3,).)) The plasmid generated by this manipulation is called pCHV24.

The "$T_5$NT-modified" central region of the CHV gD gene was then cloned into pCHV24. This was accomplished by cloning a 240 bp BglII-digested PCR fragment, containing the "$T_5$NT-modified" central region of the CHV gD gene, into the BglII site of pCHV24. (This PCR fragment was generated from the plasmid, pCHV18, with the oligonucleotides, CHVP83 (SEQ ID NO:124; 5'-TTAGATCTAGATTCCTTACACCATTCCATAAAAG-TTGGTTCAAATTTATCTTCTTTAGAG AAATAACAAGTTTCTCGTGGTAATTGAACCAT-AAAATCAGTATAGAAAAC-3') and CHVP84 (SEQ ID NO:125; 5'-TATTTTGATTGTGATCC-3').) The plasmid generated by this manipulation is called pCHV25.

The C3 flanking arm was then replaced with the C6 flanking arm. This was accomplished by cloning the 1,160 bp EcoRI-Asp718 fragment of pCHV21, containing the C6 flanking arm, into the 4,100 bp EcoRI-Asp718 fragment of pCHV25. The plasmid generated by this manipulation is called pCHV26. The DNA sequence of the H6-promoted gD gene in pCHV26 (SEQ ID NO:107, 108) is shown in FIG. 28. The DNA sequence of the ALVAC C6 flanking arms (SEQ ID NO:107, 108) is shown in FIG. 24.

pCHV26 was used in in vitro recombination experiments with ALVAC as the rescuing virus to yield vCP294.

Figure 29:
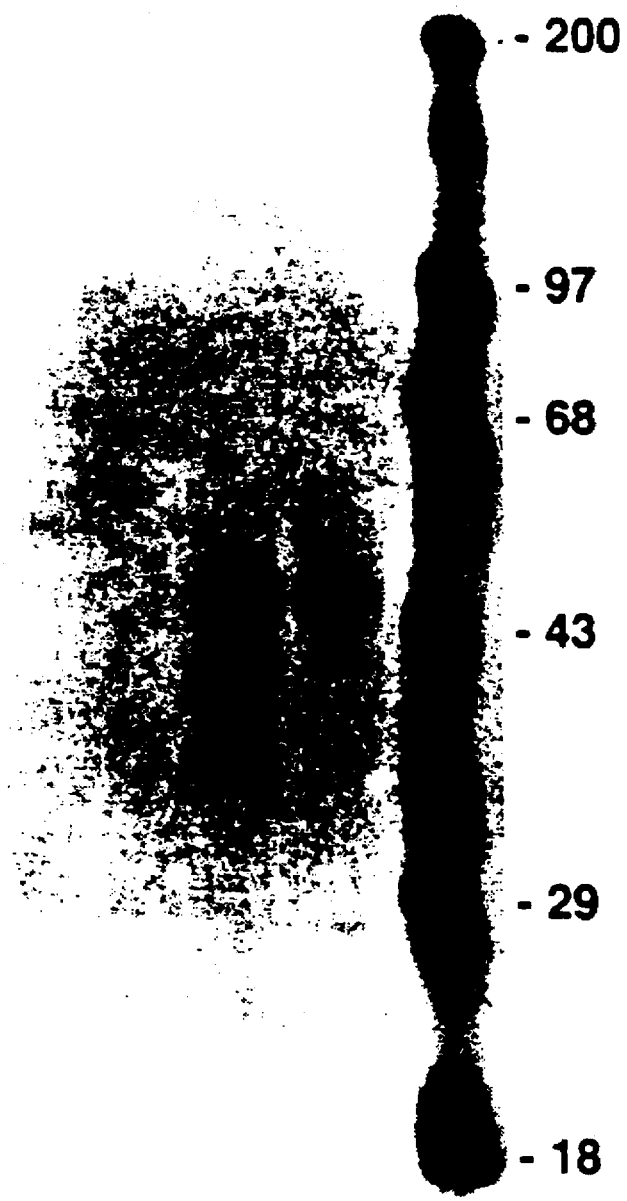
FIG. 29 shows the immunoprecipitation analysis of vCP294-infected cells (Lysates from $^{35}$S-labeled mock-infected cells (lane A), ALVAC-infected cells (lane B), vCP294-infected cells (lane C) and CHV-infected cells (lane D) were immunoprecipitated with a CHV gD-specific monoclonal antibody, 208D11 (obtained from Rhone Merieux, Lyon, France), and resolved on an SDS-polyacrylamide gel. Molecular weight standards are resolved in lane E).

Immunoprecipitation analysis was performed to determine whether vCP294 expresses CHV gD. MDCK cell monolayers were either mock infected or infected with the parental virus (ALVAC) (m.o.i.=15 PFU/cell), vCP294 (m.o.i.=15 PFU/cell) or CHV (m.o.i.=10 PFU/cell). Following an hour adsorption period, the inoculum was removed and the cells were overlayed with 2 mls of modified Eagle's medium (minus cysteine) containing 2% dialyzed fetal bovine serum and [$^{35}$S]-cysteine (50 µCi/ml). The lysates were harvested at 18 hrs post-infection in 1 ml 3× buffer A (450 mM NaCl, 3% NP-40, 30 mM Tris (pH=7.4), 3 mM EDTA, 0.03% Na-Azide and 0.6 mg/ml PMSF) and analyzed for CHV gD expression using a 1:100 dilution of a gD-specific monoclonal antibody, 208D11 (obtained from Dr. Michel Riviere, Rhone Merieux, Lyon, France). Lysates, precleared with normal mouse sera and a goat anti-mouse-protein A-sepharose complex, were incubated overnight at 4° C. with a monoclonal antibody-goat anti-mouse-protein A-sepharose complex and washed 4× with 1 × buffer A and 2× with a LiC$_2$/urea buffer. Precipitated proteins were dissociated from the immune complexes by the addition of 2× Laemmli's buffer (125 mM Tris (pH=6.8), 4% SDS, 20% glycerol, 10% 2-mercaptoethanol) and boiling for 5 min. Proteins were fractionated on an SDS-polyacrylamide gel, fixed and treated with 1M Na-salicylate for fluorography. Proteins of similar size were precipitated from CHV-infected cells (lane D) and vCP294-infected cells (lane C), but were not precipitated from mock-infected cells (lane A) or ALVAC-infected cells (lane B) (FIG. 29). These results indicate that vCP294 expresses CHV gD.

Having thus described in detail preferred embodiments of the present invention, it is to be understood that the invention defined by the appended claims is not to be limited by particular details set forth in the above description as many apparent variations thereof are possible without departing from the spirit or scope thereof.

The recombinants can be used to stimulate an antibody or immune response in pups and adult dogs against CHV and, so too can the expression products which can be isolated from cells infected by the recombinants. Further, the recombinants or the expression products therefrom can be used to generate antibodies in an animal administered the recombinants or the expression products therefrom and, the antibodies can be further used as described herein.

REFERENCES

1. Ackermann, M., R. Longnecker, B. Roizman, and L. Pereira, Virology 150, 207–220 (1986).
2. Allen, G. P. and M. R. Yeargan, J. Virol. 61, 2454–2461 (1987).
3. Allen, G. P. and J. T. Bryans, In: Progress in Veterinary Microbiology and Immunology, Vol. 2, ed. R. Pandey (Basel), pp. 78–144 (1986).
4. Allen, G. P., and L. D. Coogle, J. Virol. 62, 2850–2858 (1988).
5. Altenburger, W., C-P. Suter and J. Altenburger, Archives Virol. 105, 15–27 (1989).
6. Appel, M., In Virus Infections of Vertebrates, vol. 1, pp. 5–15. Edited by M. Appel. Amsterdam-Oxford-New York-Tokyo: Elsevier Science Publishers (1987).
7. Audonnet, J. -C., Winslow, J., Allen, G. & Paoletti, E., Journal of General Virology 71, 2969–2978 (1990).
8. Avery, R. J., and J. Niven., Infect. and Immun. 26, 795–801 (1979).
9. Babiuk, L. A., J. L'Italien, S. van Drunen Littel-van den Hurk, T. Zamb, M. J. P. Lawman, G. Hughes, and G. A. Gifford, J. Virol. 159, 57–66 (1987).
10. Baer, R., A. T. Bankier, M. D. Biggin, P. L. Deininger,, P. J. Farrell, T. J. Gibson, G. Hatfull, G. S. Hudson, S. C. Satchwell, C. Seguin, P. S. Tuffnell, and B. G. Barrell, Nature 310, 207–211 (1984).
11. Baines, J., and B. Roizman, J. Virol. 67, 1441–1452 (1993).
12. Balachandran, N., S. Bacchetti, and W. E. Rawls, Infect. Immun. 37, 1132–1137 (1982).
13. Bause, E., Biochemical Journal 209, 331–336 (1983).
14. Behbehani, A. M., Microbiological Reviews 47, 455–509 (1983).
15. Ben-Porat, T., J. DeMarchi, J. Pendrys, R. A. Veach, and A. S. Kaplan, J. Virol. 57, 191–196 (1986).
16. Ben-Porat, T. and A. S. Kaplan, In: The Herpesviruses, vol. 3, ed. B. Roizman (Plenum Publishing Corp., New York) pp. 105–173 (1985).
17. Ben-Porat, T., F. J. Rixon, and M. L. Blankenship, Virology 95, 285–294 (1979).
18. Bergoin, M., and Dales, S., In Comparative Virology, eds. K. Maramorosch and E. Kurstak, (Academic Press, NY) pp. 169–205 (1971).
19. Betman, P. W., D. Dowbenko, L. A. Lasky, and C. C. Simonsen, Science 222, 524–527 (1983).
20. Bertholet, C., Drillien, R., and Wittek, R., Proc. Natl. Acad. Sci. USA 82, 2096–2100 (1985).
21. Blewett, E. & Misra, V., Journal of General Virology 72, 2083–2090 (1991).
22. Blobel, G., Proceedings of the National Academy of Sciences, U.S.A. 77, 1496–1500 (1980).
23. Boursnell, M. E. G., P. F. Green, J. I. A. Campbell, A. Deuter, R. W. Peters., F. M. Tomley, A. C. R. Samson, P. Chambers, P. T. Emmerson, and M. M. Binns, J. Gen. Virol. 71, 621–628 (1990a).
24. Boursnell, M. E. G., P. F. Green, J. I. A. Campbell, A. Deuter, R. W. Peters, F. M. Tomley, A. C. R. Samson, P. T. Emmerson, and M. M. Binns, Veterinary Microbiology 23 305–316 (1990b).
25. Boursnell, M. E. G., P. F. Green, A. C. R. Samson, J. I. A. Campbell, A. Deuter, R. W. Peters, N. S. Millar, P. T. Emmerson, and M. M. Binns, Virology 178, 297–300. (1990c).
26. Brockmeier, S., Lager, K., Tartaglia, J., Riviere, M., Paoletti, E. & Mengeling, W., Veterinary Microbiology 38, 41–58 (1993).
27. Buller, R. M. L., G. L. Smith, Cremer, K., Notkins, A. L., and Moss, B., Nature 317, 813–815 (1985).
28. Buller, R. M. L., Chakrabarti, S., Cooper, J. A., Twardzik, D. R., and Moss, B., J. Virol. 62, 866–874 (1988).
29. Bzik, D. J., B.A. Fox, N. A. DeLuca, and S. Person, Virology 133, 301–307 (1984).
30. Cadoz, M., A. Strady, B. Meignier, J. Taylor, J. Tartaglia, E. Paoletti and S. Plotkin, The Lancet, 339, 1429 (1992).
31. Cantin, E. M., R. Eberle, J. L. Baldick, B. Moss, D. E. Willey, A. L. Notkins, and H. Openshaw, Proc. Natl. Acad. Sci. USA 84, 5908–5912 (1987).
32. Carmichael, L., Strandberg, J. & Barnes, F., Proceedings of the Society for Experimental Biology and Medicine, 120, 644–650 (1965).
33. Carmichael, L., Journal of the American Veterinary Medical Association 156, 1714–1721 (1970).

34. Chambers, P., N. S. Millar, and P. T. Emmerson, J. Gen. Virol. 67, 2685–2694 (1986).
35. Chan, W., Immunol. 49, 343–352 (1983).
36. Child, S. J., Palumbo, G. J., Buller, R. M. L., and Hruby, D. E. Virology 174, 625–629 (1990).
37. Clewell, D. B., J. Bacteriol. 110, 667–676 (1972).
38. Clewell, D. B. and D. R. Helinski, Proc. Natl. Acad. Sci. USA 62, 1159–1166 (1969).
39. Colinas, R. J., R. C. Condit and E. Paoletti, Virus Research 18, 49–70 (1990).
40. Compton, T., In: Cell Biology of Virus Entry, Replication, and Pathogenesis, eds. Compans, R. W., A. Helenius, and M. B. A. Oldstone (Alan R. Liss, Inc.) pp. 45–56 (1989).
41. Cooney E. L., Corrier A. C., Greenberg P. D., et al., Lancet 337, 567–572 (1991).
42. Corden, J., Wasylyk, B., Buchwalder, A., Sassone-Corsi, P., Kedinger, C. & Chambon, P., Science 209, 1406–1414 (1980).
43. Cranage, M. P., T. Kouzarides, A. T. Bankier, S. Satchwell, K. Weston, P. Tomlinson, B. Barrell, H. Hart, S. E. Bell, A. C. Minson, and G. L. Smith, EMBO J. 5, 3057–3063 (1986).
44. Cremer, K. J., M. Mackett, C. Wohlenberg, A. L. Notkins, and B. Moss, Science 228, 737–740 (1985).
45. Davis, W. B., J. A. Taylor, and J. E. Oakes, J. Infect. Dis. 140, 534–540 (1979).
46. Davison, A. J., and J. E. Scott, J. gen. Virol. 67, 1759–1816 (1986).
47. Drillien, R., F. Koehren and A. Kirn, Virology 111, 488–499 (1981).
48. Eberle, R., and R. J. Courthey, J. Virol. 35, 902–917 (1980)
49. Edbauer, C., R. Weinberg, J. Taylor, A. Rey-Senelonge, J. F. Bouquet, P. Desmettre, and E. Paoletti, Virology 179, 901–904 (1990).
50. Engelke, D. R., Hoener, P. A., and Collins, F. S., Proc. Natl. Acad. Sci. USA 85, 544–548 (1988).
51. Espion, D., S. de Henau, C. Letellier, C. -D. Wemers, R. Brasseur, J. F. Young, M. Gross, M. Rosenberg, G. Meulemans and A. Burny, Arch. Virol. 95, 79–95 (1987).
52. Etinger H. M., Altenburger W., Vaccine 9, 470–472 (1991).
53. Fargeaud, D., C. Benoit Jeannin, F. Kato, and G. Chappuis, Arch. Virol. 80, 69–82 (1984).
54. Fenner, F., Virology 5, 502–529 (1958).
55. Fitzpatrick, D. R., Babiuk, L. A. & Zamb, T. J., Virology 173, 46–57 (1989).
56. Flexnet, C., Hugen, A., and Moss, B., Nature 330, 259–262 (1987).
57. Flowers, C., Eastman, E. & O'Callaghan, D., Virology 180, 175–184 (1991).
58. Frame, M. C., H. S. Marsden, and D. J. McGeoch, J. gen. Virol. 67, 745–751 (1986).
59. Fries et al., 32nd Interscience Conference on Antimicrobial Agents and Chemotherapy, Anaheim, Calif. (October 1992).
60. Frink, R. J., M. R. Eisenberg, Gu Cohen, and E. K. Wagner, J. Virol. 45, 634–647 (1983).
61. Funahashi, S., T. Sato and H. Shida, J. Gen. Virol. 69, 35–47 (1988).
62. Garten, W., Kohama, T., and H-D. Klenk. J. Gen. Virol. 51, 207–211 (1980).
63. Ghendon, Y. Z., and Chernos, V. I., Acta Virol. 8, 359–368 (1964).
64. Gillard, S., Spehner, D., Drillien, R., and Kirn, A., Proc. Natl. Acad. Sci. USA 83, 5573–5577 (1986).
65. Glorioso, J., C. H. Schroder, G. Kumel, M. Szczesiul, and M. Levine, J. Virol. 50, 805–812 (1984).
66. Glorioso, J., U. Kees, G. Kumel, H. Kirchner, and P. Krammer, J. Immunol. 135, 575–582 (1985).
67. Goebel, S. J., Johnson, G. P., Perkus, M. E., Davis, S. W., Winslow, J. P., Paoletti, E., Virology 179, 247–266 (1990a).
68. Goebel, S. J., G. P. Johnson, M. E. Perkus, S. W. Davis, J. P. Winslow and E. Paoletti, Virology 179, 517–563 (1990b).
69. Goldstein, D. J. and S. K. Weller, Virology 166, 41–51 (1988).
70. Gretch, D. R., B. Kari, L. Rasmussen, R. C. Gehrz, and M. F. Stinski, J. Virol 62, 875–881 (1988).
71. Guo, P., Goebel, S., Davis, S., Perkus, M. E., Languet, B., Desmettre, P., Allen, G., and Paoletti, E., J. Virol. 63, 4189–4198 (1989).
72. Guo et al., J. Virol. 64, 2399–2406 (1990).
73. Hampl, H., T. Ben-Porat, L. Ehrlicher, K-O. Habermehl, and A.S. Kaplan, J. Virol. 52, 583–590 (1984).
74. Homma, M., and M. Ohuchi, J. Virol. 12, 1457–1465 (1973).
75. Honess, R. W., Journal of General Virology 65, 2077–2107 (1984).
76. Honess, R. W., Bodemer, W., Cameron, K. R., Niller, H. H. & Fleckenstein, B., Proceedings of the National Academy of Sciences, U.S.A. 83, 3604–3608 (1986).
77. Hruby, D. E., R. A. Maki, D. B. Miller and L. A. Ball, Proc. Natl. Acad. Sci. USA 80, 3411–3415 (1983).
78. Hutchinson, L., Browne, H., Wargents, V., Doris-Poynter, N., Primorac, S., Goldsmith, K., Minson, A., and D. C. Johnson. J. Virol. 66, 2240–2250 (1992).
79. Hutchinson, L., Goldsmith, K., Snoddy, A., Ghash, H., Graham, F. and D. Johnson. J. Virol. 66, 5603–5609 (1992b).
80. Hruby, D. E. and L. A. Ball, J. Virol. 43, 403–409 (1982).
81. Ichihashi, Y. and Dales, S., Virology 46, 533–543 (1971).
82. Ihara, T., Kato, A., Ueda, S., Ishihama, A. & Hirai, K., Virus Genes 3, 127–140 (1989).
83. Ishii, H., Y. Kobayashi, M. Kuroki and Y. Kodama, J. gen. Virol. 69, 1411–1414 (1988).
84. Jacobson, J. G., D. A. Leib, D. J. Goldstein, C. L. Bogard, P. A. Schaffer, S. K. Weller and D. M. Coen, Virology 173, 276–283 (1989).
85. Jamieson, A. T., G. A. Gentry aud J. H. Subak-Sharpe, J. Gen. Virol. 24, 465–480 (1974).
86. Karo, A., Sato, I., Ihara, T., Ueda, S., Ishihama, A. & Hirai, K., Gene 84, 399–405 (1989).
87. Kato, S., M. Takahashi, S. Kameyama and J. Kamahora, Biken's 2, 353–363 (1959).
88. Keller, P. M., A. J. Davison, R. S. Lowe, C. D. Bennett, and R. W. Ellis, Virology 152, 181–191 (1986).
89. Kieff, E., and D. Liebowitz, In: Virology, Second Edition, eds. Fields, B. N. et al. (Raven Press, Ltd., New York) pp. 1889–1920 (1990).
90. Kieny, M. P., Lathe, R., Drillien, R., Spehner, D., Skory, S., Schmitt, D., Wiktor, T., Koprowski, H., and Lecocq, J. P., Nature (London) 312, 163–166 (1984).
91. Klein, P., Kanehisa, M. & DuLisi, C., Biochimica Biophysica Acta 815, 468–476 (1985).
92. Konishi et al., Virology 190, 454–458 (1992).
93. Kopp, A. & Mettenleiter, T., Journal of Virology 66, 2754–2762 (1992).
94. Kost, T. A., E. V. Jones, K. M. Smith, A. P. Reed, A. L. Brown, and T. J. Miller, Virology 171, 365–376 (1989).
95. Kotwal, G. J., A. W. Hugin and B. Moss, Virology 171, 579–587 (1989a).

96. Kotwal, G. J. and B. Moss, J. Virol. 63, 600–606 (1989b).
97. Kotwal, G. J., S. N. Isaacs, R. McKenzie, M. M. Frank and B. Moss, Science 250, 827–830 (1990).
98. Kotwal, G. J. and Moss, B., Nature (Lond.) 335, 176–178 (1988).
99. Kouzarides, T., Bankier, A. T., Satchwell, S. C., Weston, K., Tomlinson, P. & Barrell, B. G., Virology 157, 397–413 (1987).
100. Kozak, M., Cell 44, 283–292 (1986).
101. Kuhn, J., Eing, B., Brossmer, R., Munk, K. & Braun, R., Journal of General Virology 69, 2847–2858 (1988).
102. Lai, A. C.-K. and B. G.-T. Pogo, Virus Res. 12, 239–250 (1989).
103. Lasky, L. A., D. Dowbenko, C. C. Simonsen, and P. W. Berman, Bio-Technology 2, 527–532 (1984).
104. Lawrence, W. C., R. C. DuUrso, C. A. Kundel, J. C. Whitbeck and L. J. Bello, J. Virol. 60, 405–414 (1986).
105. Le, L., R. Brasseur, C. Wemers, G. Meulemans, and A. Burny, Virus Genes 1, 333–350 (1988).
106. Long, D., Cohen, G., Muggeridge, M. & Eisenberg, R., Journal of Virology 64, 5542–5552 (1990).
107. Long, D., Wilcox, W., Abrams, W., Cohen, G. & Eisenberg, R., Journal of Virology 66, 6668–6685 (1992).
108. Longnecker, R., S. Chatterjee, R. Whitley, and B. Roizman, Proc. Natl. Acad. Sci. USA 84, 4303–4307 (1987).
109. Maeda, K., Horimoto, T., Norimine, J., Kawaguchi, Y., Tomonaga, K., Niikura, M., Kai, C., Takahashi, E. & Mikami, T., Archives of Virology 127, 387–397.
110. Mandecki, W., Proc. Natl. Acad. Sci. USA 83, 7177–7182 (1986).
111. Maniatis, T., E. F. Fritsch, and J. Sambrook, Molecular Cloning: A Laboratory Manual, (Cold Spring Harbor Laboratory, New York) (1982).
112. Marchioli, C. C., R. J. Yancey, Jr., R. C. Wardley, D. R. Thomsen and L. E. Post, Am. J. Vet. Res. 48, 1577–1583 (1987).
113. Marchioli, C., R. J. Yancey, Jr., J. G. Timmins, L. E. Post, B. R. Young, and D. A. Povendo, Am. J. Vet. Res. 49, 860–864 (1988).
114. Marchioli, C. C., R. J. Yancey, Jr., E. A. Petrovskis, J. G. Timmins, and L. E. Post, J. Virol. 61, 3977–3982 (1987).
115. Matthews, R. E. F., Intervirology 17, 42–44 (1982).
116. McGeoch, D. J., M. A. Dalrymple, A. J. Davison, A. Dolan, M. C. Frame, D. McNab, L. J. Perry, J. E. Scott, and P. Taylor, J. gen. Virol. 69, 1531–1574 (1988).
117. McGinnes, L. W., and T. G. Morrison, Virus Research 5, 343–356 (1986).
118. McLaughlin-Taylor, E., D. E. Willey, E. M. Cantin, R. Eberle, B. Moss, and H. Openshaw, J. gen. Virol. 69, 731–1734 (1988).
119. Meas, R. K., S. L. Fritsch, L. L. Herr, and P. A. Rota, J. Virol. 51, 259–262 (1984).
120. Merz, D. C., A. Scheid, and P. Choppin, J. Exper. Med. 151, 275–288 (1980).
121. Misra, V., R. M. Blumenthal and L. A. Babiuk, J. Virol. 40, 367–378 (1981).
122. Morgan, A. J., M. Mackett, S. Finerty, J. R. Arrand, F. T. Scullion and M. A. Epstein, J. Med. Virol. 25, 189–195 (1988).
123. Moss, B., E. Winters and J. A. Cooper, J. Virol. 40, 387–395 (1981).
124. Nagai, Y., M. D. Klenk, and R. Rott, Virology 72, 494–508 (1976).
125. Nagai, Y., T. Yoshida, M. Hamaguchi, H. Naruse, M. Iinuma, K. Maeno, and T. Matsumoto, Microbiol. Immunol. 24, 173–177 (1980).
126. Nazerian, K., Lee, L., Yanagida, N. & Ogawa, R., Journal of Virology 66, 1409–1413 (1992).
127. Nicolson, L. & Onions, D. E., Virology 179, 378–387 (1990).
128. Norrby, E., and Y. Gollmar, Infect. and Immun. 11, 231–239 (1975).
129. Oakes, J. E., and H. Rosemond-Hornbeak, Infect. Immun. 21, 489–495 (1978).
130. Ogawa, R., N. Yanagida, S. Saeki, S. Saito, S. Ohkawa, H. Gotoh, K. Kodama, K. Kamogawa, K. Sawaguchi and Y. Iritani, Vaccine S, 486–490 (1990).
131. Paez, E., S. Dallo and M. Esteban, Proc. Natl. Acad. Sci. USA 82, 3365–3369 (1985).
132. Palumbo, G. J., Pickup, D. J., Fredrickson, T. N., Mcintyre, L. J., and Buller, R. M. L., Virology 172, 262–273 (1989).
133. Panicali, D., S. W. Davis, S. R. Mercer, and E. Paoletti, J. Virol. 37, 1000–1010 (1981).
134. Panicali, D. and E. Paoletti, Proc. Natl. Acad. Sci. USA 79, 4927–4931 (1982).
135. Panicali, D., Davis, S. W., Mercer, S. R., and Paoletti, E., J. Virol. 37, 1000–1010 (1981).
136. Paoletti, E., B. R. Lipinskas, C. Samsonoff, S. Mercer, and D. Panicali, Proc. Natl. Acad. Sci. USA 81, 193–197 (1984).
137. Papp-Vid, G., and J. B. Derbyshire, Can. J. Comp. Med. 43, 231–233 (1979).
138. Patel, D. D. and Pickup, D. J., EMBO 6, 3787–3794 (1987).
139. Patel, D. D., Ray, C. A., Drucker, R. P., and Pickup, D. J., Proc. Natl. Acad. Sci. USA 85, 9431–9435 (1988).
140. Pearson, W. R. & Lipman, D. J., proceedings of the National Academy of Sciences 85, 2444–2448 (1988).
141. Pellett, P. E., M. D. Biggin, B. L. Barrell, and B. Roizman, J. Virol. 56, 807–813 (1985).
142. Perkus M. E., Piccini A., Lipinskas B. R., et al., Science 229, 981–984 (1985).
143. Perkus, M. E., K. Limbach, and E. Paoletti, J. Virol. 63, 3829–3836 (1989).
144. Perkus, M. E., A. Piccini, B. R. Lipinskas, and E. Paoletti, Science 229, 981–984 (1985).
145. Perkus, M. E., Goebel, S. J., Davis, S. W., Johnson, G. P., Limbach, K., Norton, E. K., and paoletti, E., Virology 179, 276–286 (1990).
146. Perkus, M. E., D. Panicali, S. Mercer and E. Paoletti, Virology 152, 285–297 (1986).
147. Perkus, M. E., Limbach, K., and Paoletti, E., J. Virol. 63, 3829–3836 (1989).
148. Perkus, M. E., S. J. Goebel, S. W. Davis, G. P. Johnson, E. K. Norton and E. Paoletti, Virology 180, 406–410 (1991).
149. Petrovskis, E. A., J. G. Timmins, M. A. Armentrout, C. C. Marchioli, R. J. Yancey, Jr., and L. E. Post, J. Virol. 59, 216–223 (1986).
150. Petrovskis, E. A., J. G. Timmins, and L. E. Post, J. Virol. 60, 185–193 (1986).
151. Piccini, A., M. E. Perkus, and E. Paoletti, Methods in Enzymology 153, 545–563 (1987).
152. Piccini, A., M. E. Perkus, and E. Paoletti, In: Methods in Enzymology, Vol. 153, eds. Wu, R., and L. Grossman (Academic Press) pp. 545–563 (1987).
153. Pickup, D. J., B. S. Ink, W. Hu, C. A. Ray and W. K. Joklik, Proc. Natl. Acad. Sci. USA 83, 7698–7702 (1986).
154. Pickup, D. J., B. S. Ink, B. L. Parsons, W. Hu and W. K. Joklik, Proc. Natl. Acad. Sci. USA 81, 6817–6821 (1984).
155. Pizer, L., Cohen, G. & Eisenberg, R., Journal of Virology 34, 142–153 (1980).

156. Plummer, G., Goodheart, C., Henson, D. & Bowling, C., Virology 39, 134–137 (1969).
157. Proudfoot, N. J. & Brownlee, G. G., Nature 163, 211–214 (1976).
158. Reed, L. J. and Muench, H., Am. J. Hyg. 27, 493–497 (1938).
159. Richman, D. D., A. Buckmaster, S. Bell, C. Hodgman and A.C. Minson, J. Virol. 57, 647–655 (1986).
160. Riggio, M. P., A. A. Cullinane, and D. E. Onions, J. Virol. 63, 1123–1133 (1989).
161. Riviere, M., Tartaglia, J., Perkus, M. E., Norton, E. K., Bongermino, C. M., Lacoste, F., Duret, C., Desmettre, P. & Paoletti, E., Journal of Virology 66, 3424–3434 (1992).
162. Robbins, A. K., R. J. Watson, M. E. Whealy, W. W. Hays, and L. W. Enquist, J. Virol. 58, 339–347 (1986).
163. Robbins, A. K., D. J. Dorney, M. W. Wathen, M. E. Whealey, C. Gold, R. J. Watson, L. E. Holland, S. D. Weed, M. Levine, J. C. Glorioso, and L. W. Enquist, J. Virol. 2691–2701 (1987).
164. Roizman, B. and A. E. Sears, In: Virology, eds. Fields, B. N. and D. M. Knipe (Raven Press, Ltd., New York) pp. 1795–1841 (1990).
165. Roizman, B., In The Herpesviruses, vol. 1, pp. 1–23, Ed. B. Roizman, New York & London: Plenum Press (1982).
166. Rooney, J. F., C. Wohlenberg, K. J. Cremer, B. Moss, and A. L. Notkins, J. Virol. 62, 1530–1534 (1988).
167. Rosenthal, K. L., J. R. Smiley, S. South, and D. C. Johnson, J. Virol. 61, 2438–2447 (1987).
168. Ross, L., Sanderson, M., Scott, S., Binns, M., Doel, T. & Milne, B., Journal of General Virology 70, 1789–1804 (1989).
169. Rota, P. A., R. K. Maes, and W. T. Ruyechan, Virology 154, 168–179 (1986).
170. Rubenstein, A. S. and A. S. Kaplan, Virology 66, 385–392 (1975).
171. Sanger, F., S. Nicklen, and A. Coulson, Proc. Natl. Acad. Sci. USA 74, 5463–5467 (1977).
172. Schmidtt, J. F. C. and H. G. Stunnenberg, J. Virol. 62 1889–1897 (1988).
173. Seligmann, E. B., In Laboratory Techniques in Rabies, eds. M. M. Kaplan and H. Koprowski, (World Health Organization, Geneva) pp. 279–285 (1973).
174. Shapira, S. K., Chou, J., Richaud, F. V. and Casadaban, M. J., Gene 25, 71–82 (1983).
175. Shida, H., Virology 150, 451–462 (1986).
176. Shida, H., T. Tochikura, T. Sato, T. Konno, K. Hirayoshi, M. Seki, Y. Ito, M. Hatanaka, Y. Hinuma, M. Sugimoto, F. Takahashi-Nishimaki, T. Maruyama, K. Miki, K. Suzuki, M. Morita, H. Sashiyama and M. Hayami, EMBO 6, 3379–3384 (1987).
177. Shida, H., Hinuma, Y., Hatanaka, M., Morita, M., Kidokoro, M., Suzuki, K., Maruyzam, T., Takahashi-Nishimaki, F., Sugimoto, M., Kitamura, R., Miyazawa, T., and Hayami, M., J. Virol. 62, 4474–4480 (1988).
178. Shimizu, M., K. Satou, and N. Nishioka, Arch. Virol. 104, 169–174 (1989).
179. Sinclair, R., R. F. Cook, and J. A. Mumford, J. gen. Virol. 70, 455–459 (1989).
180. Slabaugh, M., N. Roseman, R. Davis and C. Mathews, J. Virol. 62, 519–527 (1988).
181. Smith, J. S., P. A. Yager and G. M. Baer, In Laboratory Techniques in Rabies, eds. M. M. Kaplan and H. Koprowski (WHO Geneva) pp. 354–357 (1973).
182. Sodora, D., Cohen, G., Muggeridge, M. & Eisenberg, R., Journal of Virology 65, 4424–4431 (1991).
183. Spaete, R., Saxena, A., Scott, P., Long, G., Probert, W., Britt, W., Gibson W., Rasmussen, L. & Pachl, C., Journal of Virology 64, 2922–2931 (1990).
184. Spear, P.G., In: The Basis for Serodiagnosis and Vaccines, Immunochemistry of Viruses, Vol. 2, eds. M. H. V. Van Regenmortel and A. R. Neurath (New York), pp. 425–443 (1985a).
185. Spear, P. G., In: The Herpesvirus, Vol. 3, ed. B. Roizman (New York), pp. 315–356 (1985b).
186. Stanberry, L. R., S. Kit and M. G. Myers, J. Virol. 55, 322–328 (1985).
187. Stevely, W. S., J. Virol. 22, 232–234 (1977).
188. Stokes, A., G. P. Allen, L. A. Pullen, and P. K. Murray, J. gen. Virol. 70, 1173–1183 (1989).
189. Sullivan, V. and G. L. Smith, J. gen. Virol. 68, 2587–2598 (1987).
190. Sullivan, V. and G. L. Smith, J. gen. Virol. 69, 859–867 (1988).
191. Swain, M. A., R. W. Peet, and D. A. Galloway, J. Virol, 53, 561–569 (1985).
192. Tabor, S., and C. C. Richardson, Proc. Natl. Acad. Sci. USA 84, 4767–4771 (1987).
193. Tartaglia, J. & E. Paoletti, In Immunochemistry of Viruses, II. The Basis for Serodiagnosis and Vaccines. M. H. V. van Regenmortel & A. R. Neurath, Eds. 125–151. Elsevier Science Publishers, Amsterdam (1990).
194. Tartaglia, J., J. Taylor, W.I. Cox, J.-C. Audonnet, M. E. Perkus, A. Radaelli, C. de Giuli Morghen, B. Meignier, M. Riviere, K. Weinhold & E. Paoletti, In *AIDS Research Reviews*, W. Koff, F. Wong-Staal & R. C. Kenedy, Eds., Vol. 3, Marcel Dekker, NY (In press)(1993a).
195. Tartaglia, J., Perkus, M. E., Taylor, J., Norton, E. K., Audonnet, J.-C., Cox, W. I., Davis, S. W., Van Der Hoeyen, J., Meignier, B., Riviere, M., Languet, B., Paoletti, E., Virology 188, 217–232 (1992).
196. Tartaglia, J., Jarrett, O., Desmettre, P., Paoletti, E. (1993b) J. Virol., in press.
197. Taylor, J., C. Trimarchi, R. Weinberg, B. Languet, F. Guillemin, P. Desmettre and E. Paoletti, Vaccine 9, 190–193 (1991b).
198. Taylor, J., C. Trimarchi, R. Weinberg, B. Languet, F. Guillemin, P. Desmettre & E. Paoletti, Vaccine 9, 190 (1991).
199. Taylor, J., Weinberg, R., Kawaoka, Y., Webster, R. G., and Paoletti, E., Vaccine 6, 504–508 (1988a).
200. Taylor, J., R. Weinberg, B. Lanquet, P. Desmettre, and E. Paoletti, Vaccine 6, 497–503 (1988b).
201. Taylor, J., R. Weinberg, J. Tartaglia, C. Richardson, G. Alkhatib, D. Briedis, M. Appel, E. Norton & E. Paoletti, Virology 187, 321–328 (1992).
202. Taylor, G., E. J. Stott, G. Wertz and A. Ball, J. Gen. Virol. 72, 125–130 (1991a).
203. Taylor, J., Edbauer, C., Rey-Senelonge, A., Bouquet, J.-F., Norton, E., Goebel, S., Desmettre, P., Paoletti, E., J. Virol. 64, 1441–1450 (1990).
204. Telford, E. A., Watson, M. S., McBride, K. & Davison, A. J. (1992). The DNA sequence of equine herpesvirus-1. Virology 189, 304–316.
205. Tikoo, S. K., Fitzpatrick, D. R., Babiuk, L. A. & Zamb, T. J., Journal of Virology 64, 5132–5142 (1990).
206. Toyoda, T., T. Sakaguchi, K. Imai, N. M. Inocencio, B. Gotoh, M. Hamaguchi, and Y. Nagai, Virology 158, 242–247 (1987).
207. Wachsman, M., L. Aurelian, J. C. R. Hunter, M. E. Perkus, and E. Paoletti, Bioscience Reports 8, 323–334 (1988).
208. Wachsman, M., J. H. Luo, L. Aurelian, M. E. Perkus, and E. Paoletti, J. gen. Virol. 70, 2513–2520 (1989).
209. Wachsman, M., L. Aurelian, C. C. Smith, B. R. Lipinskas, M. E. Perkus, and E. Paoletti, J. Infect. Dis. 155, 1188–1197 (1987).

210. Wathen, M. W. and L. M. K. Wathen, J. Virol. 58, 173–178 (1986).
211. Wathen, M. W. and L. M. K. Wathen, J. Virol. 51, 57–62 (1984).
212. Wathen, L. M. K., K. B. Platt, M. W. Wathen, R. A. Van Deusen, C. A. Whetstone, and E. C. Pirtle, Virus Res. 4, 19–29 (1985).
213. Weir, J. P., M. Bennett, E. M. Allen, K. L. Elkins, S. Martin, and B. T. Rouse, J. gen. Virol. 70, 2587–2594 (1989).
214. Weir, J. P. and B. Moss, J. Virol. 46, 530–537 (1983).
215. Whalley, J. M., G. R. Robertson, N. A. Scott, G. C. Hudson, C. W. Bell, and L. M. Woodworth, J. gen. Virol. 70, 383–394 (1989).
216. Whealy, M. E., A. K. Robbins and L. W. Enquist, J. Virol. 63, 4055–4059 (1989).
217. Whirbeck, J. C., L. Z. Bello, and W. C. Lawrence, J. Virol. 62, 3319–3327 (1988).
218. Wilcox, W. C., Long, D., Sodora, D. L., Eisenberg, R. J. & Cohen, G. H., Journal of Virology 62, 1941–1947 (1988).
219. Wittmann, G. and H.-J. Rziha, In: Herpesvirus Diseases of Cattle, Horses and Pigs, ed. G. Wittmann (Kluwer Academic Publishers) pp. 230–325 (1989).
220. Xuan, X., Horimoto, T., Limcumpao, J. A., Takumi, A., Tohya, Y., Takahashi, E. & Mikami, T., Archives of Virology 116, 185–195 (1991).
221. Zamb, T., Abstract No. 330, 68th Annual Meeting of Conference of Research Workers in Animal Disease, 16 and 17 Nov. 1987, Chicago, Ill., USA (1987).
222. Zarling, J. M., P. A. Moran, R. L. Burke, C. Pachl, P. W. Berman, and L. A. Lasky, J. Immunol. 136, 4669–4673 (1986a).
223. Zarling, J. M., P. A. Moran, L. A. Lasky, and B. Moss, J. Virol. 59, 506–509 (1986b).
224. Zezulak, K. M., and P. G. Spear, J. Virol. 49, 741–747 (1984).
225. Zhou, J., L. Crawford, L. McLean, X. Sun, M. Stanley, N. Almond and G. L. Smith, J. Gen. Virol. 71, 2185–2190 (1990).

What is claimed is:

1. A synthetic canine herpesvirus glycoprotein gB, gC or gD isolated from in vitro expression of a vector containing an isolated nucleic acid having a sequence set forth in SEQ ID NO:1, SEQ ID NO:11 or SEQ ID NO:18 and coding for canine herpesvirus gB, gC or gD glycoprotein.

2. The glycoprotein of claim 1 wherein the isolated nucleic acid has a sequence of SEQ ID NO:18.

3. The glycoprotein of claim 1 wherein the isolated nucleic acid is DNA.

4. The glycoprotein of claim 1 wherein the isolated nucleic acid having a sequence set forth in SEQ ID NO:1 codes for canine herpesvirus gB glycoprotein.

5. The glycoprotein of claim 1 wherein the isolated nucleic acid having a sequence as set forth in SEQ ID NO:11 codes for canine herpesvirus gC glycoprotein.

6. The glycoprotein of claim 1 wherein the isolated nucleic acid having a sequence as set forth in SEQ ID NO:18 codes for canine herpesvirus gD glycoprotein.

7. The glycoprotein of claim 1 wherein the vector is a poxvirus.

8. The glycoprotein of claim 7 wherein the poxvirus is an avipox virus or a vaccinia virus.

9. The glycoprotein of claim 8 wherein the poxvirus is a vaccinia virus.

10. The glycoprotein of claim 9 wherein deleted from the vaccinia virus are genetic functions including a C7L–K1L open reading frame, or, a host range region.

11. The glycoprotein of claim 10 wherein at least one additional open reading frame of the vaccinia virus is deleted; and, the additional open reading frame is selected from the group consisting of: J2R, B13R+B14R, A26L, A56R, and I4L.

12. The glycoprotein of claim 10 wherein at least one additional open reading frame of the vaccinia virus is deleted; and, the additional open reading frame is selected from the group consisting of: a thymidine kinase gene, a hemorrhagic region, an A type inclusion body region, a hemagglutinin gene, and a large subunit, ribonucleotide reductase.

13. The glycoprotein of claim 11 wherein J2R, B13R+B14R, A26L, A56R, C7L–K1L and I4L are deleted from the vaccinia virus.

14. The glycoprotein of claim 12 wherein a thymidine kinase gene, a hemorrhagic region, an A type inclusion body region, a hemagglutinin gene, a host range region, and a large subunit, ribonucleotide reductase are deleted from the vaccinia virus.

15. The glycoprotein of claim 13 wherein the vector is a NYVAC recombinant virus.

16. The glycoprotein of claim 14 wherein the vector is a NYVAC recombinant virus.

17. The glycoprotein of claim 8 wherein said virus is a canarypox virus.

18. The glycoprotein of claim 17 wherein the canarypox virus is a Rentschler vaccine strain which was attenuated through more than 200 serial passages on chick embryo fibroblasts, a master seed therefrom was subjected to four successive plaque purifications under agar, from which a plaque clone was amplified through five additional passages.

* * * * *

SEQUENCE LISTING ( 1 ) GENERAL INFORMATION:

( i i i ) NUMBER OF SEQUENCES: 128

( 2 ) INFORMATION FOR SEQ ID NO:1:

( i ) SEQUENCE CHARACTERISTICS:
( A ) LENGTH: 3000 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

```
TTTCTGGAT  TTCAGCTATG  TCCTTCGGGA  GTTTATATAA  CTTATGAAGA  AAACTGTCCT    60
TTGGTAGCAG  TTTTACAAAG  CGGTGTAAAT  TGCGAAATTG  GACCAACTAC  AACTGTAATA   120
TACGACAGTG  ATATTTTTTC  TCTTCTTTAT  ACCGTTCTTC  AAAAATTGGC  TCCTGGTGTT   180
AATATAGAAA  TTTGATAAGT  ATGTTTCAT   TGTATCTATA  TATTTTTTT   ATTATTTATA   240
CTTAATAAT   ATGTGATCCA  ACAACACCGG  AAAGTACTAT  TAATCCATTA  AATCATCACA   300
ATTTATCAAC  ACCTAAACCT  ACTTCGGATG  ATATTCGTGA  AATTTTACGT  GAATCCCAAA   360
TTGAATCTGA  TGATACATCA  ACATTTTACA  TGTGCCCACC  ACCATCGGGA  TCAACATTGG   420
TGCGTTTGGA  GCCACCTAGA  GCATGTCCTA  ACTATAAACT  TGGTAAAAAT  TTACAGAAG    480
GAATTGCTGT  AATATTTAAG  GAAATATTT   CTCCTTATAA  ATTTAAAGCT  AATATATACT   540
ACAAAAATAT  TATTATCACC  ACTGTATGGT  CTGGAAGCAC  ATATGCAGTA  ATTACTAATA   600
GATATACAGA  TCGTGTACCT  ATAGGTGTTC  CTGAAATTAC  AGAGTTGATT  GATAGAAGAG   660
GTATGTGTTT  ATCAAAGCT   GATTATATTC  GTAATAATTA  TGAATTTACC  GCATTTGATA   720
AGGATGAAGA  CCCCAGAGAA  GTTCATTTAA  AGCCTTCAAA  GTTAATACA   CCAGGATCCC   780
GTGGATGGCA  TACAGTTAAT  GATACTTACA  CAAAAATTGG  GGGTTCTGGA  TTTTATCATT   840
CTGGAACATC  TGTAAATTGT  ATAGTTGAAG  AAGTTGATGC  CAGATCTGTT  TATCCATATG   900
ATTCATTTGC  TATCTCCACC  GGGGATATAA  TTCATATGTC  CCCTTTTTT   GGATTACGAG   960
ATGGTGCTCA  TACTGAATAT  ATTAGTTATT  CAACTGATAG  ATTTCAACAA  ATAGAAGGTT  1020
```

-continued

| | | | | | | |
|---|---|---|---|---|---|---|
| ATTATCCTAT | CGACTTAGAT | ACTAGACTAC | AGCTTGGTGC | ACCAGTTTCT | AGGAATTTTT | 1080 |
| TAACAACACA | ACACGTTACT | GTTGCTTGGA | ATTGGGTTCC | AAAAATTCGT | GAAGTGTGTA | 1140 |
| CTTTGGCTAA | ATGGCGTGAA | ATTGATGAAA | TTATTCGTGA | TGAGTATAAG | GGATCTTACA | 1200 |
| GATTTACAGC | AAAATCAATA | TCTGCAACAT | TTATTTCTGA | TACTACTCAA | TTTGATATTG | 1260 |
| ATCGTGTAAA | GTTAAGTGAT | TGTGCCAAAC | GTGAAGCCAT | AGAAGCTATT | GATAAGATCT | 1320 |
| ACAAAAAAAA | ATATAATAAA | ACTCATATTC | AAACAGGAGA | ATTGGAAACA | TACTTGGCTA | 1380 |
| GAGGGGGATT | TATTATAGCA | TTTAGACCAA | TGATTAGTAA | TGAGTTAGCA | AAATTGTATA | 1440 |
| TAAATGAGTT | AGTAAGATCT | AATCGTACGG | TTGATTTGAA | ATCTCTTTTA | AATCCATCTG | 1500 |
| TAAGAGGGGG | GGCTAGAAAG | AGAAGATCAG | TAGAGGAAAA | TAAAAGATCA | AAACGTAATA | 1560 |
| TTGAAGGTGG | TATTGAAAAT | GTAAATAATT | CAACAATAAT | TAAGACAACT | TCATCTGTTC | 1620 |
| ATTTTGCTAT | GCTTCAGTTT | GCCTATGATC | ATATTCAATC | ACATGTTAAT | GAAATGCTTA | 1680 |
| GTAGAATTGC | AACTGCATGG | TGTAATCTTC | AAAATAAAGA | GAGAACCCTT | TGGAATGAAG | 1740 |
| TTATGAAACT | TAATCCAACT | AGTGTGGCTT | CGGTTGCTAT | GGATCAAAGA | GTTTCAGCAC | 1800 |
| GAATGTTAGG | GGATGTTCTT | GCAGTTACTC | AATGTGTTAA | TATATCAGGT | TCTAGTGTTT | 1860 |
| TTATTCAAAA | TTCCATGCGT | GTTTTAGGGT | CAACAACTAC | ATGTTACAGT | CGTCCTCTTA | 1920 |
| TATCATTTAA | AGCACTAGAA | AACTCAACTA | ACTATATTGA | AGGACAACTT | GGGGAAAATA | 1980 |
| ATGAACTATT | AGTAGAACGA | AAGCTAATTG | AACCATGTAC | AGCTAACCAT | AAAAGATATT | 2040 |
| TTAAATTTGG | TGCAGATTAT | GTATATTTTG | AAAACTATGC | ATATGTTCGA | AAGGTACCTC | 2100 |
| TTAATGAAAT | TGAAATGATC | AGTGCATATG | TAGATCTTAA | TATTACATTA | CTTGAGGATC | 2160 |
| GTGAATTTTT | ACCACTAGAG | GTATATACTC | GAGCAGAGTT | AGAAGATACA | GGACTATTGG | 2220 |
| ACTATAGTGA | GATTCAACGT | AGAAATCAAC | TACATGCACT | TAAGTTTTAT | GATATTGACA | 2280 |
| GTGTTGTAAA | AGTTGATAAT | AATGTTGTAA | TTATGAGGGG | CATTGCAAAT | TTTTTCCAAG | 2340 |
| GACTTGGAGA | TGTTGGAGCG | GGATTTGGAA | AAGTTGTTTT | GGGTGCTGCA | AATGCTGTTA | 2400 |
| TTGCAACTGT | TTCTGGAGTG | TCCTCGTTTC | TTAATAACCC | ATTTGGGGCG | CTAGCCGTTG | 2460 |
| GATTGCTGAT | TTTAGCTGGA | CTATTTGCAG | CGTTTTTGGC | TTATAGATAT | GTTCTAAAC | 2520 |
| TTAAGTCAAA | TCCAATGAAA | GCACTATACC | CAGTAACTAC | AAAAAATTTA | AAGAAAGTG | 2580 |
| TTAAGAATGG | TAATTCTGGA | AATAATAGTG | ATGGAGAAGA | AAATGATGAT | AATATCGATG | 2640 |
| AAGAAAAGCT | TCAACAAGCT | AAAGAAATGA | TTAAATATAT | GTCTCTAGTT | TCTGCTATGG | 2700 |
| AACAGCAGGA | ACATAAAGCT | ATTAAAAAAA | ATAGTGGCCC | TGCCCTTCTA | GCAAGTCACA | 2760 |
| TTACAAACCT | ATCTCTTAAA | CATCGTGGTC | CAAAATACAA | ACGTTTGAAA | AATGTAAATG | 2820 |
| AAAATGAAAG | TAAAGTTTAA | TAAAAAATTT | AAATATTACG | TAAAATTTTC | TGACTCTGCC | 2880 |
| CACTTTTTTT | ATAATATAAA | TTTTAGAAAA | TTTTACTCAT | TTTATTATCT | TTTATAAACC | 2940 |
| TCCAACTATT | TATAAAGGAT | AATAAATGGA | CATTTCTGCG | GTGCCTGTAT | ATCCTACTAA | 3000 |

( 2 ) INFORMATION FOR SEQ ID NO:2:

( i ) SEQUENCE CHARACTERISTICS:
        ( A ) LENGTH: 879 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( x i ) SEQUENCE DESCRIPTION: SEQ ID NO:2:

| | | | | | | | | | | | | | | |
|---|---|---|---|---|---|---|---|---|---|---|---|---|---|---|
| Met 1 | Phe | Ser | Leu | Tyr 5 | Leu | Tyr | Ile | Phe | Phe 10 | Ile | Ile | Tyr | Thr | Leu Ile 15 |
| Ile | Cys | Asp | Pro 20 | Thr | Thr | Pro | Glu | Ser 25 | Thr | Ile | Asn | Pro | Leu 30 | Asn His |
| His | Asn | Leu 35 | Ser | Thr | Pro | Lys | Pro 40 | Thr | Ser | Asp | Asp | Ile 45 | Arg | Glu Ile |
| Leu | Arg 50 | Glu | Ser | Gln | Ile 55 | Glu | Ser | Asp | Asp | Thr 60 | Ser | Thr | Phe | Tyr Met |
| Cys 65 | Pro | Pro | Pro | Ser | Gly 70 | Ser | Thr | Leu | Val | Arg 75 | Leu | Glu | Pro | Pro Arg 80 |
| Ala | Cys | Pro | Asn | Tyr 85 | Lys | Leu | Gly | Lys | Asn 90 | Phe | Thr | Glu | Gly | Ile Ala 95 |
| Val | Ile | Phe | Lys 100 | Glu | Asn | Ile | Ser | Pro 105 | Tyr | Lys | Phe | Lys | Ala 110 | Asn Ile |
| Tyr | Tyr | Lys 115 | Asn | Ile | Ile | Ile | Thr 120 | Thr | Val | Trp | Ser | Gly 125 | Ser | Thr Tyr |
| Ala | Val 130 | Ile | Thr | Asn | Arg | Tyr 135 | Thr | Asp | Arg | Val | Pro 140 | Ile | Gly | Val Pro |
| Glu 145 | Ile | Thr | Glu | Leu | Ile 150 | Asp | Arg | Arg | Gly | Met 155 | Cys | Leu | Ser | Lys Ala 160 |
| Asp | Tyr | Ile | Arg | Asn 165 | Asn | Tyr | Glu | Phe | Thr 170 | Ala | Phe | Asp | Lys | Asp Glu 175 |
| Asp | Pro | Arg | Glu 180 | Val | His | Leu | Lys | Pro 185 | Ser | Lys | Phe | Asn | Thr 190 | Pro Gly |
| Ser | Arg | Gly 195 | Trp | His | Thr | Val | Asn 200 | Asp | Thr | Tyr | Thr | Lys 205 | Ile | Gly Gly |
| Ser | Gly 210 | Phe | Tyr | His | Ser | Gly 215 | Thr | Ser | Val | Asn | Cys 220 | Ile | Val | Glu Glu |
| Val 225 | Asp | Ala | Arg | Ser | Val 230 | Tyr | Pro | Tyr | Asp | Ser 235 | Phe | Ala | Ile | Ser Thr 240 |
| Gly | Asp | Ile | Ile | His 245 | Met | Ser | Pro | Phe | Phe 250 | Gly | Leu | Arg | Asp | Gly Ala 255 |
| His | Thr | Glu | Tyr 260 | Ile | Ser | Tyr | Ser | Thr 265 | Asp | Arg | Phe | Gln | Gln 270 | Ile Glu |
| Gly | Tyr | Tyr 275 | Pro | Ile | Asp | Leu | Asp 280 | Thr | Arg | Leu | Gln | Leu 285 | Gly | Ala Pro |
| Val | Ser 290 | Arg | Asn | Phe | Leu | Thr 295 | Thr | Gln | His | Val | Thr 300 | Val | Ala | Trp Asn |
| Trp 305 | Val | Pro | Lys | Ile | Arg 310 | Glu | Val | Cys | Thr | Leu 315 | Ala | Lys | Trp | Arg Glu 320 |
| Ile | Asp | Glu | Ile | Ile 325 | Arg | Asp | Glu | Tyr | Lys 330 | Gly | Ser | Tyr | Arg | Phe Thr 335 |
| Ala | Lys | Ser | Ile 340 | Ser | Ala | Thr | Phe | Ile 345 | Ser | Asp | Thr | Thr | Gln 350 | Phe Asp |
| Ile | Asp | Arg 355 | Val | Lys | Leu | Ser | Asp 360 | Cys | Ala | Lys | Arg | Glu 365 | Ala | Ile Glu |
| Ala | Ile 370 | Asp | Lys | Ile | Tyr | Lys 375 | Lys | Lys | Tyr | Asn | Lys 380 | Thr | His | Ile Gln |
| Thr 385 | Gly | Glu | Leu | Glu | Thr 390 | Tyr | Leu | Ala | Arg | Gly 395 | Gly | Phe | Ile | Ile Ala 400 |
| Phe | Arg | Pro | Met | Ile 405 | Ser | Asn | Glu | Leu | Ala 410 | Lys | Leu | Tyr | Ile | Asn Glu 415 |

```
Leu Val Arg Ser Asn Arg Thr Val Asp Leu Lys Ser Leu Leu Asn Pro
        420                 425                 430

Ser Val Arg Gly Gly Ala Arg Lys Arg Arg Ser Val Glu Glu Asn Lys
        435                 440                 445

Arg Ser Lys Arg Asn Ile Glu Gly Gly Ile Glu Asn Val Asn Asn Ser
        450                 455                 460

Thr Ile Ile Lys Thr Thr Ser Ser Val His Phe Ala Met Leu Gln Phe
465                 470                 475                 480

Ala Tyr Asp His Ile Gln Ser His Val Asn Glu Met Leu Ser Arg Ile
                485                 490                 495

Ala Thr Ala Trp Cys Asn Leu Gln Asn Lys Glu Arg Thr Leu Trp Asn
            500                 505                 510

Glu Val Met Lys Leu Asn Pro Thr Ser Val Ala Ser Val Ala Met Asp
            515                 520                 525

Gln Arg Val Ser Ala Arg Met Leu Gly Asp Val Leu Ala Val Thr Gln
530                 535                 540

Cys Val Asn Ile Ser Gly Ser Ser Val Phe Ile Gln Asn Ser Met Arg
545                 550                 555                 560

Val Leu Gly Ser Thr Thr Thr Cys Tyr Ser Arg Pro Leu Ile Ser Phe
                565                 570                 575

Lys Ala Leu Glu Asn Ser Thr Asn Tyr Ile Glu Gly Gln Leu Gly Glu
            580                 585                 590

Asn Asn Glu Leu Leu Val Glu Arg Lys Leu Ile Glu Pro Cys Thr Ala
        595                 600                 605

Asn His Lys Arg Tyr Phe Lys Phe Gly Ala Asp Tyr Val Tyr Phe Glu
    610                 615                 620

Asn Tyr Ala Tyr Val Arg Lys Val Pro Leu Asn Glu Ile Glu Met Ile
625                 630                 635                 640

Ser Ala Tyr Val Asp Leu Asn Ile Thr Leu Leu Glu Asp Arg Glu Phe
                645                 650                 655

Leu Pro Leu Glu Val Tyr Thr Arg Ala Glu Leu Glu Asp Thr Gly Leu
            660                 665                 670

Leu Asp Tyr Ser Glu Ile Gln Arg Arg Asn Gln Leu His Ala Leu Lys
        675                 680                 685

Phe Tyr Asp Ile Asp Ser Val Val Lys Val Asp Asn Asn Val Val Ile
    690                 695                 700

Met Arg Gly Ile Ala Asn Phe Phe Gln Gly Leu Gly Asp Val Gly Ala
705                 710                 715                 720

Gly Phe Gly Lys Val Val Leu Gly Ala Ala Asn Ala Val Ile Ala Thr
                725                 730                 735

Val Ser Gly Val Ser Ser Phe Leu Asn Asn Pro Phe Gly Ala Leu Ala
            740                 745                 750

Val Gly Leu Leu Ile Leu Ala Gly Leu Phe Ala Ala Phe Leu Ala Tyr
        755                 760                 765

Arg Tyr Val Ser Lys Leu Lys Ser Asn Pro Met Lys Ala Leu Tyr Pro
    770                 775                 780

Val Thr Thr Lys Asn Leu Lys Glu Ser Val Lys Asn Gly Asn Ser Gly
785                 790                 795                 800

Asn Asn Ser Asp Gly Glu Glu Asn Asp Asp Asn Ile Asp Glu Glu Lys
                805                 810                 815

Leu Gln Gln Ala Lys Glu Met Ile Lys Tyr Met Ser Leu Val Ser Ala
            820                 825                 830

Met Glu Gln Gln Glu His Lys Ala Ile Lys Lys Asn Ser Gly Pro Ala
        835                 840                 845
```

|     |     |     |     |     |     |     |     |     |     |     |     |     |     |     |
|---|---|---|---|---|---|---|---|---|---|---|---|---|---|---|
| Leu | Leu | Ala | Ser | His | Ile | Thr | Asn | Leu | Ser | Leu | Lys | His | Arg | Gly | Pro |
|     | 850 |     |     |     | 855 |     |     |     |     | 860 |     |     |     |     |
| Lys | Tyr | Lys | Arg | Leu | Lys | Asn | Val | Asn | Glu | Asn | Glu | Ser | Lys | Val |
| 865 |     |     |     |     | 870 |     |     |     |     | 875 |     |     |     |     |

(2) INFORMATION FOR SEQ ID NO:3:

(i) SEQUENCE CHARACTERISTICS:
        (A) LENGTH: 879 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:3:

| Met | Phe | Ser | Leu | Tyr | Leu | Tyr | Ile | Phe | Phe | Ile | Ile | Tyr | Thr | Leu | Ile |
| 1 |     |     |     | 5 |     |     |     |     | 10 |     |     |     |     | 15 |     |
| Ile | Cys | Asp | Pro | Thr | Thr | Pro | Glu | Ser | Thr | Ile | Asn | Pro | Leu | Asn | His |
|     |     |     | 20 |     |     |     |     | 25 |     |     |     |     | 30 |     |     |
| His | Asn | Leu | Ser | Thr | Pro | Lys | Pro | Thr | Ser | Asp | Asp | Ile | Arg | Glu | Ile |
|     |     |     | 35 |     |     |     | 40 |     |     |     |     | 45 |     |     |     |
| Leu | Arg | Glu | Ser | Gln | Ile | Glu | Ser | Asp | Asp | Thr | Ser | Thr | Phe | Tyr | Met |
|     | 50 |     |     |     |     | 55 |     |     |     |     | 60 |     |     |     |     |
| Cys | Pro | Pro | Pro | Ser | Gly | Ser | Thr | Leu | Val | Arg | Leu | Glu | Pro | Pro | Arg |
| 65 |     |     |     |     | 70 |     |     |     |     | 75 |     |     |     |     | 80 |
| Ala | Cys | Pro | Asn | Tyr | Lys | Leu | Gly | Lys | Asn | Phe | Thr | Glu | Gly | Ile | Ala |
|     |     |     |     | 85 |     |     |     |     | 90 |     |     |     |     | 95 |     |
| Val | Ile | Phe | Lys | Glu | Asn | Ile | Ser | Pro | Tyr | Lys | Phe | Lys | Ala | Asn | Ile |
|     |     |     | 100 |     |     |     |     | 105 |     |     |     |     | 110 |     |     |
| Tyr | Tyr | Lys | Asn | Ile | Ile | Ile | Thr | Thr | Val | Trp | Ser | Gly | Ser | Thr | Tyr |
|     |     |     | 115 |     |     |     |     | 120 |     |     |     |     | 125 |     |     |
| Ala | Val | Ile | Thr | Asn | Arg | Tyr | Thr | Asp | Arg | Val | Pro | Ile | Gly | Val | Pro |
|     | 130 |     |     |     |     | 135 |     |     |     |     | 140 |     |     |     |     |
| Glu | Ile | Thr | Glu | Leu | Ile | Asp | Arg | Arg | Gly | Met | Cys | Leu | Ser | Lys | Ala |
| 145 |     |     |     |     | 150 |     |     |     |     | 155 |     |     |     |     | 160 |
| Asp | Tyr | Ile | Arg | Asn | Asn | Tyr | Glu | Phe | Thr | Ala | Phe | Asp | Lys | Asp | Glu |
|     |     |     |     | 165 |     |     |     |     | 170 |     |     |     |     | 175 |     |
| Asp | Pro | Arg | Glu | Val | His | Leu | Lys | Pro | Ser | Lys | Phe | Asn | Thr | Pro | Gly |
|     |     |     | 180 |     |     |     |     | 185 |     |     |     |     | 190 |     |     |
| Ser | Arg | Gly | Trp | His | Thr | Val | Asn | Asp | Thr | Tyr | Thr | Lys | Ile | Gly | Gly |
|     |     | 195 |     |     |     |     | 200 |     |     |     |     | 205 |     |     |     |
| Ser | Gly | Phe | Tyr | His | Ser | Gly | Thr | Ser | Val | Asn | Cys | Ile | Val | Glu | Glu |
|     | 210 |     |     |     |     | 215 |     |     |     |     | 220 |     |     |     |     |
| Val | Asp | Ala | Arg | Ser | Val | Tyr | Pro | Tyr | Asp | Ser | Phe | Ala | Ile | Ser | Thr |
| 225 |     |     |     |     | 230 |     |     |     |     | 235 |     |     |     |     | 240 |
| Gly | Asp | Ile | Ile | His | Met | Ser | Pro | Phe | Phe | Gly | Leu | Arg | Asp | Gly | Ala |
|     |     |     |     | 245 |     |     |     |     | 250 |     |     |     |     | 255 |     |
| His | Thr | Glu | Tyr | Ile | Ser | Tyr | Ser | Thr | Asp | Arg | Phe | Gln | Gln | Ile | Glu |
|     |     |     | 260 |     |     |     |     | 265 |     |     |     |     | 270 |     |     |
| Gly | Tyr | Tyr | Pro | Ile | Asp | Leu | Asp | Thr | Arg | Leu | Gln | Leu | Gly | Ala | Pro |
|     |     | 275 |     |     |     |     | 280 |     |     |     |     | 285 |     |     |     |
| Val | Ser | Arg | Asn | Phe | Leu | Thr | Thr | Gln | His | Val | Thr | Val | Ala | Trp | Asn |
|     | 290 |     |     |     |     | 295 |     |     |     |     | 300 |     |     |     |     |
| Trp | Val | Pro | Lys | Ile | Arg | Glu | Val | Cys | Thr | Leu | Ala | Lys | Trp | Arg | Glu |

-continued

|     |     |     | 305 |     |     |     | 310 |     |     |     | 315 |     |     |     | 320 |
| --- | --- | --- | --- | --- | --- | --- | --- | --- | --- | --- | --- | --- | --- | --- | --- |
| Ile | Asp | Glu | Ile | Ile | Arg | Asp | Glu | Tyr | Lys | Gly | Ser | Tyr | Arg | Phe | Thr |
|     |     |     |     | 325 |     |     |     | 330 |     |     |     |     |     | 335 |     |
| Ala | Lys | Ser | Ile | Ser | Ala | Thr | Phe | Ile | Ser | Asp | Thr | Thr | Gln | Phe | Asp |
|     |     |     | 340 |     |     |     |     | 345 |     |     |     |     | 350 |     |     |
| Ile | Asp | Arg | Val | Lys | Leu | Ser | Asp | Cys | Ala | Lys | Arg | Glu | Ala | Ile | Glu |
|     |     | 355 |     |     |     |     | 360 |     |     |     |     | 365 |     |     |     |
| Ala | Ile | Asp | Lys | Ile | Tyr | Lys | Lys | Tyr | Asn | Lys | Thr | His | Ile | Gln |
|     | 370 |     |     |     |     | 375 |     |     |     |     | 380 |     |     |     |
| Thr | Gly | Glu | Leu | Glu | Thr | Tyr | Leu | Ala | Arg | Gly | Gly | Phe | Ile | Ile | Ala |
| 385 |     |     |     |     | 390 |     |     |     |     | 395 |     |     |     |     | 400 |
| Phe | Arg | Pro | Met | Ile | Ser | Asn | Glu | Leu | Ala | Lys | Leu | Tyr | Ile | Asn | Glu |
|     |     |     |     | 405 |     |     |     |     | 410 |     |     |     |     | 415 |     |
| Leu | Val | Arg | Ser | Asn | Arg | Thr | Val | Asp | Leu | Lys | Ser | Leu | Leu | Asn | Pro |
|     |     |     | 420 |     |     |     |     | 425 |     |     |     |     | 430 |     |     |
| Ser | Val | Arg | Gly | Gly | Ala | Arg | Lys | Arg | Arg | Ser | Val | Glu | Glu | Asn | Lys |
|     |     | 435 |     |     |     |     | 440 |     |     |     |     | 445 |     |     |     |
| Arg | Ser | Lys | Arg | Asn | Ile | Glu | Gly | Gly | Ile | Glu | Asn | Val | Asn | Asn | Ser |
|     | 450 |     |     |     |     | 455 |     |     |     |     | 460 |     |     |     |     |
| Thr | Ile | Ile | Lys | Thr | Thr | Ser | Ser | Val | His | Phe | Ala | Met | Leu | Gln | Phe |
| 465 |     |     |     |     | 470 |     |     |     |     | 475 |     |     |     |     | 480 |
| Ala | Tyr | Asp | His | Ile | Gln | Ser | His | Val | Asn | Glu | Met | Leu | Ser | Arg | Ile |
|     |     |     |     | 485 |     |     |     |     | 490 |     |     |     |     | 495 |     |
| Ala | Thr | Ala | Trp | Cys | Asn | Leu | Gln | Asn | Lys | Glu | Arg | Thr | Leu | Trp | Asn |
|     |     |     | 500 |     |     |     |     | 505 |     |     |     |     | 510 |     |     |
| Glu | Val | Met | Lys | Leu | Asn | Pro | Thr | Ser | Val | Ala | Ser | Val | Ala | Met | Asp |
|     |     |     | 515 |     |     |     |     | 520 |     |     |     |     | 525 |     |     |
| Gln | Arg | Val | Ser | Ala | Arg | Met | Leu | Gly | Asp | Val | Leu | Ala | Val | Thr | Gln |
|     | 530 |     |     |     |     | 535 |     |     |     |     |     | 540 |     |     |     |
| Cys | Val | Asn | Ile | Ser | Gly | Ser | Ser | Val | Phe | Ile | Gln | Asn | Ser | Met | Arg |
| 545 |     |     |     |     | 550 |     |     |     |     | 555 |     |     |     |     | 560 |
| Val | Leu | Gly | Ser | Thr | Thr | Thr | Cys | Tyr | Ser | Arg | Pro | Leu | Ile | Ser | Phe |
|     |     |     |     | 565 |     |     |     |     | 570 |     |     |     |     | 575 |     |
| Lys | Ala | Leu | Glu | Asn | Ser | Thr | Asn | Tyr | Ile | Glu | Gly | Gln | Leu | Gly | Glu |
|     |     |     | 580 |     |     |     |     | 585 |     |     |     |     | 590 |     |     |
| Asn | Asn | Glu | Leu | Leu | Val | Glu | Arg | Lys | Leu | Ile | Glu | Pro | Cys | Thr | Ala |
|     |     | 595 |     |     |     |     | 600 |     |     |     |     | 605 |     |     |     |
| Asn | His | Lys | Arg | Tyr | Phe | Lys | Phe | Gly | Ala | Asp | Tyr | Val | Tyr | Phe | Glu |
|     | 610 |     |     |     |     | 615 |     |     |     |     | 620 |     |     |     |     |
| Asn | Tyr | Ala | Tyr | Val | Arg | Lys | Val | Pro | Leu | Asn | Glu | Ile | Glu | Met | Ile |
| 625 |     |     |     |     | 630 |     |     |     |     | 635 |     |     |     |     | 640 |
| Ser | Ala | Tyr | Val | Asp | Leu | Asn | Ile | Thr | Leu | Leu | Glu | Asp | Arg | Glu | Phe |
|     |     |     |     | 645 |     |     |     |     | 650 |     |     |     |     | 655 |     |
| Leu | Pro | Leu | Glu | Val | Tyr | Thr | Arg | Ala | Glu | Leu | Glu | Asp | Thr | Gly | Leu |
|     |     |     | 660 |     |     |     |     | 665 |     |     |     |     | 670 |     |     |
| Leu | Asp | Tyr | Ser | Glu | Ile | Gln | Arg | Arg | Asn | Gln | Leu | His | Ala | Leu | Lys |
|     |     | 675 |     |     |     |     | 680 |     |     |     |     | 685 |     |     |     |
| Phe | Tyr | Asp | Ile | Asp | Ser | Val | Val | Lys | Val | Asp | Asn | Asn | Val | Val | Ile |
|     | 690 |     |     |     |     | 695 |     |     |     |     | 700 |     |     |     |     |
| Met | Arg | Gly | Ile | Ala | Asn | Phe | Phe | Gln | Gly | Leu | Gly | Asp | Val | Gly | Ala |
| 705 |     |     |     |     | 710 |     |     |     |     | 715 |     |     |     |     | 720 |
| Gly | Phe | Gly | Lys | Val | Val | Leu | Gly | Ala | Ala | Asn | Ala | Val | Ile | Ala | Thr |
|     |     |     |     | 725 |     |     |     |     | 730 |     |     |     |     | 735 |     |

```
Val  Ser  Gly  Val  Ser  Ser  Phe  Leu  Asn  Asn  Pro  Phe  Gly  Ala  Leu  Ala
               740                     745                    750

Val  Gly  Leu  Leu  Ile  Leu  Ala  Gly  Leu  Phe  Ala  Ala  Phe  Leu  Ala  Tyr
               755                     760                    765

Arg  Tyr  Val  Ser  Lys  Leu  Lys  Ser  Asn  Pro  Met  Lys  Ala  Leu  Tyr  Pro
     770                     775                    780

Val  Thr  Thr  Lys  Asn  Leu  Lys  Glu  Ser  Val  Lys  Asn  Gly  Asn  Ser  Gly
785                     790                    795                         800

Asn  Asn  Ser  Asp  Gly  Glu  Glu  Asn  Asp  Asp  Asn  Ile  Asp  Glu  Glu  Lys
                    805                     810                    815

Leu  Gln  Gln  Ala  Lys  Glu  Met  Ile  Lys  Tyr  Met  Ser  Leu  Val  Ser  Ala
               820                     825                    830

Met  Glu  Gln  Gln  Glu  His  Lys  Ala  Ile  Lys  Lys  Asn  Ser  Gly  Pro  Ala
               835                     840                    845

Leu  Leu  Ala  Ser  His  Ile  Thr  Asn  Leu  Ser  Leu  Lys  His  Arg  Gly  Pro
     850                     855                    860

Lys  Tyr  Lys  Arg  Leu  Lys  Asn  Val  Asn  Glu  Asn  Glu  Ser  Lys  Val
865                     870                    875
```

( 2 ) INFORMATION FOR SEQ ID NO:4:

( i ) SEQUENCE CHARACTERISTICS:
        ( A ) LENGTH: 1041 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:4:

```
Met  Ser  Thr  Arg  Gly  Asp  Leu  Gly  Lys  Arg  Arg  Gly  Ser  Arg  Trp
1                   5                    10                   15

Gln  Gly  His  Ser  Gly  Tyr  Phe  Arg  Gln  Arg  Cys  Phe  Phe  Pro  Ser  Leu
               20                     25                    30

Leu  Gly  Ile  Ala  Ala  Thr  Gly  Ser  Arg  His  Gly  Asn  Gly  Ser  Ser  Gly
               35                     40                    45

Leu  Thr  Arg  Leu  Ala  Arg  Tyr  Val  Ser  Phe  Ile  Trp  Ile  Val  Leu  Phe
     50                     55                    60

Leu  Val  Gly  Pro  Arg  Pro  Val  Glu  Gly  Gln  Ser  Gly  Ser  Thr  Ser  Glu
65                       70                   75                          80

Gln  Pro  Arg  Arg  Thr  Val  Ala  Thr  Pro  Glu  Val  Gly  Gly  Thr  Pro  Pro
               85                     90                    95

Lys  Pro  Thr  Thr  Asp  Pro  Thr  Asp  Met  Ser  Asp  Met  Arg  Glu  Ala  Leu
               100                    105                   110

Arg  Ala  Ser  Gln  Ile  Glu  Ala  Asn  Gly  Pro  Ser  Thr  Phe  Tyr  Met  Cys
     115                    120                   125

Pro  Pro  Pro  Ser  Gly  Ser  Thr  Val  Val  Arg  Leu  Glu  Pro  Pro  Arg  Ala
     130                    135                   140

Cys  Pro  Asp  Tyr  Lys  Leu  Gly  Lys  Asn  Phe  Thr  Glu  Gly  Ile  Ala  Val
145                     150                   155                        160

Ile  Phe  Lys  Glu  Asn  Ile  Ala  Pro  Tyr  Lys  Phe  Lys  Ala  Asn  Ile  Tyr
               165                    170                   175

Tyr  Lys  Asn  Ile  Ile  Met  Thr  Thr  Val  Trp  Ser  Gly  Ser  Ser  Tyr  Ala
               180                    185                   190

Val  Thr  Thr  Asn  Arg  Tyr  Thr  Asp  Arg  Val  Pro  Val  Lys  Val  Gln  Glu
     195                    200                   205
```

| | | | | | | | | | | | | | | |
|---|---|---|---|---|---|---|---|---|---|---|---|---|---|---|
| Ile | Thr | Asp | Leu | Ile | Asp | Arg | Arg | Gly | Met | Cys | Leu | Ser | Lys | Ala | Asp |
| | 210 | | | | | 215 | | | | | 220 | | | | |
| Tyr | Val | Arg | Asn | Asn | Tyr | Gln | Phe | Thr | Ala | Phe | Asp | Arg | Asp | Glu | Asp |
| 225 | | | | | 230 | | | | | 235 | | | | | 240 |
| Pro | Arg | Glu | Leu | Pro | Leu | Lys | Pro | Ser | Lys | Phe | Asn | Thr | Pro | Gln | Ser |
| | | | | 245 | | | | | 250 | | | | | 255 | |
| Arg | Gly | Trp | His | Thr | Tyr | Lys | Phe | Lys | Ala | Thr | Val | Tyr | Tyr | Lys | Asp |
| | | | 260 | | | | | 265 | | | | | 270 | | |
| Val | Ile | Val | Ser | Thr | Ala | Trp | Ala | Gly | Ser | Ser | Tyr | Thr | Gln | Ile | Thr |
| | | 275 | | | | | 280 | | | | | 285 | | | |
| Asn | Arg | Tyr | Ala | Asp | Arg | Val | Pro | Ile | Pro | Val | Ser | Glu | Ile | Thr | Asp |
| | 290 | | | | | 295 | | | | | 300 | | | | |
| Thr | Ile | Asp | Lys | Phe | Gly | Lys | Cys | Ser | Ser | Lys | Ala | Thr | Tyr | Val | Arg |
| 305 | | | | | 310 | | | | | 315 | | | | | 320 |
| Asn | Asn | His | Lys | Val | Glu | Ala | Phe | Asn | Glu | Asp | Lys | Asn | Pro | Gln | Asp |
| | | | | 325 | | | | | 330 | | | | | 335 | |
| Met | Pro | Leu | Ile | Ala | Ser | Lys | Tyr | Asn | Ser | Val | Gly | Ser | Lys | Ala | Trp |
| | | | 340 | | | | | 345 | | | | | 350 | | |
| His | Thr | Thr | Asn | Glu | Thr | Tyr | Thr | Lys | Ile | Gly | Ala | Ala | Gly | Phe | His |
| | | 355 | | | | | 360 | | | | | 365 | | | |
| His | Ser | Gly | Thr | Ser | Val | Asn | Cys | Ile | Val | Glu | Glu | Val | Asp | Ala | Arg |
| | 370 | | | | | 375 | | | | | 380 | | | | |
| Ser | Val | Tyr | Pro | Tyr | Asp | Ser | Phe | Ala | Ile | Ser | Thr | Gly | Asp | Val | Ile |
| 385 | | | | | 390 | | | | | 395 | | | | | 400 |
| His | Met | Ser | Pro | Phe | Phe | Gly | Leu | Arg | Asp | Gly | Ala | His | Val | Glu | His |
| | | | | 405 | | | | | 410 | | | | | 415 | |
| Thr | Ser | Tyr | Ser | Ser | Asp | Arg | Phe | Gln | Gln | Ile | Glu | Gly | Tyr | Tyr | Pro |
| | | | 420 | | | | | 425 | | | | | 430 | | |
| Ile | Asp | Leu | Asp | Thr | Arg | Leu | Gln | Leu | Gly | Ala | Pro | Val | Ser | Arg | Asn |
| | | 435 | | | | | 440 | | | | | 445 | | | |
| Phe | Leu | Glu | Thr | Pro | His | Val | Thr | Val | Ala | Trp | Asn | Trp | Thr | Pro | Lys |
| | 450 | | | | | 455 | | | | | 460 | | | | |
| Cys | Gly | Arg | Val | Cys | Thr | Leu | Ala | Lys | Trp | Arg | Glu | Ile | Asp | Glu | Met |
| 465 | | | | | 470 | | | | | 475 | | | | | 480 |
| Leu | Arg | Asp | Glu | Tyr | Gln | Gly | Ser | Tyr | Arg | Phe | Thr | Val | Lys | Thr | Ile |
| | | | | 485 | | | | | 490 | | | | | 495 | |
| Ser | Ala | Thr | Phe | Ile | Ser | Asn | Thr | Ser | Gln | Phe | Glu | Ile | Asn | Arg | Ile |
| | | | 500 | | | | | 505 | | | | | 510 | | |
| Arg | Leu | Gly | Asp | Cys | Ala | Thr | Lys | Glu | Ala | Ala | Glu | Ala | Ile | Asp | Arg |
| | | 515 | | | | | 520 | | | | | 525 | | | |
| Ile | Tyr | Lys | Ser | Lys | Tyr | Ser | Lys | Thr | His | Ile | Gln | Thr | Gly | Thr | Leu |
| | 530 | | | | | 535 | | | | | 540 | | | | |
| Glu | Thr | Tyr | Leu | Ala | Arg | Gly | Gly | Phe | Leu | Ile | Ala | Phe | Arg | Pro | Met |
| 545 | | | | | 550 | | | | | 555 | | | | | 560 |
| Ile | Ser | Asn | Glu | Leu | Ala | Lys | Leu | Tyr | Ile | Asn | Glu | Leu | Ala | Arg | Ser |
| | | | | 565 | | | | | 570 | | | | | 575 | |
| Asn | Arg | Thr | Val | Asp | Leu | Ser | Ala | Leu | Leu | Asn | Pro | Ser | Gly | Glu | Thr |
| | | | 580 | | | | | 585 | | | | | 590 | | |
| Val | Gln | Arg | Thr | Arg | Gly | Ser | Val | Pro | Ser | Asn | Gln | His | His | Arg | Ser |
| | | 595 | | | | | 600 | | | | | 605 | | | |
| Arg | Arg | Ser | Thr | Ile | Glu | Gly | Gly | Ile | Glu | Thr | Val | Asn | Asn | Ala | Ser |
| | 610 | | | | | 615 | | | | | 620 | | | | |
| Leu | Leu | Lys | Thr | Thr | Ser | Ser | Val | Glu | Phe | Ala | Met | Ile | Gln | Phe | Ala |

```
625                         630                         635                         640
Tyr Asp Tyr Ile Gln Ala His Val Asn Glu Met Leu Ser Arg Ile Ala
                645                 650                 655

Thr Ala Trp Cys Thr Leu Gln Asn Arg Glu His Val Leu Trp Thr Glu
                660                 665                 670

Thr Leu Lys Leu Asn Pro Gly Gly Val Val Ser Met Ala Leu Glu Arg
            675                 680                 685

Arg Val Ser Ala Arg Leu Leu Gly Asp Ala Val Ala Val Thr Gln Cys
        690                 695                 700

Val Asn Ile Ser Ser Gly His Val Tyr Ile Gln Asn Ser Met Arg Val
705                 710                 715                 720

Thr Gly Ser Ser Thr Thr Cys Tyr Ser Arg Pro Leu Val Ser Phe Arg
                725                 730                 735

Ala Leu Asn Asp Ser Glu Tyr Ile Glu Gly Gln Leu Gly Glu Asn Asn
            740                 745                 750

Asp Leu Leu Val Glu Arg Lys Leu Ile Glu Pro Cys Thr Val Asn Asn
        755                 760                 765

Lys Arg Tyr Phe Lys Phe Gly Ala Asp Tyr Val Tyr Phe Glu Asp Tyr
770                 775                 780

Ala Tyr Val Arg Lys Val Pro Leu Ser Glu Ile Glu Leu Ile Ser Ala
785                 790                 795                 800

Tyr Val Asp Leu Asn Leu Thr Leu Leu Glu Asp Arg Glu Phe Leu Pro
                805                 810                 815

Leu Glu Val Tyr Thr Arg Ala Glu Leu Glu Asp Thr Gly Leu Leu Asp
            820                 825                 830

Tyr Ser Glu Ile Gln Arg Arg Asn Gln Leu His Ala Leu Lys Phe Tyr
        835                 840                 845

Asp Ile Asp Ser Ile Val Arg Val Asp Asn Asn Leu Val Ile Met Arg
850                 855                 860

Gly Met Ala Asn Phe Phe Gln Gly Leu Gly Asp Val Gly Ala Gly Phe
865                 870                 875                 880

Gly Lys Val Val Leu Gly Ala Ala Ser Ala Val Ile Ser Thr Val Ser
                885                 890                 895

Gly Val Ser Ser Phe Leu Asn Asn Pro Phe Gly Ala Leu Ala Val Gly
            900                 905                 910

Leu Leu Ile Leu Ala Gly Ile Val Ala Ala Phe Leu Ala Tyr Arg Tyr
        915                 920                 925

Ile Ser Arg Leu Arg Ala Asn Pro Met Lys Ala Leu Tyr Pro Val Thr
930                 935                 940

Thr Arg Asn Leu Lys Gln Thr Ala Lys Ser Pro Ala Ser Thr Ala Gly
945                 950                 955                 960

Gly Asp Ser Asp Pro Gly Val Asp Asp Phe Asp Glu Glu Lys Leu Met
                965                 970                 975

Gln Ala Arg Glu Met Ile Lys Tyr Met Ser Leu Val Ser Ala Met Glu
            980                 985                 990

Gln Gln Glu His Lys Ala Met Lys Lys Asn Lys Gly Pro Ala Ile Leu
        995                 1000                1005

Thr Ser His Leu Thr Asn Met Ala Leu Arg Arg Arg Gly Pro Lys Tyr
        1010                1015                1020

Gln Arg Leu Asn Asn Leu Asp Ser Gly Asp Asp Thr Glu Thr Asn Leu
1025                1030                1035                1040

Val
```

( 2 ) INFORMATION FOR SEQ ID NO:5:

( i ) SEQUENCE CHARACTERISTICS:
        ( A ) LENGTH: 980 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:5:

```
Met Ser Ser Gly Cys Arg Ser Val Gly Gly Ser Thr Trp Gly Asn Trp
1               5                   10                  15

Arg Gly Asp Gly Gly Asp Leu Arg Gln Arg Arg Val Leu Ser Pro Val
            20                  25                  30

Cys Ser Ala Pro Ala Ala Gly Ser Trp Ile Gly Ser Gln Leu Gly Asn
        35                  40                  45

Val Gly Asn Leu Leu Ala Thr Pro His Pro Leu Gly Lys Pro Ala Ser
    50                  55                  60

Ser Arg Val Gly Thr Ile Val Leu Ala Cys Leu Leu Phe Gly Ser
65                  70                  75                  80

Cys Val Val Arg Ala Val Pro Thr Thr Pro Ser Pro Pro Thr Ser Thr
                85                  90                  95

Pro Thr Ser Met Ser Thr His Ser His Gly Thr Val Asp Pro Thr Leu
            100                 105                 110

Leu Pro Thr Glu Thr Pro Asp Pro Leu Arg Leu Ala Val Arg Glu Ser
        115                 120                 125

Gly Ile Leu Ala Glu Asp Gly Asp Phe Tyr Thr Cys Pro Pro Pro Thr
    130                 135                 140

Gly Ser Thr Val Val Arg Ile Glu Pro Pro Arg Thr Cys Pro Lys Phe
145                 150                 155                 160

Asp Leu Gly Arg Asn Phe Thr Glu Gly Ile Ala Val Ile Phe Lys Glu
                165                 170                 175

Asn Ile Ala Pro Tyr Lys Phe Arg Ala Asn Val Tyr Tyr Lys Asp Ile
            180                 185                 190

Val Val Thr Arg Val Trp Lys Gly Tyr Ser His Thr Ser Leu Ser Asp
        195                 200                 205

Arg Tyr Asn Asp Arg Val Pro Val Ser Val Glu Glu Ile Phe Gly Leu
    210                 215                 220

Ile Asp Ser Lys Gly Lys Cys Ser Ser Lys Ala Glu Tyr Leu Arg Asp
225                 230                 235                 240

Asn Ile Met His His Ala Tyr His Asp Asp Glu Asp Glu Val Glu Leu
                245                 250                 255

Asp Leu Cys Arg Pro Ser Leu Gln Leu Arg Gly Ala Arg Ala Trp Gln
            260                 265                 270

Thr Thr Asn Asp Thr Thr Ser Tyr Val Gly Trp Met Pro Trp Arg His
        275                 280                 285

Tyr Thr Ser Thr Ser Val Asn Cys Ile Val Glu Glu Val Glu Ala Arg
    290                 295                 300

Ser Val Tyr Pro Tyr Asp Ser Phe Ala Leu Ser Thr Gly Asp Ile Val
305                 310                 315                 320

Tyr Ala Ser Pro Phe Tyr Gly Leu Arg Ala Ala Ala Arg Ile Glu His
                325                 330                 335

Asn Ser Tyr Ala Gln Glu Arg Phe Arg Gln Val Glu Gly Tyr Arg Pro
            340                 345                 350
```

Arg Asp Leu Asp Ser Lys Leu Gln Ala Glu Glu Pro Val Thr Lys Asn
        355                 360                 365

Phe Ile Thr Thr Pro His Val Thr Val Ser Trp Asn Trp Thr Glu Lys
        370                 375                 380

Lys Val Glu Ala Cys Thr Leu Thr Lys Trp Lys Glu Val Asp Glu Leu
385                 390                 395                 400

Val Arg Asp Glu Phe Arg Gly Ser Tyr Arg Phe Thr Ile Arg Ser Ile
                405                 410                 415

Ser Ser Thr Phe Ile Ser Asn Thr Thr Gln Phe Lys Leu Glu Ser Ala
                420                 425                 430

Pro Leu Thr Glu Cys Val Ser Lys Glu Ala Lys Glu Ala Ile Asp Ser
            435                 440                 445

Ile Tyr Lys Lys Gln Tyr Glu Ser Thr His Val Phe Ser Gly Asp Val
        450                 455                 460

Glu Tyr Tyr Leu Ala Arg Gly Gly Phe Leu Ile Ala Phe Arg Pro Met
465                 470                 475                 480

Leu Ser Asn Glu Leu Ala Arg Leu Tyr Leu Asn Glu Leu Val Arg Ser
                485                 490                 495

Asn Arg Thr Tyr Asp Leu Lys Asn Leu Leu Asn Pro Asn Ala Asn Asn
            500                 505                 510

Asn Asn Asn Thr Thr Arg Arg Arg Arg Ser Leu Leu Ser Val Pro Glu
        515                 520                 525

Pro Gln Pro Thr Gln Asp Gly Val His Arg Glu Gln Ile Leu His Arg
    530                 535                 540

Leu His Lys Arg Ala Val Glu Ala Thr Ala Gly Thr Asp Ser Ser Asn
545                 550                 555                 560

Val Thr Ala Lys Gln Leu Glu Leu Ile Lys Thr Thr Ser Ser Ile Glu
            565                 570                 575

Phe Ala Met Leu Gln Phe Ala Tyr Asp His Ile Gln Ser His Val Asn
            580                 585                 590

Glu Met Leu Ser Arg Ile Ala Thr Ala Trp Cys Thr Leu Gln Asn Lys
        595                 600                 605

Glu Arg Thr Leu Trp Asn Glu Met Val Lys Ile Asn Pro Ser Ala Ile
    610                 615                 620

Val Ser Ala Thr Leu Asp Glu Arg Val Ala Ala Arg Val Leu Gly Asp
625                 630                 635                 640

Val Ile Ala Ile Thr His Cys Ala Lys Ile Glu Gly Asn Val Tyr Leu
            645                 650                 655

Gln Asn Ser Met Arg Ser Met Asp Ser Asn Thr Cys Tyr Ser Arg Pro
            660                 665                 670

Pro Val Thr Phe Thr Ile Thr Lys Asn Ala Asn Asn Arg Gly Ser Ile
        675                 680                 685

Glu Gly Gln Leu Gly Glu Glu Asn Glu Ile Phe Thr Glu Arg Lys Leu
    690                 695                 700

Ile Glu Pro Cys Ala Leu Asn Gln Lys Arg Tyr Phe Lys Phe Gly Lys
705                 710                 715                 720

Glu Tyr Val Tyr Tyr Glu Asn Tyr Thr Phe Val Arg Lys Val Pro Pro
                725                 730                 735

Thr Glu Ile Glu Val Ile Ser Thr Tyr Val Glu Leu Asn Leu Thr Leu
            740                 745                 750

Leu Glu Asp Arg Glu Phe Leu Pro Leu Glu Val Tyr Thr Arg Ala Glu
        755                 760                 765

Leu Glu Asp Thr Gly Leu Leu Asp Tyr Ser Glu Ile Gln Arg Arg Asn
    770                 775                 780

| | | | | | | | | | | | | | | |
|---|---|---|---|---|---|---|---|---|---|---|---|---|---|---|
| Gln 785 | Leu | His | Ala | Leu | Arg 790 | Phe | Tyr | Asp | Ile 795 | Asp | Ser | Val | Val | Asn Val 800 |
| Asp | Asn | Thr | Ala 805 | Val | Ile | Met | Gln | Ile 810 | Ala | Ser | Phe | Phe | Lys 815 | Gly |
| Leu | Gly | Lys | Val 820 | Gly | Glu | Ala | Val | Gly 825 | Thr | Leu | Val | Leu | Gly 830 | Ala Ala |
| Gly | Ala | Val 835 | Val | Ser | Thr | Val | Ser 840 | Gly | Ile | Ala | Ser | Phe 845 | Leu | Asn Asn |
| Pro | Phe 850 | Gly | Gly | Leu | Ala | Ile 855 | Gly | Leu | Leu | Val | Ile 860 | Ala | Gly | Leu Val |
| Ala 865 | Ala | Phe | Phe | Ala | Tyr 870 | Arg | Tyr | Val | Met 875 | Gln | Ile | Arg | Ser | Asn Pro 880 |
| Met | Lys | Ala | Leu | Tyr 885 | Pro | Ile | Thr | Thr | Lys 890 | Ala | Leu | Lys | Asn 895 | Lys Ala |
| Lys | Thr | Ser | Tyr 900 | Gly | Gln | Asn | Glu | Glu 905 | Asp | Asp | Gly | Ser | Asp 910 | Phe Asp |
| Glu | Ala | Lys 915 | Leu | Glu | Glu | Ala | Arg 920 | Glu | Met | Ile | Lys | Tyr 925 | Met | Ser Met |
| Val | Ser 930 | Ala | Leu | Glu | Lys | Gln 935 | Glu | Lys | Lys | Ala | Ile 940 | Lys | Lys | Asn Ser |
| Gly 945 | Val | Gly | Leu | Ile | Ala 950 | Ser | Asn | Val | Ser | Lys 955 | Leu | Ala | Leu | Arg Arg 960 |
| Arg | Gly | Pro | Lys | Tyr 965 | Thr | Arg | Leu | Gln | Gln 970 | Asn | Asp | Thr | Met | Glu Asn 975 |
| Glu | Lys | Met | Val 980 | | | | | | | | | | | |

(2) INFORMATION FOR SEQ ID NO:6:

(i) SEQUENCE CHARACTERISTICS:
    (A) LENGTH: 913 amino acids
    (B) TYPE: amino acid
    (C) STRANDEDNESS: single
    (D) TOPOLOGY: linear (ii) MOLECULE TYPE: peptide (v) FRAGMENT TYPE: N-terminal (xi) SEQUENCE DESCRIPTION: SEQ ID NO:6:

| | | | | | | | | | | | | | | |
|---|---|---|---|---|---|---|---|---|---|---|---|---|---|---|
| Met 1 | Pro | Ala | Gly | Gly 5 | Gly | Leu | Trp | Arg | Gly 10 | Pro | Arg | Gly | His 15 | Arg Pro |
| Gly | His | His | Gly 20 | Gly | Ala | Gly | Leu | Gly 25 | Arg | Leu | Trp | Pro | Ala 30 | Pro His |
| His | Ala | Ala 35 | Ala | Ala | Arg | Gly | Ala 40 | Val | Ala | Leu | Ala | Leu 45 | Leu | Leu Leu |
| Ala | Leu 50 | Ala | Ala | Ala | Pro | Pro 55 | Cys | Gly | Ala | Ala | Val 60 | Thr | Arg | Ala |
| Ala 65 | Ser | Ala | Ser | Pro 70 | Thr | Pro | Gly | Thr | Gly 75 | Ala | Thr | Pro | Asn | Asp Val 80 |
| Ser | Ala | Glu | Ala | Ser 85 | Leu | Glu | Glu | Ile | Glu 90 | Ala | Phe | Ser | Pro 95 | Gly Pro |
| Ser | Glu | Ala | Pro 100 | Asp | Gly | Glu | Tyr | Gly 105 | Asp | Leu | Asp | Ala | Arg 110 | Thr Ala |
| Val | Arg | Ala 115 | Ala | Ala | Thr | Glu | Arg 120 | Asp | Arg | Phe | Tyr | Val 125 | Cys | Pro Pro |
| Pro | Ser | Gly | Ser | Thr | Val | Val | Arg | Leu | Glu | Pro | Glu | Gln | Ala | Cys Pro |

|     |     |     |     |     |     |     |     |     |     |     |     |     |     |     |
|---|---|---|---|---|---|---|---|---|---|---|---|---|---|---|
| | | | | 130 | | | | | 135 | | | | 140 | |
| Glu 145 | Tyr | Ser | Gln | Gly | Arg 150 | Asn | Phe | Thr | Glu | Gly 155 | Ile | Ala | Val | Leu | Phe 160 |
| Lys | Glu | Asn | Ile | Ala 165 | Pro | His | Lys | Phe | Lys 170 | Ala | His | Ile | Tyr | Tyr 175 | Lys |
| Asn | Val | Ile | Val 180 | Thr | Thr | Val | Trp | Ser 185 | Gly | Ser | Thr | Tyr | Ala 190 | Ala | Ile |
| Thr | Asn | Arg 195 | Phe | Thr | Asp | Arg | Val 200 | Pro | Val | Pro | Val | Gln 205 | Glu | Ile | Thr |
| Asp | Val 210 | Ile | Asp | Arg | Arg | Gly 215 | Lys | Cys | Val | Ser | Lys 220 | Ala | Glu | Tyr | Val |
| Arg 225 | Asn | Asn | His | Lys | Val 230 | Thr | Ala | Phe | Asp | Arg 235 | Asp | Glu | Asn | Pro | Val 240 |
| Glu | Val | Asp | Leu | Arg 245 | Pro | Ser | Arg | Leu | Asn 250 | Ala | Leu | Gly | Thr | Arg 255 | Gly |
| Trp | His | Thr | Thr 260 | Asn | Asp | Thr | Tyr | Thr 265 | Lys | Ile | Gly | Ala | Ala 270 | Gly | Phe |
| Tyr | His | Thr 275 | Gly | Thr | Ser | Val | Asn 280 | Cys | Ile | Val | Glu | Glu 285 | Val | Glu | Ala |
| Arg | Ser 290 | Val | Tyr | Pro | Tyr | Asp 295 | Ser | Phe | Ala | Leu | Ser 300 | Thr | Gly | Asp | Ile |
| Val 305 | Tyr | Met | Ser | Pro | Phe 310 | Tyr | Gly | Leu | Arg | Glu 315 | Gly | Ala | His | Gly | Glu 320 |
| His | Ile | Gly | Tyr | Ala 325 | Pro | Gly | Arg | Phe | Gln 330 | Gln | Val | Glu | His | Tyr 335 | Tyr |
| Pro | Ile | Asp | Leu 340 | Asp | Ser | Arg | Leu | Arg 345 | Ala | Ser | Glu | Ser | Val 350 | Thr | Arg |
| Asn | Phe | Leu | Arg 355 | Thr | Pro | His | Phe | Thr 360 | Val | Ala | Trp | Asp 365 | Trp | Ala | Pro |
| Lys | Thr 370 | Arg | Arg | Val | Cys | Ser 375 | Leu | Ala | Lys | Trp | Arg 380 | Glu | Ala | Glu | Glu |
| Met 385 | Thr | Arg | Asp | Glu | Thr 390 | Arg | Asp | Gly | Ser | Phe 395 | Arg | Phe | Thr | Ser | Arg 400 |
| Ala | Leu | Gly | Ala | Ser 405 | Phe | Val | Ser | Asp | Val 410 | Thr | Gln | Leu | Asp | Leu 415 | Gln |
| Arg | Val | His | Leu 420 | Gly | Asp | Cys | Val | Leu 425 | Arg | Glu | Ala | Ser | Glu 430 | Ala | Ile |
| Asp | Ala | Ile | Tyr 435 | Arg | Arg | Arg | Tyr | Asn 440 | Ser | Thr | His | Val | Leu 445 | Ala | Gly |
| Asp | Arg 450 | Pro | Glu | Val | Tyr | Leu 455 | Ala | Arg | Gly | Gly | Phe 460 | Val | Val | Ala | Phe |
| Arg 465 | Pro | Leu | Ile | Ser | Asn 470 | Glu | Leu | Ala | Gln | Leu 475 | Tyr | Ala | Arg | Glu | Leu 480 |
| Glu | Arg | Leu | Gly | Leu 485 | Ala | Gly | Val | Val | Gly 490 | Pro | Ala | Ala | Pro | Ala 495 | Ala |
| Ala | Arg | Arg | Ala 500 | Arg | Arg | Ser | Pro | Gly 505 | Pro | Ala | Gly | Thr | Pro 510 | Glu | Pro |
| Pro | Ala | Val 515 | Asn | Gly | Thr | Gly | His 520 | Leu | Arg | Ile | Thr | Thr 525 | Gly | Ser | Ala |
| Glu | Phe 530 | Ala | Arg | Leu | Gln | Phe 535 | Thr | Tyr | Asp | His | Ile 540 | Gln | Ala | His | Val |
| Asn 545 | Asp | Met | Leu | Gly | Arg 550 | Ile | Ala | Ala | Ala | Trp 555 | Cys | Glu | Leu | Gln | Asn 560 |

-continued

| | | | | | | | | | | | | | | |
|---|---|---|---|---|---|---|---|---|---|---|---|---|---|---|
| Lys | Asp | Arg | Thr | Leu | Trp | Ser | Glu | Met | Ser | Arg | Leu | Asn | Pro | Ser | Ala |
| | | | | 565 | | | | 570 | | | | | | 575 | |
| Val | Ala | Thr | Ala | Ala | Leu | Gly | Gln | Arg | Val | Ser | Ala | Arg | Met | Leu | Gly |
| | | | 580 | | | | | 585 | | | | | 590 | | |
| Asp | Val | Met | Ala | Ile | Ser | Arg | Cys | Val | Glu | Val | Arg | Gly | Gly | Val | Tyr |
| | | | 595 | | | | 600 | | | | | 605 | | | |
| Val | Gln | Asn | Ser | Met | Arg | Val | Pro | Gly | Glu | Arg | Gly | Thr | Cys | Tyr | Ser |
| | 610 | | | | | 615 | | | | | 620 | | | | |
| Arg | Pro | Leu | Val | Thr | Phe | Glu | His | Asn | Gly | Thr | Gly | Val | Ile | Glu | Gly |
| 625 | | | | | 630 | | | | | 635 | | | | | 640 |
| Gln | Leu | Gly | Asp | Asp | Asn | Glu | Leu | Leu | Ile | Ser | Arg | Asp | Leu | Ile | Glu |
| | | | | 645 | | | | | 650 | | | | | 655 | |
| Pro | Cys | Thr | Gly | Asn | His | Arg | Arg | Tyr | Phe | Lys | Leu | Gly | Ser | Gly | Tyr |
| | | | 660 | | | | | 665 | | | | | 670 | | |
| Val | Tyr | Tyr | Glu | Asp | Tyr | Asn | Tyr | Val | Arg | Met | Val | Glu | Val | Pro | Glu |
| | | 675 | | | | | 680 | | | | | 685 | | | |
| Thr | Ile | Ser | Thr | Arg | Val | Thr | Leu | Asn | Leu | Thr | Leu | Leu | Glu | Asp | Arg |
| | | 690 | | | | | 695 | | | | | 700 | | | |
| Glu | Phe | Leu | Pro | Leu | Glu | Val | Tyr | Thr | Arg | Glu | Glu | Leu | Ala | Asp | Thr |
| 705 | | | | | 710 | | | | | 715 | | | | | 720 |
| Gly | Leu | Leu | Asp | Tyr | Ser | Glu | Ile | Gln | Arg | Arg | Asn | Gln | Leu | His | Ala |
| | | | | 725 | | | | | 730 | | | | | 735 | |
| Leu | Lys | Phe | Tyr | Asp | Ile | Asp | Arg | Val | Lys | Val | Asp | His | Asn | Val |
| | | | 740 | | | | | 745 | | | | 750 | | | |
| Val | Leu | Leu | Arg | Gly | Ile | Ala | Asn | Phe | Phe | Gln | Gly | Leu | Gly | Asp | Val |
| | | | 755 | | | | | 760 | | | | | 765 | | |
| Gly | Ala | Ala | Val | Gly | Lys | Val | Val | Leu | Gly | Ala | Thr | Gly | Ala | Val | Ile |
| | 770 | | | | | 775 | | | | | 780 | | | | |
| Ser | Ala | Val | Gly | Gly | Met | Val | Ser | Phe | Leu | Ser | Asn | Pro | Phe | Gly | Ala |
| 785 | | | | | 790 | | | | | 795 | | | | | 800 |
| Leu | Ala | Ile | Gly | Leu | Leu | Val | Leu | Ala | Gly | Leu | Val | Ala | Ala | Phe | Leu |
| | | | | 805 | | | | | 810 | | | | | 815 | |
| Ala | Tyr | Arg | His | Ile | Ser | Arg | Leu | Arg | Arg | Asn | Pro | Met | Lys | Ala | Leu |
| | | | 820 | | | | | 825 | | | | | 830 | | |
| Tyr | Pro | Val | Thr | Thr | Lys | Thr | Leu | Lys | Glu | Asp | Gly | Val | Asp | Glu | Gly |
| | | 835 | | | | | 840 | | | | | 845 | | | |
| Asp | Val | Asp | Glu | Ala | Lys | Leu | Asp | Gln | Ala | Arg | Asp | Met | Ile | Arg | Tyr |
| | 850 | | | | | 855 | | | | | 860 | | | | |
| Met | Ser | Ile | Val | Ser | Ala | Leu | Glu | Gln | Gln | Glu | His | Lys | Ala | Arg | Lys |
| 865 | | | | | 870 | | | | | 875 | | | | | 880 |
| Lys | Asn | Ser | Gly | Pro | Ala | Leu | Leu | Ala | Ser | Arg | Val | Gly | Ala | Met | Ala |
| | | | | 885 | | | | | 890 | | | | | 895 | |
| Thr | Arg | Arg | Arg | His | Tyr | Gln | Arg | Leu | Glu | Ser | Glu | Asp | Pro | Asp | Ala |
| | | | 900 | | | | | 905 | | | | | 910 | | |
| Leu | | | | | | | | | | | | | | | |

( 2 ) INFORMATION FOR SEQ ID NO:7:

( i ) SEQUENCE CHARACTERISTICS:
        ( A ) LENGTH: 868 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:7:

```
Met Phe Val Thr Ala Val Val Ser Val Ser Pro Ser Ser Phe Tyr Glu
 1               5               10              15

Ser Leu Gln Val Glu Pro Thr Gln Ser Glu Asp Ile Thr Arg Ser Ala
             20              25              30

His Leu Gly Asp Gly Asp Glu Ile Arg Glu Ala Ile His Lys Ser Gln
         35              40              45

Asp Ala Glu Thr Lys Pro Thr Phe Tyr Val Cys Pro Pro Thr Gly
     50              55              60

Ser Thr Ile Val Arg Leu Glu Pro Thr Arg Thr Cys Pro Asp Tyr His
 65              70              75              80

Leu Gly Lys Asn Phe Thr Glu Gly Ile Ala Val Val Tyr Lys Glu Asn
                 85              90              95

Ile Ala Ala Tyr Lys Phe Lys Ala Thr Val Tyr Tyr Lys Asp Val Ile
             100             105             110

Val Ser Thr Ala Trp Ala Gly Ser Ser Tyr Thr Gln Ile Thr Asn Arg
         115             120             125

Tyr Ala Asp Arg Val Pro Ile Pro Val Ser Glu Ile Thr Asp Thr Ile
     130             135             140

Asp Lys Phe Gly Lys Cys Ser Ser Lys Ala Thr Tyr Val Arg Asn Asn
 145             150             155             160

His Lys Val Glu Ala Phe Asn Glu Asp Lys Asn Pro Gln Asp Met Pro
                 165             170             175

Leu Ile Ala Ser Lys Tyr Asn Ser Val Gly Ser Lys Ala Trp His Thr
             180             185             190

Thr Asn Asp Thr Tyr Met Val Ala Gly Thr Pro Gly Thr Tyr Arg Thr
         195             200             205

Gly Thr Ser Val Asn Cys Ile Ile Glu Glu Val Glu Ala Arg Ser Ile
     210             215             220

Phe Pro Tyr Asp Ser Phe Gly Leu Ser Thr Gly Asp Ile Ile Tyr Met
 225             230             235             240

Ser Pro Phe Phe Gly Leu Arg Asp Gly Ala Tyr Arg Glu His Ser Asn
                 245             250             255

Tyr Ala Met Asp Arg Phe His Gln Phe Glu Gly Tyr Arg Gln Arg Asp
             260             265             270

Leu Asp Thr Arg Ala Leu Leu Glu Pro Ala Ala Arg Asn Phe Leu Val
         275             280             285

Thr Pro His Leu Thr Val Gly Trp Asn Trp Lys Pro Lys Arg Thr Glu
     290             295             300

Val Cys Ser Leu Val Lys Trp Arg Glu Val Glu Asp Val Val Arg Asp
 305             310             315             320

Glu Tyr Ala His Asn Phe Arg Phe Thr Met Lys Thr Leu Ser Thr Thr
                 325             330             335

Phe Ile Ser Glu Thr Asn Glu Phe Asn Leu Asn Gln Ile His Leu Ser
             340             345             350

Gln Cys Val Lys Glu Glu Ala Arg Ala Ile Ile Asn Arg Ile Tyr Thr
         355             360             365

Thr Arg Tyr Asn Ser Ser His Val Arg Thr Gly Asp Ile Gln Thr Tyr
     370             375             380

Leu Ala Arg Gly Gly Phe Val Val Phe Gln Pro Leu Leu Ser Asn
 385             390             395             400

Ser Leu Ala Arg Leu Tyr Leu Gln Glu Leu Val Arg Glu Asn Thr Asn
             405             410             415
```

| | | | | | | | | | | | | | | |
|---|---|---|---|---|---|---|---|---|---|---|---|---|---|---|
| His | Ser | Pro | Gln<br>420 | Lys | His | Pro | Thr | Arg<br>425 | Asn | Thr | Arg | Ser | Arg<br>430 | Ser |
| Val | Pro | Val<br>435 | Glu | Leu | Arg | Ala | Asn<br>440 | Arg | Thr | Ile | Thr | Thr<br>445 | Ser | Ser |
| Val | Glu<br>450 | Phe | Ala | Met | Leu | Gln<br>455 | Phe | Thr | Tyr | Asp | His<br>460 | Ile | Gln | Glu | His |
| Val<br>465 | Asn | Glu | Met | Leu | Ala<br>470 | Arg | Ile | Ser | Ser | Ser<br>475 | Trp | Cys | Gln | Leu | Gln<br>480 |
| Asn | Arg | Glu | Arg | Ala<br>485 | Leu | Trp | Ser | Gly | Leu<br>490 | Phe | Pro | Ile | Asn | Pro<br>495 | Ser |
| Ala | Leu | Ala | Ser<br>500 | Thr | Ile | Leu | Asp | Gln<br>505 | Arg | Val | Lys | Ala | Arg<br>510 | Ile | Leu |
| Gly | Asp | Val<br>515 | Ile | Ser | Val | Ser | Asn<br>520 | Cys | Pro | Glu | Leu | Gly<br>525 | Ser | Asp | Thr |
| Arg | Ile<br>530 | Ile | Leu | Gln | Asn | Ser<br>535 | Met | Arg | Val | Ser | Gly<br>540 | Ser | Thr | Thr | Arg |
| Cys<br>545 | Tyr | Ser | Arg | Pro | Leu<br>550 | Ile | Ser | Ile | Val | Ser<br>555 | Leu | Asn | Gly | Ser | Gly<br>560 |
| Thr | Val | Glu | Gly | Gln<br>565 | Leu | Gly | Thr | Asp | Asn<br>570 | Glu | Leu | Ile | Met | Ser<br>575 | Arg |
| Asp | Leu | Leu | Glu<br>580 | Pro | Cys | Val | Ala | Asn<br>585 | His | Lys | Arg | Tyr | Phe<br>590 | Leu | Phe |
| Gly | His | His<br>595 | Tyr | Val | Tyr | Tyr | Glu<br>600 | Asp | Tyr | Arg | Tyr | Val<br>605 | Arg | Glu | Ile |
| Ala | Val<br>610 | His | Asp | Val | Gly | Met<br>615 | Ile | Ser | Thr | Tyr | Val<br>620 | Asp | Leu | Asn | Leu |
| Thr<br>625 | Leu | Leu | Lys | Asp | Arg<br>630 | Glu | Phe | Met | Pro | Leu<br>635 | Gln | Val | Tyr | Thr | Arg<br>640 |
| Asp | Glu | Leu | Arg | Asp<br>645 | Thr | Gly | Leu | Leu | Asp<br>650 | Tyr | Ser | Glu | Ile | Gln<br>655 | Arg |
| Arg | Asn | Gln | Met<br>660 | His | Ser | Leu | Arg | Phe<br>665 | Tyr | Asp | Ile | Asp | Lys<br>670 | Val | Val |
| Gln | Tyr | Asp<br>675 | Ser | Gly | Thr | Ala | Ile<br>680 | Met | Gln | Gly | Met | Ala<br>685 | Gln | Phe | Phe |
| Gln | Gly<br>690 | Leu | Gly | Thr | Ala | Gly<br>695 | Gln | Ala | Val | Gly | His<br>700 | Val | Val | Leu | Gly |
| Ala<br>705 | Thr | Gly | Ala | Leu | Leu<br>710 | Ser | Thr | Val | His | Gly<br>715 | Phe | Thr | Thr | Phe | Leu<br>720 |
| Ser | Asn | Pro | Phe | Gly<br>725 | Ala | Leu | Ala | Val | Gly<br>730 | Leu | Leu | Val | Leu | Ala<br>735 | Gly |
| Leu | Val | Ala | Ala<br>740 | Phe | Phe | Ala | Tyr | Arg<br>745 | Tyr | Val | Leu | Lys | Leu<br>750 | Lys | Thr |
| Ser | Pro | Met<br>755 | Lys | Ala | Leu | Tyr | Pro<br>760 | Leu | Thr | Thr | Lys | Gly<br>765 | Leu | Lys | Gln |
| Leu | Pro<br>770 | Glu | Gly | Met | Asp | Pro<br>775 | Phe | Ala | Glu | Lys | Pro<br>780 | Asn | Ala | Thr | Asp |
| Thr<br>785 | Pro | Ile | Glu | Glu | Ile<br>790 | Gly | Asp | Ser | Gln | Asn<br>795 | Thr | Glu | Pro | Ser | Val<br>800 |
| Asn | Ser | Gly | Phe | Asp<br>805 | Pro | Asp | Lys | Phe | Arg<br>810 | Glu | Ala | Gln | Glu | Met<br>815 | Ile |
| Lys | Tyr | Met | Thr<br>820 | Leu | Val | Ser | Ala | Ala<br>825 | Glu | Arg | Gln | Glu | Ser<br>830 | Lys | Ala |
| Arg | Lys | Lys | Asn | Lys | Thr | Ser | Ala | Leu | Leu | Thr | Ser | Arg | Leu | Thr | Gly |

835                         840                              845

Leu  Ala  Leu  Arg  Asn  Arg  Arg  Gly  Tyr  Ser  Arg  Val  Arg  Thr  Glu  Asn
                 850                         855                 860

Val  Thr  Gly  Val
       865

(2) INFORMATION FOR SEQ ID NO:8:

(i) SEQUENCE CHARACTERISTICS:
        (A) LENGTH: 903 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:8:

Met  His  Gln  Gly  Ala  Pro  Ser  Trp  Gly  Arg  Arg  Trp  Phe  Val  Val  Trp
       1                   5                        10                       15

Ala  Leu  Leu  Gly  Leu  Thr  Leu  Gly  Val  Leu  Val  Ala  Ser  Ala  Ala  Pro
                      20                       25                      30

Ser  Ser  Pro  Gly  Thr  Pro  Gly  Val  Ala  Arg  Asp  Pro  Gly  Gly  Glu  Arg
                 35                       40                      45

Gly  Pro  Cys  His  Ser  Gly  Ala  Ala  Ala  Leu  Gly  Ala  Ala  Pro  Thr  Gly
            50                       55                      60

Asp  Pro  Lys  Pro  Lys  Lys  Asn  Lys  Lys  Pro  Lys  Asn  Pro  Thr  Pro  Pro
       65                      70                      75                      80

Arg  Pro  Ala  Gly  Asp  Asn  Ala  Thr  Val  Ala  Ala  Gly  His  Ala  Thr  Leu
                           85                      90                      95

Arg  Glu  His  Leu  Arg  Asp  Ile  Lys  Ala  Glu  Asn  Thr  Asp  Ala  Asn  Phe
                           100                     105                     110

Tyr  Val  Cys  Pro  Pro  Pro  Thr  Gly  Ala  Thr  Val  Val  Gln  Phe  Glu  Gln
                 115                          120                     125

Pro  Arg  Arg  Cys  Pro  Thr  Arg  Pro  Glu  Gly  Gln  Asn  Tyr  Thr  Glu  Gly
            130                          135                     140

Ile  Ala  Val  Val  Phe  Lys  Glu  Asn  Ile  Ala  Pro  Tyr  Lys  Phe  Lys  Ala
       145                     150                     155                     160

Thr  Met  Tyr  Tyr  Lys  Asp  Val  Thr  Val  Ser  Gln  Val  Trp  Phe  Gly  His
                           165                     170                     175

Arg  Tyr  Ser  Gln  Phe  Met  Gly  Ile  Phe  Glu  Asp  Arg  Ala  Pro  Val  Pro
                      180                     185                     190

Phe  Glu  Glu  Val  Ile  Asp  Lys  Ile  Asn  Ala  Lys  Gly  Val  Cys  Arg  Ser
                 195                     200                     205

Thr  Ala  Lys  Tyr  Val  Arg  Asn  Asn  Leu  Glu  Thr  Thr  Ala  Phe  His  Arg
            210                     215                     220

Asp  Asp  His  Glu  Thr  Asp  Met  Glu  Leu  Lys  Pro  Ala  Asn  Ala  Ala  Thr
       225                     230                     235                     240

Arg  Thr  Ser  Arg  Gly  Trp  His  Thr  Thr  Asp  Leu  Lys  Tyr  Asn  Pro  Ser
                           245                     250                     255

Arg  Val  Glu  Ala  Phe  His  Arg  Tyr  Gly  Thr  Thr  Val  Asn  Cys  Ile  Val
                      260                     265                     270

Glu  Glu  Val  Asp  Ala  Arg  Ser  Val  Tyr  Pro  Tyr  Asp  Glu  Phe  Val  Leu
                 275                     280                     285

Ala  Thr  Gly  Asp  Phe  Val  Tyr  Met  Ser  Pro  Phe  Tyr  Gly  Tyr  Arg  Glu
            290                     295                     300

| | | | | | | | | | | | | | | |
|---|---|---|---|---|---|---|---|---|---|---|---|---|---|---|
| Gly | Ser | His | Thr | Glu | His | Thr | Thr | Tyr | Ala | Ala | Asp | Arg | Phe | Lys | Gln |
| 305 | | | | 310 | | | | | 315 | | | | | | 320 |
| Val | Asp | Gly | Phe | Tyr | Ala | Arg | Asp | Leu | Thr | Thr | Lys | Ala | Arg | Ala | Thr |
| | | | | 325 | | | | | 330 | | | | | 335 | |
| Ala | Pro | Thr | Thr | Arg | Asn | Leu | Leu | Thr | Thr | Pro | Lys | Phe | Thr | Val | Ala |
| | | | 340 | | | | | 345 | | | | | 350 | | |
| Trp | Asp | Trp | Val | Pro | Lys | Arg | Pro | Ser | Val | Cys | Thr | Met | Thr | Lys | Trp |
| | | | 355 | | | | 360 | | | | | 365 | | | |
| Gln | Glu | Val | Asp | Glu | Met | Leu | Arg | Ser | Glu | Tyr | Gly | Gly | Ser | Phe | Arg |
| | 370 | | | | | 375 | | | | | 380 | | | | |
| Phe | Ser | Ser | Asp | Ala | Ile | Ser | Thr | Thr | Phe | Thr | Thr | Asn | Leu | Thr | Glu |
| 385 | | | | | 390 | | | | | 395 | | | | | 400 |
| Tyr | Pro | Leu | Ser | Arg | Val | Asp | Leu | Gly | Asp | Cys | Ile | Gly | Lys | Asp | Ala |
| | | | | 405 | | | | | 410 | | | | | 415 | |
| Arg | Asp | Ala | Met | Asp | Arg | Ile | Phe | Ala | Arg | Arg | Tyr | Asn | Ala | Thr | His |
| | | | 420 | | | | | 425 | | | | | 430 | | |
| Ile | Lys | Val | Gly | Gln | Pro | Gln | Tyr | Tyr | Leu | Ala | Asn | Gly | Gly | Phe | Leu |
| | | | 435 | | | | 440 | | | | | 445 | | | |
| Ile | Ala | Tyr | Gln | Pro | Leu | Leu | Ser | Asn | Thr | Leu | Ala | Glu | Leu | Tyr | Val |
| | | | 450 | | | | 455 | | | | | 460 | | | |
| Arg | Glu | His | Leu | Arg | Glu | Gln | Ser | Arg | Lys | Pro | Pro | Asn | Pro | Thr | Pro |
| 465 | | | | | 470 | | | | | 475 | | | | | 480 |
| Pro | Pro | Pro | Gly | Ala | Ser | Ala | Asn | Ala | Ser | Val | Glu | Arg | Ile | Lys | Thr |
| | | | | 485 | | | | | 490 | | | | | 495 | |
| Thr | Ser | Ser | Ile | Glu | Phe | Ala | Arg | Leu | Gln | Phe | Thr | Tyr | Asn | His | Ile |
| | | | 500 | | | | | 505 | | | | | 510 | | |
| Gln | Arg | His | Val | Asn | Asp | Met | Leu | Gly | Arg | Val | Ala | Ile | Ala | Trp | Cys |
| | | 515 | | | | | 520 | | | | | 525 | | | |
| Glu | Leu | Gln | Asn | His | Glu | Leu | Thr | Leu | Trp | Asn | Glu | Ala | Arg | Lys | Leu |
| | 530 | | | | | 535 | | | | | 540 | | | | |
| Asn | Pro | Asn | Ala | Ile | Ala | Ser | Val | Thr | Val | Gly | Arg | Arg | Val | Ser | Ala |
| 545 | | | | | 550 | | | | | 555 | | | | | 560 |
| Arg | Met | Leu | Gly | Asp | Val | Met | Ala | Val | Ser | Thr | Cys | Val | Pro | Val | Ala |
| | | | | 565 | | | | | 570 | | | | | 575 | |
| Ala | Asp | Asn | Val | Ile | Val | Gln | Asn | Ser | Met | Arg | Ile | Ser | Ser | Arg | Pro |
| | | | 580 | | | | | 585 | | | | | 590 | | |
| Gly | Ala | Cys | Tyr | Ser | Arg | Pro | Leu | Val | Ser | Phe | Arg | Tyr | Glu | Asp | Gln |
| | | 595 | | | | | 600 | | | | | 605 | | | |
| Gly | Pro | Leu | Val | Glu | Gly | Gln | Leu | Gly | Glu | Asn | Asn | Glu | Leu | Arg | Leu |
| | 610 | | | | | 615 | | | | | 620 | | | | |
| Thr | Arg | Asp | Ala | Ile | Glu | Pro | Cys | Thr | Val | Gly | His | Arg | Arg | Tyr | Phe |
| 625 | | | | | 630 | | | | | 635 | | | | | 640 |
| Thr | Phe | Gly | Gly | Gly | Tyr | Val | Tyr | Phe | Glu | Glu | Tyr | Ala | Tyr | Ser | His |
| | | | | 645 | | | | | 650 | | | | | 655 | |
| Gln | Leu | Ser | Arg | Ala | Asp | Ile | Thr | Thr | Val | Ser | Thr | Phe | Ile | Asp | Leu |
| | | | 660 | | | | | 665 | | | | | 670 | | |
| Asn | Ile | Thr | Met | Leu | Glu | Asp | His | Glu | Phe | Val | Pro | Leu | Glu | Val | Tyr |
| | | 675 | | | | | 680 | | | | | 685 | | | |
| Thr | Arg | His | Glu | Ile | Lys | Asp | Ser | Gly | Leu | Leu | Asp | Tyr | Thr | Glu | Val |
| | 690 | | | | | 695 | | | | | 700 | | | | |
| Gln | Arg | Arg | Asn | Gln | Leu | His | Asp | Leu | Arg | Phe | Ala | Asp | Ile | Asp | Thr |
| 705 | | | | | 710 | | | | | 715 | | | | | 720 |
| Val | Ile | His | Ala | Asp | Ala | Asn | Ala | Ala | Met | Phe | Ala | Gly | Leu | Gly | Ala |
| | | | | 725 | | | | | 730 | | | | | 735 | |

```
Phe  Phe  Glu  Gly  Met  Gly  Asp  Leu  Gly  Arg  Ala  Val  Gly  Lys  Val  Val
               740                 745                      750

Met  Gly  Leu  Val  Gly  Gly  Val  Val  Ser  Ala  Val  Ser  Gly  Val  Ser  Ser
          755                 760                      765

Phe  Met  Ser  Asn  Pro  Phe  Gly  Ala  Leu  Ala  Val  Gly  Leu  Leu  Val  Leu
     770                 775                      780

Ala  Gly  Leu  Ala  Ala  Ala  Phe  Phe  Ala  Phe  Arg  Tyr  Val  Met  Arg  Leu
785                      790                 795                           800

Gln  Ser  Asn  Pro  Met  Lys  Ala  Leu  Tyr  Pro  Leu  Thr  Thr  Lys  Glu  Leu
               805                      810                           815

Lys  Asn  Pro  Thr  Asn  Pro  Asp  Ala  Ser  Gly  Glu  Gly  Glu  Gly  Gly  Gly
               820                      825                      830

Asp  Phe  Asp  Glu  Ala  Lys  Leu  Ala  Glu  Ala  Arg  Glu  Met  Ile  Arg  Tyr
          835                      840                 845

Met  Ala  Leu  Val  Ser  Ala  Met  Glu  Arg  Thr  Glu  His  Lys  Ala  Lys  Lys
     850                      855                      860

Lys  Gly  Thr  Ser  Arg  Leu  Leu  Ser  Ala  Lys  Val  Thr  Asp  Met  Val  Met
865                      870                 875                           880

Arg  Lys  Arg  Arg  Asn  Thr  Asn  Tyr  Thr  Gln  Val  Pro  Asn  Lys  Asp  Gly
               885                      890                      895

Asp  Ala  Asp  Glu  Asp  Asp  Leu
               900
```

( 2 ) INFORMATION FOR SEQ ID NO:9:

( i ) SEQUENCE CHARACTERISTICS:
        ( A ) LENGTH: 906 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:9:

```
Met  Glu  Ser  Arg  Ile  Trp  Cys  Leu  Val  Val  Cys  Val  Asn  Leu  Cys  Ile
1                   5                   10                       15

Val  Cys  Leu  Gly  Ala  Ala  Val  Ser  Ser  Ser  Thr  Ser  His  Ala  Thr
               20                  25                      30

Ser  Ser  Thr  His  Asn  Gly  Ser  His  Thr  Ser  Arg  Thr  Thr  Ser  Ala  Gln
          35                  40                      45

Thr  Arg  Ser  Val  Tyr  Ser  Gln  His  Val  Thr  Ser  Ser  Glu  Ala  Val  Ser
     50                      55                      60

His  Arg  Ala  Asn  Glu  Thr  Ile  Tyr  Asn  Thr  Thr  Leu  Lys  Tyr  Gly  Asp
65                       70                      75                       80

Val  Val  Gly  Val  Asn  Thr  Thr  Lys  Tyr  Pro  Tyr  Arg  Val  Cys  Ser  Met
               85                       90                      95

Ala  Gln  Gly  Thr  Asp  Leu  Ile  Arg  Phe  Glu  Arg  Asn  Ile  Ile  Cys  Thr
               100                      105                      110

Ser  Met  Lys  Pro  Ile  Asn  Glu  Asp  Leu  Asp  Glu  Gly  Ile  Met  Val  Val
          115                      120                      125

Tyr  Lys  Arg  Asn  Ile  Val  Ala  His  Thr  Phe  Lys  Val  Arg  Val  Tyr  Gln
     130                      135                      140

Lys  Val  Leu  Thr  Phe  Arg  Arg  Ser  Tyr  Ala  Tyr  Ile  Tyr  Thr  Thr  Tyr
145                      150                      155                      160

Leu  Leu  Gly  Ser  Asn  Thr  Glu  Tyr  Val  Ala  Pro  Pro  Met  Trp  Glu  Ile
```

```
                         165                          170                             175
        His  His  Ile  Asn  Lys  Phe  Ala  Gln  Cys  Tyr  Ser  Ser  Tyr  Ser  Arg  Val
                       180                      185                190
        Ile  Gly  Gly  Thr  Val  Phe  Val  Ala  Tyr  His  Arg  Asp  Ser  Tyr  Glu  Asn
                  195                      200                205
        Lys  Thr  Met  Gln  Leu  Ile  Pro  Asp  Asp  Tyr  Ser  Asn  Thr  His  Ser  Thr
             210                      215                     220
        Arg  Tyr  Val  Thr  Val  Lys  Asp  Gln  Trp  His  Ser  Arg  Gly  Ser  Thr  Trp
        225                      230                     235                          240
        Leu  Tyr  Arg  Glu  Thr  Cys  Asn  Leu  Asn  Cys  Met  Leu  Thr  Ile  Thr  Thr
                            245                     250                          255
        Ala  Arg  Ser  Lys  Tyr  Pro  Tyr  His  Phe  Ala  Thr  Ser  Thr  Gly  Asp
                       260                      265                270
        Val  Val  Tyr  Ile  Ser  Pro  Phe  Tyr  Asn  Gly  Thr  Asn  Arg  Asn  Ala  Ser
                  275                      280                285
        Tyr  Phe  Gly  Glu  Asn  Ala  Asp  Lys  Phe  Phe  Ile  Phe  Pro  Asn  Tyr  Thr
             290                      295                     300
        Ile  Val  Ser  Asp  Phe  Gly  Arg  Pro  Asn  Ala  Ala  Pro  Glu  Thr  His  Arg
        305                      310                     315                          320
        Leu  Val  Ala  Phe  Leu  Glu  Arg  Ala  Asp  Ser  Val  Ile  Ser  Trp  Asp  Ile
                            325                     330                          335
        Gln  Asp  Glu  Lys  Asn  Val  Thr  Cys  Gln  Leu  Thr  Phe  Trp  Glu  Ala  Ser
                       340                      345                350
        Glu  Arg  Thr  Ile  Arg  Ser  Glu  Ala  Glu  Asp  Ser  Tyr  His  Phe  Ser  Ser
                  355                      360                365
        Ala  Lys  Met  Thr  Ala  Thr  Phe  Leu  Ser  Lys  Lys  Gln  Glu  Val  Asn  Met
             370                      375                     380
        Ser  Asp  Ser  Ala  Leu  Asp  Cys  Val  Arg  Asp  Glu  Ala  Ile  Asn  Lys  Leu
        385                      390                     395                          400
        Gln  Gln  Ile  Phe  Asn  Thr  Ser  Tyr  Asn  Gln  Thr  Tyr  Glu  Lys  Tyr  Gly
                            405                     410                          415
        Asn  Val  Ser  Val  Phe  Glu  Thr  Ser  Gly  Gly  Leu  Val  Val  Phe  Trp  Gln
                       420                      425                430
        Gly  Ile  Lys  Gln  Lys  Ser  Leu  Val  Glu  Leu  Glu  Arg  Leu  Ala  Asn  Arg
                  435                      440                445
        Ser  Ser  Leu  Asn  Ile  Thr  His  Arg  Thr  Arg  Arg  Ser  Thr  Ser  Asp  Asn
             450                      455                     460
        Asn  Thr  Thr  His  Leu  Ser  Ser  Met  Glu  Ser  Val  His  Asn  Leu  Val  Tyr
        465                      470                     475                          480
        Ala  Gln  Leu  Gln  Phe  Thr  Tyr  Asp  Thr  Leu  Arg  Gly  Tyr  Ile  Asn  Arg
                            485                     490                          495
        Ala  Leu  Ala  Gln  Ile  Ala  Glu  Ala  Trp  Cys  Val  Asp  Gln  Arg  Arg  Thr
                       500                      505                510
        Leu  Glu  Val  Phe  Lys  Glu  Leu  Ser  Lys  Ile  Asn  Pro  Ser  Ala  Ile  Leu
                  515                      520                525
        Ser  Ala  Ile  Tyr  Asn  Lys  Pro  Ile  Ala  Ala  Arg  Phe  Met  Gly  Asp  Val
             530                      535                     540
        Leu  Gly  Leu  Ala  Ser  Cys  Val  Thr  Ile  Asn  Gln  Thr  Ser  Val  Lys  Val
        545                      550                     555                          560
        Leu  Arg  Asp  Met  Asn  Val  Lys  Glu  Ser  Pro  Gly  Arg  Cys  Tyr  Ser  Arg
                            565                     570                          575
        Pro  Val  Val  Ile  Phe  Asn  Phe  Ala  Asn  Ser  Ser  Tyr  Val  Gln  Tyr  Gly
                       580                      585                590
```

```
Gln Leu Gly Glu Asp Asn Glu Ile Leu Leu Gly Asn His Arg Thr Glu
        595                 600                 605

Glu Cys Gln Leu Pro Ser Leu Lys Ile Phe Ile Ala Gly Asn Ser Ala
    610                 615                 620

Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
                645                 650                 655

Asn Thr Asp Phe Arg Val Leu Glu Leu Tyr Ser Gln Lys Glu Leu Arg
            660                 665                 670

Ser Ser Asn Val Phe Asp Leu Glu Glu Ile Met Arg Glu Phe Asn Ser
        675                 680                 685

Tyr Lys Gln Arg Val Lys Tyr Val Glu Asp Lys Val Val Asp Pro Leu
    690                 695                 700

Pro Pro Tyr Leu Lys Gly Leu Asp Asp Leu Met Ser Gly Leu Gly Ala
705                 710                 715                 720

Ala Gly Lys Ala Val Gly Val Ala Ile Gly Ala Val Gly Gly Ala Val
                725                 730                 735

Ala Ser Val Val Glu Gly Val Ala Thr Phe Leu Lys Asn Pro Phe Gly
            740                 745                 750

Ala Phe Thr Ile Ile Leu Val Ala Ile Ala Val Val Ile Ile Thr Tyr
        755                 760                 765

Leu Ile Tyr Thr Arg Gln Arg Arg Leu Cys Thr Gln Pro Leu Gln Asn
    770                 775                 780

Leu Phe Pro Tyr Leu Val Ser Ala Asp Gly Thr Val Thr Ser Gly
785                 790                 795                 800

Ser Thr Lys Asp Thr Ser Leu Gln Ala Pro Pro Ser Tyr Glu Glu Ser
                805                 810                 815

Val Tyr Asn Ser Gly Arg Lys Gly Pro Gly Pro Pro Ser Ser Asp Ala
            820                 825                 830

Ser Thr Ala Ala Pro Pro Tyr Thr Asn Glu Gln Ala Tyr Gln Met Leu
        835                 840                 845

Leu Ala Leu Ala Arg Leu Asp Ala Glu Gln Arg Ala Gln Gln Asn Gly
    850                 855                 860

Thr Asp Ser Leu Asp Gly Gln Thr Gly Thr Gln Asp Lys Gly Gln Lys
865                 870                 875                 880

Pro Asn Leu Leu Asp Arg Leu Arg His Arg Lys Asn Gly Tyr Arg His
                885                 890                 895

Leu Lys Asp Ser Asp Glu Glu Glu Asn Val
            900                 905
```

( 2 ) INFORMATION FOR SEQ ID NO:10:

( i ) SEQUENCE CHARACTERISTICS:
        ( A ) LENGTH: 857 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:10:

```
Met Thr Arg Arg Arg Val Leu Ser Val Val Leu Leu Ala Ala Leu
1               5                   10                  15

Ala Cys Arg Leu Gly Ala Gln Thr Pro Glu Gln Pro Ala Pro Pro Ala
            20                  25                  30
```

| | | | | | | | | | | | | | |
|---|---|---|---|---|---|---|---|---|---|---|---|---|---|
|Thr|Thr|Val|Gln|Pro|Thr|Ala|Thr|Arg|Gln|Gln|Thr|Ser|Phe|Pro|Phe|
| | |35| | |40| | | | | |45| | | | |
|Arg|Val|Cys|Glu|Leu|Ser|Ser|His|Gly|Asp|Leu|Phe|Arg|Phe|Ser|Ser|
| |50| | | | |55| | | |60| | | | | |
|Asp|Ile|Gln|Cys|Pro|Ser|Phe|Gly|Thr|Arg|Glu|Asn|His|Thr|Glu|Gly|
|65| | | | |70| | | |75| | | | | |80|
|Leu|Leu|Met|Val|Phe|Lys|Asp|Asn|Ile|Ile|Pro|Tyr|Ser|Phe|Lys|Val|
| | | | |85| | | |90| | | | |95| | |
|Arg|Ser|Tyr|Thr|Lys|Ile|Val|Thr|Asn|Ile|Leu|Ile|Tyr|Asn|Gly|Trp|
| | | |100| | | |105| | | | |110| | | |
|Tyr|Ala|Asp|Ser|Val|Thr|Asn|Arg|His|Glu|Glu|Lys|Phe|Ser|Val|Asp|
| | |115| | | |120| | | | |125| | | | |
|Ser|Tyr|Glu|Thr|Asp|Gln|Met|Asp|Thr|Ile|Tyr|Gln|Cys|Tyr|Asn|Ala|
| |130| | | | |135| | | |140| | | | | |
|Val|Lys|Met|Thr|Lys|Asp|Gly|Leu|Thr|Arg|Val|Tyr|Val|Asp|Arg|Asp|
|145| | | | |150| | | |155| | | | | |160|
|Gly|Val|Asn|Ile|Thr|Val|Asn|Leu|Lys|Pro|Thr|Gly|Gly|Leu|Ala|Asn|
| | | | |165| | | |170| | | | |175| | |
|Gly|Val|Arg|Arg|Tyr|Ala|Ser|Gln|Thr|Glu|Leu|Tyr|Asp|Ala|Pro|Gly|
| | | |180| | | |185| | | | |190| | | |
|Trp|Leu|Ile|Trp|Thr|Tyr|Arg|Thr|Arg|Thr|Thr|Val|Asn|Cys|Leu|Ile|
| | |195| | | |200| | | | |205| | | | |
|Thr|Asp|Met|Met|Ala|Lys|Ser|Asn|Ser|Pro|Phe|Asp|Phe|Phe|Val|Thr|
| |210| | | | |215| | | |220| | | | | |
|Thr|Thr|Gly|Gln|Thr|Val|Glu|Met|Ser|Pro|Phe|Tyr|Asp|Gly|Lys|Asn|
|225| | | | |230| | | |235| | | | | |240|
|Lys|Glu|Thr|Phe|His|Glu|Arg|Ala|Asp|Ser|Phe|His|Val|Arg|Thr|Asn|
| | | |245| | | |250| | | | |255| | | |
|Tyr|Lys|Ile|Val|Asp|Tyr|Asp|Asn|Arg|Gly|Thr|Asn|Pro|Gln|Gly|Glu|
| | | |260| | | |265| | | | |270| | | |
|Arg|Arg|Ala|Phe|Leu|Asp|Lys|Gly|Thr|Tyr|Thr|Leu|Ser|Trp|Lys|Leu|
| | |275| | | |280| | | | |285| | | | |
|Glu|Asn|Arg|Thr|Ala|Tyr|Cys|Pro|Leu|Gln|His|Trp|Gln|Thr|Phe|Asp|
| |290| | | | |295| | | |300| | | | | |
|Ser|Thr|Ile|Ala|Thr|Glu|Thr|Gly|Lys|Ser|Ile|His|Phe|Val|Thr|Asp|
|305| | | | |310| | | |315| | | | | |320|
|Glu|Gly|Thr|Ser|Ser|Phe|Val|Thr|Asn|Thr|Thr|Val|Gly|Ile|Glu|Leu|
| | | | |325| | | |330| | | | |335| | |
|Pro|Asp|Ala|Phe|Lys|Cys|Ile|Glu|Glu|Gln|Val|Asn|Lys|Thr|Met|His|
| | | |340| | | |345| | | | |350| | | |
|Glu|Lys|Tyr|Glu|Ala|Val|Gln|Asp|Arg|Tyr|Thr|Lys|Gly|Gln|Glu|Ala|
| | |355| | | |360| | | | |365| | | | |
|Ile|Thr|Tyr|Phe|Ile|Thr|Ser|Gly|Gly|Leu|Leu|Leu|Ala|Trp|Leu|Pro|
| |370| | | | |375| | | |380| | | | | |
|Leu|Thr|Pro|Arg|Ser|Leu|Ala|Thr|Val|Lys|Asn|Leu|Thr|Glu|Leu|Thr|
|385| | | | |390| | | |395| | | | | |400|
|Thr|Pro|Thr|Ser|Ser|Pro|Pro|Ser|Ser|Pro|Ser|Pro|Ala|Pro|Ser|
| | | | |405| | | |410| | | | |415| |
|Ala|Ala|Arg|Gly|Ser|Thr|Pro|Ala|Ala|Val|Leu|Arg|Arg|Arg|Arg|
| | | |420| | | |425| | | | |430| | |
|Asp|Ala|Gly|Asn|Ala|Thr|Thr|Pro|Val|Pro|Pro|Thr|Ala|Pro|Gly|Lys|
| | |435| | | |440| | | | |445| | | | |
|Ser|Leu|Gly|Thr|Leu|Asn|Asn|Pro|Ala|Thr|Val|Gln|Ile|Gln|Phe|Ala|

-continued

```
                    450                          455                         460
Tyr  Asp  Ser  Leu  Arg  Arg  Gln  Ile  Asn  Arg  Met  Leu  Gly  Asp  Leu  Ala
465                      470                      475                      480

Arg  Ala  Trp  Cys  Leu  Glu  Gln  Lys  Arg  Gln  Asn  Met  Val  Leu  Arg  Glu
                    485                      490                      495

Leu  Thr  Lys  Ile  Asn  Pro  Thr  Thr  Val  Met  Ser  Ser  Ile  Tyr  Gly  Lys
                    500                      505                      510

Ala  Val  Ala  Ala  Lys  Arg  Leu  Gly  Asp  Val  Ile  Ser  Val  Ser  Gln  Cys
                    515                      520                      525

Val  Pro  Val  Asn  Gln  Ala  Thr  Val  Thr  Leu  Arg  Lys  Ser  Met  Arg  Val
          530                      535                      540

Pro  Gly  Ser  Glu  Thr  Met  Cys  Tyr  Ser  Arg  Pro  Leu  Val  Ser  Phe  Ser
545                      550                      555                      560

Phe  Ile  Asn  Asp  Thr  Lys  Thr  Tyr  Glu  Gly  Gln  Leu  Gly  Thr  Asp  Asn
                    565                      570                      575

Glu  Ile  Phe  Leu  Thr  Lys  Lys  Met  Thr  Glu  Val  Cys  Gln  Ala  Thr  Ser
                    580                      585                      590

Gln  Tyr  Tyr  Phe  Gln  Ser  Gly  Asn  Glu  Ile  His  Val  Tyr  Asn  Asp  Tyr
          595                      600                      605

His  His  Phe  Lys  Thr  Ile  Glu  Leu  Asp  Gly  Ile  Ala  Thr  Leu  Gln  Thr
     610                      615                      620

Phe  Ile  Ser  Leu  Asn  Thr  Ser  Leu  Ile  Glu  Asn  Ile  Asp  Phe  Ala  Ser
625                      630                      635                      640

Leu  Glu  Leu  Tyr  Ser  Arg  Asp  Glu  Gln  Arg  Ala  Ser  Asn  Val  Phe  Asp
                    645                      650                      655

Leu  Glu  Gly  Ile  Phe  Arg  Glu  Tyr  Asn  Phe  Gln  Ala  Gln  Asn  Ile  Ala
                    660                      665                      670

Gly  Leu  Arg  Lys  Asp  Leu  Asp  Asn  Ala  Val  Ser  Asn  Gly  Arg  Asn  Gln
          675                      680                      685

Phe  Val  Asp  Gly  Leu  Gly  Glu  Leu  Met  Asp  Ser  Leu  Gly  Ser  Val  Gly
          690                      695                      700

Gln  Ser  Ile  Thr  Asn  Leu  Val  Ser  Thr  Val  Gly  Gly  Leu  Phe  Ser  Ser
705                      710                      715                      720

Leu  Val  Ser  Gly  Phe  Ile  Ser  Phe  Phe  Lys  Asn  Pro  Phe  Gly  Gly  Met
                    725                      730                      735

Leu  Ile  Leu  Val  Leu  Val  Ala  Gly  Val  Val  Ile  Leu  Val  Ile  Ser  Leu
                    740                      745                      750

Thr  Arg  Arg  Thr  Arg  Gln  Met  Ser  Gln  Gln  Pro  Val  Gln  Met  Leu  Tyr
          755                      760                      765

Pro  Gly  Ile  Asp  Glu  Leu  Ala  Gln  Gln  His  Ala  Ser  Gly  Glu  Gly  Pro
     770                      775                      780

Gly  Ile  Asn  Pro  Ile  Ser  Lys  Thr  Glu  Leu  Gln  Ala  Ile  Met  Leu  Ala
785                      790                      795                      800

Leu  His  Glu  Gln  Asn  Gln  Glu  Gln  Lys  Arg  Ala  Ala  Gln  Arg  Ala  Ala
                    805                      810                      815

Gly  Pro  Ser  Val  Ala  Ser  Arg  Ala  Leu  Gln  Ala  Ala  Arg  Asp  Arg  Phe
               820                      825                      830

Pro  Gly  Leu  Arg  Arg  Arg  Arg  Tyr  His  Asp  Pro  Glu  Thr  Ala  Ala  Ala
          835                      840                      845

Leu  Leu  Gly  Glu  Ala  Glu  Thr  Glu  Phe
          850                      855
```

( 2 ) INFORMATION FOR SEQ ID NO:11:

( i ) SEQUENCE CHARACTERISTICS:
  ( A ) LENGTH: 2280 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:11:

| | | | | | |
|---|---|---|---|---|---|
| CGAGCCCTAA | TTATTGGTTT | GTATATGACT | GTTGGAATTT | GTTACATTTT | TATTAAAACA | 60 |
| ATAAATTAAA | TTTTTAAAC | TATATTACGG | TTGTGTGTGT | TTTAAGTTTT | AAATAAAGCA | 120 |
| ATATTTCGAA | TTCACATTTA | TCAAAAACAT | TAAAACCCAA | CACAAAAAAA | TTTCTATAAT | 180 |
| CATTAAGGTA | ATAAGTCAAA | ATGAGTTTTA | AAAATTTTTA | TCTAATATAT | GTAATTATAA | 240 |
| TTTTTATAAA | CTCGATAATA | ACTTCGGCAT | CTACATCCAA | ACCTTCAACA | CCTACCATAA | 300 |
| TTCCAACTTC | AGCAAATGAA | TCACCTGCTT | CCATAGATAC | AACTATAACA | AAACCTATAT | 360 |
| CTACAGAGGC | AAATAATTTA | AAATCAGTAA | GTACCTCAAT | TAAACCACCT | AAAAACTTAA | 420 |
| AAAAAAAATT | ACTTAAATCT | AAATGTAGAG | ATAATGTTAT | TTATAGGCCA | TATTTTAGTC | 480 |
| AATTAGAAAT | TAACTGTACT | ATAACTAAAA | AGCAAAATTT | AAGTAATCCT | TTAATTGAGT | 540 |
| TATGGTTTAA | AGAACTTTCT | ACATATAATA | AAACCAATGA | AAATGTTGAA | AGTTTAAAAA | 600 |
| CAGATATATC | AAAAAATATT | TTATTATTTT | CGACAAAAAA | TAATAGTGAT | AACTTTTATA | 660 |
| ATGATTTTTT | ATTAGGTATA | CAAAATCAAC | CAGTAAATTA | TAAACTTTAC | GGTTCCCAAT | 720 |
| TTTATGATAA | TGGAAACATA | TTACTAAATA | TAAAGTCGGT | TGACTTTAAA | ACCTCTGGAA | 780 |
| TATATACTTG | GAAACTATAT | AATTCAAATA | ATGAAAGTAT | TTTTGAAACT | TTTAAAATTC | 840 |
| AAGTATATGC | ATATCATTCC | CCAAATGTAA | ACTTAAAATC | AAACCCAAGT | TTATATAATG | 900 |
| AAAACTACAG | CGCTATTTGT | ACAATAGCAA | ATTACTTTCC | ATTGGAATCT | ACGGAAATAT | 960 |
| TTTGGTTTAA | CGATGGACAA | CCTATTGATA | AAAAATATAT | AGATGAAACT | TATAGTGTAT | 1020 |
| GGATTGACGG | TCTTATAACA | CGCACTTCAA | TATTATCCCT | TCCCTTTTCC | GAAGCCATGG | 1080 |
| AAAGCCCCCC | CAATTTGCGA | TGTAATGTTG | AATGGTATAA | AAATTCAAAG | GCATCAAAAA | 1140 |
| AATTTTCAAA | TACCGTTATT | CCAAAAGTTT | ACTATAAACC | TTTTATATCT | ATAAAATTTG | 1200 |
| ATAATGGTTT | AGCTATTTGT | GATGCTAAAT | GTGTTTCCCG | TGAAAATAAT | AAATTACAAT | 1260 |
| GGTTAGTTAA | AGATATACCT | ATAAATGGTG | ATGATATTAT | AAGCGGCCCC | TGTTTAAACC | 1320 |
| ACCCTGGTTT | GGTCAATATT | CAAAATAAAA | TAGATATATC | GGATTATGAT | GAACCTGTTA | 1380 |
| CCTATAAATG | TTCAATTATT | GGTTATCCAA | TAATTTTTCC | CAACTTTTAT | GATGAAAAGG | 1440 |
| TGTTTGATGC | ATCGGATGAA | AATGTTAGTA | AATCGATGTT | AATAAGTATT | ACCACAATAA | 1500 |
| TTGGTGGAGC | CATTTTTGTT | ATAGTATTGA | TTTTTATAAC | AGCTTTATGT | TTTTATTGTT | 1560 |
| CAAAAAATAA | TAAGATCTAA | TATCAATATT | TACGTAAATG | GATTATATAA | TGTTATATTC | 1620 |
| GTGTTATTAT | GATTTATAAG | TTCATCAAAT | TTAAAAATTT | GTATAGTATT | AAGATTTTTA | 1680 |
| ATAGGGGTAT | CGTTTAATAT | GGCTCAGTTA | GTTTTAACTG | ATATTCCCCT | CGAAGATGTG | 1740 |
| GAAAATAAAA | ATACTTCATC | CGACGAAGAA | ACAACTAACT | TAAACCAGAA | AAAATCAACA | 1800 |
| TGTCAATGTT | TATGTGTTAC | CCTTGGATTT | TTTGCAGCTG | GAATTTTATT | AACCATAGCT | 1860 |
| GCAATAATTT | TTACTTTTAT | TTTTACAGTA | CCATTAGAAA | TGCTTGGATC | TATTAATTGT | 1920 |
| CCTCCATCTA | CATTTGGTAT | TGATAATGTT | TGTATCGAAC | CAATAAAAAA | ATCTATTAAT | 1980 |
| TCTTATTCAG | AATTATCTAA | AATATGTTAT | GATAGATTGT | CAAATCCGAT | AAATCAGAGT | 2040 |
| ACTATTAACT | CCTTATTAAC | TGTTTTAAAT | ATGTTTGCAG | ATAAAAACTA | TGAAAATGTT | 2100 |

```
TATAATTGTA ATACAATGAG TGAAAAAACA TGTAATTCAT CAATAGCTAT TTGTCAAACT    2160

AATCATCCAC TAAGTTCATT GGGAAATTTT GTTATTAAAA TTAGAAAAAT TTTTGGGTTT    2220

AAATAATAAA TAAAATAAAT AAACATTACT TTTGTTTTT GTCTTTATTA AACAGTTGTA     2280
```

( 2 ) INFORMATION FOR SEQ ID NO:12:

( i ) SEQUENCE CHARACTERISTICS:
        ( A ) LENGTH: 459 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: internal ( x i ) SEQUENCE DESCRIPTION: SEQ ID NO:12:

```
Met Ser Phe Lys Asn Phe Tyr Leu Ile Tyr Val Ile Ile Ile Phe Ile
 1           5                  10                  15

Asn Ser Ile Ile Thr Ser Ala Ser Thr Ser Lys Pro Ser Thr Pro Thr
            20                  25                  30

Ile Ile Pro Thr Ser Ala Asn Glu Ser Pro Ala Ser Ile Asp Thr Thr
        35                  40                  45

Ile Thr Lys Pro Ile Ser Thr Glu Ala Asn Asn Leu Lys Ser Val Ser
    50                  55                  60

Thr Ser Ile Lys Pro Pro Lys Asn Leu Lys Lys Lys Leu Leu Lys Ser
65                  70                  75                  80

Lys Cys Arg Asp Asn Val Ile Tyr Arg Pro Tyr Phe Ser Gln Leu Glu
                85                  90                  95

Ile Asn Cys Thr Ile Thr Lys Lys Gln Asn Leu Ser Asn Pro Leu Ile
            100                 105                 110

Glu Leu Trp Phe Lys Glu Leu Ser Thr Tyr Asn Lys Thr Asn Glu Asn
        115                 120                 125

Val Glu Ser Leu Lys Thr Asp Ile Ser Lys Asn Ile Leu Leu Phe Ser
    130                 135                 140

Thr Lys Asn Asn Ser Asp Asn Phe Tyr Asn Asp Phe Leu Leu Gly Ile
145                 150                 155                 160

Gln Asn Gln Pro Val Asn Tyr Lys Leu Tyr Gly Ser Gln Phe Tyr Asp
                165                 170                 175

Asn Gly Asn Ile Leu Leu Asn Ile Lys Ser Val Asp Phe Lys Thr Ser
            180                 185                 190

Gly Ile Tyr Thr Trp Lys Leu Tyr Asn Ser Asn Asn Glu Ser Ile Phe
        195                 200                 205

Glu Thr Phe Lys Ile Gln Val Tyr Ala Tyr His Ser Pro Asn Val Asn
    210                 215                 220

Leu Lys Ser Asn Pro Ser Leu Tyr Asn Glu Asn Tyr Ser Ala Ile Cys
225                 230                 235                 240

Thr Ile Ala Asn Tyr Phe Pro Leu Glu Ser Thr Glu Ile Phe Trp Phe
                245                 250                 255

Asn Asp Gly Gln Pro Ile Asp Lys Lys Tyr Ile Asp Glu Thr Tyr Ser
            260                 265                 270

Val Trp Ile Asp Gly Leu Ile Thr Arg Thr Ser Ile Leu Ser Leu Pro
        275                 280                 285

Phe Ser Glu Ala Met Glu Ser Pro Pro Asn Leu Arg Cys Asn Val Glu
    290                 295                 300

Trp Tyr Lys Asn Ser Lys Ala Ser Lys Lys Phe Ser Asn Thr Val Ile
305                 310                 315                 320
```

```
        Pro  Lys  Val  Tyr  Tyr  Lys  Pro  Phe  Ile  Ser  Ile  Lys  Phe  Asp  Asn  Gly
                            325                      330                      335

Leu  Ala  Ile  Cys  Asp  Ala  Lys  Cys  Val  Ser  Arg  Glu  Asn  Asn  Lys  Leu
                            340                      345                      350

Gln  Trp  Leu  Val  Lys  Asp  Ile  Pro  Ile  Asn  Gly  Asp  Asp  Ile  Ile  Ser
                            355                      360                      365

Gly  Pro  Cys  Leu  Asn  His  Pro  Gly  Leu  Val  Asn  Ile  Gln  Asn  Lys  Ile
                  370                      375                      380

Asp  Ile  Ser  Asp  Tyr  Asp  Glu  Pro  Val  Thr  Tyr  Lys  Cys  Ser  Ile  Ile
        385                      390                      395                           400

Gly  Tyr  Pro  Ile  Ile  Phe  Pro  Asn  Phe  Tyr  Asp  Glu  Lys  Val  Phe  Asp
                            405                      410                      415

Ala  Ser  Asp  Glu  Asn  Val  Ser  Lys  Ser  Met  Leu  Ile  Ser  Ile  Thr  Thr
                            420                      425                      430

Ile  Ile  Gly  Gly  Ala  Ile  Phe  Val  Ile  Val  Leu  Ile  Phe  Ile  Thr  Ala
                            435                      440                      445

Leu  Cys  Phe  Tyr  Cys  Ser  Lys  Asn  Asn  Lys  Ile
                  450                      455
```

( 2 ) INFORMATION FOR SEQ ID NO:13:

( i ) SEQUENCE CHARACTERISTICS:
       ( A ) LENGTH: 175 amino acids
       ( B ) TYPE: amino acid
       ( C ) STRANDEDNESS: single
       ( D ) TOPOLOGY: linear ( i i ) MOLECULE TYPE: peptide ( v ) FRAGMENT TYPE: internal ( x i ) SEQUENCE DESCRIPTION: SEQ ID NO:13:

```
        Met  Ala  Gln  Leu  Val  Leu  Thr  Asp  Ile  Pro  Leu  Glu  Asp  Val  Glu  Asn
        1                   5                        10                       15

Lys  Asn  Thr  Ser  Ser  Asp  Glu  Glu  Thr  Thr  Asn  Leu  Asn  Gln  Lys  Lys
                            20                       25                       30

Ser  Thr  Cys  Gln  Cys  Leu  Cys  Val  Thr  Leu  Gly  Phe  Phe  Ala  Ala  Gly
                  35                       40                       45

Ile  Leu  Leu  Thr  Ile  Ala  Ala  Ile  Ile  Phe  Thr  Phe  Ile  Phe  Thr  Val
                  50                       55                       60

Pro  Leu  Glu  Met  Leu  Gly  Ser  Ile  Asn  Cys  Pro  Pro  Ser  Thr  Phe  Gly
        65                            70                      75                      80

Ile  Asp  Asn  Val  Cys  Ile  Glu  Pro  Ile  Lys  Lys  Ser  Ile  Asn  Ser  Tyr
                            85                       90                       95

Ser  Glu  Leu  Ser  Lys  Ile  Cys  Tyr  Asp  Arg  Leu  Ser  Asn  Pro  Ile  Asn
                            100                      105                      110

Gln  Ser  Thr  Ile  Asn  Ser  Leu  Leu  Thr  Val  Leu  Asn  Met  Phe  Ala  Asp
                  115                      120                      125

Lys  Asn  Tyr  Glu  Asn  Val  Tyr  Asn  Cys  Asn  Thr  Met  Ser  Glu  Lys  Thr
                  130                      135                      140

Cys  Asn  Ser  Ser  Ile  Ala  Ile  Cys  Gln  Thr  Asn  His  Pro  Leu  Ser  Ser
        145                      150                      155                           160

Leu  Gly  Asn  Phe  Val  Ile  Lys  Ile  Arg  Lys  Ile  Phe  Gly  Phe  Lys
                            165                      170                      175
```

( 2 ) INFORMATION FOR SEQ ID NO:14:

( i ) SEQUENCE CHARACTERISTICS:

( A ) LENGTH: 459 amino acids
( B ) TYPE: amino acid
( C ) STRANDEDNESS: single
( D ) TOPOLOGY: linear ( i i ) MOLECULE TYPE: peptide ( v ) FRAGMENT TYPE: N-terminal ( x i ) SEQUENCE DESCRIPTION: SEQ ID NO:14:

| Met | Ser | Phe | Lys | Asn | Phe | Tyr | Leu | Ile | Tyr | Val | Ile | Ile | Ile | Phe | Ile |
|---|---|---|---|---|---|---|---|---|---|---|---|---|---|---|---|
| 1 | | | | 5 | | | | | 10 | | | | | 15 | |
| Asn | Ser | Ile | Ile | Thr | Ser | Ala | Ser | Thr | Ser | Lys | Pro | Ser | Thr | Pro | Thr |
| | | | 20 | | | | 25 | | | | | | 30 | | |
| Ile | Ile | Pro | Thr | Ser | Ala | Asn | Glu | Ser | Pro | Ala | Ser | Ile | Asp | Thr | Thr |
| | | | 35 | | | | 40 | | | | | 45 | | | |
| Ile | Thr | Lys | Pro | Ile | Ser | Thr | Glu | Ala | Asn | Asn | Leu | Lys | Ser | Val | Ser |
| | 50 | | | | | 55 | | | | | 60 | | | | |
| Thr | Ser | Ile | Lys | Pro | Pro | Lys | Asn | Leu | Lys | Lys | Lys | Leu | Leu | Lys | Ser |
| 65 | | | | | 70 | | | | | 75 | | | | | 80 |
| Lys | Cys | Arg | Asp | Asn | Val | Ile | Tyr | Arg | Pro | Tyr | Phe | Ser | Gln | Leu | Glu |
| | | | | 85 | | | | | 90 | | | | | 95 | |
| Ile | Asn | Cys | Thr | Ile | Thr | Lys | Lys | Gln | Asn | Leu | Ser | Asn | Pro | Leu | Ile |
| | | | 100 | | | | | 105 | | | | | 110 | | |
| Glu | Leu | Trp | Phe | Lys | Glu | Leu | Ser | Thr | Tyr | Asn | Lys | Thr | Asn | Glu | Asn |
| | | | 115 | | | | 120 | | | | | 125 | | | |
| Val | Glu | Ser | Leu | Lys | Thr | Asp | Ile | Ser | Lys | Asn | Ile | Leu | Leu | Phe | Ser |
| | 130 | | | | | 135 | | | | | 140 | | | | |
| Thr | Lys | Asn | Asn | Ser | Asp | Asn | Phe | Tyr | Asn | Asp | Phe | Leu | Leu | Gly | Ile |
| 145 | | | | | 150 | | | | | 155 | | | | | 160 |
| Gln | Asn | Gln | Pro | Val | Asn | Tyr | Lys | Leu | Tyr | Gly | Ser | Gln | Phe | Tyr | Asp |
| | | | | 165 | | | | | 170 | | | | | 175 | |
| Asn | Gly | Asn | Ile | Leu | Leu | Asn | Ile | Lys | Ser | Val | Asp | Phe | Lys | Thr | Ser |
| | | | 180 | | | | | 185 | | | | | 190 | | |
| Gly | Ile | Tyr | Thr | Trp | Lys | Leu | Tyr | Asn | Ser | Asn | Asn | Glu | Ser | Ile | Phe |
| | | | 195 | | | | 200 | | | | | 205 | | | |
| Glu | Thr | Phe | Lys | Ile | Gln | Val | Tyr | Ala | Tyr | His | Ser | Pro | Asn | Val | Asn |
| | 210 | | | | | 215 | | | | | 220 | | | | |
| Leu | Lys | Ser | Asn | Pro | Ser | Leu | Tyr | Asn | Glu | Asn | Tyr | Ser | Ala | Ile | Cys |
| 225 | | | | | 230 | | | | | 235 | | | | | 240 |
| Thr | Ile | Ala | Asn | Tyr | Phe | Pro | Leu | Glu | Ser | Thr | Glu | Ile | Phe | Trp | Phe |
| | | | | 245 | | | | | 250 | | | | | 255 | |
| Asn | Asp | Gly | Gln | Pro | Ile | Asp | Lys | Lys | Tyr | Ile | Asp | Glu | Thr | Tyr | Ser |
| | | | 260 | | | | | 265 | | | | | 270 | | |
| Val | Trp | Ile | Asp | Gly | Leu | Ile | Thr | Arg | Thr | Ser | Ile | Leu | Ser | Leu | Pro |
| | | 275 | | | | | 280 | | | | | 285 | | | |
| Phe | Ser | Glu | Ala | Met | Glu | Ser | Pro | Pro | Asn | Leu | Arg | Cys | Asn | Val | Glu |
| | 290 | | | | | 295 | | | | | 300 | | | | |
| Trp | Tyr | Lys | Asn | Ser | Lys | Ala | Ser | Lys | Lys | Phe | Ser | Asn | Thr | Val | Ile |
| 305 | | | | | 310 | | | | | 315 | | | | | 320 |
| Pro | Lys | Val | Tyr | Tyr | Lys | Pro | Phe | Ile | Ser | Ile | Lys | Phe | Asp | Asn | Gly |
| | | | | 325 | | | | | 330 | | | | | 335 | |
| Leu | Ala | Ile | Cys | Asp | Ala | Lys | Cys | Val | Ser | Arg | Glu | Asn | Asn | Lys | Leu |
| | | | 340 | | | | | 345 | | | | | 350 | | |
| Gln | Trp | Leu | Val | Lys | Asp | Ile | Pro | Ile | Asn | Gly | Asp | Asp | Ile | Ile | Ser |
| | | | 355 | | | | | 360 | | | | | 365 | | |

```
        Gly  Pro  Cys  Leu  Asn  His  Pro  Gly  Leu  Val  Asn  Ile  Gln  Asn  Lys  Ile
             370                 375                 380

Asp  Ile  Ser  Asp  Tyr  Asp  Glu  Pro  Val  Thr  Tyr  Lys  Cys  Ser  Ile  Ile
        385                      390                 395                           400

Gly  Tyr  Pro  Ile  Ile  Phe  Pro  Asn  Phe  Tyr  Asp  Glu  Lys  Val  Phe  Asp
                            405                 410                           415

Ala  Ser  Asp  Glu  Asn  Val  Ser  Lys  Ser  Met  Leu  Ile  Ser  Ile  Thr  Thr
                       420                      425                      430

Ile  Ile  Gly  Gly  Ala  Ile  Phe  Val  Ile  Val  Leu  Ile  Phe  Ile  Thr  Ala
                       435                 440                      445

Leu  Cys  Phe  Tyr  Cys  Ser  Lys  Asn  Asn  Lys  Ile
             450                      455
```

( 2 ) INFORMATION FOR SEQ ID NO:15:

( i ) SEQUENCE CHARACTERISTICS:
      ( A ) LENGTH: 533 amino acids
      ( B ) TYPE: amino acid
      ( C ) STRANDEDNESS: single
      ( D ) TOPOLOGY: linear ( i i ) MOLECULE TYPE: peptide ( v ) FRAGMENT TYPE: N-terminal ( x i ) SEQUENCE DESCRIPTION: SEQ ID NO:15:

```
        Met  Arg  Arg  Tyr  Arg  Met  Gly  Arg  Gly  Ile  Tyr  Leu  Leu  Tyr  Ile  Cys
        1                   5                        10                          15

Leu  Leu  Tyr  Thr  Tyr  Leu  Gln  Phe  Gly  Thr  Ser  Ser  Thr  Thr  Ala  Val
                       20                      25                      30

Ser  Ile  Glu  Asn  Ser  Asp  Asn  Ser  Thr  Ala  Glu  Met  Leu  Ser  Ser  Thr
                       35                      40                      45

Ser  Met  Ser  Ala  Thr  Thr  Pro  Ile  Ser  Gln  Pro  Thr  Ser  Pro  Phe  Thr
             50                      55                      60

Thr  Pro  Thr  Arg  Arg  Ser  Thr  Asn  Ile  Ala  Thr  Ser  Ser  Ser  Thr  Thr
        65                       70                      75                           80

Gln  Ala  Ser  Gln  Pro  Thr  Ser  Thr  Leu  Thr  Thr  Leu  Thr  Arg  Ser  Ser
                            85                      90                           95

Thr  Thr  Ile  Ala  Thr  Ser  Pro  Ser  Thr  Thr  Gln  Ala  Ala  Thr  Phe  Ile
                       100                     105                     110

Gly  Ser  Ser  Thr  Asp  Ser  Asn  Thr  Thr  Leu  Leu  Lys  Thr  Thr  Lys  Lys
                       115                     120                     125

Pro  Lys  Arg  Lys  Lys  Asn  Lys  Asn  Asn  Gly  Ala  Arg  Phe  Lys  Leu  Asp
                  130                     135                     140

Cys  Gly  Tyr  Lys  Gly  Val  Ile  Tyr  Arg  Pro  Tyr  Phe  Ser  Pro  Leu  Gln
        145                     150                     155                          160

Leu  Asn  Cys  Thr  Leu  Pro  Thr  Glu  Pro  His  Ile  Thr  Asn  Pro  Ile  Asp
                            165                     170                          175

Phe  Glu  Ile  Trp  Phe  Lys  Pro  Arg  Thr  Arg  Phe  Gly  Asp  Phe  Leu  Gly
                       180                     185                     190

Asp  Lys  Glu  Asp  Phe  Val  Gly  Asn  His  Thr  Arg  Thr  Ser  Ile  Leu  Leu
                  195                     200                     205

Phe  Ser  Ser  Arg  Asn  Gly  Ser  Val  Asn  Ser  Met  Asp  Leu  Gly  Asp  Ala
             210                     215                     220

Thr  Leu  Gly  Ile  Leu  Gln  Ser  Arg  Ile  Pro  Asp  Tyr  Thr  Leu  Tyr  Asn
        225                     230                     235                          240

Ile  Pro  Ile  Gln  His  Thr  Glu  Ala  Met  Ser  Leu  Gly  Ile  Lys  Ser  Val
                       245                     250                          255
```

```
Glu  Ser  Ala  Thr  Ser  Gly  Val  Tyr  Thr  Trp  Arg  Val  Tyr  Gly  Gly  Asp
               260                 265                      270

Gly  Leu  Asn  Lys  Thr  Val  Leu  Gly  Gln  Val  Asn  Val  Ser  Val  Val  Ala
          275                 280                      285

Tyr  His  Pro  Pro  Ser  Val  Asn  Leu  Thr  Pro  Arg  Ala  Ser  Leu  Phe  Asn
     290                 295                      300

Lys  Thr  Phe  Glu  Ala  Val  Cys  Ala  Val  Ala  Asn  Tyr  Phe  Pro  Arg  Ser
305                 310                      315                           320

Thr  Lys  Leu  Thr  Trp  Tyr  Leu  Asp  Gly  Lys  Pro  Ile  Glu  Arg  Gln  Tyr
               325                      330                      335

Ile  Ser  Asp  Thr  Ala  Ser  Val  Trp  Ile  Asp  Gly  Leu  Ile  Thr  Arg  Ser
               340                 345                      350

Ser  Val  Leu  Ala  Ile  Pro  Thr  Thr  Glu  Thr  Asp  Ser  Glu  Lys  Pro  Asp
          355                      360                      365

Ile  Arg  Cys  Asp  Leu  Glu  Trp  His  Glu  Ser  Pro  Val  Ser  Tyr  Lys  Arg
          370                 375                      380

Phe  Thr  Lys  Ser  Val  Ala  Pro  Asp  Val  Tyr  Tyr  Pro  Pro  Thr  Val  Ser
385                      390                      395                      400

Val  Thr  Phe  Ala  Asp  Thr  Arg  Ala  Ile  Cys  Asp  Val  Lys  Cys  Val  Pro
                    405                      410                      415

Arg  Asp  Gly  Ile  Ser  Leu  Met  Trp  Lys  Ile  Gly  Asn  Tyr  His  Leu  Pro
               420                 425                      430

Lys  Ala  Met  Ser  Ala  Asp  Ile  Leu  Ile  Thr  Gly  Pro  Cys  Ile  Glu  Arg
          435                      440                      445

Pro  Gly  Leu  Val  Asn  Ile  Gln  Ser  Met  Cys  Asp  Ile  Ser  Glu  Thr  Asp
     450                      455                      460

Gly  Pro  Val  Ser  Tyr  Thr  Cys  Gln  Thr  Ile  Gly  Tyr  Pro  Pro  Ile  Leu
465                      470                      475                      480

Pro  Gly  Phe  Tyr  Asp  Thr  Gln  Val  Tyr  Asp  Ala  Ser  Pro  Glu  Ile  Val
                    485                      490                      495

Ser  Glu  Ser  Met  Leu  Val  Ser  Val  Val  Ala  Val  Ile  Leu  Gly  Ala  Val
               500                      505                      510

Leu  Ile  Thr  Val  Phe  Ile  Phe  Ile  Thr  Ala  Leu  Cys  Leu  Tyr  Tyr  Ser
          515                      520                      525

His  Pro  Arg  Arg  Leu
          530
```

( 2 ) INFORMATION FOR SEQ ID NO:16:

( i ) SEQUENCE CHARACTERISTICS:
        ( A ) LENGTH: 468 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:16:

```
Met  Trp  Leu  Pro  Asn  Leu  Val  Arg  Phe  Val  Ala  Val  Ala  Tyr  Leu  Ile
1                   5                   10                      15

Cys  Ala  Gly  Ala  Ile  Leu  Thr  Tyr  Ala  Ser  Gly  Ala  Ser  Ala  Ser  Ser
               20                  25                      30

Ser  Gln  Ser  Thr  Pro  Ala  Thr  Pro  Thr  His  Thr  Thr  Pro  Asn  Leu  Thr
          35                  40                      45

Thr  Ala  His  Gly  Ala  Gly  Ser  Asp  Asn  Thr  Thr  Asn  Ala  Asn  Gly  Thr
```

|     |     |     |     |     |     |     |     |     |     |     |     |     |     |     |
|-----|-----|-----|-----|-----|-----|-----|-----|-----|-----|-----|-----|-----|-----|-----|
| | | | | 50 | | | | | 55 | | | | 60 | |
| Glu 65 | Ser | Thr | His | Ser | His 70 | Glu | Thr | Thr | Ile 75 | Thr | Cys | Thr | Lys | Ser Leu 80 |
| Ile | Ser | Val | Pro | Tyr 85 | Tyr | Lys | Ser | Val | Asp 90 | Met | Asn | Cys | Thr | Thr Ser 95 |
| Val | Gly | Val | Asn 100 | Tyr | Ser | Glu | Tyr | Arg 105 | Leu | Glu | Ile | Tyr | Leu 110 | Asn Gln |
| Arg | Thr | Pro 115 | Phe | Ser | Gly | Thr | Pro 120 | Pro | Gly | Asp | Glu | Glu 125 | Asn | Tyr Ile |
| Asn | His 130 | Asn | Ala | Thr | Lys | Asp 135 | Gln | Thr | Leu | Leu | Leu 140 | Phe | Ser | Thr Ala |
| Glu 145 | Arg | Lys | Lys | Ser | Arg 150 | Arg | Gly | Asp | Leu | Ser 155 | Val | His | Pro | Ser Leu 160 |
| Lys | Gly | Glu | Asn | Tyr 165 | Arg | Ala | Thr | Cys | Val 170 | Val | Ala | Ser | Tyr | Phe Pro 175 |
| His | Ser | Ser | Val 180 | Lys | Leu | Arg | Trp | Tyr 185 | Lys | Asn | Ala | Arg | Glu 190 | Val Asp |
| Phe | Thr | Lys 195 | Tyr | Val | Thr | Asn | Ala 200 | Ser | Ser | Val | Trp | Val 205 | Asp | Gly Leu |
| Ile | Thr 210 | Arg | Ile | Ser | Thr | Val 215 | Ser | Ile | Pro | Val | Asp 220 | Pro | Glu | Glu Glu |
| Tyr 225 | Thr | Gly | Gln | Leu | Gly 230 | Val | Ile | Pro | Asp | Arg 235 | Leu | Pro | Lys | Arg Gln 240 |
| Leu | Phe | Asn | Leu | Pro 245 | Leu | His | Thr | Glu | Gly 250 | Gly | Thr | Lys | Phe | Pro Leu 255 |
| Thr | Ile | Lys | Ser 260 | Val | Asp | Trp | Arg | Thr 265 | Ala | Gly | Ile | Tyr | Val 270 | Trp Ser |
| Leu | Tyr | Ala 275 | Lys | Asn | Gly | Thr | Leu 280 | Val | Asn | Ser | Thr | Ser 285 | Val | Thr Val |
| Ser | Thr 290 | Tyr | Asn | Ala | Pro | Leu 295 | Leu | Pro | Ser | Leu | Arg 300 | Cys | Ser | Ile Asp |
| Trp 305 | Tyr | Arg | Asp | Glu | Val 310 | Ser | Phe | Ala | Arg | Ile 315 | Ala | Lys | Ala | Gly Thr 320 |
| Pro | Ser | Val | Phe | Val 325 | Ala | Pro | Thr | Val | Ser 330 | Val | Ser | Val | Glu | Asp Gly 335 |
| Asp | Ala | Val | Cys 340 | Thr | Ala | Lys | Cys | Val 345 | Pro | Ser | Thr | Gly | Val 350 | Phe Val |
| Ser | Trp | Ser 355 | Val | Asn | Asp | His | Leu 360 | Pro | Gly | Val | Pro | Ser 365 | Gln | Asp Met |
| Thr | Thr 370 | Gly | Val | Cys | Pro | Ser 375 | His | Ser | Gly | Leu | Val 380 | Asn | Met | Gln Ser |
| Arg 385 | Arg | Pro | Leu | Ser | Glu 390 | Glu | Asn | Gly | Glu | Arg 395 | Glu | Tyr | Ser | Cys Ile 400 |
| Ile | Glu | Gly | Tyr | Pro 405 | Asp | Gly | Leu | Pro | Met 410 | Phe | Ser | Asp | Thr | Val Val 415 |
| Tyr | Asp | Ala | Ser 420 | Pro | Ile | Val | Glu | Asp 425 | Arg | Pro | Val | Leu | Thr 430 | Ser Ile |
| Ile | Ala | Val 435 | Thr | Cys | Gly | Ala | Ala 440 | Ala | Leu | Ala | Leu | Val 445 | Val | Leu Ile |
| Thr | Ala 450 | Val | Cys | Phe | Tyr | Cys 455 | Ser | Lys | Pro | Ser | Gln 460 | Ala | Pro | Tyr Lys |
| Lys 465 | Ser | Asp | Phe | | | | | | | | | | | |

( 2 ) INFORMATION FOR SEQ ID NO:17:

( i ) SEQUENCE CHARACTERISTICS:
        ( A ) LENGTH: 511 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:17:

```
Met Ala Pro Gly Arg Val Gly Leu Ala Val Val Leu Trp Ser Leu Leu
 1               5                  10                  15
Trp Leu Gly Ala Gly Val Ser Gly Gly Ser Glu Thr Ala Ser Thr Gly
            20                  25                  30
Pro Thr Ile Thr Ala Gly Ala Val Thr Asn Ala Ser Glu Ala Pro Thr
        35                  40                  45
Ser Gly Ser Pro Gly Ser Ala Ala Ser Pro Glu Val Thr Pro Thr Ser
     50                 55                  60
Thr Pro Asn Pro Asn Asn Val Thr Gln Asn Lys Thr Thr Pro Thr Glu
 65                 70                  75                  80
Pro Ala Ser Pro Pro Thr Thr Pro Lys Pro Thr Ser Thr Pro Lys Ser
                85                  90                  95
Pro Pro Thr Ser Thr Pro Asp Pro Lys Pro Lys Asn Asn Thr Thr Pro
            100                 105                 110
Ala Lys Ser Gly Arg Pro Thr Lys Pro Pro Gly Pro Val Trp Cys Asp
        115                 120                 125
Arg Arg Asp Pro Leu Ala Arg Tyr Gly Ser Arg Val Gln Ile Arg Cys
130                 135                 140
Arg Phe Arg Asn Ser Thr Arg Met Glu Phe Arg Leu Gln Ile Trp Arg
145                 150                 155                 160
Tyr Ser Met Gly Pro Ser Pro Pro Ile Ala Pro Ala Pro Asp Leu Glu
                165                 170                 175
Glu Val Leu Thr Asn Ile Thr Ala Pro Pro Gly Gly Leu Leu Val Tyr
            180                 185                 190
Asp Ser Ala Pro Asn Leu Thr Asp Pro His Val Leu Trp Ala Glu Gly
        195                 200                 205
Ala Gly Pro Gly Ala Asp Pro Pro Leu Tyr Ser Val Thr Gly Pro Leu
    210                 215                 220
Pro Thr Gln Arg Leu Ile Ile Gly Glu Val Thr Pro Ala Thr Gln Gly
225                 230                 235                 240
Met Tyr Tyr Leu Ala Trp Gly Arg Met Asp Ser Pro His Glu Tyr Gly
                245                 250                 255
Thr Trp Val Arg Val Arg Met Phe Arg Pro Pro Ser Leu Thr Leu Gln
            260                 265                 270
Pro His Ala Val Met Glu Gly Gln Pro Phe Lys Ala Thr Cys Thr Ala
        275                 280                 285
Ala Ala Tyr Tyr Pro Arg Asn Pro Val Glu Phe Val Trp Phe Glu Asp
    290                 295                 300
Asp His Gln Val Phe Asn Pro Gly Gln Ile Asp Thr Gln Thr His Glu
305                 310                 315                 320
His Pro Asp Gly Phe Thr Thr Val Ser Thr Val Thr Ser Glu Ala Val
                325                 330                 335
Gly Gly Gln Val Pro Pro Arg Thr Phe Thr Cys Gln Met Thr Trp His
            340                 345                 350
```

| | | | | | | | | | | | | | | |
|---|---|---|---|---|---|---|---|---|---|---|---|---|---|---|
|Arg|Asp|Ser<br>355|Val|Thr|Phe|Ser|Arg<br>360|Arg|Asn|Ala|Thr|Gly<br>365|Leu|Ala|Leu|
|Val|Leu<br>370|Pro|Arg|Pro|Thr|Ile<br>375|Thr|Met|Glu|Phe|Gly<br>380|Val|Arg|Ile|Val|
|Val<br>385|Cys|Thr|Ala|Gly|Cys<br>390|Val|Pro|Glu|Gly|Val<br>395|Thr|Phe|Ala|Trp|Phe<br>400|
|Leu|Gly|Asp|Asp|Pro<br>405|Ser|Pro|Ala|Ala|Lys<br>410|Ser|Ala|Val|Thr|Ala<br>415|Gln|
|Glu|Ser|Cys|Asp<br>420|His|Pro|Gly|Leu|Ala<br>425|Thr|Val|Arg|Ser|Thr<br>430|Leu|Pro|
|Ile|Ser|Tyr<br>435|Asp|Tyr|Ser|Glu|Tyr<br>440|Ile|Cys|Arg|Leu|Thr<br>445|Gly|Tyr|Pro|
|Ala|Gly<br>450|Ile|Pro|Val|Leu|Glu<br>455|His|His|Gly|Ser|His<br>460|Gln|Pro|Pro|Pro|
|Arg<br>465|Asp|Pro|Thr|Glu|Arg<br>470|Gln|Val|Ile|Glu|Ala<br>475|Ile|Glu|Trp|Val|Gly<br>480|
|Ile|Gly|Ile|Gly|Val<br>485|Leu|Ala|Ala|Gly|Val<br>490|Leu|Val|Val|Thr|Ala<br>495|Ile|
|Val|Tyr|Val|Val<br>500|Arg|Thr|Ser|Gln|Ser<br>505|Arg|Gln|Arg|His|Arg<br>510|Arg| |

( 2 ) INFORMATION FOR SEQ ID NO:18:

( i ) SEQUENCE CHARACTERISTICS:
        ( A ) LENGTH: 1320 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

```
GATATTTAAT AAAACTATTA TGAAACTTCT TATAACTTAT TTGTTTTTAT TAAATGGGTT      60
GGGTTGGTTT TAAAATTACA TACGTGTATT AAGAATTAAC ATCATAAAGG ACACACCCAT     120
GAAAAACATT TAAATTCTAT TAATTTGAAC GGATTAAACA TTTTCTCATT TTAAGAGTTG     180
CTACGACTTT TGATAGTAAA ATGATTAAAC TTCTATTTAT CTTATTTTAT TTTAACCCAA     240
TAACTGGATA TAAATGGGTA GACCCTCCTC GTAGGTATAA TTACACCGTT TTAAGAATGA     300
TTCCAGATAT TCCAAATCCA ATGGATCCTT CTAAAAACGC TGAAGTTCGG TATGTAACTT     360
CTACTGACCC ATGTGATATG GTTGCTTTGA TTTCTAATCC AAATATAGAA TCTACAATTA     420
AAACGATTCA ATTTGTGCAA AAGAAAAAAT TTACAATGC ATCTCTTAGT TGGTTTAAAG     480
TTGGAGATGA TTGTACATAT CCAATATATT TAATTCAATA TTTTGATTGT GATCCTCAAA     540
GAGAATTTGG CATATGTTTA AAAAGATCTC CAGATTTTTG GAAACCATCG TTAGTTGGTT     600
ACACATTTTT AACTGATGAT GAATTGGGAT TAGTTTAGC TGCCCCCGCT CCATTAATC      660
AAGGTCAATA TAGACGGGTT ATTCAAATTG AAAATGAAGT TTTTTATACT GATTTTATGG     720
TTCAATTACC ACGAGAAACT TGTTATTTTT CTAAAGAAGA TAAATTTGAA CCAACTTTTA     780
TGGAATGGTG TAAGGAATCT AGATCTGTAG GAGCATCAAA AGTTGACGAT GAACTTTTTT     840
ATCTAAATAG AGCTGGTCCC CAAACCCTGC TTAAATATTA TGTTATTAAA GATTTTATA     900
GACTTAACGG TAGAGAACCT CCAATAAAAT TTAAAGAAGC TCTTAGATAC GATATACCAT     960
ATAAAGTGAA TGATAAATTT GATGATGAAT TACCATCGAG GCCACATATT AGTAATACTA    1020
TTAATAAAAC TATTAAAGAA ATTGTAAATC TTGAAGATTA TTTTAAAAAT ACAAATGTTA    1080
```

-continued

```
TAGATACTAC TACCCCAACA CCAATAAATA ATACCCCAAA AAATATAACC GTGGGAATTG      1140

TTATAATTAT ATTAATAATA CTATTTATAA TTGGATTTTT TGTTTATAAA AGACAAAAAA      1200

TATATAATAA TTATAAAAAA TTAACAACAA ATGTTTAGCC TTTATAAATT AATTTACAGA      1260

ATAAACAACT GGGCGGTCTT TTGTTTAATA AAAATTCATG TACCTACAAC TTTTATTCAC      1320
```

( 2 ) INFORMATION FOR SEQ ID NO:19:

( i ) SEQUENCE CHARACTERISTICS:
        ( A ) LENGTH: 345 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:19:

```
Met Ile Lys Leu Leu Phe Ile Leu Phe Tyr Phe Asn Pro Ile Thr Gly
 1               5                  10                  15

Tyr Lys Trp Val Asp Pro Pro Arg Arg Tyr Asn Tyr Thr Val Leu Arg
                20                  25                  30

Met Ile Pro Asp Ile Pro Asn Pro Met Asp Pro Ser Lys Asn Ala Glu
            35                  40                  45

Val Arg Tyr Val Thr Ser Thr Asp Pro Cys Asp Met Val Ala Leu Ile
        50                  55                  60

Ser Asn Pro Asn Ile Glu Ser Thr Ile Lys Thr Ile Gln Phe Val Gln
65                  70                  75                  80

Lys Lys Lys Phe Tyr Asn Ala Ser Leu Ser Trp Phe Lys Val Gly Asp
                85                  90                  95

Asp Cys Thr Tyr Pro Ile Tyr Leu Ile Gln Tyr Phe Asp Cys Asp Pro
            100                 105                 110

Gln Arg Glu Phe Gly Ile Cys Leu Lys Arg Ser Pro Asp Phe Trp Lys
        115                 120                 125

Pro Ser Leu Val Gly Tyr Thr Phe Leu Thr Asp Asp Glu Leu Gly Leu
    130                 135                 140

Val Leu Ala Ala Pro Ala Pro Phe Asn Gln Gly Gln Tyr Arg Arg Val
145                 150                 155                 160

Ile Gln Ile Glu Asn Glu Val Phe Tyr Thr Asp Phe Met Val Gln Leu
                165                 170                 175

Pro Arg Glu Thr Cys Tyr Phe Ser Lys Glu Asp Lys Phe Glu Pro Thr
            180                 185                 190

Phe Met Glu Trp Cys Lys Glu Ser Arg Ser Val Gly Ala Ser Lys Val
        195                 200                 205

Asp Asp Glu Leu Phe Tyr Leu Asn Arg Ala Gly Pro Gln Thr Leu Leu
    210                 215                 220

Lys Tyr Tyr Val Ile Lys Asp Phe Tyr Arg Leu Asn Gly Arg Glu Pro
225                 230                 235                 240

Pro Ile Lys Phe Lys Glu Ala Leu Arg Tyr Asp Ile Pro Tyr Lys Val
                245                 250                 255

Asn Asp Lys Phe Asp Asp Glu Leu Pro Ser Arg Pro His Ile Ser Asn
            260                 265                 270

Thr Ile Asn Lys Thr Ile Lys Glu Ile Val Asn Leu Glu Asp Tyr Phe
        275                 280                 285

Lys Asn Thr Asn Val Ile Asp Thr Thr Thr Pro Thr Pro Ile Asn Asn
    290                 295                 300
```

```
       Thr  Pro  Lys  Asn  Ile  Thr  Val  Gly  Ile  Val  Ile  Ile  Ile  Leu  Ile  Ile
       305                      310                      315                          320

Leu  Phe  Ile  Ile  Gly  Phe  Phe  Val  Tyr  Lys  Arg  Gln  Lys  Ile  Tyr  Asn
                           325                      330                      335

Asn  Tyr  Lys  Lys  Leu  Thr  Thr  Asn  Val
                      340                      345
```

( 2 ) INFORMATION FOR SEQ ID NO:20:

( i ) SEQUENCE CHARACTERISTICS:
        ( A ) LENGTH: 345 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:20:

```
       Met  Ile  Lys  Leu  Leu  Phe  Ile  Leu  Phe  Tyr  Phe  Asn  Pro  Ile  Thr  Gly
       1                   5                        10                       15

Tyr  Lys  Trp  Val  Asp  Pro  Pro  Arg  Arg  Tyr  Asn  Tyr  Thr  Val  Leu  Arg
                      20                       25                       30

Met  Ile  Pro  Asp  Ile  Pro  Asn  Pro  Met  Asp  Pro  Ser  Lys  Asn  Ala  Glu
                      35                       40                       45

Val  Arg  Tyr  Val  Thr  Ser  Thr  Asp  Pro  Cys  Asp  Met  Val  Ala  Leu  Ile
            50                       55                       60

Ser  Asn  Pro  Asn  Ile  Glu  Ser  Thr  Ile  Lys  Thr  Ile  Gln  Phe  Val  Gln
       65                       70                       75                        80

Lys  Lys  Lys  Phe  Tyr  Asn  Ala  Ser  Leu  Ser  Trp  Phe  Lys  Val  Gly  Asp
                           85                       90                       95

Asp  Cys  Thr  Tyr  Pro  Ile  Tyr  Leu  Ile  Gln  Tyr  Phe  Asp  Cys  Asp  Pro
                      100                      105                      110

Gln  Arg  Glu  Phe  Gly  Ile  Cys  Leu  Lys  Arg  Ser  Pro  Asp  Phe  Trp  Lys
                 115                      120                      125

Pro  Ser  Leu  Val  Gly  Tyr  Thr  Phe  Leu  Thr  Asp  Asp  Glu  Leu  Gly  Leu
            130                      135                      140

Val  Leu  Ala  Ala  Pro  Ala  Pro  Phe  Asn  Gln  Gly  Gln  Tyr  Arg  Arg  Val
       145                      150                      155                       160

Ile  Gln  Ile  Glu  Asn  Glu  Val  Phe  Tyr  Thr  Asp  Phe  Met  Val  Gln  Leu
                           165                      170                      175

Pro  Arg  Glu  Thr  Cys  Tyr  Phe  Ser  Lys  Glu  Asp  Lys  Phe  Glu  Pro  Thr
                      180                      185                      190

Phe  Met  Glu  Trp  Cys  Lys  Glu  Ser  Arg  Ser  Val  Gly  Ala  Ser  Lys  Val
                 195                      200                      205

Asp  Asp  Glu  Leu  Phe  Tyr  Leu  Asn  Arg  Ala  Gly  Pro  Gln  Thr  Leu  Leu
            210                      215                      220

Lys  Tyr  Tyr  Val  Ile  Lys  Asp  Phe  Tyr  Arg  Leu  Asn  Gly  Arg  Glu  Pro
       225                      230                      235                       240

Pro  Ile  Lys  Phe  Lys  Glu  Ala  Leu  Arg  Tyr  Asp  Ile  Pro  Tyr  Lys  Val
                      245                      250                      255

Asn  Asp  Lys  Phe  Asp  Asp  Glu  Leu  Pro  Ser  Arg  Pro  His  Ile  Ser  Asn
                      260                      265                      270

Thr  Ile  Asn  Lys  Thr  Ile  Lys  Glu  Ile  Val  Asn  Leu  Glu  Asp  Tyr  Phe
                 275                      280                      285

Lys  Asn  Thr  Asn  Val  Ile  Asp  Thr  Thr  Thr  Pro  Thr  Pro  Ile  Asn  Asn
            290                      295                      300
```

```
        Thr   Pro   Lys   Asn   Ile   Thr   Val   Gly   Ile   Val   Ile   Ile   Ile   Leu   Ile   Ile
        305                           310                           315                           320

Leu   Phe   Ile   Ile   Gly   Phe   Phe   Val   Tyr   Lys   Arg   Gln   Lys   Ile   Tyr   Asn
                                325                           330                           335

Asn   Tyr   Lys   Lys   Leu   Thr   Thr   Asn   Val
                          340                           345
```

( 2 ) INFORMATION FOR SEQ ID NO:21:

( i ) SEQUENCE CHARACTERISTICS:
        ( A ) LENGTH: 374 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:21:

```
        Met   Met   Thr   Arg   Leu   His   Phe   Trp   Trp   Cys   Gly   Ile   Phe   Ala   Val   Leu
        1                       5                           10                          15

Lys   Tyr   Leu   Val   Cys   Thr   Ser   Ser   Leu   Thr   Thr   Thr   Pro   Lys   Thr   Thr
                          20                          25                          30

Thr   Val   Tyr   Val   Lys   Gly   Phe   Asn   Ile   Pro   Pro   Leu   Arg   Tyr   Asn   Tyr
                    35                          40                          45

Thr   Gln   Ala   Arg   Ile   Val   Pro   Lys   Ile   Pro   Gln   Ala   Met   Asp   Pro   Lys
              50                          55                          60

Ile   Thr   Ala   Glu   Val   Arg   Tyr   Val   Thr   Ser   Met   Asp   Ser   Cys   Gly   Met
        65                      70                          75                          80

Val   Ala   Leu   Ile   Ser   Glu   Pro   Asp   Ile   Asp   Ala   Thr   Ile   Arg   Thr   Ile
                          85                          90                          95

Gln   Leu   Ser   Gln   Lys   Lys   Thr   Tyr   Asn   Ala   Thr   Ile   Ser   Trp   Phe   Lys
                          100                         105                         110

Val   Thr   Gln   Gly   Cys   Glu   Tyr   Pro   Met   Phe   Leu   Met   Asp   Met   Arg   Leu
                    115                         120                         125

Cys   Asp   Pro   Lys   Arg   Glu   Phe   Gly   Ile   Cys   Ala   Leu   Arg   Ser   Pro   Ser
              130                         135                         140

Tyr   Trp   Leu   Glu   Pro   Leu   Thr   Lys   Tyr   Met   Phe   Leu   Thr   Asp   Asp   Glu
        145                         150                         155                         160

Leu   Gly   Leu   Ile   Met   Met   Ala   Pro   Ala   Gln   Phe   Asn   Gln   Gly   Gln   Tyr
                          165                         170                         175

Arg   Arg   Val   Ile   Thr   Ile   Asp   Gly   Ser   Met   Phe   Tyr   Thr   Asp   Phe   Met
                    180                         185                         190

Val   Gln   Leu   Ser   Pro   Thr   Pro   Cys   Trp   Phe   Ala   Lys   Pro   Asp   Arg   Tyr
              195                         200                         205

Glu   Glu   Ile   Leu   His   Glu   Trp   Cys   Arg   Asn   Val   Lys   Thr   Ile   Gly   Leu
        210                         215                         220

Asp   Gly   Ala   Arg   Asp   Tyr   His   Tyr   Tyr   Trp   Val   Pro   Tyr   Asn   Pro   Gln
        225                         230                         235                         240

Pro   His   His   Lys   Ala   Val   Leu   Leu   Tyr   Trp   Tyr   Arg   Thr   His   Gly   Arg
                          245                         250                         255

Glu   Pro   Pro   Val   Arg   Phe   Gln   Glu   Ala   Ile   Arg   Tyr   Asp   Arg   Pro   Ala
                    260                         265                         270

Ile   Pro   Ser   Gly   Ser   Glu   Asp   Ser   Lys   Arg   Ser   Asn   Asp   Ser   Arg   Gly
                    275                         280                         285

Glu   Ser   Ser   Gly   Pro   Asn   Trp   Ile   Asp   Ile   Glu   Asn   Tyr   Thr   Pro   Lys
```

|   | 290 |   |   |   | 295 |   |   |   | 300 |   |   |   |   |
|---|---|---|---|---|---|---|---|---|---|---|---|---|---|

Asn Asn Val Pro Ile Ile Ile Ser Asp Asp Asp Val Pro Thr Ala Pro
305                 310             315                 320

Pro Lys Gly Met Asn Asn Gln Ser Val Val Ile Pro Ala Ile Val Leu
                325             330             335

Ser Cys Leu Ile Ile Ala Leu Ile Leu Gly Val Ile Tyr Tyr Ile Leu
        340             345             350

Arg Val Lys Arg Ser Arg Ser Thr Ala Tyr Gln Gln Leu Pro Ile Ile
        355             360             365

His Thr Thr His His Pro
    370

(2) INFORMATION FOR SEQ ID NO:22:

(i) SEQUENCE CHARACTERISTICS:
        (A) LENGTH: 442 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:22:

Met Pro Ala Val Leu Leu Val Leu Tyr Val Asn Pro Pro Pro Ser Val
1               5               10              15

Cys Ile Leu Thr Gln Lys Leu Ser Leu Gly Leu Tyr Asn Gln Trp Trp
            20              25              30

Arg Val Cys Arg Ser Val Pro Pro Trp Tyr Val Phe Phe Asn Lys
        35              40              45

Arg Ser Met Ser Thr Phe Lys Leu Met Met Asp Gly Arg Leu Val Phe
    50              55              60

Ala Met Ala Ile Ala Ile Leu Ser Val Val Leu Ser Cys Gly Thr Cys
65              70              75              80

Glu Lys Ala Lys Arg Ala Val Arg Gly Arg Gln Asp Arg Pro Lys Glu
            85              90              95

Phe Pro Pro Pro Arg Tyr Asn Tyr Thr Ile Leu Thr Arg Tyr Asn Ala
            100             105             110

Thr Ala Leu Ala Ser Pro Phe Ile Asn Asp Gln Val Lys Asn Val Asp
        115             120             125

Leu Arg Ile Val Thr Ala Thr Arg Pro Cys Glu Met Ile Ala Leu Ile
    130             135             140

Ala Lys Thr Asn Ile Asp Ser Ile Leu Lys Glu Leu Ala Ala Ala Gln
145             150             155             160

Lys Thr Tyr Ser Ala Arg Leu Thr Trp Phe Lys Ile Met Pro Thr Cys
            165             170             175

Ala Thr Pro Ile His Asp Val Ser Tyr Met Lys Cys Asn Pro Lys Leu
        180             185             190

Ser Phe Ala Met Cys Asp Glu Arg Ser Asp Ile Leu Trp Gln Ala Ser
    195             200             205

Leu Ile Thr Met Ala Ala Glu Thr Asp Asp Glu Leu Gly Leu Val Leu
    210             215             220

Ala Ala Pro Ala His Ser Ala Ser Gly Leu Tyr Arg Arg Val Ile Glu
225             230             235             240

Ile Asp Gly Arg Arg Ile Tyr Thr Asp Phe Ser Val Thr Ile Pro Ser
            245             250             255

Glu Arg Cys Pro Ile Ala Phe Glu Leu Asn Phe Gly Asn Pro Asp Arg
            260                 265                 270

Cys Lys Thr Pro Glu Gln Tyr Ser Arg Gly Glu Val Phe Thr Arg Arg
        275                 280                 285

Phe Leu Gly Glu Phe Asn Phe Pro Gln Gly Glu His Met Thr Trp Val
    290                 295                 300

Lys Phe Trp Phe Val Tyr Asp Gly Gly Asn Leu Pro Val Gln Phe Tyr
305                 310                 315                 320

Glu Ala Gln Ala Phe Ala Arg Pro Val Pro Pro Asp Asn His Pro Gly
                325                 330                 335

Phe Asp Ser Val Glu Ser Glu Ile Thr Gln Asn Lys Thr Asp Pro Lys
                340                 345                 350

Pro Gly Gln Ala Asp Pro Lys Pro Asn Gln Pro Phe Lys Trp Pro Ser
            355                 360                 365

Ile Lys His Leu Val Pro Arg Leu Asp Glu Val Asp Glu Val Ile Glu
            370                 375                 380

Pro Val Thr Lys Pro Pro Lys Thr Ser Lys Ser Asn Ser Thr Phe Val
385                 390                 395                 400

Gly Ile Ser Val Gly Leu Gly Ile Ala Gly Leu Val Leu Val Gly Val
                405                 410                 415

Ile Leu Tyr Val Cys Leu Arg Arg Lys Lys Glu Leu Lys Val Cys Thr
                420                 425                 430

Glu Arg Leu Asp Ser Pro Thr Leu Asp Leu
            435                 440

( 2 ) INFORMATION FOR SEQ ID NO:23:

( i ) SEQUENCE CHARACTERISTICS:
      ( A ) LENGTH: 393 amino acids
      ( B ) TYPE: amino acid
      ( C ) STRANDEDNESS: single
      ( D ) TOPOLOGY: linear ( i i ) MOLECULE TYPE: peptide ( v ) FRAGMENT TYPE: N-terminal ( x i ) SEQUENCE DESCRIPTION: SEQ ID NO:23:

Met Gly Gly Ala Ala Ala Arg Leu Gly Ala Val Ile Leu Phe Val Val
1               5                   10                  15

Ile Val Gly Leu His Gly Val Arg Gly Lys Tyr Ala Leu Ala Asp Ala
            20                  25                  30

Ser Leu Lys Met Ala Asp Pro Asn Arg Phe Arg Gly Lys Asp Leu Pro
        35                  40                  45

Val Leu Asp Gln Leu Thr Asp Pro Pro Gly Val Arg Arg Val Tyr His
    50                  55                  60

Ile Gln Ala Gly Leu Pro Asn Pro Phe Gln Pro Pro Ser Leu Pro Ile
65                  70                  75                  80

Thr Val Tyr Arg Arg Val Glu Arg Ala Cys Arg Ser Val Leu Leu Asn
                85                  90                  95

Ala Pro Ser Glu Ala Pro Gln Ile Val Arg Gly Ala Ser Glu Asp Val
            100                 105                 110

Arg Lys Gln Pro Tyr Asn Leu Thr Ile Ala Trp Phe Arg Met Gly Gly
        115                 120                 125

Asn Cys Ala Ile Pro Ile Thr Val Met Glu Tyr Thr Glu Cys Ser Tyr
    130                 135                 140

Asn Lys Ser Leu Gly Ala Cys Pro Ile Arg Thr Gln Pro Arg Trp Asn
145                 150                 155                 160

|     |     |     |     |     |     |     |     |     |     |     |     |     |     |     |
|---|---|---|---|---|---|---|---|---|---|---|---|---|---|---|
| Tyr | Tyr | Asp | Ser | Phe<br>165 | Ser | Ala | Val | Ser | Glu<br>170 | Asp | Asn | Leu | Gly | Phe<br>175 | Leu |

Tyr Tyr Asp Ser Phe Ser Ala Val Ser Glu Asp Asn Leu Gly Phe Leu
                    165                 170                 175

Met His Ala Pro Ala Phe Glu Thr Ala Gly Thr Tyr Leu Arg Leu Val
            180                 185                 190

Lys Ile Asn Asp Trp Thr Glu Ile Thr Gln Phe Ile Leu Glu His Arg
            195                 200                 205

Ala Lys Gly Ser Cys Lys Tyr Thr Leu Pro Leu Arg Ile Pro Pro Ser
    210                 215                 220

Ala Cys Leu Ser Pro Gln Ala Tyr Gln Gln Gly Val Thr Val Asp Ser
225                 230                 235                 240

Ile Gly Met Leu Pro Arg Phe Ile Pro Glu Asn Gln Arg Thr Val Ala
            245                 250                 255

Val Tyr Ser Leu Lys Ile Ala Gly Trp His Gly Pro Arg Ala Pro Tyr
            260                 265                 270

Thr Ser Thr Leu Leu Pro Pro Glu Leu Pro Glu Thr Pro Asn Ala Thr
            275                 280                 285

Gln Pro Glu Leu Ala Pro Glu Asp Pro Glu Asp Ser Ala Leu Leu Glu
            290                 295                 300

Asp Pro Val Gly Thr Val Ala Pro Gln Ile Pro Pro Asn Trp His Ile
305                 310                 315                 320

Pro Ser Ile Gln Asp Ala Ala Thr Pro Tyr His Pro Pro Ala Thr Pro
                325                 330                 335

Asn Asn Met Gly Leu Ile Ala Gly Ala Val Gly Gly Ser Leu Leu Ala
            340                 345                 350

Ala Leu Val Ile Cys Gly Ile Val Tyr Trp Met Arg Arg Arg Thr Arg
            355                 360                 365

Lys Ala Pro Lys Arg Ile Arg Leu Pro His Ile Arg Glu Asp Asp Gln
    370                 375                 380

Pro Ser Ser His Gln Pro Leu Phe Tyr
385                 390

( 2 ) INFORMATION FOR SEQ ID NO:24:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:24:

TAATTAACTA GCTACCCGGG                                          20

( 2 ) INFORMATION FOR SEQ ID NO:25:

( i ) SEQUENCE CHARACTERISTICS:
      ( A ) LENGTH: 28 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:25:

GTACATTAAT TGATCGATGG GCCCTTAA                               28

( 2 ) INFORMATION FOR SEQ ID NO:26:

( i ) SEQUENCE CHARACTERISTICS:

( A ) LENGTH: 73 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:26:

AGCTTCCCGG GTAAGTAATA CGTCAAGGAG AAAACGAAAC GATCTGTAGT TAGCGGCCGC    60

CTAATTAACT AAT    73

( 2 ) INFORMATION FOR SEQ ID NO:27:

( i ) SEQUENCE CHARACTERISTICS:
          ( A ) LENGTH: 69 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:27:

AGGGCCCATT CATTATGCAG TTCCTCTTTT GCTTTGCTAG ACATCAATCG CCGGCGGATT    60

AATTGATTA    69

( 2 ) INFORMATION FOR SEQ ID NO:28:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:28:

TTAGTTAATT AGGCGGCCGC    20

( 2 ) INFORMATION FOR SEQ ID NO:29:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:29:

CGATTACTAT GAAGGATCCG TT    22

( 2 ) INFORMATION FOR SEQ ID NO:30:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:30:

TAATGATACT TCCTAGGCAA    20

( 2 ) INFORMATION FOR SEQ ID NO:31:

( i ) SEQUENCE CHARACTERISTICS:
          ( A ) LENGTH: 41 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:31:

CGATTACTAG ATCTGAGCTC CCCGGGCTCG AGGGATCCGT T    41

(2) INFORMATION FOR SEQ ID NO:32:

(i) SEQUENCE CHARACTERISTICS:
    (A) LENGTH: 39 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:32:

TAATGATCTA GACTCGAGGG GCCCGAGCTC CCTAGGCAA    39

(2) INFORMATION FOR SEQ ID NO:33:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:33:

GATCCGAATT CTAGCT    16

(2) INFORMATION FOR SEQ ID NO:34:

(i) SEQUENCE CHARACTERISTICS:
    (A) LENGTH: 12 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:34:

GCTTAAGATC GA    12

(2) INFORMATION FOR SEQ ID NO:35:

(i) SEQUENCE CHARACTERISTICS:
    (A) LENGTH: 75 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:35:

TATGAGTAAC TTAACTCTTT TGTTAATTAA AAGTATATTC AAAAAATAAG TTATATAAAT    60

AGATCTGAAT TCGTT    75

(2) INFORMATION FOR SEQ ID NO:36:

(i) SEQUENCE CHARACTERISTICS:
    (A) LENGTH: 73 base pairs
    (B) TYPE: nucleic acid
    (C) STRANDEDNESS: single
    (D) TOPOLOGY: linear ( i i ) MOLECULE TYPE: cDNA ( x i ) SEQUENCE DESCRIPTION: SEQ ID NO:36:

ACTCATTGAA TTGAGAAAAC AATTAATTTT CATATAAGTT TTTTATTCAA TATATTTATC    60

TAGACTTAAG CAA    73

( 2 ) INFORMATION FOR SEQ ID NO:37:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:37:

AAAATGGGCG TGGATTGTTA ACTTTATATA ACTTATTTTT TGAATATAC    49

( 2 ) INFORMATION FOR SEQ ID NO:38:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:38:

ACACGAATGA TTTCTAAAG TATTTGGAAA GTTTATAGG TAGTTGATAG AACAAAATAC    60

ATAATTT    67

( 2 ) INFORMATION FOR SEQ ID NO:39:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:39:

TGTGCTTACT AAAAGATTTC ATAAACCTTT CAAAATATCC ATCAACTATC T    51

( 2 ) INFORMATION FOR SEQ ID NO:40:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:40:

TGTAAAAATA AATCACTTTT TATACTAAGA TCTCCCGGGC TGCAGC    46

( 2 ) INFORMATION FOR SEQ ID NO:41:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear

5,688,920

171 172

-continued ( i i ) MOLECULE TYPE: cDNA ( x i ) SEQUENCE DESCRIPTION: SEQ ID NO:41:

```
TGTTTTATGT ATTAAAACAT TTTTATTTAG TGAAAAATAT GATTCTAGAG GGCCCGACGT    60
CGCCGG                                                              66
```

( 2 ) INFORMATION FOR SEQ ID NO:42:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:42:

```
TTTCTGTATA TTTGCACCAA TTTAGATCTT ACTCAAAATA TGTAACAATA              50
```

( 2 ) INFORMATION FOR SEQ ID NO:43:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:43:

```
TGTCATTTAA CACTATACTC ATATTAATAA AAATAATATT TATT                    44
```

( 2 ) INFORMATION FOR SEQ ID NO:44:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:44:

```
GATCCTGAGT ACTTTGTAAT ATAATGATAT ATATTTCAC TTTATCTCAT TTGAGAATAA    60
AAAGATCTTA GG                                                       72
```

( 2 ) INFORMATION FOR SEQ ID NO:45:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:45:

```
GACTCATGAA ACATTATATT ACTATATATA AAAGTGAAAT AGAGTAAACT CTTATTTTC    60
TAGAATCCTT AA                                                       72
```

( 2 ) INFORMATION FOR SEQ ID NO:46:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:46:

GATCCAGATC TCCCGGGAAA AAAATTATTT AACTTTTCAT TAATAGGGAT TTGACGTATG    60

TAGCGTACTA GG    72

( 2 ) INFORMATION FOR SEQ ID NO:47:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:47:

GTCTAGAGGG CCCTTTTTTT AATAAATTGA AAAGTAATTA TCCCTAAACT GCATACTACG    60

CATGATCCTT AA    72

( 2 ) INFORMATION FOR SEQ ID NO:48:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:48:

GGGAGATCTC TCGAGCTGCA GGGCGCCGGA TCCTTTTTCT    40

( 2 ) INFORMATION FOR SEQ ID NO:49:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:49:

CCCTCTAGAG AGCTCGACGT CCCGCGGCCT AGGAAAAAGA    40

( 2 ) INFORMATION FOR SEQ ID NO:50:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:50:

CGATATCCGT TAAGTTTGTA TCGTAATGGG CTCCAGATCT TCTACCAGGA TCCCGGTAC    59

( 2 ) INFORMATION FOR SEQ ID NO:51:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:51:

CGGGATCCTG GTAGAAGATC TGGAGCCCAT TACGATACAA ACTTAACGGA TATCG    55

( 2 ) INFORMATION FOR SEQ ID NO:52:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:52:

AATTCGAGCT CCCCGGG    17

( 2 ) INFORMATION FOR SEQ ID NO:53:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:53:

CCCGGGGAGC TCG    13

( 2 ) INFORMATION FOR SEQ ID NO:54:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:54:

CTTTTTATAA AAAGTTAACT ACGTAG    26

( 2 ) INFORMATION FOR SEQ ID NO:55:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:55:

GATCCTACGT AGTTAACTTT TTATAAAAAG AGCT    34

( 2 ) INFORMATION FOR SEQ ID NO:56:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:56:

CTTAACTCAG CTGACTATCC    20

( 2 ) INFORMATION FOR SEQ ID NO:57:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:57:

```
TACGTAGTTA ACTTTTTATA AAAATCATAT TTTTGTAGTG GCTC                          44
```

( 2 ) INFORMATION FOR SEQ ID NO:58:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:58:

```
AATTCAGGAT CGTTCCTTTA CTAGTTGAGA TTCTCAAGGA TGATGGGATT TAATTTTTAT          60

AAGCTTG                                                                   67
```

( 2 ) INFORMATION FOR SEQ ID NO:59:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:59:

```
AATTCAAGCT TATAAAAATT AAATCCCATC ATCCTTGAGA ATCTCAACTA GTAAAGGAAC          60

GATCCTG                                                                   67
```

( 2 ) INFORMATION FOR SEQ ID NO:60:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:60:

```
CTAGACACTT TATGTTTTTT AATATCCGGT CTTAAAAGCT TCCCGGGGAT CCTTATACGG          60

GGAATAAT                                                                  68
```

( 2 ) INFORMATION FOR SEQ ID NO:61:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:61:

| ATTATTCCCC | GTATAAGGAT | CCCCCGGGAA | GCTTTTAAGA | CCGGATATTA | AAAAACATAA | 60 |
| AGTGT | | | | | | 65 |

(2) INFORMATION FOR SEQ ID NO:62:

(i) SEQUENCE CHARACTERISTICS:
        (A) LENGTH: 3209 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:62:

| TGAATGTTAA | ATGTTATACT | TTGGATGAAG | CTATAAATAT | GCATTGGAAA | AATAATCCAT | 60 |
| TTAAAGAAAG | GATTCAAATA | CTACAAAACC | TAAGCGATAA | TATGTTAACT | AAGCTTATTC | 120 |
| TTAACGACGC | TTTAAATATA | CACAAATAAA | CATAATTTTT | GTATAACCTA | ACAAATAACT | 180 |
| AAAACATAAA | AATAATAAAA | GGAAATGTAA | TATCGTAATT | ATTTACTCA | GGAATGGGGT | 240 |
| TAAATATTTA | TATCACGTGT | ATATCTATAC | TGTTATCGTA | TACTCTTTAC | AATTACTATT | 300 |
| ACGAATATGC | AAGAGATAAT | AAGATTACGT | ATTTAAGAGA | ATCTTGTCAT | GATAATTGGG | 360 |
| TACGACATAG | TGATAAATGC | TATTTCGCAT | CGTTACATAA | AGTCAGTTGG | AAAGATGGAT | 420 |
| TTGACAGATG | TAACTTAATA | GGTGCAAAAA | TGTTAAATAA | CAGCATTCTA | TCGGAAGATA | 480 |
| GGATACCAGT | TATATTATAC | AAAAATCACT | GGTTGGATAA | AACAGATTCT | GCAATATTCG | 540 |
| TAAAAGATGA | AGATTACTGC | GAATTTGTAA | ACTATGACAA | TAAAAAGCCA | TTTATCTCAA | 600 |
| CGACATCGTG | TAATTCTTCC | ATGTTTTATG | TATGTGTTTC | AGATATTATG | AGATTACTAT | 660 |
| AAACTTTTTG | TATACTTATA | TTCCGTAAAC | TATATTAATC | ATGAAGAAAA | TGAAAAAGTA | 720 |
| TAGAAGCTGT | TCACGAGCGG | TTGTTGAAAA | CAACAAAATT | ATACATTCAA | GATGGCTTAC | 780 |
| ATATACGTCT | GTGAGGCTAT | CATGGATAAT | GACAATGCAT | CTCTAAATAG | GTTTTTGGAC | 840 |
| AATGGATTCG | ACCCTAACAC | GGAATATGGT | ACTCTACAAT | CTCCTCTTGA | AATGGCTGTA | 900 |
| ATGTTCAAGA | ATACCGAGGC | TATAAAAATC | TTGATGAGGT | ATGGAGCTAA | ACCTGTAGTT | 960 |
| ACTGAATGCA | CAACTTCTTG | TCTGCATGAT | GCGGTGTTGA | GAGACGACTA | CAAAATAGTG | 1020 |
| AAAGATCTGT | TGAAGAATAA | CTATGTAAAC | AATGTTCTTT | ACAGCGGAGG | CTTTACTCCT | 1080 |
| TTGTGTTTGG | CAGCTTACCT | TAACAAAGTT | AATTTGGTTA | AACTTCTATT | GGCTCATTCG | 1140 |
| GCGGATGTAG | ATATTTCAAA | CACGGATCGG | TTAACTCCTC | TACATATAGC | CGTATCAAAT | 1200 |
| AAAAATTTAA | CAATGGTTAA | ACTTCTATTG | AACAAGGTG | CTGATACTGA | CTTGCTGGAT | 1260 |
| AACATGGGAC | GTACTCCTTT | AATGATCGCT | GTACAATCTG | GAAATATTGA | AATATGTAGC | 1320 |
| ACACTACTTA | AAAAAAATAA | AATGTCCAGA | ACTGGGAAAA | ATTGATCTTG | CCAGCTGTAA | 1380 |
| TTCATGGTAG | AAAAGAAGTG | CTCAGGCTAC | TTTTCAACAA | AGGAGCAGAT | GTAAACTACA | 1440 |
| TCTTTGAAAG | AAATGGAAAA | TCATATACTG | TTTTGGAATT | GATTAAAGAA | AGTTACTCTG | 1500 |
| AGACACAAAA | GAGGTAGCTG | AAGTGGTACT | CTCAAAATGC | AGAACGATGA | CTGCGAAGCA | 1560 |
| AGAAGTAGAG | AAATAACACT | TTATGACTTT | CTTAGTTGTA | GAAAGATAG | AGATATAATG | 1620 |
| ATGGTCATAA | ATAACTCTGA | TATTGCAAGT | AAATGCAATA | ATAAGTTAGA | TTTATTTAAA | 1680 |
| AGGATAGTTA | AAAATAGAAA | AAAAGAGTTA | ATTTGTAGGG | TTAAAATAAT | ACATAAGATC | 1740 |
| TTAAAATTTA | TAAATACGCA | TAATAATAAA | AATAGATTAT | ACTTATTACC | TTCAGAGATA | 1800 |
| AAATTTAAGA | TATTTACTTA | TTTAACTTAT | AAAGATCTAA | AATGCATAAT | TTCTAAATAA | 1860 |
| TGAAAAAAAA | GTACATCATG | AGCAACGCGT | TAGTATATTT | TACAATGGAG | ATTAACGCTC | 1920 |

| | | | | | |
|---|---|---|---|---|---|
| TATACCGTTC | TATGTTTATT | GATTCAGATG | ATGTTTTAGA | AAAGAAAGTT | ATTGAATATG | 1980 |
| AAAACTTTAA | TGAAGATGAA | GATGACGACG | ATGATTATTG | TTGTAAATCT | GTTTTAGATG | 2040 |
| AAGAAGATGA | CGCGCTAAAG | TATACTATGG | TTACAAAGTA | TAAGTCTATA | CTACTAATGG | 2100 |
| CGACTTGTGC | AAGAAGGTAT | AGTATAGTGA | AAATGTTGTT | AGATTATGAT | TATGAAAAAC | 2160 |
| CAAATAAATC | AGATCCATAT | CTAAAGGTAT | CTCCTTTGCA | CATAATTTCA | TCTATTCCTA | 2220 |
| GTTAGAATA  | CTTTTCATTA | TATTTGTTTA | CAGCTGAAGA | CGAAAAAAAT | ATATCGATAA | 2280 |
| TAGAAGATTA | TGTTAACTCT | GCTAATAAGA | TGAAATTGAA | TGAGTCTGTG | ATAATAGCTA | 2340 |
| TAATCAGAGA | AGTTCTAAAA | GGAAATAAAA | ATCTAACTGA | TCAGGATATA | AAAACATTGG | 2400 |
| CTGATGAAAT | CAACAAGGAG | GAACTGAATA | TAGCTAAACT | ATTGTTAGAT | AGAGGGGCCA | 2460 |
| AAGTAAATTA | CAAGGATGTT | TACGGTTCTT | CAGCTCTCCA | TAGAGCTGCT | ATTGGTAGGA | 2520 |
| AACAGGATAT | GATAAAGCTG | TTAATCGATC | ATGGAGCTGA | TGTAAACTCT | TAACTATTG  | 2580 |
| CTAAAGATAA | TCTTATTAAA | AAAAAATAAT | ATCACGTTTA | GTAATATTAA | AATATATTAA | 2640 |
| TAACTCTATT | ACTAATAACT | CCAGTGGATA | TGAACATAAT | ACGAAGTTTA | TACATTCTCA | 2700 |
| TCAAAATCTT | ATTGACATCA | AGTTAGATTG | TGAAAATGAG | ATTATGAAAT | TAAGGAATAC | 2760 |
| AAAAATAGGA | TGTAAGAACT | TACTAGAATG | TTTTATCAAT | AATGATATGA | ATACAGTATC | 2820 |
| TAGGGCTATA | AACAATGAAA | CGATTAAAAA | TTATAAAAAT | CATTTCCCTA | TATATAATAC | 2880 |
| GCTCATAGAA | AAATTCATTT | CTGAAAGTAT | ACTAAGACAC | GAATTATTGG | ATGGAGTTAT | 2940 |
| AAATTCTTTT | CAAGGATTCA | ATAATAAATT | GCCTTACGAG | ATTCAGTACA | TTATACTGGA | 3000 |
| GAATCTTAAT | AACCATGAAC | TAAAAAAAAT | TTTAGATAAT | ATACATTAAA | AAGGTAAATA | 3060 |
| GATCATCTGT | TATTATAAGC | AAAGATGCTT | GTTGCCAATA | ATATACAACA | GGTATTTGTT | 3120 |
| TTTATTTTA  | ACTACATATT | TGATGTTCAT | TCTCTTTATA | TAGTATACAC | AGAAAATTCA | 3180 |
| TAATCCACTT | AGAATTTCTA | GTTATCTAG  | | | | 3209 |

(2) INFORMATION FOR SEQ ID NO:63:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:63:

GCTTCCCGGG AATTCTAGCT AGCTAGTTT    29

(2) INFORMATION FOR SEQ ID NO:64:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:64:

ACTCTCAAAA GCTTCCCGGG AATTCTAGCT AGCTAGTTTT TATAAA    46

(2) INFORMATION FOR SEQ ID NO:65:

(i) SEQUENCE CHARACTERISTICS:
        (A) LENGTH: 50 base pairs ( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:65:

GATCTTTATA AAAACTAGCT AGCTAGAATT CCCGGGAAGC TTTTGAGAGT    50

( 2 ) INFORMATION FOR SEQ ID NO:66:

( i ) SEQUENCE CHARACTERISTICS:
( A ) LENGTH: 71 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:66:

CTGAAATTAT TCATTATCG CGATATCCGT TAAGTTTGTA TCGTAATGGT TCCTCAGGCT    60

CTCCTGTTTG T    71

( 2 ) INFORMATION FOR SEQ ID NO:67:

( i ) SEQUENCE CHARACTERISTICS:
( A ) LENGTH: 48 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:67:

CATTACGATA CAAACTTAAC GGATATCGCG ATAATGAAAT AATTTCAG    48

( 2 ) INFORMATION FOR SEQ ID NO:68:

( i ) SEQUENCE CHARACTERISTICS:
( A ) LENGTH: 73 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:68:

ACCCCTTCTG GTTTTCCGT TGTGTTTGG GAAATTCCCT ATTTACACGA TCCCAGACAA    60

GCTTAGATCT CAG    73

( 2 ) INFORMATION FOR SEQ ID NO:69:

( i ) SEQUENCE CHARACTERISTICS:
( A ) LENGTH: 51 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:69:

CTGAGATCTA AGCTTGTCTG GGATCGTGTA AATAGGGAAT TTCCCAAAAC A    51

( 2 ) INFORMATION FOR SEQ ID NO:70:

( i ) SEQUENCE CHARACTERISTICS:
( A ) LENGTH: 45 base pairs
( B ) TYPE: nucleic acid ( C ) STRANDEDNESS: single
            ( D ) TOPOLOGY: linear ( i i ) MOLECULE TYPE: cDNA ( x i ) SEQUENCE DESCRIPTION: SEQ ID NO:70:

CAACGGAAAA ACCAGAAGGG GTACAAACAG GAGAGCCTGA GGAAC                                45

( 2 ) INFORMATION FOR SEQ ID NO:71:

( i ) SEQUENCE CHARACTERISTICS:
            ( A ) LENGTH: 11 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:71:

GGATCCCCGG G                                                                    11

( 2 ) INFORMATION FOR SEQ ID NO:72:

( i ) SEQUENCE CHARACTERISTICS:
            ( A ) LENGTH: 3659 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:72:

GATATCTGTG GTCTATATAT ACTACACCCT ACCGATATTA ACCAACGAGT TTCTCACAAG     60

AAAACTTGTT TAGTAGATAG AGATTCTTTG ATTGTGTTTA AAGAAGTAC CAGTAAAAAG      120

TGTGGCATAT GCATAGAAGA AATAAACAAA AAACATATTT CCGAACAGTA TTTTGGAATT     180

CTCCCAAGTT GTAAACATAT TTTTTGCCTA TCATGTATAA GACGTTGGGC AGATACTACC     240

AGAAATACAG ATACTGAAAA TACGTGTCCT GAATGTAGAA TAGTTTTTCC TTTCATAATA     300

CCCAGTAGGT ATTGGATAGA TAATAAATAT GATAAAAAAA TATTATATAA TAGATATAAG     360

AAAATGATTT TTACAAAAAT ACCTATAAGA ACAATAAAAA TATAATTACA TTTACGGAAA     420

ATAGCTGGTT TTAGTTTACC AACTTAGAGT AATTATCATA TTGAATCTAT ATTGTTTTTT    480

AGTTATATAA AAACATGATT AGCCCCCAAT CGGATGAAAA TATAAAGAT GTTGAGAATT     540

TCGAATACAA CAAAAGAGG AATCGTACGT TGTCCATATC CAAACATATA AATAAAATT      600

CAAAAGTAGT ATTATACTGG ATGTTTAGAG ATCAACGTGT ACAAGATAAT TGGGCTTTAA    660

TTTACGCACA ACGATTAGCG TTAAAACTCA AAATACCTCT AAGAATATGC TTTTGTGTCG    720

TGCCAAAATT TCACACTACT ACTTCTAGAC ACTTTATGTT TTTAATATCC GGTCTTAAAG   780

AAGTCGCGGA AGAATGTAAA AGACTATGTA TAGGGTTTTC ATTGATATAT GGCGTACCAA    840

AAGTAATAAT TCCGTGTATA GTAAAAAAAT ACAGAGTCGG AGTAATCATA ACGGATTTCT    900

TTCCATTACG TGTTCCCGAA AGATTAATGA AACAGACTGT AATATCTCTT CCAGATAACA    960

TACCTTTTAT ACAAGTAGAC GCTCATAATA TAGTACCTTG TTGGGAAGCT TCTGATAAAG    1020

AAGAATACGG TGCACGAACT TTAAGAAAAA AGATATTTGA TAAATTATAT GAATATATGA    1080

CAGAATTTCC TGTTGTTCGT AAACATCCAT ACGGTCCATT TTCTATATCT ATTGCAAAAC    1140

CCAAAAATAT ATCATTAGAC AAGACGGTAT TACCCGTAAA ATGGGCAACG CCTGGAACAA    1200

AAGCTGGAAT AATTGTTTTA AAAGAATTTA TAAAAAACAG ATTACCGTCA TACGACGCGG    1260

ATCATAACAA TCCTACGTGT GACGCTTTGA GTAACTTATC TCCGTGGCTA CATTTTGGTC    1320

```
ATGTATCCGC ACAACGTGTT GCCTTAGAAG TATTAAAATG TATACGAGAA AGCAAAAAAA    1380
ACGTTGAAAC GTTTATAGAT GAAATAATTG TAAGAAGAGA ACTATCGGAT AATTTTTGTT    1440
ACTATAACAA ACATTATGAT AGTATCCAGT CTACTCATTC ATGGGTTAGA AAAACATTAG    1500
AAGATCACAT TAATGATCCT AGAAAGTATA TATATTCCAT TAAACAACTC GAAAAGCGG     1560
AAACTCATGA TCCTCTATGG AACGCGTCAC AAATGCAGAT GGTGAGAGAA GGAAAAATGC    1620
ATAGTTTTTT ACGAATGTAT TGGGCTAAGA AGATACTTGA ATGGACTAGA ACACCTGAAG    1680
ACGCTTTGAG TTATAGTATC TATTTGAACA ACAAGTACGA ACTAGACGGC ACGGATCCTA    1740
ACGGATACGT AGGTTGTATG TGGTCTATTT GCGGATTACA CGATAGAGCG TGGAAAGCAA    1800
GACCGATATT TGGAAAGATA AGATATATGA ATTATGAGAG TTCTAAGAAG AAATTTGATG    1860
TTGCTGTATT TATACAGAAA TACAATTAAG ATAAATAATA TACAGCATTG TAACCATCGT    1920
CATCCGTTAT ACGGGGAATA ATATTACCAT ACAGTATTAT TAAATTTCT TACGAAGAAT     1980
ATAGATCGGT ATTTATCGTT AGTTTATTTT ACATTATTA ATTAAACATG TCTACTATTA     2040
CCTGTTATGG AAATGACAAA TTTAGTTATA TAATTTATGA TAAAATTAAG ATAATAATAA    2100
TGAAATCAAA TAATTATGTA AATGCTACTA GATTATGTGA ATTACGAGGA AGAAAGTTTA    2160
CGAACTGGAA AAAATTAAGT GAATCTAAAA TATTAGTCGA TAATGTAAAA AAAATAAATG    2220
ATAAAACTAA CCAGTTAAAA ACGGATATGA TTATATACGT TAAGGATATT GATCATAAAG    2280
GAAGAGATAC TTGCGGTTAC TATGTACACC AAGATCTGGT ATCTTCTATA TCAAATTGGA    2340
TATCTCCGTT ATTCGCCGTT AAGGTAAATA AAATTATTAA CTATTATATA TGTAATGAAT    2400
ATGATATACG ACTTAGCGAA ATGGAATCTG ATATGACAGA AGTAATAGAT GTAGTTGATA    2460
AATTAGTAGG AGGATACAAT GATGAAATAG CAGAAATAAT ATATTTGTTT AATAAATTTA    2520
TAGAAAAATA TATTGCTAAC ATATCGTTAT CAACTGAATT ATCTAGTATA TTAAATAATT    2580
TTATAAATTT TATAAATTTT AATAAAAAAT ACAATAACGA CATAAAGATA TTTAATCTTT    2640
AATTCTTGAT CTGAAAAACA CATCTATAAA ACTAGATAAA AAGTTATTCG ATAAAGATAA    2700
TAATGAATCG AACGATGAAA AATTGGAAAC AGAAGTTGAT AAGCTAATTT TTTTCATCTA    2760
AATAGTATTA TTTTATTGAA GTACGAAGTT TTACGTTAGA TAAATAATAA AGGTCGATTT    2820
TTACTTTGTT AAATATCAAA TATGTCATTA TCTGATAAAG ATACAAAAAC ACACGGTGAT    2880
TATCAACCAT CTAACGAACA GATATTACAA AAAATACGTC GGACTATGGA AAACGAAGCT    2940
GATAGCCTCA ATAGAAGAAG CATTAAAGAA ATTGTTGTAG ATGTTATGAA GAATTGGGAT    3000
CATCCTCAAC GAAGAAATAG ATAAAGTTCT AAACTGGAAA AATGATACAT TAAACGATTT    3060
AGATCATCTA AATACAGATG ATAATATTAA GGAAATCATA CAATGTCTGA TTAGAGAATT    3120
TGCGTTTAAA AAGATCAATT CTATTATGTA TAGTTATGCT ATGGTAAAAC TCAATTCAGA    3180
TAACGAACAT TGAAAGATAA AATTAAGGAT TATTTTATAG AAACTATTCT TAAAGACAAA    3240
CGTGGTTATA AACAAAGCC ATTACCCGGA TTGGAAACTA AAATACTAGA TAGTATTATA     3300
AGATTTAAA AACATAAAAT TAATAGGTTT TTATAGATTG ACTTATTATA TACAATATGG     3360
ATAAAAGATA TATATCAACT AGAAAGTTGA ATGACGGATT CTTAATTTTA TATTATGATT    3420
CAATAGAAAT TATTGTCATG TCGTGTAATC ATTTTATAAA TATATCAGCG TTACTAGCTA    3480
AGAAAAACAA GGACTTTAAT GAATGGCTAA AGATAGAATC ATTTAGAGAA ATAATAGATA    3540
CTTAGATAA AATTAATTAC GATCTAGGAC AACGATATTG TGAAGAACTT ACGGCGCATC     3600
ACATTCCAGT GTAATTATTG AGGTCAAAGC TAGTAACTTA ATAGATGACA GGACAGCTG     3659
```

-continued ( 2 ) INFORMATION FOR SEQ ID NO:73:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:73:

```
TCATTATCGC  GATATCCGTG  TTAACTAGCT  AGCTAATTTT  TATTCCCGGG  ATCCTTATCA        60
```

( 2 ) INFORMATION FOR SEQ ID NO:74:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:74:

```
GTATAAGGAT  CCCGGGAATA  AAAATTAGCT  AGCTAGTTAA  CACGGATATC  GCGATAATGA        60
```

( 2 ) INFORMATION FOR SEQ ID NO:75:

( i ) SEQUENCE CHARACTERISTICS:
        ( A ) LENGTH: 2356 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:75:

```
TGTCTGGACT  AACTGATTTC  ATGGAACAAT  TTTCATCAAA  AATATCAGTT  ATACCTAGTT        60
CTACAAAGAC  AGAACTTTGA  TGTTATGTTT  GTGTTTGTAT  AGAAAATTTT  GGGATACTAA       120
CTGATATTTC  TGAATATTTC  TGAATATTTC  ATGTTACTTA  CTTACTCCTA  TCTTAGACGA       180
TAATAAAATT  CGAGGCGTAA  TATGTTTTTC  CAAATATTTG  AAATTCTTAT  ACGTATCGGC       240
GAAGAAAAGT  AACATACTAT  AAGTGTTATG  CAAGTAAGGT  ATGTAATGA   TATTGGATTT       300
AATTTCATTG  ACAATACATA  TGTCCAAACA  TTCCACTCGT  AATTATGTAC  GGAACGACTT       360
TAGTTAAATA  CTTAGTCACA  AAAAACTTAT  GACTGTCATT  ATCTGAAAAC  GGTGATTCCC       420
ATAAATCAGA  ATACTTAATA  TTAAATAGAA  TGCTCGCTTC  TGGAGGTTTC  CGGATACTAG       480
ATAACATATC  TTCTGTATTA  TAGTTTAATT  CACTCATTTT  ATTACATAAT  ACAGTAACAT       540
CTCCCGAAAC  CAATGATGTT  ATATTAGATT  TACTTACATA  CTTCTTGTAA  CTATCATGAA       600
TACGTTTGTT  ATGATCTATA  AAGAAGATGG  ATGTATATTC  TGTTCTAGAT  AGCAAGTTCT       660
TTAAGTTATT  CTTTGTCTGT  ATTACTATCA  TCGTCTTCAT  CATCGTCTAA  AGGTAGCATT       720
ATATAATAAA  TCTAATAGTT  GATTTCTCGA  TCTATCAGTA  CTCGCTTTCA  ATAACATTTT       780
TACTATAAGC  ATAATAGAAG  GCGGTGATAT  CACTATATTT  TTATCGGGTA  TTCTTTTAGT       840
AATTAGTTAG  TTCGTAGAAT  TTCGTAGAGA  TAAAAGCCAA  TTTGTTGTTG  ATACTGCTTA       900
CGTTACTCAT  GTTTCTTGTT  TCTGTTAATT  AACAGGTATA  CCCTTACAAT  AAGTTTAATT       960
AACTTTTAGG  TTTTTGTGAA  GAACTTTTAG  CTTCTAGTTC  CCTTATCCAT  AATTGGGTCT      1020
TAGATCTAGA  TTCTTCCCAT  GTATAAGGG   GGACATACCC  AAAATCTTTA  AATGCTTTGT      1080
CCGTTTCTAT  AGTAAATGTC  GTACATTCCT  TAATCAAAGT  ATAAGGATTT  AGTAAAGGCG      1140
```

| | | | | | |
|---|---|---|---|---|---|
|TGTAAGAACA|AATAGGTGAT|AGTAATACTC|TTAAACCTTT|ATTAATATTA|GCGATAAACC|1200
|TTAAACACCA|TAAAGGAAGA|CATGTATTCC|GTAGATCCAT|CCCTAATTGA|TTAAAGAAAT|1260
|GCATGTTAAA|ATCATGATAA|TGTTCAGTAG|GAGAGGTATC|GTAACAGTAA|TACACGTTAT|1320
|TGCAGAGAGG|ACTATGTTGA|CCATTTTCTA|TCATATTTCT|TGCTGCTAAA|ATATGCATCC|1380
|AAGCTACGTT|TCCTGCATAG|ACTCTGCTAT|GAAATACTTT|ATCATCCGCA|TATTTATACA|1440
|TTTTCCTGCT|TTTATACGAT|CTTCTGTATA|AAGTTCTAG|TACTGGACAG|TATTCTCCGA|1500
|AAACACCTAA|TGGGCGTAGC|GACAAGTGCA|TAATCTAAGT|CCTATATTAG|ACATAGTACC|1560
|GTTAGCTTCT|AGTATATATT|TCTCAGATAA|CTTGTTTACT|AAGAGGATAA|GCCTCTTTAT|1620
|GGTTAGATTG|ATAATACGTA|TTCTCGTTTC|CTCTTATCAT|CGCATCTCCG|GAGAAAGTTA|1680
|GGACCTACCG|CAGAATAACT|ACTCGTATAT|ACTAAGACTC|TTACGCCGTT|ATACAGACAA|1740
|GAATCTACTA|CGTTCTTCGT|TCCGTTGATA|TTAACGTCCA|TTATAGAGTC|GTTAGTAAAC|1800
|TTACCCGCTA|CATCATTTAT|CGAAGCAATA|TGAATGACCA|CATCTGCTGA|TCTAAGCGCT|1860
|TCGTCCAAAG|TACTTTTATT|TCTAACATCT|CCAATCACGG|GAACTATCTT|TATTATATTA|1920
|CATTTTCTA|CAAGATCTAG|TAACCATTGG|TCGATTCTAA|TATCGTAAAC|ACGAACTTCT|1980
|TTTTAAAGAG|GATTCGAACA|AGATAAGATT|ATTTATAATG|TGTCTACCTA|AAAATCCACA|2040
|CCCTCCGGTT|ACCACGTATA|CTAGTGTACG|CATTTGAGT|ATTAACTATA|TAAGACCAAA|2100
|ATTATATTTT|CATTTCTGT|TATATTATAC|TATATAATAA|AAACAAATAA|ATATACGAAT|2160
|ATTATAAGAA|ATTTAGAACA|CGTTATTAAA|GTATTGCCTT|TTTTATTAAC|GGCGTGTTCT|2220
|TGTAATTGCC|GTTAGAATA|GTCTTTATTT|ACTTTAGATA|ACTCTTCTAT|CATAACCGTC|2280
|TCCTTATTCC|AATCTTCTTC|AGAAGTACAT|GAGTACTTAC|CGAAGTTTAT|CATCATAGAG|2340
|ATTATATATG|AAGAAA| | | | |2356

( 2 ) INFORMATION FOR SEQ ID NO:76:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:76:

GACAATCTAA GTCCTATATT AGAC      24

( 2 ) INFORMATION FOR SEQ ID NO:77:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:77:

GGATTTTTAG GTAGACAC      18

( 2 ) INFORMATION FOR SEQ ID NO:78:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear (i i) MOLECULE TYPE: cDNA (x i) SEQUENCE DESCRIPTION: SEQ ID NO:78:

TCATCGTCTT CATCATCG                                                     18

(2) INFORMATION FOR SEQ ID NO:79:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:79:

GTCTTAAACT TATTGTAAGG GTATACCTG                                         29

(2) INFORMATION FOR SEQ ID NO:80:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:80:

AACGATTAGT TAGTTACTAA AAGCTTGCTG CAGCCCGGGT TTTTTATTAG TTTAGTTAGT        60

C                                                                       61

(2) INFORMATION FOR SEQ ID NO:81:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:81:

GACTAACTAA CTAATAAAAA ACCCGGGCTG CAGCAAGCTT TTTGTAACTA ACTAATCGTT        60

(2) INFORMATION FOR SEQ ID NO:82:

(i) SEQUENCE CHARACTERISTICS:
        (A) LENGTH: 99 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:82:

GCACGGAACA AAGCTTATCG CGATATCCGT TAAGTTTGTA TCGTAATGCT ATCAATCACG        60

ATTCTGTTCC TGCTCATAGC AGAGGGCTCA TCTCAGAAT                              99

(2) INFORMATION FOR SEQ ID NO:83:

(i) SEQUENCE CHARACTERISTICS:
        (A) LENGTH: 99 base pairs
        (B) TYPE: nucleic acid
        (C) STRANDEDNESS: single
        (D) TOPOLOGY: linear ( i i ) MOLECULE TYPE: cDNA ( x i ) SEQUENCE DESCRIPTION: SEQ ID NO:83:

| ATTCTGAGAT | GAGCCCTCTG | CTATGAGCAG | GAACAGAATC | GTGATTGATA | GCATTACGAT | 60 |
| ACAAACTTAA | CGGATATCGC | GATAAGCTTT | GTTCCGTGC | | | 99 |

( 2 ) INFORMATION FOR SEQ ID NO:84:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:84:

| GAAAAATTTA | AAGTCGACCT | GTTTGTTGA | GTTGTTTGCG | TGGTAACCAA | TGCAAATCTG | 60 |
| GTCACT | | | | | | 66 |

( 2 ) INFORMATION FOR SEQ ID NO:85:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:85:

| TCTAGCAAGA | CTGACTATTG | CAAAAGAAG | CACTATTTCC | TCCATTACGA | TACAAACTTA | 60 |
| ACGGAT | | | | | | 66 |

( 2 ) INFORMATION FOR SEQ ID NO:86:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:86:

| ATCCGTTAAG | TTTGTATCGT | AATGGAGGAA | ATAGTGCTTC | TTTTTGCAAT | AGTCAGTCTT | 60 |
| GCTAGAAGTG | ACCAGATTTG | CATTGGT | | | | 87 |

( 2 ) INFORMATION FOR SEQ ID NO:87:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:87:

| TACCACGCAA | ACAACTCAAC | AAAACAGGTC | GACTTTAAAT | TTTTCTGCA | 49 |

( 2 ) INFORMATION FOR SEQ ID NO:88:

( i ) SEQUENCE CHARACTERISTICS:
        ( A ) LENGTH: 132 base pairs
        ( B ) TYPE: nucleic acid (C) STRANDEDNESS: single
(D) TOPOLOGY: linear (ii) MOLECULE TYPE: cDNA (xi) SEQUENCE DESCRIPTION: SEQ ID NO:88:

GTACAGGTCG ACAAGCTTCC CGGGTATCGC GATATCCGTT AAGTTTGTAT CGTAATGAAT    60

ACTCAAATTC TAATACTCAC TCTTGTGGCA GCCATTCACA CAAATGCAGA CAAAATCTGC   120

CTTGGACATC AT                                                      132

(2) INFORMATION FOR SEQ ID NO:89:

(i) SEQUENCE CHARACTERISTICS:
    (A) LENGTH: 132 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:89:

ATGATGTCCA AGGCAGATTT TGTCTGCATT TGTGTGAATG GCTGCCACAA GAGTGAGTAT    60

TAGAATTTGA GTATTCATTA CGATACAAAC TTAACGGATA TCGCGATACC CGGGAAGCTT   120

GTCGACCTGT AC                                                      132

(2) INFORMATION FOR SEQ ID NO:90:

(i) SEQUENCE CHARACTERISTICS:
    (A) LENGTH: 51 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:90:

ATAACATGCG GTGCACCATT TGTATATAAG TTAACGAATT CCAAGTCAAG C              51

(2) INFORMATION FOR SEQ ID NO:91:

(i) SEQUENCE CHARACTERISTICS:
    (A) LENGTH: 51 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:91:

GCTTGACTTG GAATTCGTTA ACTTATATAC AAATGGTGCA CCGCATGTTA T              51

(2) INFORMATION FOR SEQ ID NO:92:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:92:

TAAGAATGGT AATTCT                                                    16

(2) INFORMATION FOR SEQ ID NO:93:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:93:

TTCCCGGGTT AAACTTTACT TTCATTTTC       29

( 2 ) INFORMATION FOR SEQ ID NO:94:

( i ) SEQUENCE CHARACTERISTICS:
        ( A ) LENGTH: 88 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:94:

TTGTCGACTG AGATAAAGTG AAAATATATA TCATTATATT ACAAAGTACA ATTATTTAGG       60

TTTAATCATG TTTTCATTGT ATCTATAT       88

( 2 ) INFORMATION FOR SEQ ID NO:95:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:95:

TTAGTACTTT CCGGTGTTGT TGGATCACAT ATTATTAAAG TATAAATAAT AAAGAA       56

( 2 ) INFORMATION FOR SEQ ID NO:96:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:96:

TGGAATGAAG TTATGAAACT       20

( 2 ) INFORMATION FOR SEQ ID NO:97:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:97:

TGCACTGATC ATTTCAATTT C       21

( 2 ) INFORMATION FOR SEQ ID NO:98:

( i ) SEQUENCE CHARACTERISTICS:
        ( A ) LENGTH: 28 base pairs
        ( B ) TYPE: nucleic acid ( C ) STRANDEDNESS: single
( D ) TOPOLOGY: linear ( i i ) MOLECULE TYPE: cDNA ( x i ) SEQUENCE DESCRIPTION: SEQ ID NO:98:

TGGAATTTTG AATGAAAACA CTAGAACC 28

( 2 ) INFORMATION FOR SEQ ID NO:99:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:99:

TTCTAGTGTT TTCATTCAAA ATTCCAT 27

( 2 ) INFORMATION FOR SEQ ID NO:100:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:100:

CCTTCAAAGT TTAATACACC 20

( 2 ) INFORMATION FOR SEQ ID NO:101:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:101:

TATGGCTTCA CGTTTGGCAC 20

( 2 ) INFORMATION FOR SEQ ID NO:102:

( i ) SEQUENCE CHARACTERISTICS:
( A ) LENGTH: 49 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:102:

CACCGGGGAT ATAATTCATA TGTCCCTTT CTTTGGATTA CGAGATGGT 49

( 2 ) INFORMATION FOR SEQ ID NO:103:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:103:

| | | | | |
|---|---|---|---|---|
| CCATCTCGTA | ATCCAAAGAA | AGGGGACATA | TGAAT | 35 |

( 2 ) INFORMATION FOR SEQ ID NO:104:

( i ) SEQUENCE CHARACTERISTICS:
      ( A ) LENGTH: 2951 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:104:

| | | | | | |
|---|---|---|---|---|---|
| AGTACAATAA | AAAGTATTAA | ATAAAATAC | TTACTTACGA | AAAAATGACT | AATTAGCTAT | 60 |
| AAAAACCCGG | GAAAGGATCC | TGATCCTTTT | TCTGGGTAAG | TAATACGTCA | AGGAGAAAAC | 120 |
| GAAACGATCT | GTAGTTAGCG | GCCAAACTCG | AGGTCGACTG | AGATAAAGTG | AAAATATATA | 180 |
| TCATTATATT | ACAAAGTACA | ATTATTTAGG | TTAATCATG | TTTTCATTGT | ATCTATATAT | 240 |
| TTTTTTATT | ATTTATACTT | TAATAATATG | TGATCCAACA | ACACCGGAAA | GTACTATTAA | 300 |
| TCCATTAAAT | CATCACAATT | TATCAACACC | TAAACCTACT | TCGGATGATA | TTCGTGAAAT | 360 |
| TTTACGTGAA | TCCCAAATTG | AATCTGATGA | TACATCAACA | TTTTACATGT | GCCCACCACC | 420 |
| ATCGGGATCA | ACATTGGTGC | GTTTGGAGCC | ACCTAGAGCA | TGTCCTAACT | ATAAACTTGG | 480 |
| TAAAAATTTT | ACAGAAGGAA | TTGCTGTAAT | ATTTAAGGAA | AATATTTCTC | CTTATAAATT | 540 |
| TAAAGCTAAT | ATATACTACA | AAAATATTAT | TATCACCACT | GTATGGTCTG | GAAGCACATA | 600 |
| TGCAGTAATT | ACTAATAGAT | ATACAGATCG | TGTACCTATA | GGTGTTCCTG | AAATTACAGA | 660 |
| GTTGATTGAT | AGAAGAGGTA | TGTGTTTATC | AAAAGCTGAT | TATATTCGTA | ATAATTATGA | 720 |
| ATTACCGCA | TTTGATAAGG | ATGAAGACCC | CAGAGAAGTT | CATTTAAAGC | CTTCAAAGTT | 780 |
| TAATACACCA | GGATCCCGTG | GATGGCATAC | AGTTAATGAT | ACTTACACAA | AAATTGGGGG | 840 |
| TTCTGGATTT | TATCATTCTG | GAACATCTGT | AAATTGTATA | GTTGAAGAAG | TTGATGCCAG | 900 |
| ATCTGTTTAT | CCATATGATT | CATTTGCTAT | CTCCACCGGG | GATATAATTC | ATATGTCCCC | 960 |
| TTTTTTTGGA | TTACGAGATG | GTGCTCATAC | TGAATATATT | AGTTATTCAA | CTGATAGATT | 1020 |
| TCAACAAATA | GAAGGTTATT | ATCCTATCGA | CTTAGATACT | AGACTACAGC | TTGGTGCACC | 1080 |
| AGTTTCTAGG | AATTTTTTAA | CAACACAACA | CGTTACTGTT | GCTTGGAATT | GGGTTCCAAA | 1140 |
| AATTCGTGAA | GTGTGTACTT | TGGCTAAATG | GCGTGAAATT | GATGAAATTA | TTCGTGATGA | 1200 |
| GTATAAGGGA | TCTTACAGAT | TTACAGCAAA | ATCAATATCT | GCAACATTTA | TTTCTGATAC | 1260 |
| TACTCAATTT | GATATTGATC | GTGTAAAGTT | AAGTGATTGT | GCCAAACGTG | AAGCCATAGA | 1320 |
| AGCTATTGAT | AAGATCTACA | AAAAAAAATA | TAATAAAACT | CATATTCAAA | CAGGAGAATT | 1380 |
| GGAAACATAC | TTGGCTAGAG | GGGGATTTAT | TATAGCATTT | AGACCAATGA | TTAGTAATGA | 1440 |
| GTTAGCAAAA | TTGTATATAA | ATGAGTTAGT | AAGATCTAAT | CGTACGGTTG | ATTTGAAATC | 1500 |
| TCTTTTAAAT | CCATCTGTAA | GAGGGGGGGC | TAGAAAGAGA | AGATCAGTAG | AGGAAAATAA | 1560 |
| AAGATCAAAA | CGTAATATTG | AAGGTGGTAT | TGAAAATGTA | AATAATTCAA | CAATAATTAA | 1620 |
| GACAACTTCA | TCTGTTCATT | TTGCTATGCT | TCAGTTTGCC | TATGATCATA | TTCAATCACA | 1680 |
| TGTTAATGAA | ATGCTTAGTA | GAATTGCAAC | TGCATGGTGT | AATCTTCAAA | ATAAAGAGAG | 1740 |
| AACCCTTTGG | AATGAAGTTA | TGAAACTTAA | TCCAACTAGT | GTGGCTTCGG | TTGCTATGGA | 1800 |
| TCAAAGAGTT | TCAGCACGAA | TGTTAGGGGA | TGTTCTTGCA | GTTACTCAAT | GTGTTAATAT | 1860 |
| ATCAGGTTCT | AGTGTTTTTA | TTCAAAATTC | CATGCGTGTT | TTAGGGTCAA | CAACTACATG | 1920 |

| | | | | | |
|---|---|---|---|---|---|
| TTACAGTCGT | CCTCTTATAT | CATTTAAAGC | ACTAGAAAAC | TCAACTAACT | ATATTGAAGG | 1980 |
| ACAACTTGGG | GAAAATAATG | AACTATTAGT | AGAACGAAAG | CTAATTGAAC | CATGTACAGC | 2040 |
| TAACCATAAA | AGATATTTTA | AATTTGGTGC | AGATTATGTA | TATTTTGAAA | ACTATGCATA | 2100 |
| TGTTCGAAAG | GTACCTCTTA | ATGAAATTGA | AATGATCAGT | GCATATGTAG | ATCTTAATAT | 2160 |
| TACATTACTT | GAGGATCGTG | AATTTTTACC | ACTAGAGGTA | TATACTCGAG | CAGAGTTAGA | 2220 |
| AGATACAGGA | CTATTGGACT | ATAGTGAGAT | TCAACGTAGA | AATCAACTAC | ATGCACTTAA | 2280 |
| GTTTTATGAT | ATTGACAGTG | TTGTAAAAGT | TGATAATAAT | GTTGTAATTA | TGAGGGGCAT | 2340 |
| TGCAAATTTT | TTCCAAGGAC | TTGGAGATGT | TGGAGCGGGA | TTTGGAAAAG | TTGTTTTGGG | 2400 |
| TGCTGCAAAT | GCTGTTATTG | CAACTGTTTC | TGGAGTGTCC | TCGTTTCTTA | ATAACCCATT | 2460 |
| TGGGGCGCTA | GCCGTTGGAT | TGCTGATTTT | AGCTGGACTA | TTTGCAGCGT | TTTTGGCTTA | 2520 |
| TAGATATGTT | TCTAAACTTA | AGTCAAATCC | AATGAAAGCA | CTATACCCAG | TAACTACAAA | 2580 |
| AAATTTAAAA | GAAAGTGTTA | AGAATGGTAA | TTCTGGAAAT | AATAGTGATG | GAGAAGAAAA | 2640 |
| TGATGATAAT | ATCGATGAAG | AAAAGCTTCA | ACAAGCTAAA | GAATGATTA | AATATATGTC | 2700 |
| TCTAGTTTCT | GCTATGGAAC | AGCAGGAACA | TAAAGCTATT | AAAAAAAATA | GTGGCCCTGC | 2760 |
| CCTTCTAGCA | AGTCACATTA | CAAACCTATC | TCTTAAACAT | CGTGGTCCAA | AATACAAACG | 2820 |
| TTTGAAAAAT | GTAAATGAAA | ATGAAAGTAA | AGTTTAACCC | GGGTACCGAG | CTCGAATTCT | 2880 |
| TTTTATTGAT | TAACTAGTCA | AATGAGTATA | TATAATTGAA | AAAGTAAAAT | ATAAATCATA | 2940 |
| TAATAATGAA | A | | | | | 2951 |

(2) INFORMATION FOR SEQ ID NO:105:

(i) SEQUENCE CHARACTERISTICS:
        (A) LENGTH: 2951 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:105:

| | | | | | |
|---|---|---|---|---|---|
| TCATGTTATT | TTTCATAATT | TATTTTTATG | AATGAATGCT | TTTTTACTGA | TTAATCGATA | 60 |
| TTTTTGGGCC | CTTTCCTAGG | ACTAGGAAAA | AGACCCATTC | ATTATGCAGT | TCCTCTTTTG | 120 |
| CTTTGCTAGA | CATCAATCGC | CGGTTTGAGC | TCCAGCTGAC | TCTATTTCAC | TTTTATATAT | 180 |
| AGTAATATAA | TGTTTCATGT | TAATAAATCC | AAATTAGTAC | AAAAGTAACA | TAGATATATA | 240 |
| AAAAAAATAA | TAAATATGAA | ATTATTATAC | ACTAGGTTGT | TGTGGCCTTT | CATGATAATT | 300 |
| AGGTAATTTA | GTAGTGTTAA | ATAGTTGTGG | ATTTGGATGA | AGCCTACTAT | AAGCACTTTA | 360 |
| AAATGCACTT | AGGGTTTAAC | TTAGACTACT | ATGTAGTTGT | AAAATGTACA | CGGGTGGTGG | 420 |
| TAGCCCTAGT | TGTAACCACG | CAAACCTCGG | TGGATCTCGT | ACAGGATTGA | TATTTGAACC | 480 |
| ATTTTTAAAA | TGTCTTCCTT | AACGACATTA | TAAATTCCTT | TTATAAAGAG | GAATATTTAA | 540 |
| ATTCGATTA | TATATGATGT | TTTTATAATA | ATAGTGGTGA | CATACCAGAC | CTTCGTGTAT | 600 |
| ACGTCATTAA | TGATTATCTA | TATGTCTAGC | ACATGGATAT | CCACAAGGAC | TTAATGTCT | 660 |
| CAACTAACTA | TCTTCTCCAT | ACACAAATAG | TTTTCGACTA | ATATAAGCAT | TATTAATACT | 720 |
| TAAATGGCGT | AAACTATTCC | TACTTCTGGG | GTCTCTTCAA | GTAAATTTCG | GAAGTTTCAA | 780 |
| ATTATGTGGT | CCTAGGGCAC | CTACCGTATG | TCAATTACTA | TGAATGTGTT | TTAACCCCC | 840 |
| AAGACCTAAA | ATAGTAAGAC | CTTGTAGACA | TTTAACATAT | CAACTTCTTC | AACTACGGTC | 900 |

| | | | | | |
|---|---|---|---|---|---|
| TAGACAAATA | GGTATACTAA | GTAAACGATA | GAGGTGGCCC | CTATATTAAG | TATACAGGGG | 960
| AAAAAAACCT | AATGCTCTAC | CACGAGTATG | ACTTATATAA | TCAATAAGTT | GACTATCTAA | 1020
| AGTTGTTTAT | CTTCCAATAA | TAGGATAGCT | GAATCTATGA | TCTGATGTCG | AACCACGTGG | 1080
| TCAAAGATCC | TTAAAAAATT | GTTGTGTTGT | GCAATGACAA | CGAACCTTAA | CCCAAGGTTT | 1140
| TTAAGCACTT | CACACATGAA | ACCGATTTAC | CGCACTTTAA | CTACTTTAAT | AAGCACTACT | 1200
| CATATTCCCT | AGAATGTCTA | AATGTCGTTT | TAGTTATAGA | CGTTGTAAAT | AAAGACTATG | 1260
| ATGAGTTAAA | CTATAACTAG | CACATTTCAA | TTCACTAACA | CGGTTTGCAC | TTCGGTATCT | 1320
| TCGATAACTA | TTCTAGATGT | TTTTTTTTAT | ATTATTTTGA | GTATAAGTTT | GTCCTCTTAA | 1380
| CCTTTGTATG | AACCGATCTC | CCCCTAAATA | ATATCGTAAA | TCTGGTTACT | AATCATTACT | 1440
| CAATCGTTTT | AACATATATT | TACTCAATCA | TTCTAGATTA | GCATGCCAAC | TAAACTTTAG | 1500
| AGAAAATTTA | GGTAGACATT | CTCCCCCCCG | ATCTTTCTCT | TCTAGTCATC | TCCTTTTATT | 1560
| TTCTAGTTTT | GCATTATAAC | TTCCACCATA | ACTTTTACAT | TTATTAAGTT | GTTATTAATT | 1620
| CTGTTGAAGT | AGACAAGTAA | AACGATACGA | AGTCAAACGG | ATACTAGTAT | AAGTTAGTGT | 1680
| ACAATTACTT | TACGAATCAT | CTTAACGTTG | ACGTACCACA | TTAGAAGTTT | TATTTCTCTC | 1740
| TTGGGAAACC | TTACTTCAAT | ACTTTGAATT | AGGTTGATCA | CACCGAAGCC | AACGATACCT | 1800
| AGTTTCTCAA | AGTCGTGCTT | ACAATCCCCT | ACAAGAACGT | CAATGAGTTA | CACAATTATA | 1860
| TAGTCCAAGA | TCACAAAAAT | AAGTTTAAG | GTACGCACAA | AATCCCAGTT | GTTGATGTAC | 1920
| AATGTCAGCA | GGAGAATATA | GTAAATTTCG | TGATCTTTTG | AGTTGATTGA | TATAACTTCC | 1980
| TGTTGAACCC | CTTTTATTAC | TTGATAATCA | TCTTGCTTTC | GATTAACTTG | GTACATGTCG | 2040
| ATTGGTATTT | TCTATAAAAT | TTAAACCACG | TCTAATACAT | ATAAAACTTT | TGATACGTAT | 2100
| ACAAGCTTTC | CATGGAGAAT | TACTTTAACT | TTACTAGTCA | CGTATACATC | TAGAATTATA | 2160
| ATGTAATGAA | CTCCTAGCAC | TTAAAAATGG | TGATCTCCAT | ATATGAGCTC | GTCTCAATCT | 2220
| TCTATGTCCT | GATAACCTGA | TATCACTCTA | AGTTGCATCT | TTAGTTGATG | TACGTGAATT | 2280
| CAAAATACTA | TAACTGTCAC | AACATTTTCA | ACTATTATTA | CAACATTAAT | ACTCCCCGTA | 2340
| ACGTTTAAAA | AAGGTTCCTG | AACCTCTACA | ACCTCGCCCT | AAACCTTTTC | AACAAAACCC | 2400
| ACGACGTTTA | CGACAATAAC | GTTGACAAAG | ACCTCACAGG | AGCAAAGAAT | TATTGGGTAA | 2460
| ACCCCGCGAT | CGGCAACCTA | ACGACTAAAA | TCGACCTGAT | AAACGTCGCA | AAAACCGAAT | 2520
| ATCTATACAA | AGATTTGAAT | TCAGTTTAGG | TTACTTTCGT | GATATGGGTC | ATTGATGTTT | 2580
| TTTAAATTTT | CTTTCACAAT | TCTTACCATT | AAGACCTTTA | TTATCACTAC | CTCTTCTTTT | 2640
| ACTACTATTA | TAGCTACTTC | TTTTCGAAGT | TGTTCGATTT | CTTTACTAAT | TTATATACAG | 2700
| AGATCAAAGA | CGATACCTTG | TCGTCCTTGT | ATTTCGATAA | TTTTTTTTAT | CACCGGGACG | 2760
| GGAAGATCGT | TCAGTGTAAT | GTTTGGATAG | AGAATTTGTA | GCACCAGGTT | TTATGTTTGC | 2820
| AAACTTTTTA | CATTTACTTT | TACTTTCATT | TCAAATTGGG | CCCATGGCTC | GAGCTTAAGA | 2880
| AAAATAACTA | ATTGATCAGT | TTACTCATAT | ATATTAACTT | TTTCATTTTA | TATTTAGTAT | 2940
| ATTATTACTT | T | | | | | 2951

( 2 ) INFORMATION FOR SEQ ID NO:106:

( i ) SEQUENCE CHARACTERISTICS:
    ( A ) LENGTH: 879 amino acids
    ( B ) TYPE: amino acid
    ( C ) STRANDEDNESS: single
    ( D ) TOPOLOGY: linear ( i i ) MOLECULE TYPE: peptide ( v ) FRAGMENT TYPE: internal ( x i ) SEQUENCE DESCRIPTION: SEQ ID NO:106:

| Met | Phe | Ser | Leu | Tyr | Leu | Tyr | Ile | Phe | Phe | Ile | Ile | Tyr | Thr | Leu | Ile |
|---|---|---|---|---|---|---|---|---|---|---|---|---|---|---|---|
| 1 | | | | 5 | | | | | 10 | | | | | 15 | |
| Ile | Cys | Asp | Pro | Thr | Thr | Pro | Glu | Ser | Thr | Ile | Asn | Pro | Leu | Asn | His |
| | | | 20 | | | | | 25 | | | | | 30 | | |
| His | Asn | Leu | Ser | Thr | Pro | Lys | Pro | Thr | Ser | Asp | Asp | Ile | Arg | Glu | Ile |
| | | | 35 | | | | 40 | | | | | 45 | | | |
| Leu | Arg | Glu | Ser | Gln | Ile | Glu | Ser | Asp | Asp | Thr | Ser | Thr | Phe | Tyr | Met |
| | | 50 | | | | | 55 | | | | | 60 | | | |
| Cys | Pro | Pro | Pro | Ser | Gly | Ser | Thr | Leu | Val | Arg | Leu | Glu | Pro | Pro | Arg |
| 65 | | | | | 70 | | | | | 75 | | | | | 80 |
| Ala | Cys | Pro | Asn | Tyr | Lys | Leu | Gly | Lys | Asn | Phe | Thr | Glu | Gly | Ile | Ala |
| | | | | 85 | | | | | 90 | | | | | 95 | |
| Val | Ile | Phe | Lys | Glu | Asn | Ile | Ser | Pro | Tyr | Lys | Phe | Lys | Ala | Asn | Ile |
| | | | 100 | | | | | 105 | | | | | 110 | | |
| Tyr | Tyr | Lys | Asn | Ile | Ile | Ile | Thr | Thr | Val | Trp | Ser | Gly | Ser | Thr | Tyr |
| | | 115 | | | | | 120 | | | | | 125 | | | |
| Ala | Val | Ile | Thr | Asn | Arg | Tyr | Thr | Asp | Arg | Val | Pro | Ile | Gly | Val | Pro |
| | | 130 | | | | 135 | | | | | 140 | | | | |
| Glu | Ile | Thr | Glu | Leu | Ile | Asp | Arg | Arg | Gly | Met | Cys | Leu | Ser | Lys | Ala |
| 145 | | | | | 150 | | | | | 155 | | | | | 160 |
| Asp | Tyr | Ile | Arg | Asn | Asn | Tyr | Glu | Phe | Thr | Ala | Phe | Asp | Lys | Asp | Glu |
| | | | | 165 | | | | | 170 | | | | | 175 | |
| Asp | Pro | Arg | Glu | Val | His | Leu | Lys | Pro | Ser | Lys | Phe | Asn | Thr | Pro | Gly |
| | | | 180 | | | | | 185 | | | | | 190 | | |
| Ser | Arg | Gly | Trp | His | Thr | Val | Asn | Asp | Thr | Tyr | Thr | Lys | Ile | Gly | Gly |
| | | 195 | | | | | 200 | | | | | 205 | | | |
| Ser | Gly | Phe | Tyr | His | Ser | Gly | Thr | Ser | Val | Asn | Cys | Ile | Val | Glu | Glu |
| | | 210 | | | | 215 | | | | | 220 | | | | |
| Val | Asp | Ala | Arg | Ser | Val | Tyr | Pro | Tyr | Asp | Ser | Phe | Ala | Ile | Ser | Thr |
| 225 | | | | | 230 | | | | | 235 | | | | | 240 |
| Gly | Asp | Ile | Ile | His | Met | Ser | Pro | Phe | Phe | Gly | Leu | Arg | Asp | Gly | Ala |
| | | | | 245 | | | | | 250 | | | | | 255 | |
| His | Thr | Glu | Tyr | Ile | Ser | Tyr | Ser | Thr | Asp | Arg | Phe | Gln | Gln | Ile | Glu |
| | | | 260 | | | | | 265 | | | | | 270 | | |
| Gly | Tyr | Tyr | Pro | Ile | Asp | Leu | Asp | Thr | Arg | Leu | Gln | Leu | Gly | Ala | Pro |
| | | 275 | | | | | 280 | | | | | 285 | | | |
| Val | Ser | Arg | Asn | Phe | Leu | Thr | Thr | Gln | His | Val | Thr | Val | Ala | Trp | Asn |
| | | 290 | | | | | 295 | | | | | 300 | | | |
| Trp | Val | Pro | Lys | Ile | Arg | Glu | Val | Cys | Thr | Leu | Ala | Lys | Trp | Arg | Glu |
| 305 | | | | | 310 | | | | | 315 | | | | | 320 |
| Ile | Asp | Glu | Ile | Ile | Arg | Asp | Glu | Tyr | Lys | Gly | Ser | Tyr | Arg | Phe | Thr |
| | | | | 325 | | | | | 330 | | | | | 335 | |
| Ala | Lys | Ser | Ile | Ser | Ala | Thr | Phe | Ile | Ser | Asp | Thr | Thr | Gln | Phe | Asp |
| | | | 340 | | | | | 345 | | | | | 350 | | |
| Ile | Asp | Arg | Val | Lys | Leu | Ser | Asp | Cys | Ala | Lys | Arg | Glu | Ala | Ile | Glu |
| | | 355 | | | | | 360 | | | | | 365 | | | |
| Ala | Ile | Asp | Lys | Ile | Tyr | Lys | Lys | Lys | Tyr | Asn | Lys | Thr | His | Ile | Gln |
| | | 370 | | | | | 375 | | | | | 380 | | | |
| Thr | Gly | Glu | Leu | Glu | Thr | Tyr | Leu | Ala | Arg | Gly | Gly | Phe | Ile | Ile | Ala |
| 385 | | | | | 390 | | | | | 395 | | | | | 400 |

```
Phe Arg Pro Met Ile Ser Asn Glu Leu Ala Lys Leu Tyr Ile Asn Glu
            405                 410                 415
Leu Val Arg Ser Asn Arg Thr Val Asp Leu Lys Ser Leu Leu Asn Pro
            420                 425                 430
Ser Val Arg Gly Gly Ala Arg Lys Arg Arg Ser Val Glu Glu Asn Lys
            435                 440                 445
Arg Ser Lys Arg Asn Ile Glu Gly Gly Ile Glu Asn Val Asn Asn Ser
450                         455                 460
Thr Ile Ile Lys Thr Thr Ser Ser Val His Phe Ala Met Leu Gln Phe
465                 470                 475                 480
Ala Tyr Asp His Ile Gln Ser His Val Asn Glu Met Leu Ser Arg Ile
                485                 490                 495
Ala Thr Ala Trp Cys Asn Leu Gln Asn Lys Glu Arg Thr Leu Trp Asn
            500                 505                 510
Glu Val Met Lys Leu Asn Pro Thr Ser Val Ala Ser Val Ala Met Asp
            515                 520                 525
Gln Arg Val Ser Ala Arg Met Leu Gly Asp Val Leu Ala Val Thr Gln
    530                 535                 540
Cys Val Asn Ile Ser Gly Ser Ser Val Phe Ile Gln Asn Ser Met Arg
545                 550                 555                 560
Val Leu Gly Ser Thr Thr Thr Cys Tyr Ser Arg Pro Leu Ile Ser Phe
            565                 570                 575
Lys Ala Leu Glu Asn Ser Thr Asn Tyr Ile Glu Gly Gln Leu Gly Glu
            580                 585                 590
Asn Asn Glu Leu Leu Val Glu Arg Lys Leu Ile Glu Pro Cys Thr Ala
            595                 600                 605
Asn His Lys Arg Tyr Phe Lys Phe Gly Ala Asp Tyr Val Tyr Phe Glu
    610                 615                 620
Asn Tyr Ala Tyr Val Arg Lys Val Pro Leu Asn Glu Ile Glu Met Ile
625                 630                 635                 640
Ser Ala Tyr Val Asp Leu Asn Ile Thr Leu Leu Glu Asp Arg Glu Phe
                645                 650                 655
Leu Pro Leu Glu Val Tyr Thr Arg Ala Glu Leu Glu Asp Thr Gly Leu
            660                 665                 670
Leu Asp Tyr Ser Glu Ile Gln Arg Arg Asn Gln Leu His Ala Leu Lys
        675                 680                 685
Phe Tyr Asp Ile Asp Ser Val Val Lys Val Asp Asn Asn Val Val Ile
    690                 695                 700
Met Arg Gly Ile Ala Asn Phe Phe Gln Gly Leu Gly Asp Val Gly Ala
705                 710                 715                 720
Gly Phe Gly Lys Val Val Leu Gly Ala Ala Asn Ala Val Ile Ala Thr
            725                 730                 735
Val Ser Gly Val Ser Ser Phe Leu Asn Asn Pro Phe Gly Ala Leu Ala
            740                 745                 750
Val Gly Leu Leu Ile Leu Ala Gly Leu Phe Ala Ala Phe Leu Ala Tyr
        755                 760                 765
Arg Tyr Val Ser Lys Leu Lys Ser Asn Pro Met Lys Ala Leu Tyr Pro
    770                 775                 780
Val Thr Thr Lys Asn Leu Lys Glu Ser Val Lys Asn Gly Asn Ser Gly
785                 790                 795                 800
Asn Asn Ser Asp Gly Glu Glu Asn Asp Asp Asn Ile Asp Glu Glu Lys
            805                 810                 815
Leu Gln Gln Ala Lys Glu Met Ile Lys Tyr Met Ser Leu Val Ser Ala
        820                 825                 830
```

```
Met Glu Gln Gln Glu His Lys Ala Ile Lys Lys Asn Ser Gly Pro Ala
        835                 840                 845
Leu Leu Ala Ser His Ile Thr Asn Leu Ser Leu Lys His Arg Gly Pro
        850                 855                 860
Lys Tyr Lys Arg Leu Lys Asn Val Asn Glu Asn Glu Ser Lys Val
        865             870                 875
```

( 2 ) INFORMATION FOR SEQ ID NO:107:

( i ) SEQUENCE CHARACTERISTICS:
        ( A ) LENGTH: 1615 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:107:

```
GAGCTCGCGG CCGCCTATCA AAAGTCTTAA TGAGTTAGGT GTAGATAGTA TAGATATTAC      60
TACAAAGGTA TTCATATTTC CTATCAATTC TAAAGTAGAT GATATTAATA ACTCAAAGAT     120
GATGATAGTA GATAATAGAT ACGCTCATAT AATGACTGCA AATTTGGACG GTTCACATTT     180
TAATCATCAC GCGTTCATAA GTTCAACTG  CATAGATCAA AATCTCACTA AAAGATAGC      240
CGATGTATTT GAGAGAGATT GGACATCTAA CTACGCTAAA GAAATTACAG TTATAAATAA     300
TACATAATGG ATTTGTTAT  CATCAGTTAT ATTAACATA  AGTACAATAA AAAGTATTAA     360
ATAAAAATAC TTACTTACGA AAAAATGACT AATTAGCTAT AAAACCCGG  GCTGCAGCTC     420
GAGGAATTCT TTTTATTGAT TAACTAGTCA AATGAGTATA TATAATTGAA AAAGTAAAAT     480
ATAAATCATA TAATAATGAA ACGAAATATC AGTAATAGAC AGGAACTGGC AGATTCTTCT     540
TCTAATGAAG TAAGTACTGC TAAATCTCCA AAATTAGATA AAATGATAC  AGCAAATACA     600
GCTTCATTCA ACGAATTACC TTTTAATTTT TTCAGACACA CCTTATTACA AACTAACTAA     660
GTCAGATGAT GAGAAAGTAA ATATAAATTT AACTTATGGG TATAATATAA TAAAGATTCA     720
TGATATTAAT AATTTACTTA ACGATGTTAA TAGACTTATT CCATCAACCC CTTCAAACCT     780
TTCTGGATAT TATAAAATAC CAGTTAATGA TATTAAAATA GATTGTTTAA GAGATGTAAA     840
TAATTATTTG GAGGTAAAGG ATATAAAATT AGTCTATCTT TCACATGGAA ATGAATTACC     900
TAATATTAAT AATTATGATA GGAATTTTTT AGGATTTACA GCTGTTATAT GTATCAACAA     960
TACAGGCAGA TCTATGGTTA TGGTAAAACA CTGTAACGGG AAGCAGCATT CTATGGTAAC    1020
TGGCCTATGT TTAATAGCCA GATCATTTTA CTCTATAAAC ATTTTACCAC AAATAATAGG    1080
ATCCTCTAGA TATTTAATAT TATATCTAAC AACAACAAAA AAATTTAACG ATGTATGGCC    1140
AGAAGTATTT TCTACTAATA AAGATAAAGA TAGTCTATCT TATCTACAAG ATATGAAAGA    1200
AGATAATCAT TTAGTAGTAG CTACTAATAT GGAAAGAAAT GTATACAAAA ACGTGGAAGC    1260
TTTTATATTA AATAGCATAT TACTAGAAGA TTTAAAATCT AGACTTAGTA TAACAAAACA    1320
GTTAAATGCC AATATCGATT CTATATTTCA TCATAACAGT AGTACATTAA TCAGTGATAT    1380
ACTGAAACGA TCTACAGACT CAACTATGCA AGGAATAAGC AATATGCCAA TTATGTCTAA    1440
TATTTTAACT TTAGAACTAA AACGTTCTAC CAATACTAAA AATAGGATAC GTGATAGGCT    1500
GTTAAAAGCT GCAATAAATA GTAAGGATGT AGAAGAAATA CTTTGTTCTA TACCTTCGGA    1560
GGAAAGAACT TTAGAACAAC TTAAGTTTAA TCAAACTTGT ATTTATGAAG GTACC         1615
```

( 2 ) INFORMATION FOR SEQ ID NO:108:

( i ) SEQUENCE CHARACTERISTICS:
    ( A ) LENGTH: 1615 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:108:

```
CTCGAGCGCC GGCGGATAGT TTTCAGAATT ACTCAATCCA CATCTATCAT ATCTATAATG      60
ATGTTTCCAT AAGTATAAAG GATAGTTAAG ATTTCATCTA CTATAATTAT TGAGTTTCTA     120
CTACTATCAT CTATTATCTA TGCGAGTATA TTACTGACGT TTAAACCTGC CAAGTGTAAA     180
ATTAGTAGTG CGCAAGTATT CAAAGTTGAC GTATCTAGTT TTAGAGTGAT TTTTCTATCG     240
GCTACATAAA CTCTCTCTAA CCTGTAGATT GATGCGATTT CTTAATGTC  AATATTTATT     300
ATGTATTACC TAAAACAATA GTAGTCAATA TAAATTGTAT TCATGTTATT TTTCATAATT     360
TATTTTTATG AATGAATGCT TTTTACTGA  TTAATCGATA TTTTGGGCC  CGACGTCGAG     420
CTCCTTAAGA AAAATAACTA ATTGATCAGT TTACTCATAT ATATTAACTT TTTCATTTTA     480
TATTTAGTAT ATTATTACTT TGCTTTATAG TCATTATCTG TCCTTGACCG TCTAAGAAGA     540
AGATTACTTC ATTCATGACG ATTTAGAGGT TTAATCTAT  TTTTACTATG TCGTTTATGT     600
CGAAGTAAGT TGCTTAATGG AAAATTAAAA AAGTCTGTGT GGAATAATGT TTGATTGATT     660
CAGTCTACTA CTCTTTCATT TATATTTAAA TTGAATACCC ATATTATATT ATTTCTAAGT     720
ACTATAATTA TTAAATGAAT TGCTACAATT ATCTGAATAA GGTAGTTGGG GAAGTTTGGA     780
AAGACCTATA ATATTTTATG GTCAATTACT ATAATTTTAT CTAACAAATT CTCTACATTT     840
ATTAATAAAC CTCCATTTCC TATATTTTAA TCAGATAGAA AGTGTACCTT TACTTAATGG     900
ATTATAATTA TTAATACTAT CCTTAAAAAA TCCTAAATGT CGACAATATA CATAGTTGTT     960
ATGTCCGTCT AGATACCAAT ACCATTTTGT GACATTGCCC TTCGTCGTAA GATACCATTG    1020
ACCGGATACA AATTATCGGT CTAGTAAAAT GAGATATTTG TAAAATGGTG TTTATTATCC    1080
TAGGAGATCT ATAAATTATA ATATAGATTG TTGTTGTTTT TTTAAATTGC TACATACCGG    1140
TCTTCATAAA AGATGATTAT TTCTATTTCT ATCAGATAGA ATAGATGTTC TATACTTTCT    1200
TCTATTAGTA AATCATCATC GATGATTATA CCTTTCTTTA CATATGTTTT TGCACCTTCG    1260
AAAATATAAT TTATCGTATA ATGATCTTCT AAATTTTAGA TCTGAATCAT ATTGTTTTGT    1320
CAATTTACGG TTATAGCTAA GATATAAAGT AGTATTGTCA TCATGTAATT AGTCACTATA    1380
TGACTTTGCT AGATGTCTGA GTTGATACGT TCCTTATTCG TTATACGGTT AATACAGATT    1440
ATAAAATTGA AATCTTGATT TTGCAAGATG GTTATGATTT TTATCCTATG CACTATCCGA    1500
CAATTTTCGA CGTTATTTAT CATTCCTACA TCTTCTTTAT GAAACAAGAT ATGGAAGCCT    1560
CCTTTCTTGA AATCTTGTTG AATTCAAATT AGTTTGAACA TAAATACTTC CATGG         1615
```

( 2 ) INFORMATION FOR SEQ ID NO:109:

( i ) SEQUENCE CHARACTERISTICS:
        ( A ) LENGTH: 112 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:109:

```
CGATGTTAAT AAGTATTACC ACAATAATTG GTGGAGCCAT TTCGTTATA  GTATTGATTT      60
TCATAACAGC TTTATGTTTC TATTGTTCAA AAAATAATAA GATCTAACTG CA             112
```

( 2 ) INFORMATION FOR SEQ ID NO:110:

( i ) SEQUENCE CHARACTERISTICS:
        ( A ) LENGTH: 106 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:110:

```
GTTAGATCTT ATTATTTTTT GAACAATAGA AACATAAAGC TGTTATGAAA ATCAATACTA      60
TAACGAAAAT GGCTCCACCA ATTATTGTGG TAATACTTAT TAACAT                   106
```

( 2 ) INFORMATION FOR SEQ ID NO:111:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:111:

```
CGTAGATTCC AATGGAAAGT                                                 20
```

( 2 ) INFORMATION FOR SEQ ID NO:112:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:112:

```
TTTTCGCGAT ATCCGTTAAG T                                               21
```

( 2 ) INFORMATION FOR SEQ ID NO:113:

( i ) SEQUENCE CHARACTERISTICS:
        ( A ) LENGTH: 93 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:113:

```
TTTTCGCGAT ATCCGTTAAG TTTGTATCGT AATGAGTTTT AAAAATTTCT ATCTAATATA     60
TGTAATTATA ATTTTCATAA ACTCGATAAT AAC                                  93
```

( 2 ) INFORMATION FOR SEQ ID NO:114:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:114:

```
TTTGTATACC TAATAAGAAA TCATTATAAA AGT                                  33
```

( 2 ) INFORMATION FOR SEQ ID NO:115:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:115:

```
CTTTTATAAT GATTTCTTAT TAGGTATACA AAATC                                35
```

( 2 ) INFORMATION FOR SEQ ID NO:116:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:116:

```
AATTTGCA                                                               8
```

( 2 ) INFORMATION FOR SEQ ID NO:117:

( i ) SEQUENCE CHARACTERISTICS:
        ( A ) LENGTH: 1760 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:117:

```
AGTACAATAA AAAGTATTAA ATAAAAATAC TTACTTACGA AAAAATGACT AATTAGCTAT      60
AAAAACCCGG GAAAGGATCC TGATCCTTTT TCTGGGTAAG TAATACGTCA AGGAGAAAAC     120
GAAACGATCT GTAGTTAGCG GCCAAACTCG AGGTCGACGG TATCGATAAG CTTGATTCTT     180
TATTCTATAC TTAAAAAGTG AAAATAAATA CAAAGGTTCT TGAGGGTTGT GTTAAATTGA     240
AAGCGAGAAA TAATCATAAA TTATTTCATT ATCGCGATAT CCGTTAAGTT TGTATCGTAA     300
TGAGTTTTAA AAATTTTTAT CTAATATATG TAATTATAAT TTTTATAAAC TCGATAATAA     360
CTTCGGCATC TACATCCAAA CCTTCAACAC CTACCATAAT TCCAACTTCA GCAAATGAAT     420
CACCTGCTTC CATAGATACA ACTATAACAA AACCTATATC TACAGAGGCA ATAATTTAA      480
AATCAGTAAG TACCTCAATT AAACCACCTA AAAACTTAAA AAAAAAATTA CTTAAATCTA     540
AATGTAGAGA TAATGTTATT TATAGGCCAT ATTTTAGTCA ATTAGAAATT AACTGTACTA     600
TAACTAAAAA GCAAATTTA AGTAATCCTT TAATTGAGTT ATGGTTTAAA GAACTTTCTA      660
CATATAATAA AACCAATGAA AATGTTGAAA GTTAAAAAC AGATATATCA AAAAATATTT      720
TATTATTTTC GACAAAAAAT AATAGTGATA ACTTTTATAA TGATTTTTTA TTAGGTATAC     780
AAAATCAACC AGTAAATTAT AAACTTTACG GTTCCCAATT TTATGATAAT GGAAACATAT     840
TACTAAATAT AAAGTCGGTT GACTTTAAAA CCTCTGGAAT ATATACTTGG AAACTATATA     900
ATTCAAATAA TGAAAGTATT TTTGAAACTT TTAAAATTCA AGTATATGCA TATCATTCCC     960
CAAATGTAAA CTTAAAATCA AACCCAAGTT TATATAATGA AAACTACAGC GCTATTTGTA    1020
CAATAGCAAA TTACTTTCCA TTGGAATCTA CGGAAATATT TTGGTTTAAC GATGGACAAC    1080
CTATTGATAA AAAATATATA GATGAAACTT ATAGTGTATG GATTGACGGT CTTATAACAC    1140
```

```
GCACTTCAAT ATTATCCCTT CCCTTTTCCG AAGCCATGGA AAGCCCCCCC AATTTGCGAT    1200

GTAATGTTGA ATGGTATAAA AATTCAAGG  CATCAAAAAA ATTTTCAAAT ACCGTTATTC    1260

CAAAAGTTTA CTATAAACCT TTTATATCTA TAAAATTTGA TAATGGTTTA GCTATTTGTG    1320

ATGCTAAATG TGTTTCCCGT GAAAATAATA AATTACAATG GTTAGTTAAA GATATACCTA    1380

TAAATGGTGA TGATATTATA AGCGGCCCCT GTTAAACCA  CCCTGGTTTG GTCAATATTC    1440

AAAATAAAAT AGATATATCG GATTATGATG AACCTGTTAC CTATAAATGT TCAATTATTG    1500

GTTATCCAAT AATTTTTCCC AACTTTTATG ATGAAAAGGT GTTGATGCA  TCGGATGAAA    1560

ATGTTAGTAA ATCGATGTTA ATAAGTATTA CCACAATAAT TGGTGGAGCC ATTTTGTTA    1620

TAGTATTGAT TTTTATAACA GCTTTATGTT TTATTGTTC  AAAAAATAAT AAGATCTAAC    1680

TGCAAATTCT TTTTATTGAT TAACTAGTCA AATGAGTATA TATAATTGAA AAAGTAAAAT    1740

ATAAATCATA TAATAATGAA                                               1760
```

( 2 ) INFORMATION FOR SEQ ID NO:118:

( i ) SEQUENCE CHARACTERISTICS:
        ( A ) LENGTH: 1760 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:118:

```
TCATGTTATT TTTCATAATT TATTTTTATG AATGAATGCT TTTTACTGA  TTAATCGATA      60

TTTTTGGGCC CTTTCCTAGG ACTAGGAAAA AGACCCATTC ATTATGCAGT TCCTCTTTTG     120

CTTGCTAGA  CATCAATCGC CGGTTTGAGC TCCAGCTGCC ATAGCTATTC GAACTAAGAA     180

ATAAGATATG AATTTTCAC  TTTTATTTAT GTTCCAAGA  ACTCCCAACA CAATTTAACT     240

TTCGCTCTTT ATTAGTATTT AATAAAGTAA TAGCGCTATA GGCAATTCAA ACATAGCATT     300

ACTCAAAATT TTTAAAAATA GATTATATAC ATTAATATTA AAAATATTTG AGCTATTATT     360

GAAGCCGTAG ATGTAGGTTT GGAAGTTGTG GATGGTATTA AGGTTGAAGT CGTTTACTTA     420

GTGGACGAAG GTATCTATGT TGATATTGTT TTGGATATAG ATGTCTCCGT TTATTAAATT     480

TTAGTCATTC ATGGAGTTAA TTTGGTGGAT TTTTGAATTT TTTTTTAAT  GAATTTAGAT     540

TTACATCTCT ATTACAATAA ATATCCGGTA TAAAATCAGT TAATCTTTAA TTGACATGAT     600

ATTGATTTTT CGTTTTAAAT TCATTAGGAA ATTAACTCAA TACCAAATTT CTTGAAAGAT     660

GTATATTATT TTGGTTACTT TTACAACTTT CAAATTTTTG TCTATATAGT TTTTTATAAA     720

ATAATAAAAG CTGTTTTTTA TTATCACTAT TGAAAATATT ACTAAAAAAT AATCCATATG     780

TTTTAGTTGG TCATTTAATA TTTGAAATGC CAAGGGTTAA AATACTATTA CCTTTGTATA     840

ATGATTTATA TTTCAGCCAA CTGAAATTTT GGAGACCTTA TATATGAACC TTTGATATAT     900

TAAGTTTATT ACTTCATAA  AAACTTTGAA AATTTTAAGT TCATATACGT ATAGTAAGGG     960

GTTTACATTT GAATTTTAGT TTGGGTTCAA ATATATTACT TTTGATGTCG CGATAAACAT    1020

GTTATCGTTT AATGAAAGGT AACCTAGAT  GCCTTATAA  AACCAAATTG CTACCTGTTG    1080

GATAACTATT TTTATATAT  CTACTTTGAA TATCACATAC CTAACTGCCA GAATATTGTG    1140

CGTGAAGTTA TAATAGGGAA GGGAAAAGGC TTCGGTACCT TTCGGGGGGG TTAAACGCTA    1200

CATTACAACT TACCATATTT TTAAGTTTCC GTAGTTTTTT TAAAAGTTTA TGGCAATAAG    1260

GTTTTCAAAT GATATTTGGA AAATATAGAT ATTTTAAACT ATTACCAAAT CGATAAACAC    1320
```

```
TACGATTTAC ACAAAGGGCA CTTTTATTAT TTAATGTTAC CAATCAATTT CTATATGGAT    1380

ATTTACCACT ACTATAATAT TCGCCGGGGA CAAATTTGGT GGGACCAAAC CAGTTATAAG    1440

TTTTATTTTA TCTATATAGC CTAATACTAC TTGGACAATG GATATTTACA AGTTAATAAC    1500

CAATAGGTTA TTAAAAAGGG TTGAAAATAC TACTTTTCCA CAAACTACGT AGCCTACTTT    1560

TACAATCATT TAGCTACAAT TATTCATAAT GGTGTTATTA ACCACCTCGG TAAAAACAAT    1620

ATCATAACTA AAATATTGT CGAAATACAA AATAACAAG TTTTTATTA TTCTAGATTG       1680

ACGTTAAGA AAAATAACTA ATTGATCAGT TTACTCATAT ATATTAACTT TTTCATTTTA     1740

TATTTAGTAT ATTATTACTT                                                1760
```

(2) INFORMATION FOR SEQ ID NO:119:

(i) SEQUENCE CHARACTERISTICS:
        (A) LENGTH: 319 amino acids
        (B) TYPE: amino acid
        (C) STRANDEDNESS: single
        (D) TOPOLOGY: linear (ii) MOLECULE TYPE: peptide (v) FRAGMENT TYPE: internal (xi) SEQUENCE DESCRIPTION: SEQ ID NO:119:

```
Leu Leu Phe Ser Thr Lys Asn Asn Ser Asp Asn Phe Tyr Asn Asp Phe
 1               5                  10                  15

Leu Leu Gly Ile Gln Asn Gln Pro Val Asn Tyr Lys Leu Tyr Gly Ser
            20                  25                  30

Gln Phe Tyr Asp Asn Gly Asn Ile Leu Asn Ile Lys Ser Val Asp
                35                  40                  45

Phe Lys Thr Ser Gly Ile Tyr Thr Trp Lys Leu Tyr Asn Ser Asn Asn
    50                  55                  60

Glu Ser Ile Phe Glu Thr Phe Lys Ile Gln Val Tyr Ala Tyr His Ser
65                  70                  75                  80

Pro Asn Val Asn Leu Lys Ser Asn Pro Ser Leu Tyr Asn Glu Asn Tyr
                85                  90                  95

Ser Ala Ile Cys Thr Ile Ala Asn Tyr Phe Pro Leu Glu Ser Thr Glu
               100                 105                 110

Ile Phe Trp Phe Asn Asp Gly Gln Pro Ile Asp Lys Lys Tyr Ile Asp
           115                 120                 125

Glu Thr Tyr Ser Val Trp Ile Asp Gly Leu Ile Thr Arg Thr Ser Ile
    130                 135                 140

Leu Ser Leu Pro Phe Ser Glu Ala Met Glu Ser Pro Pro Asn Leu Arg
145                 150                 155                 160

Cys Asn Val Glu Trp Tyr Lys Asn Ser Lys Ala Ser Lys Lys Phe Ser
                165                 170                 175

Asn Thr Val Ile Pro Lys Val Tyr Tyr Lys Pro Phe Ile Ser Ile Lys
                180                 185                 190

Phe Asp Asn Gly Leu Ala Ile Cys Asp Ala Lys Cys Val Ser Arg Glu
            195                 200                 205

Asn Asn Lys Leu Gln Trp Leu Val Lys Asp Ile Pro Ile Asn Gly Asp
    210                 215                 220

Asp Ile Ile Ser Gly Pro Cys Leu Asn His Pro Gly Leu Val Asn Ile
225                 230                 235                 240

Gln Asn Lys Ile Asp Ile Ser Asp Tyr Asp Glu Pro Val Thr Tyr Lys
                245                 250                 255

Cys Ser Ile Ile Gly Tyr Pro Ile Ile Phe Pro Asn Phe Tyr Asp Glu
```

|       |       | 260   |       |       |       | 265   |       |       |       | 270   |       |       |       |
|-------|-------|-------|-------|-------|-------|-------|-------|-------|-------|-------|-------|-------|-------|
| Lys   | Val   | Phe   | Asp   | Ala   | Ser   | Asp   | Glu   | Asn   | Val   | Ser   | Lys   | Ser   | Met   | Leu | Ile |
|       |       | 275   |       |       |       |       | 280   |       |       |       | 285   |       |       |
| Ser   | Ile   | Thr   | Thr   | Ile   | Ile   | Gly   | Gly   | Ala   | Ile   | Phe   | Val   | Ile   | Val   | Leu | Ile |
|       | 290   |       |       |       |       | 295   |       |       |       |       | 300   |       |       |
| Phe   | Ile   | Thr   | Ala   | Leu   | Cys   | Phe   | Tyr   | Cys   | Ser   | Lys   | Asn   | Asn   | Lys   | Ile |
| 305   |       |       |       |       | 310   |       |       |       |       | 315   |       |       |       |

( 2 ) INFORMATION FOR SEQ ID NO:120:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:120:

CGATATCCGT TAAGTTTGTA TCGTAATGAT TAAACTTCTA TTTATCTTAT TTTATTTTAA    60

CCCAATAA    68

( 2 ) INFORMATION FOR SEQ ID NO:121:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:121:

TTGGGTTAAA ATAAATAAG ATAAATAGAA GTTAATCAT TACGATACAA ACTTAACGGA    60

TATCG    65

( 2 ) INFORMATION FOR SEQ ID NO:122:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:122:

TTGAATTCCT AAACATTTGT TGTTAATTTT TTATAATTAT TATATATTTT TTGTCTTTTA    60

TAAACAAAGA AT    72

( 2 ) INFORMATION FOR SEQ ID NO:123:

( i ) SEQUENCE CHARACTERISTICS:
        ( A ) LENGTH: 101 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:123:

TTAGATCTGT AGGAGCATCA AAAGTTGACG ATGAACTTTT CTATCTAAAT AGAGCTGGTC    60

CCCAAACCCT GCTTAAATAT TATGTTATTA AAGATTCTA T    101

( 2 ) INFORMATION FOR SEQ ID NO:124:

( i ) SEQUENCE CHARACTERISTICS:
    ( A ) LENGTH: 110 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:124:

```
TTAGATCTAG ATTCCTTACA CCATTCCATA AAAGTTGGTT CAAATTTATC TTCTTTAGAG      60
AAATAACAAG TTTCTCGTGG TAATTGAACC ATAAAATCAG TATAGAAAAC                110
```

( 2 ) INFORMATION FOR SEQ ID NO:125:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:125:

```
TATTTTGATT GTGATCC                                                    17
```

( 2 ) INFORMATION FOR SEQ ID NO:126:

( i ) SEQUENCE CHARACTERISTICS:
    ( A ) LENGTH: 1415 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:126:

```
AGTACAATAA AAAGTATTAA ATAAAAATAC TTACTTACGA AAAAATGACT AATTAGCTAT      60
AAAAACCCGG GAAAGGATCC TGATCCTTTT TCTGGGTAAG TAATACGTCA AGGAGAAAAC     120
GAAACGATCT GTAGTTAGCG GCCAAACTCG AGGTCGACGG TATCGATAAG CTTGATTCTT     180
TATTCTATAC TTAAAAAGTG AAAATAAATA CAAAGGTTCT TGAGGGTTGT GTTAAATTGA     240
AAGCGAGAAA TAATCATAAA TTATTTCATT ATCGCGATAT CCGTTAAGTT TGTATCGTAA     300
TGATTAAACT TCTATTTATC TTATTTTATT TTAACCCAAT AACTGGATAT AAATGGGTAG     360
ACCCTCCTCG TAGGTATAAT TACACCGTTT TAAGAATGAT TCCAGATATT CCAAATCCAA     420
TGGATCCTTC TAAAAACGCT GAAGTTCGGT ATGTAACTTC TACTGACCCA TGTGATATGG     480
TTGCTTTGAT TTCTAATCCA AATATAGAAT CTACAATTAA AACGATTCAA TTTGTGCAAA     540
AGAAAAAATT TTACAATGCA TCTCTTAGTT GGTTTAAAGT TGGAGATGAT TGTACATATC     600
CAATATATTT AATTCAATAT TTTGATTGTG ATCCTCAAAG AGAATTTGGC ATATGTTTAA     660
AAAGATCTCC AGATTTTTGG AAACCATCGT TAGTTGGTTA CACATTTTTA ACTGATGATG     720
AATTGGGATT AGTTTTAGCT GCCCCCGCTC CATTTAATCA AGGTCAATAT AGACGGGTTA     780
TTCAAATTGA AAATGAAGTT TTTTATACTG ATTTTATGGT TCAATTACCA CGAGAAACTT     840
GTTATTTTTC TAAAGAAGAT AAATTTGAAC CAACTTTTAT GGAATGGTGT AAGGAATCTA     900
GATCTGTAGG AGCATCAAAA GTTGACGATG AACTTTTTTA TCTAAATAGA GCTGGTCCCC     960
AAACCCTGCT TAAATATTAT GTTATTAAAG ATTTTTATAG ACTTAACGGT AGAGAACCTC    1020
CAATAAAATT TAAAGAAGCT CTTAGATACG ATATACCATA TAAAGTGAAT GATAAATTTG    1080
```

```
ATGATGAATT  ACCATCGAGG  CCACATATTA  GTAATACTAT  TAATAAAACT  ATTAAAGAAA    1140

TTGTAAATCT  TGAAGATTAT  TTTAAAAATA  CAAATGTTAT  AGATACTACT  ACCCCAACAC    1200

CAATAAATAA  TACCCCAAAA  AATATAACCG  TGGGAATTGT  TATAATTATA  TTAATAATAC    1260

TATTTATAAT  TGGATTTTTT  GTTTATAAAA  GACAAAAAAT  ATATAATAAT  TATAAAAAAT    1320

TAACAACAAA  TGTTTAGGAA  TTCTTTTTAT  TGATTAACTA  GTCAAATGAG  TATATATAAT    1380

TGAAAAAGTA  AAATATAAAT  CATATAATAA  TGAAA                                1415
```

( 2 ) INFORMATION FOR SEQ ID NO:127:

( i ) SEQUENCE CHARACTERISTICS:
        ( A ) LENGTH: 1415 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:127:

```
TCATGTTATT  TTTCATAATT  TATTTTTATG  AATGAATGCT  TTTTTACTGA  TTAATCGATA      60

TTTTTGGGCC  CTTTCCTAGG  ACTAGGAAAA  AGACCCATTC  ATTATGCAGT  TCCTCTTTTG     120

CTTTGCTAGA  CATCAATCGC  CGGTTGAGC   TCCAGCTGCC  ATAGCTATTC  GAACTAAGAA    180

ATAAGATATG  AATTTTTCAC  TTTTATTTAT  GTTCCAAGA   ACTCCCAACA  CAATTTAACT    240

TTCGCTCTTT  ATTAGTATTT  AATAAAGTAA  TAGCGCTATA  GGCAATTCAA  ACATAGCATT    300

ACTAATTTGA  AGATAAATAG  AATAAAATAA  AATTGGGTTA  TTGACCTATA  TTTACCCATC    360

TGGGAGGAGC  ATCCATATTA  ATGTGGCAAA  ATTCTTACTA  AGGTCTATAA  GGTTTAGGTT    420

ACCTAGGAAG  ATTTTTGCGA  CTTCAAGCCA  TACATTGAAG  ATGACTGGGT  ACACTATACC    480

AACGAAACTA  AAGATTAGGT  TTATATCTTA  GATGTTAATT  TTGCTAAGTT  AAACACGTTT    540

TCTTTTTTAA  AATGTTACGT  AGAGAATCAA  CCAAATTTCA  ACCTCTACTA  ACATGTATAG    600

GTTATATAAA  TTAAGTTATA  AAACTAACAC  TAGGAGTTTC  TCTTAAACCG  TATACAAATT    660

TTTCTAGAGG  TCTAAAAACC  TTTGGTAGCA  ATCAACCAAT  GTGTAAAAAT  TGACTACTAC    720

TTAACCCTAA  TCAAAATCGA  CGGGGGCGAG  GTAAATTAGT  TCCAGTTATA  TCTGCCCAAT    780

AAGTTTAACT  TTTACTTCAA  AAAATATGAC  TAAAATACCA  AGTAATGGT   GCTCTTTGAA    840

CAATAAAAAG  ATTTCTTCTA  TTTAAACTTG  GTTGAAAATA  CCTTACCACA  TTCCTTAGAT    900

CTAGACATCC  TCGTAGTTTT  CAACTGCTAC  TTGAAAAAAT  AGATTTATCT  CGACCAGGGG    960

TTTGGGACGA  ATTTATAATA  CAATAATTTC  TAAAAATATC  TGAATTGCCA  TCTCTTGGAG   1020

GTTATTTAA   ATTTCTTCGA  GAATCTATGC  TATATGGTAT  ATTTCACTTA  CTATTTAAAC   1080

TACTACTTAA  TGGTAGCTCC  GGTGTATAAT  CATTATGATA  ATTATTTTGA  TAATTTCTTT   1140

AACATTTAGA  ACTTCTAATA  AAATTTTTAT  GTTACAATA   TCTATGATGA  TGGGGTTGTG   1200

GTTATTTATT  ATGGGGTTTT  TTATATTGGC  ACCCTTAACA  ATATTAATAT  AATTATTATG   1260

ATAAATATTA  ACCTAAAAAA  CAAATATTTT  CTGTTTTTA   TATATTATTA  ATATTTTTA    1320

ATTGTTGTTT  ACAAATCCTT  AAGAAAAATA  ACTAATTGAT  CAGTTACTC   ATATATATTA   1380

ACTTTTTCAT  TTTATATTTA  GTATATTATT  ACTTT                                1415
```

( 2 ) INFORMATION FOR SEQ ID NO:128:

( i ) SEQUENCE CHARACTERISTICS:
        ( A ) LENGTH: 345 amino acids
        ( B ) TYPE: amino acid
        ( C ) STRANDEDNESS: single (D) TOPOLOGY: linear (ii) MOLECULE TYPE: peptide (v) FRAGMENT TYPE: internal (xi) SEQUENCE DESCRIPTION: SEQ ID NO:128:

```
Met Ile Lys Leu Leu Phe Ile Leu Phe Tyr Phe Asn Pro Ile Thr Gly
1               5                   10                  15
Tyr Lys Trp Val Asp Pro Pro Arg Arg Tyr Asn Tyr Thr Val Leu Arg
            20              25                  30
Met Ile Pro Asp Ile Pro Asn Pro Met Asp Pro Ser Lys Asn Ala Glu
        35              40                  45
Val Arg Tyr Val Thr Ser Thr Asp Pro Cys Asp Met Val Ala Leu Ile
    50              55                  60
Ser Asn Pro Asn Ile Glu Ser Thr Ile Lys Thr Ile Gln Phe Val Gln
65              70                  75                      80
Lys Lys Lys Phe Tyr Asn Ala Ser Leu Ser Trp Phe Lys Val Gly Asp
            85                  90                  95
Asp Cys Thr Tyr Pro Ile Tyr Leu Ile Gln Tyr Phe Asp Cys Asp Pro
            100             105                 110
Gln Arg Glu Phe Gly Ile Cys Leu Lys Arg Ser Pro Asp Phe Trp Lys
        115             120                 125
Pro Ser Leu Val Gly Tyr Thr Phe Leu Thr Asp Asp Glu Leu Gly Leu
    130             135                 140
Val Leu Ala Ala Pro Ala Pro Phe Asn Gln Gly Gln Tyr Arg Arg Val
145             150                 155                     160
Ile Gln Ile Glu Asn Glu Val Phe Tyr Thr Asp Phe Met Val Gln Leu
            165                 170                 175
Pro Arg Glu Thr Cys Tyr Phe Ser Lys Glu Asp Lys Phe Glu Pro Thr
            180             185                 190
Phe Met Glu Trp Cys Lys Glu Ser Arg Ser Val Gly Ala Ser Lys Val
        195             200                 205
Asp Asp Glu Leu Phe Tyr Leu Asn Arg Ala Gly Pro Gln Thr Leu Leu
    210             215                 220
Lys Tyr Tyr Val Ile Lys Asp Phe Tyr Arg Leu Asn Gly Arg Glu Pro
225             230                 235                     240
Pro Ile Lys Phe Lys Glu Ala Leu Arg Tyr Asp Ile Pro Tyr Lys Val
            245                 250                 255
Asn Asp Lys Phe Asp Asp Glu Leu Pro Ser Arg Pro His Ile Ser Asn
            260             265                 270
Thr Ile Asn Lys Thr Ile Lys Glu Ile Val Asn Leu Glu Asp Tyr Phe
        275             280                 285
Lys Asn Thr Asn Val Ile Asp Thr Thr Thr Pro Thr Pro Ile Asn Asn
    290             295                 300
Thr Pro Lys Asn Ile Thr Val Gly Ile Val Ile Ile Ile Leu Ile Ile
305             310                 315                     320
Leu Phe Ile Ile Gly Phe Phe Val Tyr Lys Arg Gln Lys Ile Tyr Asn
            325                 330                 335
Asn Tyr Lys Lys Leu Thr Thr Asn Val
            340                 345
```